US012569551B2

(12) United States Patent
Schief et al.

(10) Patent No.: US 12,569,551 B2
(45) Date of Patent: Mar. 10, 2026

(54) MODIFIED IMMUNOGENIC PROTEINS

(71) Applicants: INTERNATIONAL AIDS VACCINE INITIATIVE, INC., New York, NY (US); THE SCRIPPS RESEARCH INSTITUTE, La Jolla, CA (US)

(72) Inventors: William Schief, La Jolla, CA (US); Manyuan Ma, La Jolla, CA (US); Jon Steichen, La Jolla, CA (US); Xiaozhen Hu, La Jolla, CA (US); Sebastian Raemisch, La Jolla, CA (US); Alessia Liguori, La Jolla, CA (US); Torben Schiffner, La Jolla, CA (US); Jordan Willis, New York, NY (US); Christopher Cottrell, La Jolla, CA (US)

(73) Assignees: International AIDS Vaccine Initiative, Inc., New York, NY (US); The SCRIPPS Research Institute, La Jolla, CA (US)

( * ) Notice: Subject to any disclaimer, the term of this patent is extended or adjusted under 35 U.S.C. 154(b) by 681 days.

(21) Appl. No.: 18/048,960

(22) Filed: Oct. 24, 2022

(65) Prior Publication Data

US 2023/0190914 A1     Jun. 22, 2023

Related U.S. Application Data

(63) Continuation-in-part of application No. PCT/US2021/030092, filed on Apr. 30, 2021.

(60) Provisional application No. 63/154,708, filed on Feb. 27, 2021, provisional application No. 63/018,198, filed on Apr. 30, 2020, provisional application No. 63/018,220, filed on Apr. 30, 2020, provisional application No. 63/018,229, filed on Apr. 30, 2020, provisional application No. 63/018,245, filed on Apr. 30, 2020, provisional application No. 63/018,254, filed on Apr. 30, 2020, provisional application No. 63/018,204, filed on Apr. 30, 2020, provisional application No. 63/018,234, filed on Apr. 30, 2020.

(51) Int. Cl.

| | |
|---|---|
| *A61K 39/00* | (2006.01) |
| *A61K 39/21* | (2006.01) |
| *A61P 31/18* | (2006.01) |
| *C07K 14/005* | (2006.01) |
| *C07K 14/08* | (2006.01) |

(52) U.S. Cl.
CPC .............. *A61K 39/21* (2013.01); *A61P 31/18* (2018.01); *C07K 14/005* (2013.01); *A61K 2039/575* (2013.01); *C12N 2740/16022* (2013.01); *C12N 2740/16034* (2013.01); *C12N 2740/16071* (2013.01)

(58) Field of Classification Search
CPC .. A61K 2039/545; A61K 38/00; A61K 39/12; A61K 39/21; A61P 31/18
See application file for complete search history.

(56) References Cited

FOREIGN PATENT DOCUMENTS

| WO | 2016/037154 A1 | 3/2016 |
|---|---|---|
| WO | 2016/205704 A2 | 12/2016 |
| WO | 2017/165674 A1 | 9/2017 |

OTHER PUBLICATIONS

Seiradake, E. et al., "Structurally encoded intraclass differences in EphA clusters drive distinct cell responses" , Nat Struct Mol Biol, 2013, 20(8):958-964.*
Joseph Jardine, et al., Rational HIV Immunogen Design to Target Specific Germline B Cell Receptors, Science(2013) 340 No. 6113, 711-716.
Joseph Jardine, et al., Supplementary Materials for: Rational HIV Immunogen Design to Target Specific Germline B Cell Receptors, Science(2013) 340 (6113) 711-716.
Communication pursuant to Rule 164(1) EPC and Supplementary Partial European Search Report issued May 8, 2024 in co-pending EP Application No. 21797527.5.
International Search Report dated Oct. 13, 2021, in International Application No. PCT/US2021/030092.

* cited by examiner

*Primary Examiner* — Barry A Chestnut
(74) *Attorney, Agent, or Firm* — Duane Morris LLP; Thomas J. Kowalski

(57)     ABSTRACT

The invention relates to germline-targeting designs, stabilization designs, and/or combinations thereof, of proteins designed with modified surfaces helpful for immunization regimens, other protein modifications and/or development of nanoparticles, methods of making and using the same, and to (a) germline-targeting priming or boosting/shepherding immunogens to initiate or guide maturation of VRC01-class responses (b) PCT64/PG9-germline-targeting designs (c) BG18-germline-targeting designs or boosting/shepherding immunogens to initiate or guide maturation of BG18-like responses, and/or (d) trimer stabilization and presentation in a membrane-bound format.

19 Claims, 36 Drawing Sheets
Specification includes a Sequence Listing.

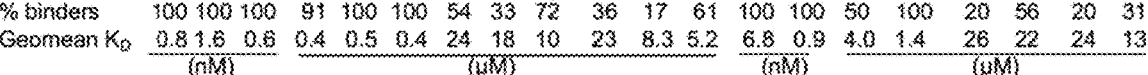
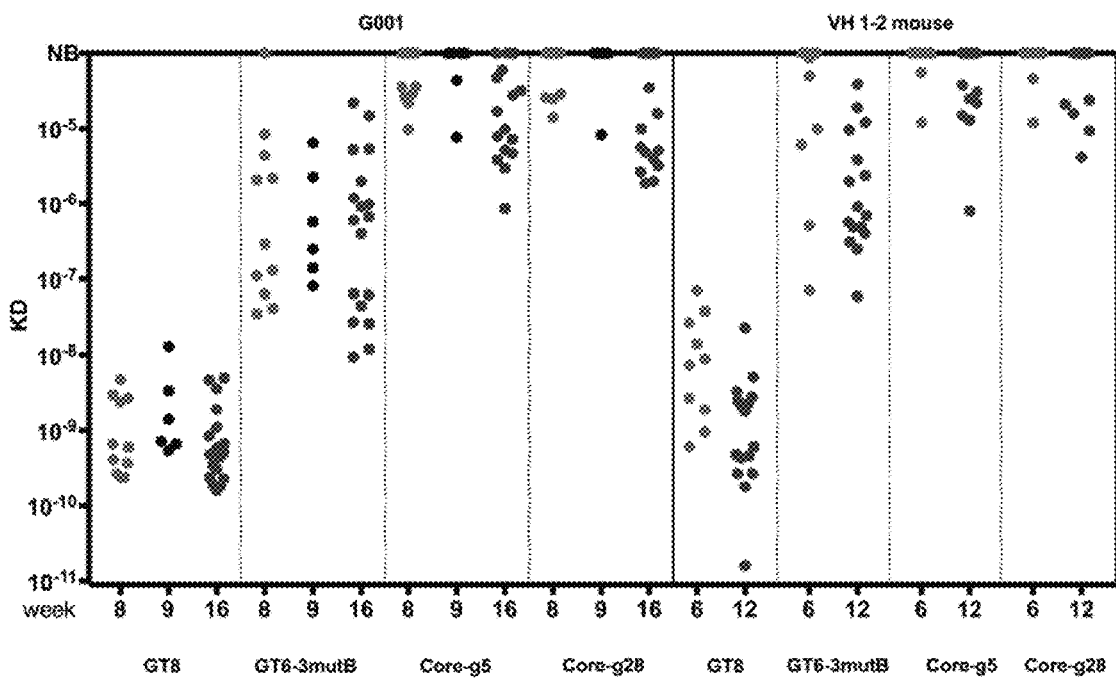
FIG. 1

BG505_MD39

BG505_ApexGT2

BG505_SOSIP_MD39_m (positive ctrl)
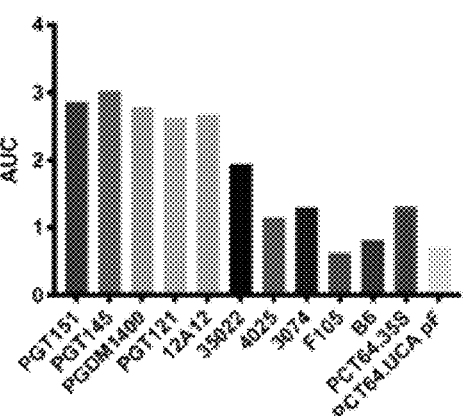
BG505.ApexGT5.2_m2
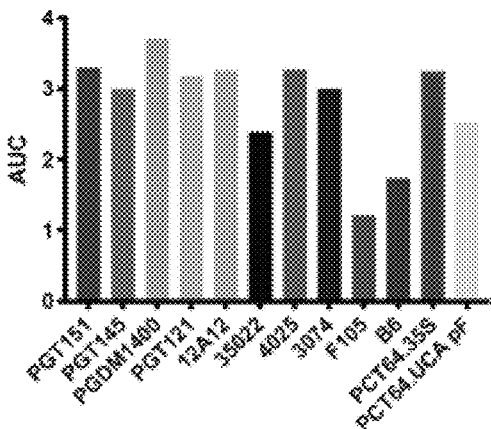
BG505.ApexGT6.2_m2
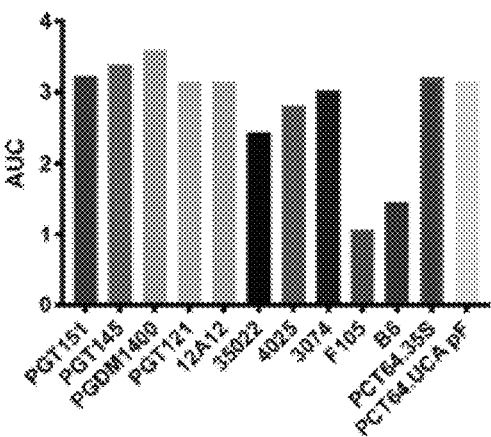
BG505.ApexGT5.2_congly_m2
BG505.ApexGT6.2_congly_m2
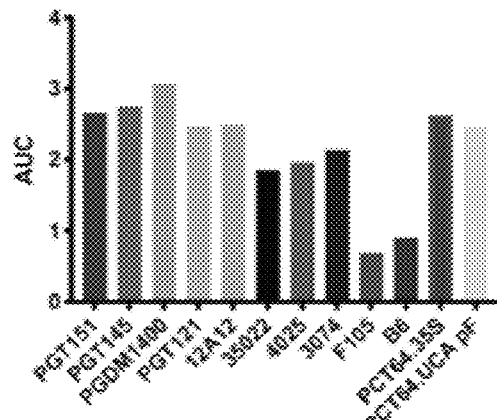
FIG. 19

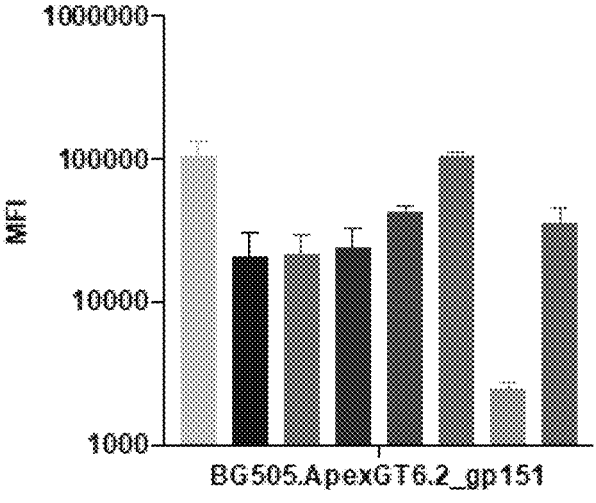
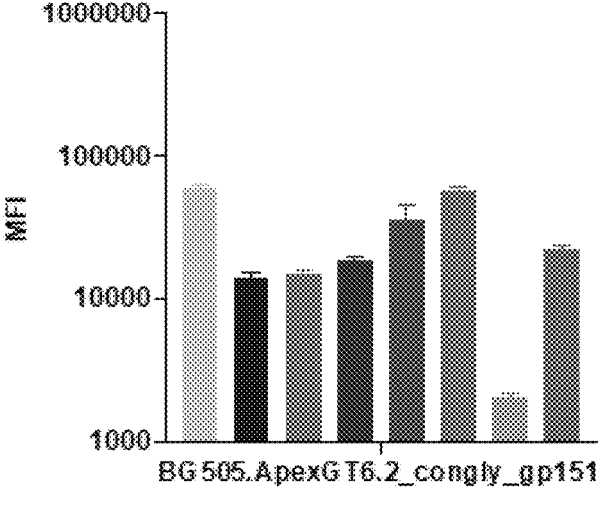
FIG. 20B

| Experiment/ sort | Immunization step (6 week intervals) | Sorting strategy | # of animals sorted | % of animals with detectable VRC01c pairs (≥1 pairs) | N VRC01 pairs sequenced | %mut VH (mean±sdev) | %mut VL (mean±sdev) |
|---|---|---|---|---|---|---|---|
| A1907/ABC203 | GT8-6G | GT8-6G | 5 | 80% | 10 | 1.9 ± 2.6 | 2.7 ± 2.1 |
| A1906/ABC202 | GT8 | GT8 | 5 | 100% | 10 | 3.7 ± 1.8 | 3.7 ± 1.7 |
| A1906/ABC202 | GT8-6G | GT8 | 5 | 80% | 11 | 2.4 ± 1.7 | 2.8 ± 1.5 |
| A1906/ABC202 | GT8-new6G | GT8 | 5 | 100% | 25 | 1.3 ± 2.1 | 2.2 ± 2.1 |
| A1906/ABC202 | GT8-6G-g123 | GT8-6G | 5 | 80% | 6 | 1.9 ± 2.8 | 1.8 ± 1.3 |
| A1907/ABC203 | GT8-6G-g123 | GT8-6G | 4 | 75% | 7 | 1.6 ± 2.5 | 3.3 ± 3.3 |
| N1807/ABC180 | GT8>placebo | GT6-3mutB | 3 | 100% | 14 | 4.1 ± 2.6 | 5.0 ± 2.6 |
| N1901/ABC181 | GT8-6G>placebo | GT6-3mutB | 4 | 100% | 29 | 5.2 ± 3.4 | 4.9 ± 2.5 |
| N1807/ABC180 | GT8>GT6-5mut | GT6-3mutB | 4 | 100% | 15 | 4.2 ± 2.7 | 3.8 ± 1.5 |
| N1901/ABC181 | GT8-6G>GT6-3mutB | GT6-3mutB | 5 | 100% | 31 | 5.3 ± 3.1 | 4.5 ± 2.3 |
| A1906/ABC214 | GT8-6G>core-g5 | core-g15 | 2 | 100% | 12 | 10.5 ± 2.5 | 7.2 ± 1.7 |
| N1807/ABC180 | GT8>core-g7 | GT6-3mutB | 4 | 100% | 16 | 9.6 ± 5.3 | 7.5 ± 1.6 |
| A1905/ABC205 | GT8-6G>core-g27 | core-g7 | 3 | 100% | 28 | 7.4 ± 3.4 | 4.9 ± 2.3 |
| A1904/ABC201 | GT8-6G>core-g28 | core-g7 | 2 | 100% | 17 | 12.2 ± 2.7 | 9.4 ± 2.3 |
| A1910/ABC230R | GT8-6Gg123>core-g28 | core-g7 | 3 | 100% | 9 | 13.8 ± 5.3 | 6.4 ± 1.4 |

MODIFIED IMMUNOGENIC PROTEINS

RELATED APPLICATIONS AND INCORPORATION BY REFERENCE

This application is a continuation-in-part of international application PCT/US2021/030092 which published as PCT Publication No. WO 2021/222706 on Nov. 4, 2021 which claims benefit of US provisional patent application Ser. Nos. 63/018,198 filed Apr. 30, 2020, 63/018,204 filed Apr. 30, 2020, 63/018,220 filed Apr. 30, 2020, 63/018,229 filed Apr. 30, 2020, 63/018,234 filed Apr. 30, 2020, 63/018,245 filed Apr. 30, 2020, 63/018,254 filed Apr. 30, 2020 and 63/154, 708 filed Feb. 27, 2021. Reference is made to international patent application PCT/US19/63903 filed Dec. 1, 2019.

FEDERAL FUNDING LEGEND

This invention was made with government support under Grant Nos. 1UM1 AI144462, 1UM1 A1100663, 1R01 AI147826, 5R01 AI113867, and 5R01 AI128836 awarded by the National Institutes of Health. The government has certain rights in the invention.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Oct. 18, 2022, is named Y7969_04060.xml and is 296,498 bytes in size.

FIELD OF THE INVENTION

The invention relates to germline-targeting designs, stabilization designs, shepherding and polishing designs, and/or combinations thereof, of proteins designed with modified surfaces helpful for immunization regimens, other protein modifications, and/or development of nanoparticles, and/or development of membrane-anchored immunogens, and methods of making and using the same.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+

T cells seriously impairs the body's ability to fight most invaders, but it has a particularly severe impact on the defenses against viruses, fungi, parasites and certain bacteria, including mycobacteria.

Viruses have evolved a variety of mechanisms to escape antibody recognition, many of which involve features of the viral surface proteins, such as high variability, steric occlusion, and glycan coating. For HIV, the dense shield of glycans that decorate the viral Env protein was once believed to be refractory to antibody recognition, shielding conserved protein epitopes of important functional significance whose greater exposure would result in increased susceptibility to antibody neutralization.

Citation or identification of any document in this application is not an admission that such document is available as prior art to the present invention.

SUMMARY OF THE INVENTION

The present invention relates to non-naturally occurring proteins, which may be involved in forming immunogenic proteins of the present invention.

The invention relates to a non-naturally occurring protein which may comprise any one of the sequences in Table 1.

The protein may have at least 90% or 95% homology or identity with the sequence of the non-naturally occurring protein(s) of the invention.

The invention also encompasses trimers which may comprise any one of the non-naturally occurring protein(s) of the invention.

The proteins of the invention may comprise an additional cysteine and/or be fused to be a multimerization motif. The proteins of the invention may also comprise a tag for purification or biotinylation, such as a his tag or a avi-tag.

The invention also encompasses nucleic acids encoding the non-naturally occurring protein(s) of the present invention, including nucleic acids that may have at least 90% or 95% homology or identity with a nucleotide encoding the sequence of the non-naturally occurring protein(s) of the invention. In one embodiment, the nucleic acid may be a RNA, advantageously a mRNA.

The invention also encompasses eliciting an immune response which may comprise systemically administering to an animal in need thereof an effective amount of any one of the non-naturally occurring protein(s) of the invention. The animal may be a mammal, advantageously a human.

The invention also encompasses a method or use of any of the herein disclosed proteins for germline-targeting immunogens to prime specific precursor B cells, boosting/shepherding immunogens to guide maturation, and/or trimer stabilization and presentation in a membrane-bound format. In one embodiment, the maturation is a VRC01-class response. In another embodiment, the germline is PCT64, PG9 or BG18 or a combination thereof.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28 (b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 is a graph that shows the binding affinities of eOD-GT8 or candidate boost immunogens for partially mature VRC01-class antibodies induced by vaccination with adjuvanted eOD-GT8 60mer either in a human clinical trial (G001) or in a mouse model (VH1-2 mouse).

FIG. 17 discloses SEQ ID NOS 159-164, 160-161 and 165, respectively, in order of appearance.

FIG. 19 shows antigenic profiles of BG505.ApexGT5.2 and BG505.ApexGT6.2 compared with WT trimers. The ELISA plate was coated with RM19R antibody overnight at 4° C. and blocked by 5% skim milk in PBST with 1% FBS. Indicated Env trimers were loaded onto the blocked plate and labelled by 10 ug/mL with 4-fold dilutions of the indicated antibodies followed by peroxidase-conjugated anti-human IgG antibodies. Plates were developed for less than 10 minutes with TMB, stopped by addition of sulfuric acid, and optical densities at 450 nm and 570 nm were measured by a plate reader (BioTek). Data were normalized by subtracting the background, AUCs were calculated in graphpad prism, and AUCs of each mAb against negative control supernatants were subtracted from AUCs for each construct. To note, PCT64.UCA pF equals PCT64.LMCA.

FIGS. 20A-20B show cell-surface antigenic profiles of BG505.ApexGT5.2 and BG505.ApexGT6.2 membrane bound trimers compared with WT trimers. The FreeStyle 293F cells (Invitrogen, Cat no. R79007) were maintained in FreeStyle 293 expression media at 1.0×106 cells/mL. Each DNA construct was transfected to cells with 293Fectin (ThermoFisher) in duplicates. Transfected cells grown for 2 days at 37° C. Cells were centrifuged at 500 g and resuspended in FACS buffer (HBSS, 1 mM EDTA, 1% BSA) and stained with Abs at 10 ug/mL for 1 h at 37° C. After washed twice with FACS buffer, cells were stained with phycoerythrin (PE)-conjugated α-human IgG (Sigma) for 20 min at 37° C. After washed twice with FACS buffer, cells were analyzed sorted on a NovoCyte (ACEA Biosciences) Analyzer. Data were normalized by subtracting the background, MFIs were calculated in FlowJo.

FIG. 27 shows summary statistics of VRC01-class B cell recovery and % mutation after priming or boosting in the VH1-2 mouse model. Groups of mice were either (i) primed at day 0 with the indicated immunogens and then sacrificed for B cell analysis at day 42, or (ii) primed at day 0 and boosted at day 42 with the indicated immunogens and then sacrificed for B cell analysis at day 84. Proteins were delivered via the IP route as 20 µg with Sigma adujvant system. Placebo was delivered via the IP route as PBS buffer with Sigma adujvant system. Cell suspensions from spleen and lymph nodes were subjected to B cell sorting and BCR sequencing, and the statistics of recovery of total VRC01-class pairs is indicated. Overall, GT8 60mer and its hyperglycosylated variants performed similarly. GT8 60mer priming followed by GT6 or placebo boost produced similar mutation levels, demonstrating that the GT6 boost immunogen did not select for substantial maturation. However, GT8 60mer priming followed by core boosting in most cases produced substantial increases in the mutation levels beyond the level generated by a placebo boost, demonstrating that certain core boost immunogens can select for increased maturation.

Figure 33:
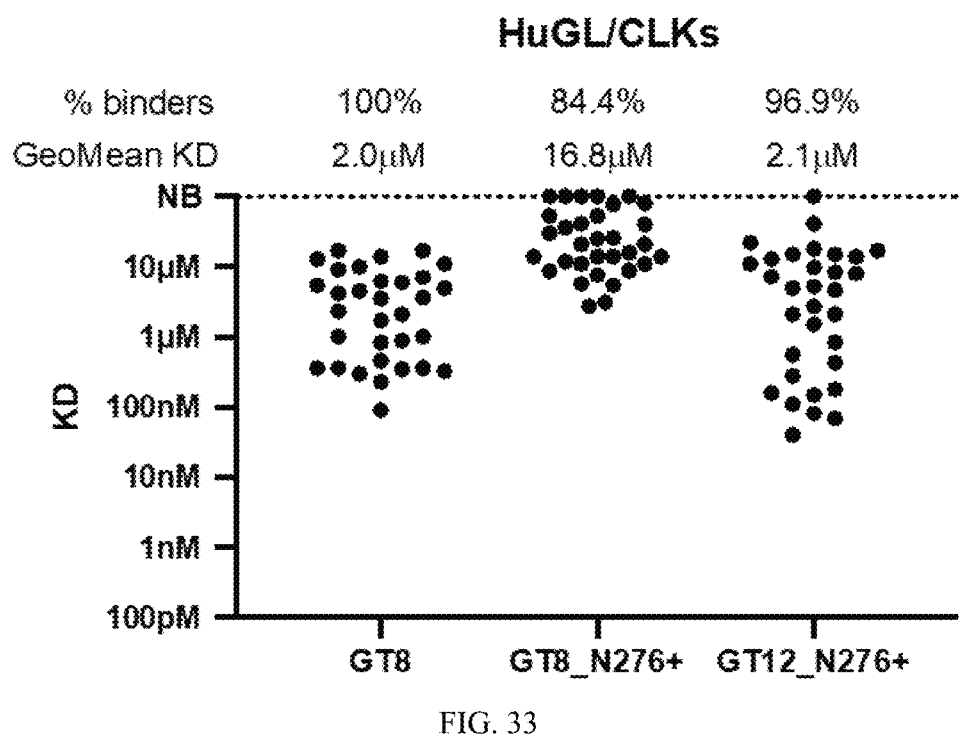

FIG. 33 shows GT12 with the N276 glycan has higher affinity to human naive VRC01-class precursor mAbs compared to GT8 with N276 glycan. eOD-GT8 was used as a probe to sort human naïve B cells. Epitope specific B cells were sorted and their B cell receptors (BCRs) sequenced. VRC01-class BCRs were expressed as IgGs, and binding to different priming candidates (GT8, GT8_N276, GT12_N276) was measured by SPR. The Kps for each antigen were determined by capturing IgG on the SPR Chip and flowing antigens as analyte. NB means no binding. The top concentration of analytes were 50 µM.

DETAILED DESCRIPTION OF THE INVENTION

Figure 2:
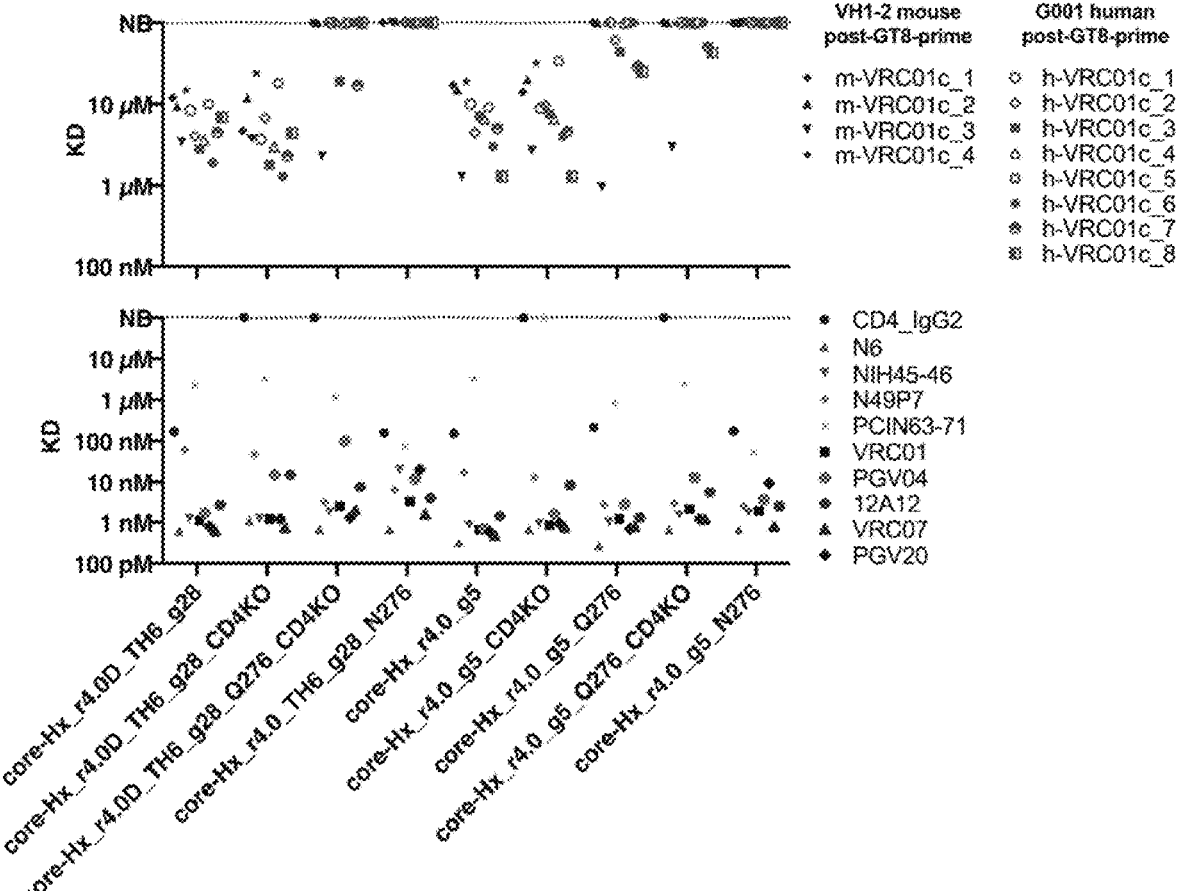
FIG. 2 is a graph that shows the antigenic profiles of candidate boost immunogens to follow eOD-GT8 60mer priming (top) and binding affinities of the highest affinity antibodies from FIG. 1 (expressed as dissociation constants, KD) of core-gp120 boost immunogen candidates for VRC01-class antibodies induced by eOD-GT8 60mer immunization in humans or a mouse model (bottom).
Figure 3:
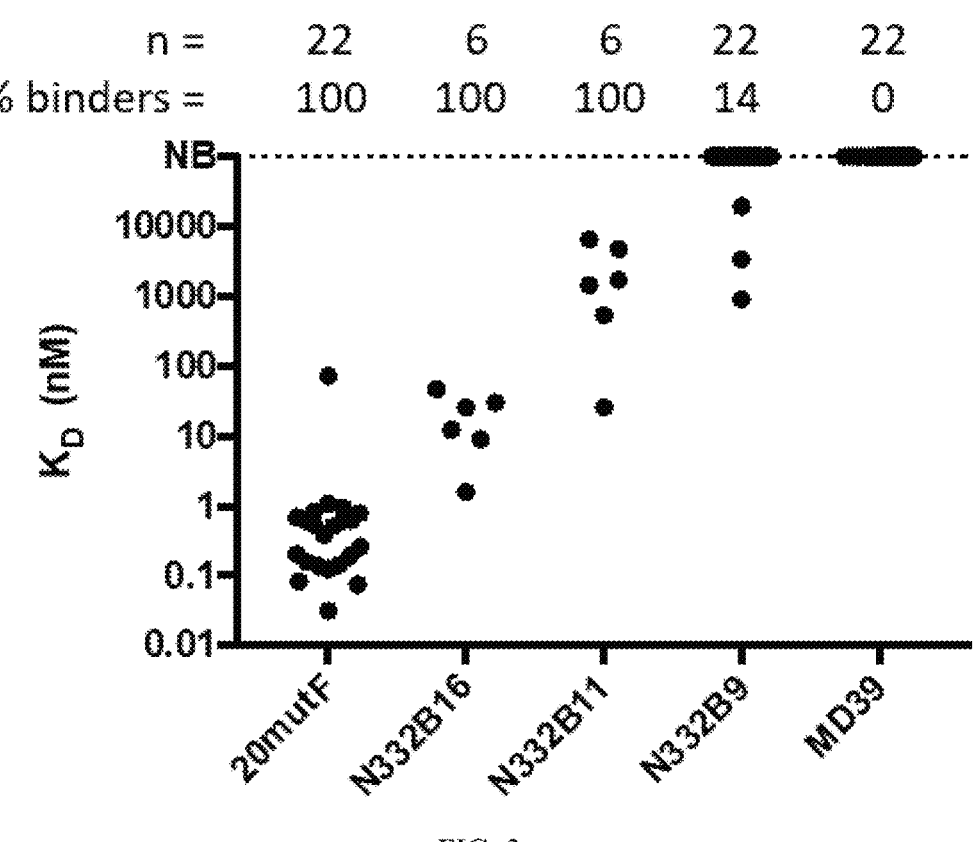
FIG. 3 shows N332B16, N332B11 and N332B9 boosting candidates. Mice that were adoptively transferred with BG18 gH knockin B cells were immunized with 20mutF (N332-GT2) nanoparticles, and antigen-specific B cells were sorted and sequenced 42 days after the prime, as described in Steichen et al. (Science. 2019 Dec. 6;366 (6470): eaax4380. doi: 10.1126/science.aax4380. Epub 2019 Oct. 31.PMID: 31672916). The isolated B cell receptors were then expressed as Fabs, and binding to 20mutF (N332-GT2), N332B11, N332B16, N332B9 and WT (MD39) trimers was measured by SPR. The Kps for each Fab were determined by capturing trimer on the SPR chip and flowing Fab as analyte. NB, no binding.
Figure 4:
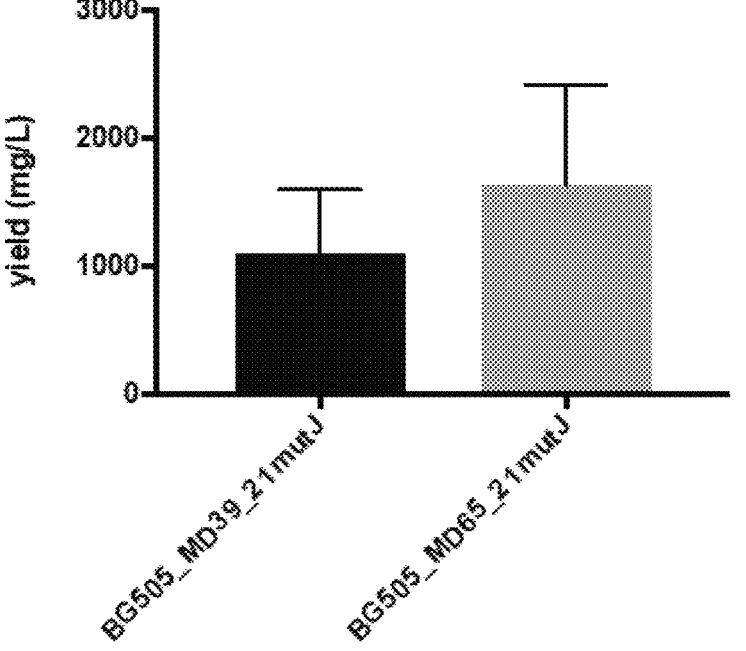
FIG. 4 shows an expression yield for BG505_MD39_21mutJ compared to BG505 MD65 21mutJ. BG505 MD39 21mutJ and BG505_MD65_21mutJ were expressed in freestyle 293F cells, cotransfected with furin and purified by either Nickel, Lectin or antibody affinity columns followed by size exclusion chromatography on a superdex200 column and the final yield of purified protein was determined by A280.
Figure 5:
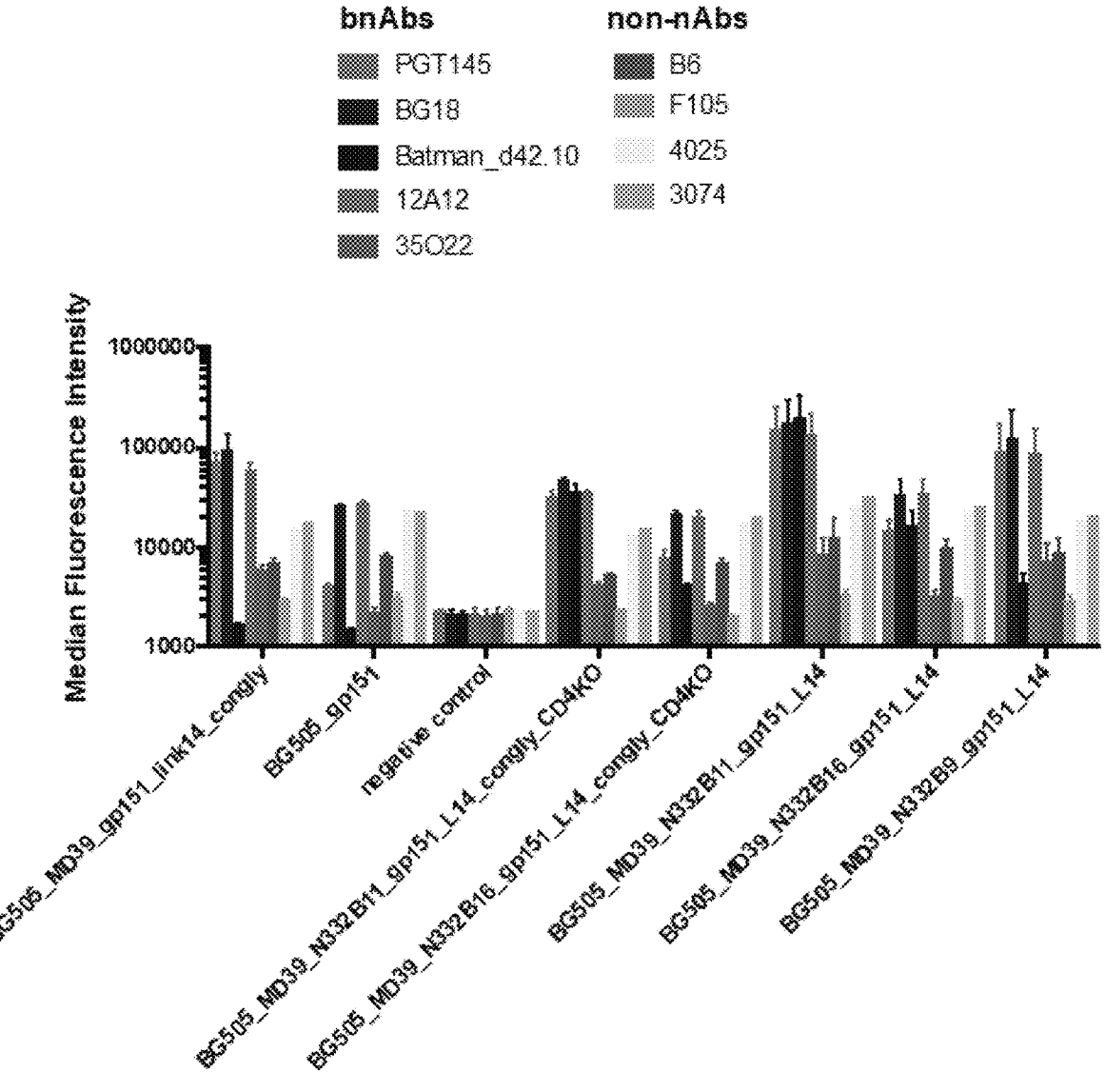
FIG. 5 shows a N332B11, N332B16, N332B9 cell surface antigenic profile. The indicated genes were transiently transfected into 293F cells and two days later the cells were stained with 10 ug/mL of the indicated FAB, which was detected with R-Phycoerythrin anti-Human IgG (Jackson ImmunoResearch) secondary on the cell surface using a NovoCyte analyzer (ACEA Biosciences). BG505_MD39_gp151_link14_congly demonstrates the antigenic profile of a well folded trimer. BG505_gp151 demonstrates the antigenic profile of a poorly folded trimer.
Figure 6:
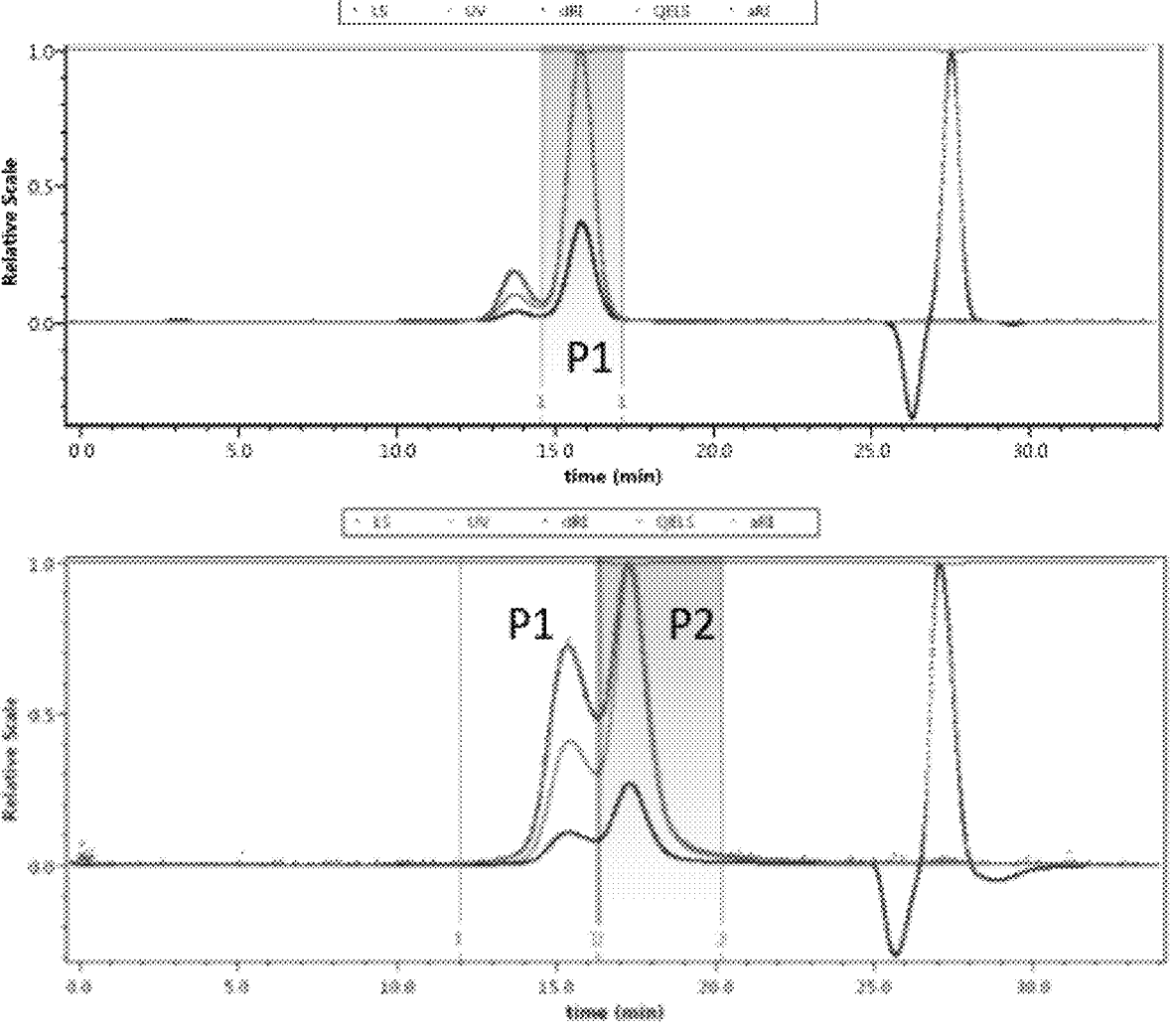
FIG. 6 shows molecular weight, SEC profile, and yield of 29mutA and 39mutA (N332-GT6). BG505_MD65 29mutA_mC and BG505_MD65_39mutA_mC (N332-GT6) were expressed in freestyle 293F cells, cotransfected with furin and purified by Nickel affinity column followed by size exclusion chromatography on a superdex200 column. The protein molecular weight was determined by analyzing the fractions by SEC+multiangle light scattering (SECMALS) using DAWN HELEOS II and Optilab T-rEX detectors (Wyatt Technology). For 29mutA the dominant peak corresponded to the MW of a trimer. For 39mutA there were two peaks which correspond closely to the MWs of a trimer and a dimer of trimers for P2 and P1, respectively. The final yield of purified protein was determined by A280. Top panel: BG505_MD65_29mutA_mC, Calculated trimer MW-218 kDa, P1-196 kDa, Yield-2.8 mg/L. Bottom panel: BG505_MD65_39mutA_mC (N332-GT6), Calculated trimer MW-214 kDa, P1-404 kDa corresponding to dimer of trimers, P2-231 kDa corresponding to trimer, Yield-4.8 mg/L.
Figures 7A, 7B:
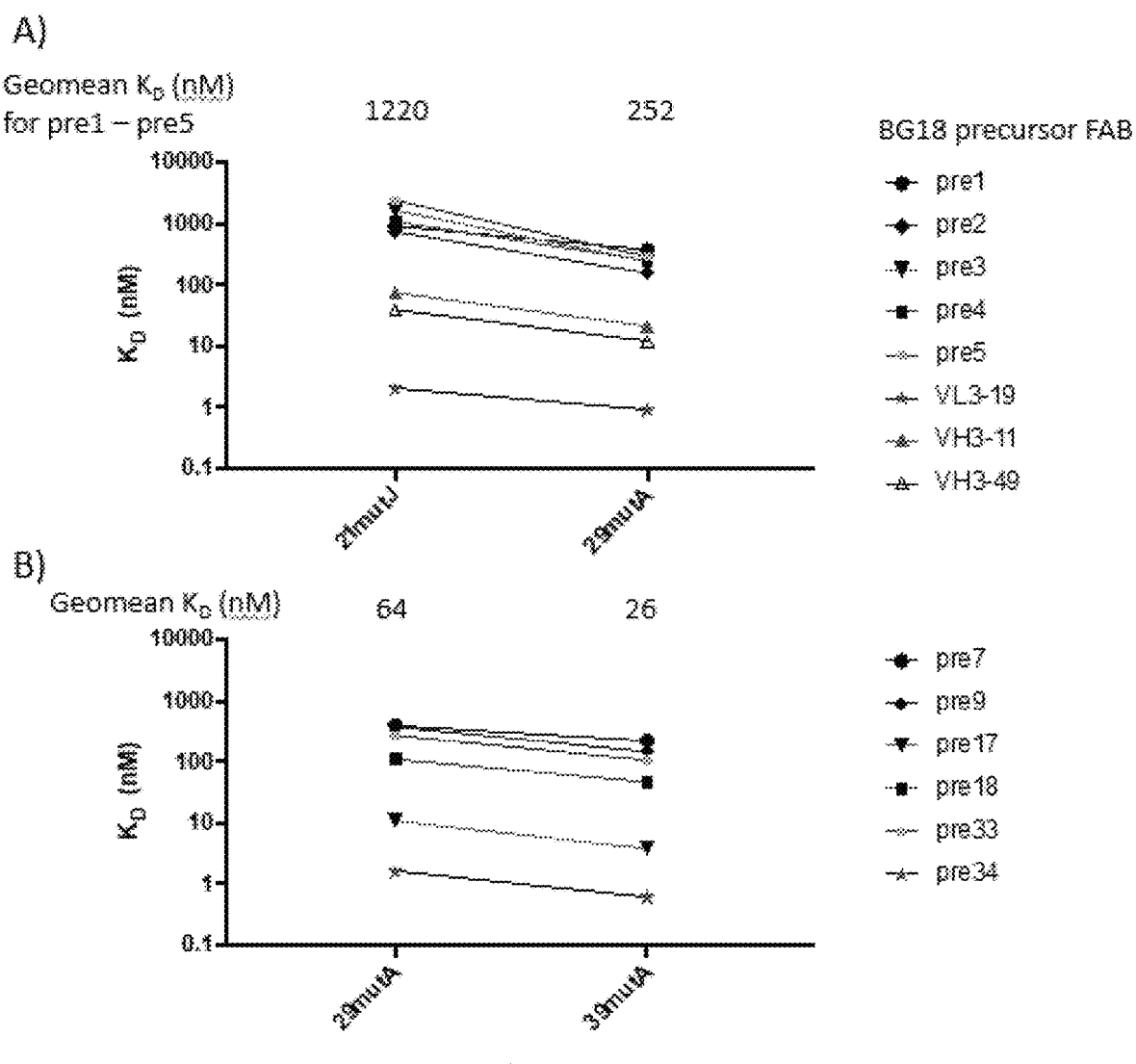
FIGS. 7A and 7B show surface plasmon resonance (SPR) measured precursor affinities for 29mutA and 39mutA (N332-GT6) compared to 21mutJ (N332-GT5). Binding affinities (Kps) were measured on A) Biacoer4000 (GE) or B) ProteOn XPR36 (Bio-Rad) by capturing the indicated His-tagged trimers (BG505_MD65_21mutJ_mC, BG505_MD65_29mutA_mC and BG505 MD65 39mutA_mC) on an anti-His mAb capture chip as ligands and flowing BG18 precursor FAB analytes with diverse HCDR3 junctions or VH genes in 1×HBS-EP running buffer (Teknova) supplemented with 1 mg/mL BSA.
Figure 8:
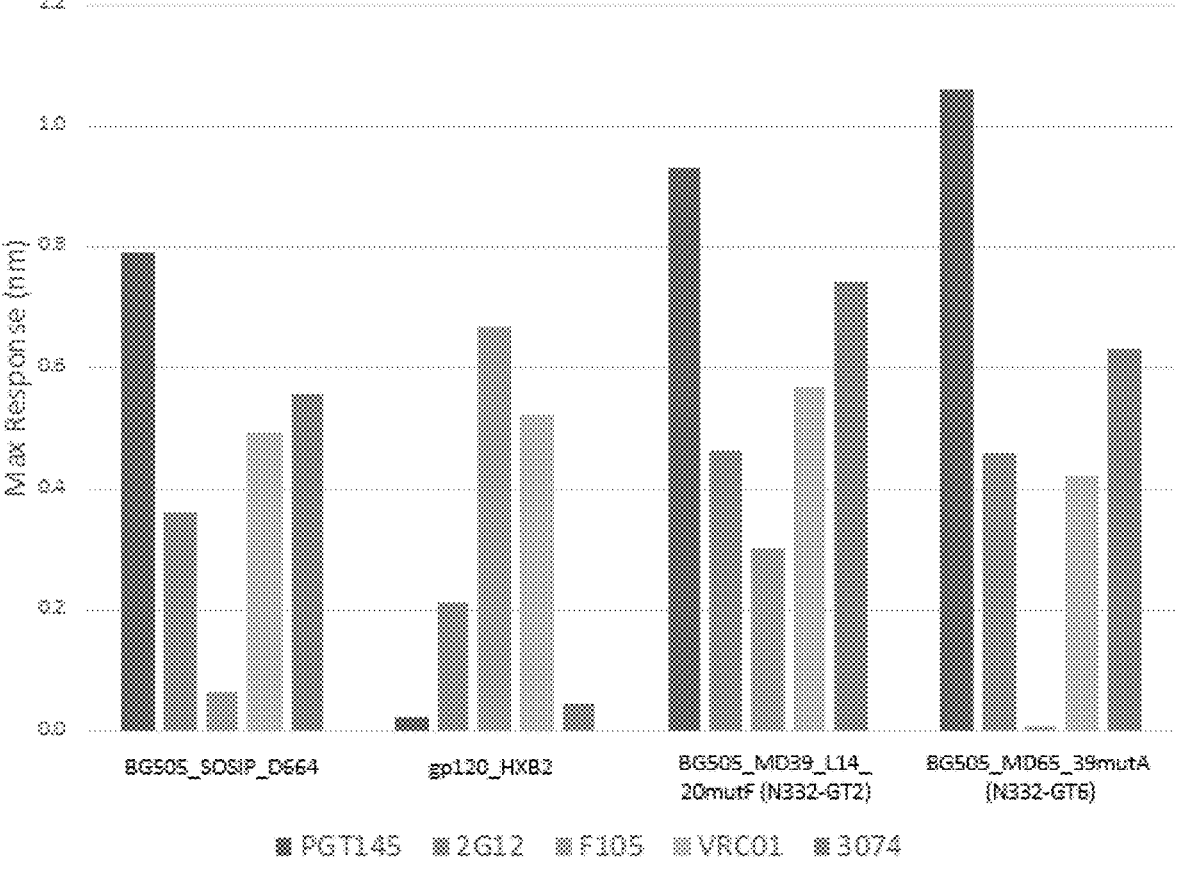
FIG. 8 shows an antigenic profile of BG505_MD65_39mutA_mC (N332-GT6) soluble trimer. The indicated Env proteins were tested for binding to broadly neutralizing antibodies (PGT145, 2G12 and VRC01) and non-neutralizing antibodies (F105 and 3074). An Octet RED instrument (FortéBio) was used to assess antibody-antigen interactions by Biolayer Interferometry. IgGs were loaded onto anti-human Fc (AHC) biosensors (FortéBio) at a concentration of 5 μg/mL in kinetics buffer (PBS, pH 7.4, 0.01% [w/v] BSA, and 0.002% [v/v] Tween 20) until a response of 1.0 nanometer (nm) shift was reached. Loaded biosensors were dipped into kinetics buffer for 1 min to acquire a baseline and then moved to wells containing 1 μM Env trimer or 3 μM Env gp120 in kinetics buffer. The Envs were allowed to associate for 180 secs before the biosensor were move back to the wells containing kinetics buffer where the baseline was acquired. Maximum response (nm shift) during the association phase was plotted for each IgG/Env pair.
Figure 9:
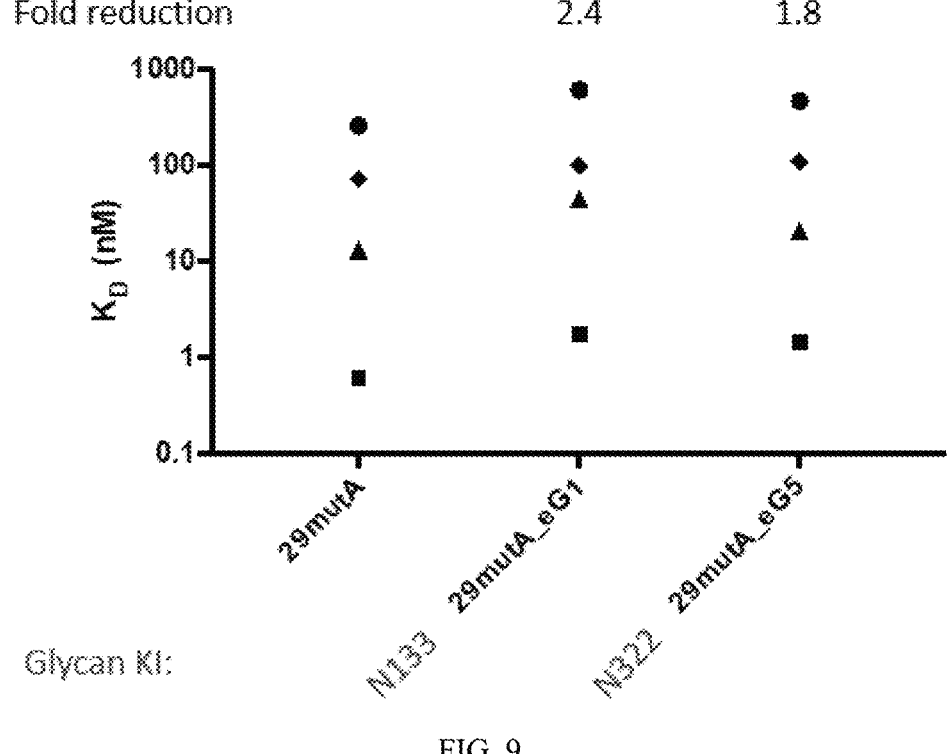
FIG. 9 shows an effect of glycan knock-ins to the BG18 epitope on 29mutA. Purified recombinant BG505_MD65_29mutA_mC with the indicated glycans knocked-in were tested for reduction in binding affinity for BG18 precursors with diverse HCDR3 junctions or alternate VH gene. SPR binding affinities (Kps) were measured on a Biacore 8000 (GE) by capturing the indicated His-tagged trimers on an anti-His mAb capture chip as ligands and flowing BG18 precursor FAB analytes in 1×HBS-EP running buffer (Teknova) supplemented with 1 mg/mL BSA.
Figure 10:
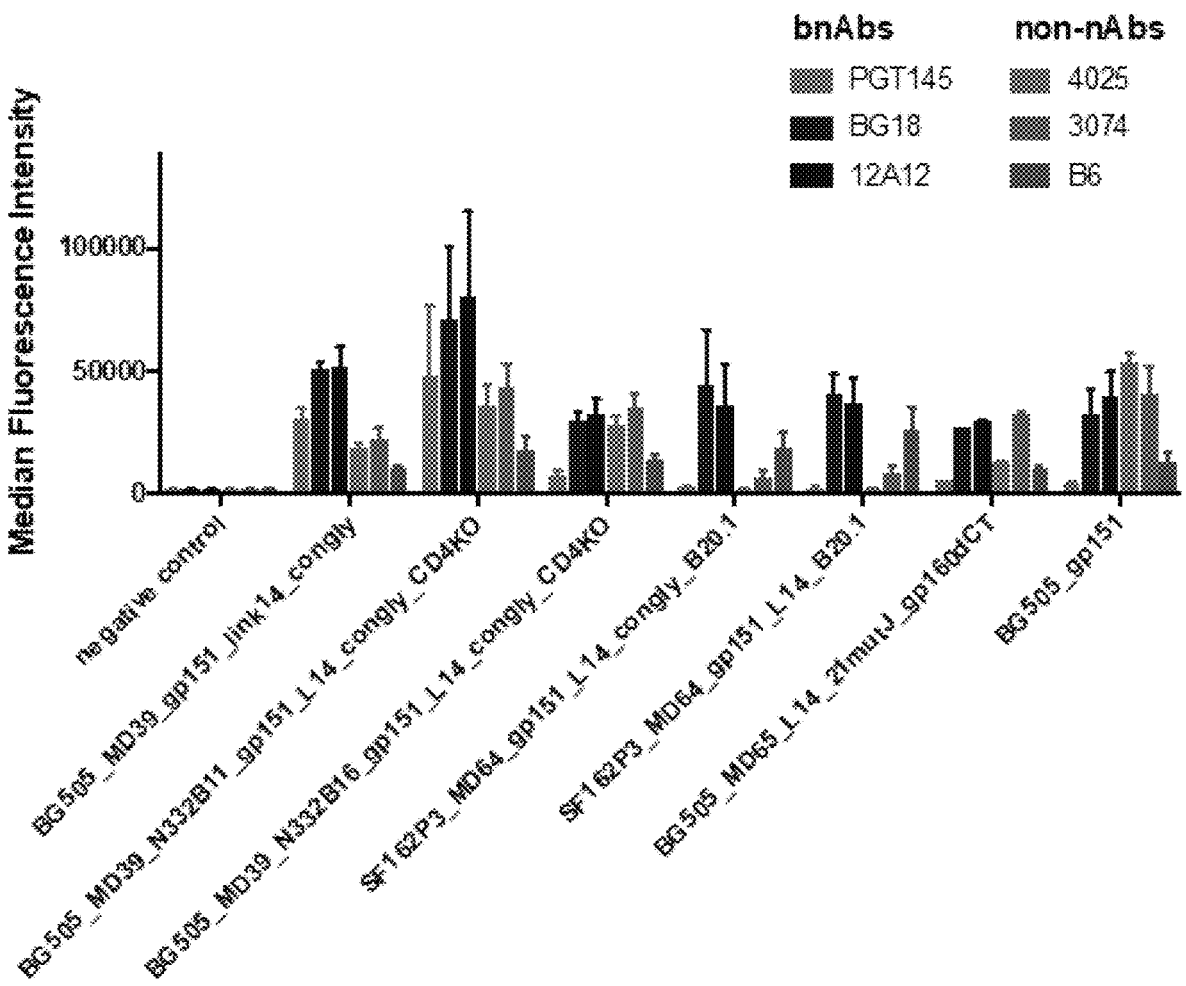
FIG. 10 shows a N332B11, N332B16, SF162P3_B20.1 cell surface antigenic profile. The indicated genes were transiently transfected into 293F cells and two days later the cells were stained with 10 ug/mL of the indicated FAB, which was detected with R-Phycoerythrin anti-Human IgG (Jackson ImmunoResearch) secondary on the cell surface using a NovoCyte analyzer (ACEA Biosciences). BG505_MD39_gp151_link14_congly_m demonstrates the antigenic profile of a well folded trimer. BG505_gp151_m demonstrates the antigenic profile of a poorly folded trimer.
Figure 11:
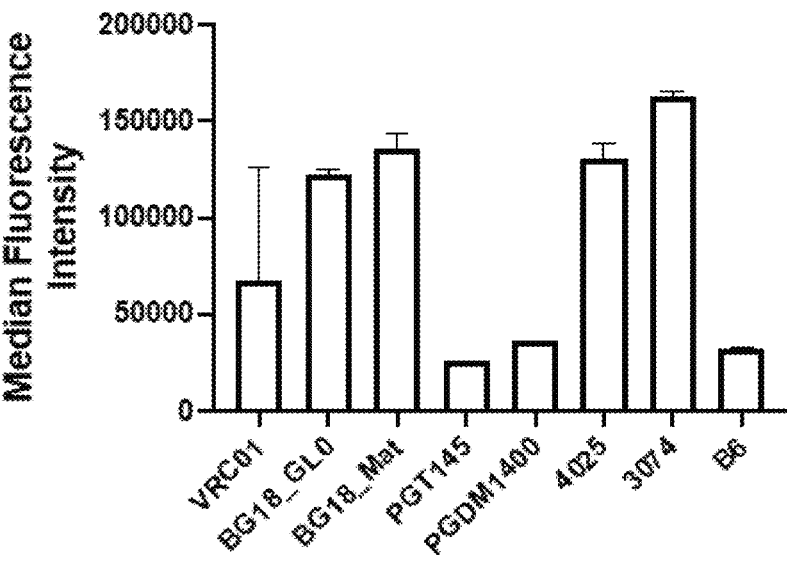
FIG. 11 shows an antigenic profile of BG505_MD65_L14_21mutJ_gp160dCT_m. Freestyle 293F cells were transfected with BG505_MD65_L14_21mutJ_gp160dCT_m. After 2 days, cells were labelled with the indicated antibodies, stained with AlexaFluor-647-conjugated anti-human IgG secondary antibody (Jackson ImmunoResearch) and Median fluorescence intensities of single cells were measured on a Novo-Cyte analyzer (ACEA Biosciences).
Figure 12:
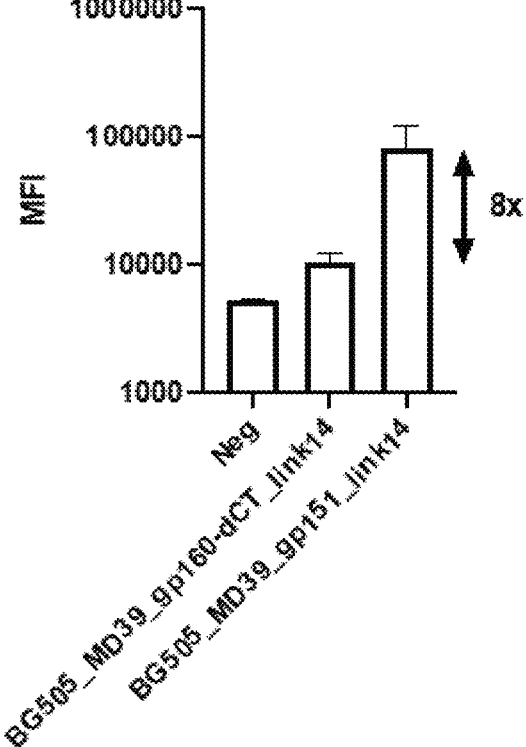
FIG. 12 shows a comparison of expression levels of gp160-dCT vs gp151. Freestyle 293F cells were transfected with the indicated Env constructs. After 2 days, cells were labelled with PGT121, stained with AlexaFluor-647-conjugated anti-human IgG secondary antibody (Jackson ImmunoResearch) and Median fluorescence intensities of single cells were measured on a NovoCyte analyzer (ACEA Biosciences).
Figure 13A:
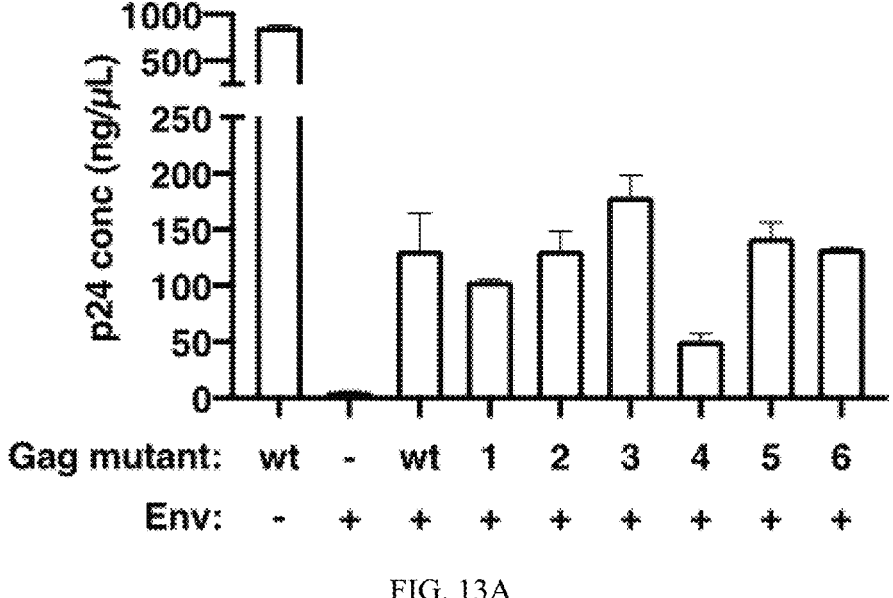
FIGS. 13A-13C show gag expression levels. The indicated GagIIIb constructs were cotransfected 1:3 with HIV-1 Envelope protein into freestyle 293F cells. Gag only and Env only served as positive (Pos) and negative (Neg) controls, respectively. After 7 days, supernatants were clarified by centrifugation, filtered through a 0.45 μm filter and Virion-associated p24 concentrations were measured using the Lentivirus-Associated p24 ELISA Kit (Cell Biolabs Inc.) according to manufacturer's instructions.
Figure 13B:
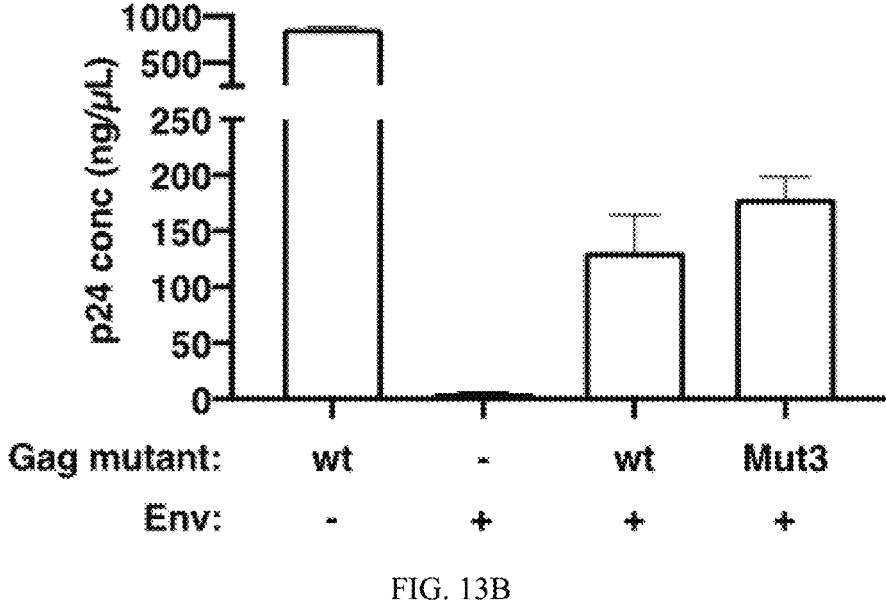
Figure 13C:
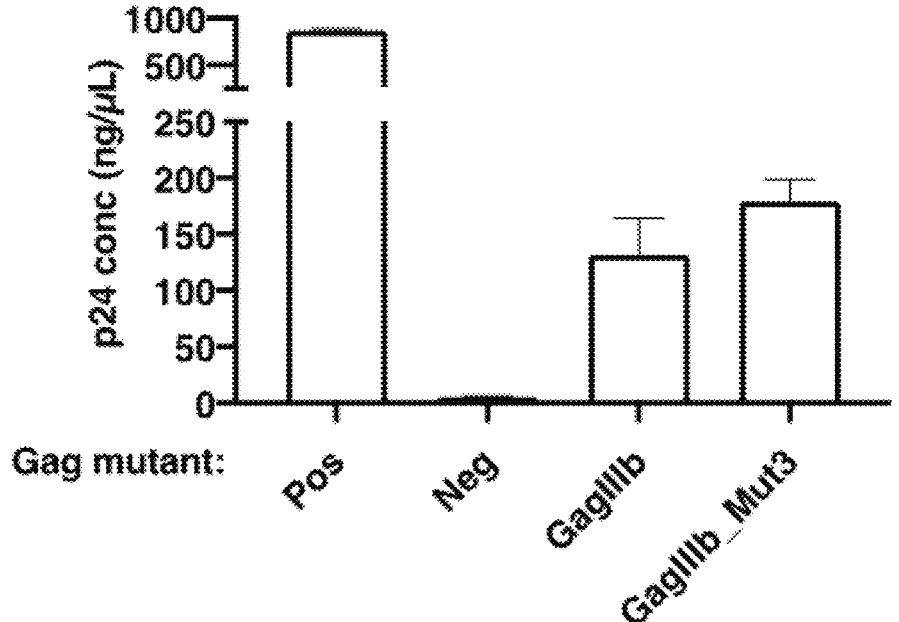
Figure 14:
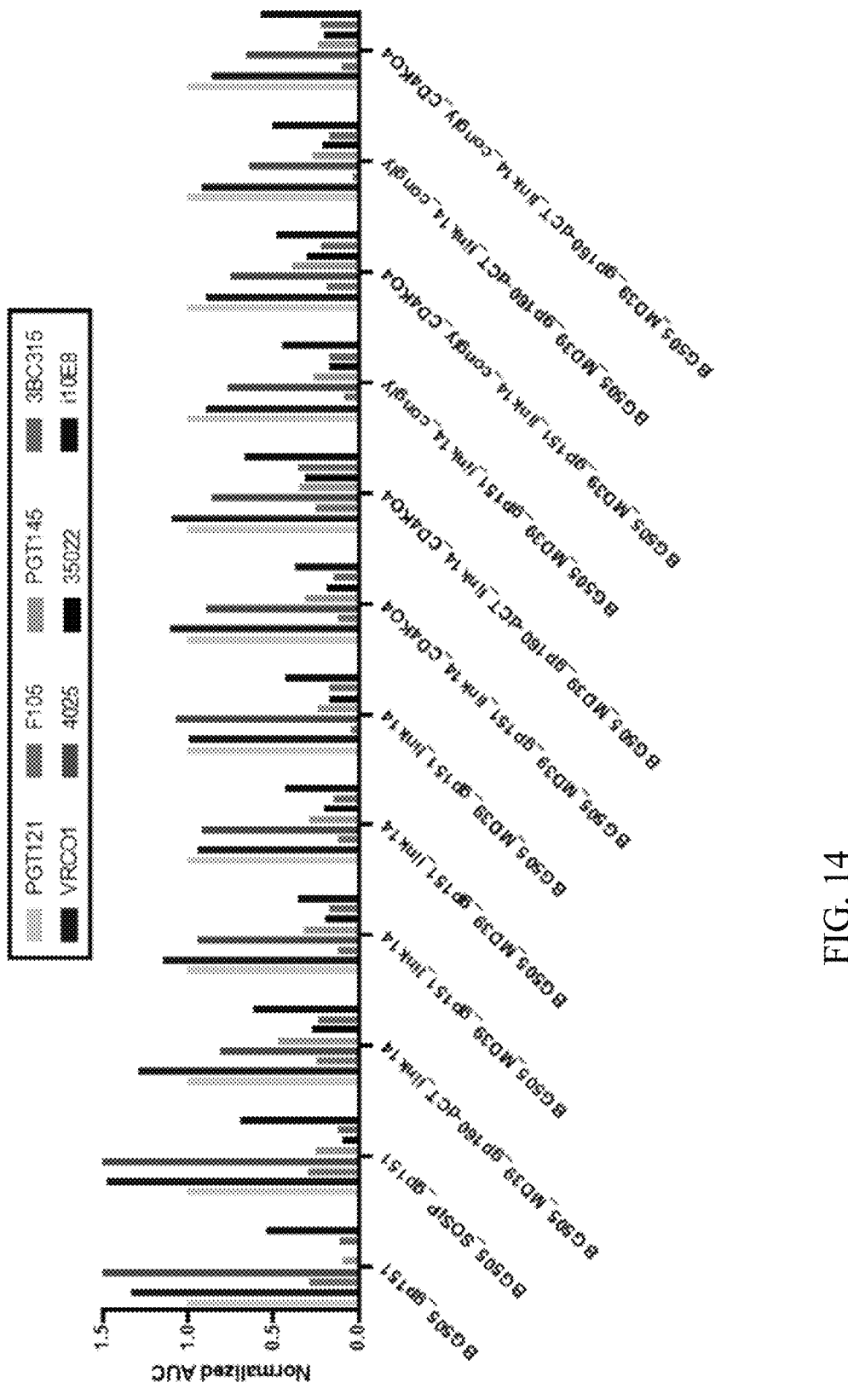
FIG. 14 shows antigenic profiles of membrane-bound BG505 trimers. The indicated constructs were co-transfected with gag-mut3 into freestyle 293F cells and in addition, Furin was cotransfected with cleave-dependent constructs BG505_gp151_m and BG505_SOSIP_gp151_m. After 6 days, supernatants were clarified by centrifugation, filtered through a 0.45 μm filter and concentrated using LentiX (Takara Bio). VLPs were coated directly onto high-binding ELISA plates, blocked with 2% BSA in PBS, and labelled with titration series of the indicated antibodies followed by peroxidase-conjugated anti-human IgG antibodies. Plates were developed for 10 minutes with TMB, stopped by addition of sulfuric acid, and optical densities were measured on a plate reader (BioTek). Data were normalized by subtracting the background, AUCs were calculated in graphpad prism, and AUCs of each mAb against negative control supernatants were subtracted from AUCs for each construct. Expression levels for each construct were normalized by dividing by the respective PGT121 signal and the normalized AUCs were plotted in prism.
Figure 15:
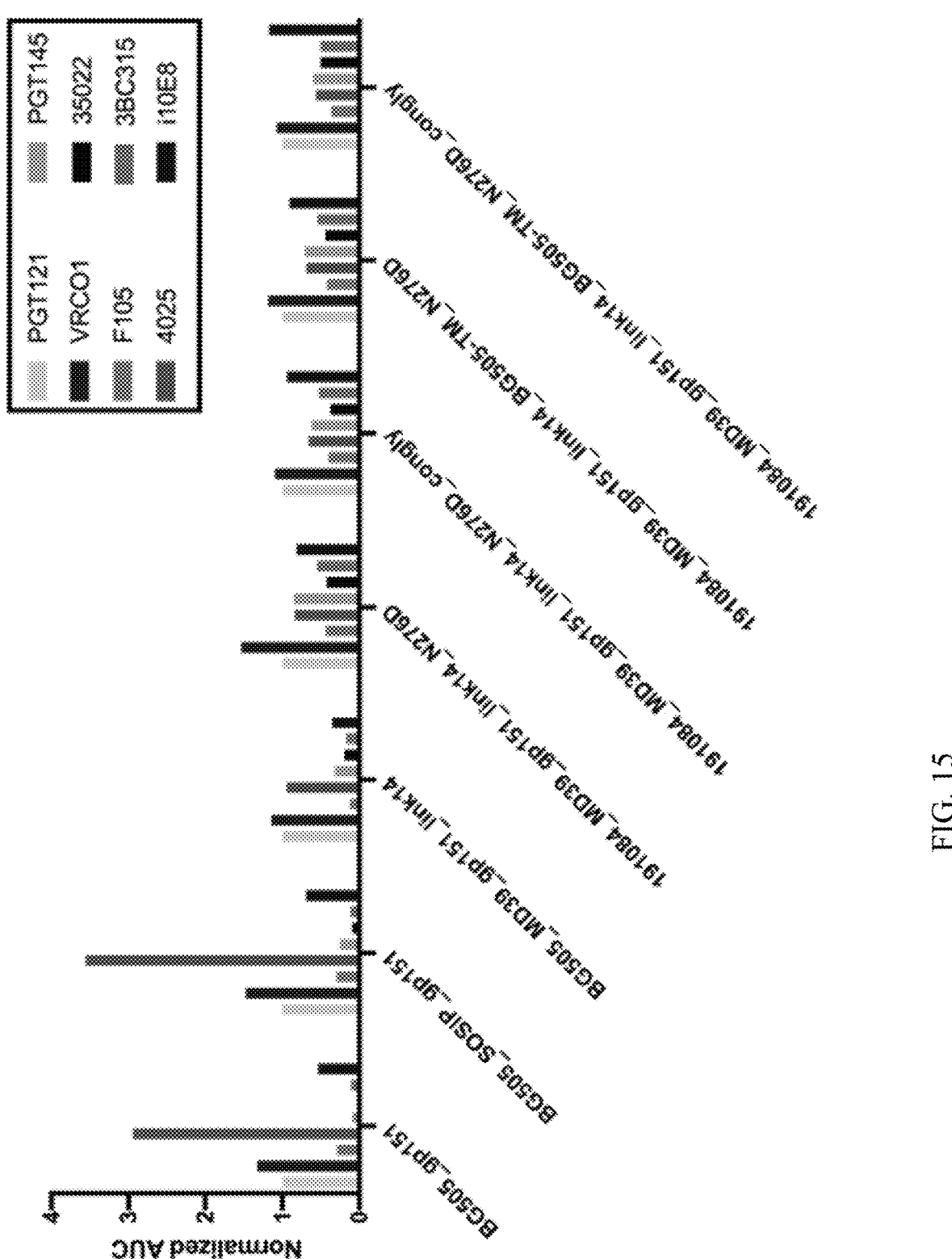
FIG. 15 shows antigenic profiles of membrane-bound 191084 trimers. The indicated constructs were co-transfected with gag-mut3 into freestyle 293F cells and in addition, Furin was cotransfected with cleave-dependent constructs BG505_gp151_m and BG505_SOSIP_gp151_m. After 6 days, supernatants were clarified by centrifugation, filtered through a 0.45 μm filter and concentrated using LentiX (Takara Bio). VLPs were coated directly onto high-binding ELISA plates, blocked with 2% BSA in PBS, and labelled with titration series of the indicated antibodies followed by peroxidase-conjugated anti-human IgG antibodies. Plates were developed for 10 minutes with TMB, stopped by addition of sulfuric acid, and optical densities were measured on a plate reader (BioTek). Data were normalized by subtracting the background, AUCs were calculated in graphpad prism, and AUCs of each mAb against negative control supernatants were subtracted from AUCs for each construct. Expression levels for each construct were normalized by dividing by the respective PGT121 signal and the normalized AUCs were plotted in prism.
Figure 16:
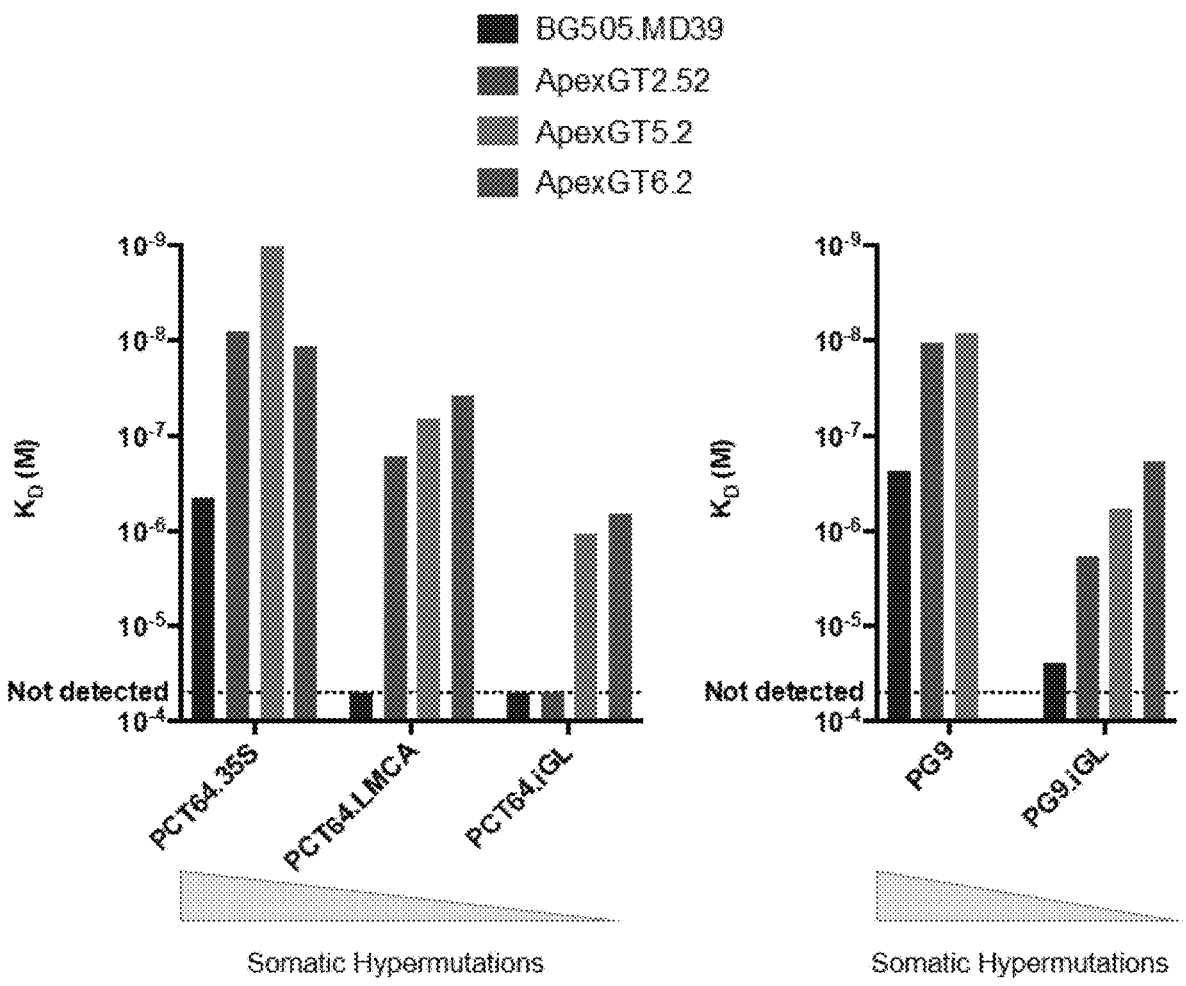
FIG. 16 shows binding affinity of BG505.ApexGT soluble protein trimers tested against PG9 and PCT64 variants ordered according to the decreasing number of somatic hypermutations. Binding affinity of WT Env trimers (BG505.MD39), ApexGT2, ApexGT5 and ApexGT6 to immobilized PG9 and PCT64 variants were measured using surface plasmon resonance at 25° C. (Bio-Rad Proteon XPR36). Binding assay was performed by loading PG9 and PCT64 antibodies at 10 ug/mL on anti-human-IgG capture with 3M MgCl2. Each Env trimer was running as ligand started at 5 uM and did 4-fold dilutions. The kinetics constant was calculated using 1:1 Langmuir binding model. To note, ApexGT6 binding against mature PG9 has not been tested.
Figure 17:
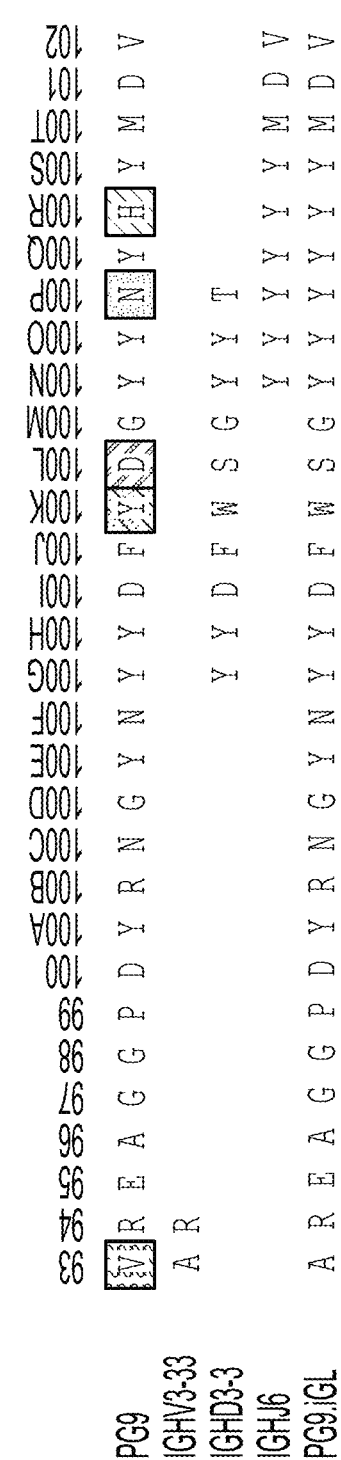
FIG. 17 shows HCDR3 sequence information of tested PCT64 and PG9 variants aligned with germline genes. Sequences were aligned by Geneious Prime, with somatic hypermutations color highlighted. PCT64.LMCA mostly has mutations reverted to the germline, while still a few remain in the HCDR3. PCT64.iGL has all templated mutations reverted to the germline, except for a non-templated aspartic acid mutation at 100G position.
Figure 18A:
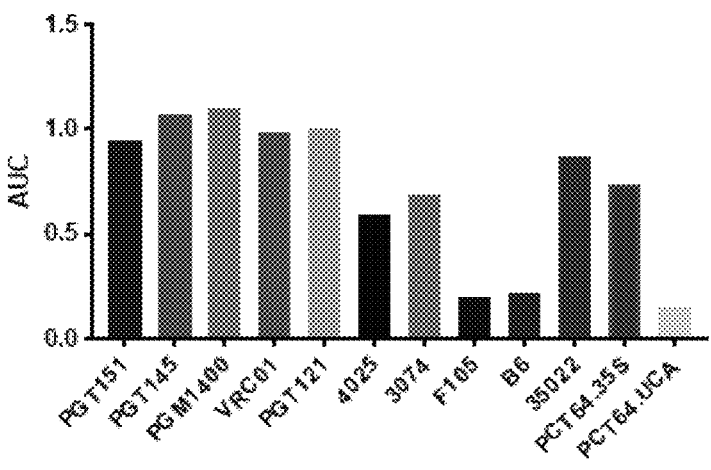
FIGS. 18A-18C show antigenic profiles of BG505.ApexGT5.2 compared with WT and ApexGT2.52 soluble protein trimers. The ELISA plate was coated with his-tag antibody overnight at 4° C. and blocked by 5% skim milk in PBST with 1% FBS. Indicated Env trimers were loaded onto the blocked plate and labelled by 10 ug/mL with 4-fold dilutions of the indicated antibodies followed by peroxidase-conjugated anti-human IgG antibodies. Plates were developed for less than 10 minutes with TMB, stopped by addition of sulfuric acid, and optical densities at 450 nm and 570 nm were measured by a plate reader (BioTek). Data were normalized by subtracting the background, AUCs were calculated in graphpad prism, and AUCs of each mAb against negative control supernatants were subtracted from AUCs for each construct. To note, PCT64.UCA equals PCT64.LMCA, BG505_ApexGT2 equals BG505.ApexGT2.52, BG505_ApexGT5 equals BG505.ApexGT5.2.
Figure 18B:
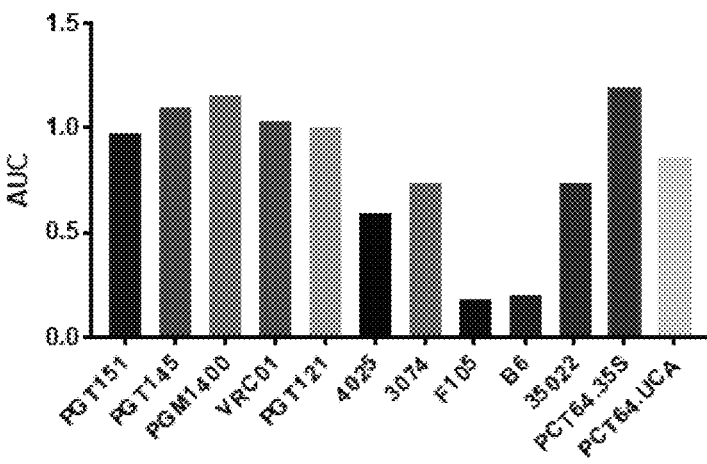
Figure 18C:
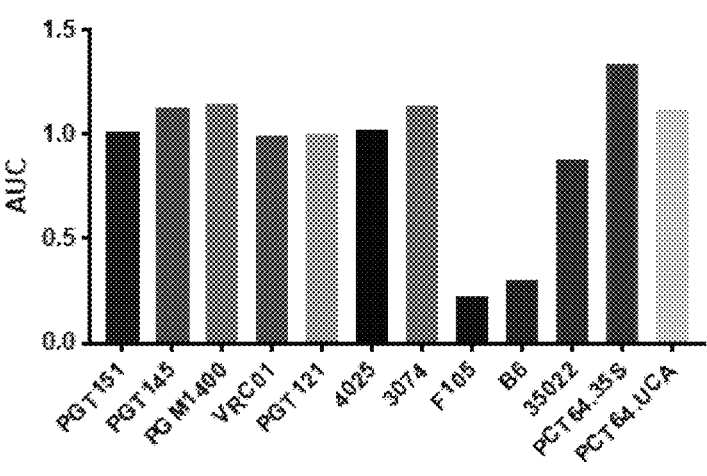
Figure 20A:
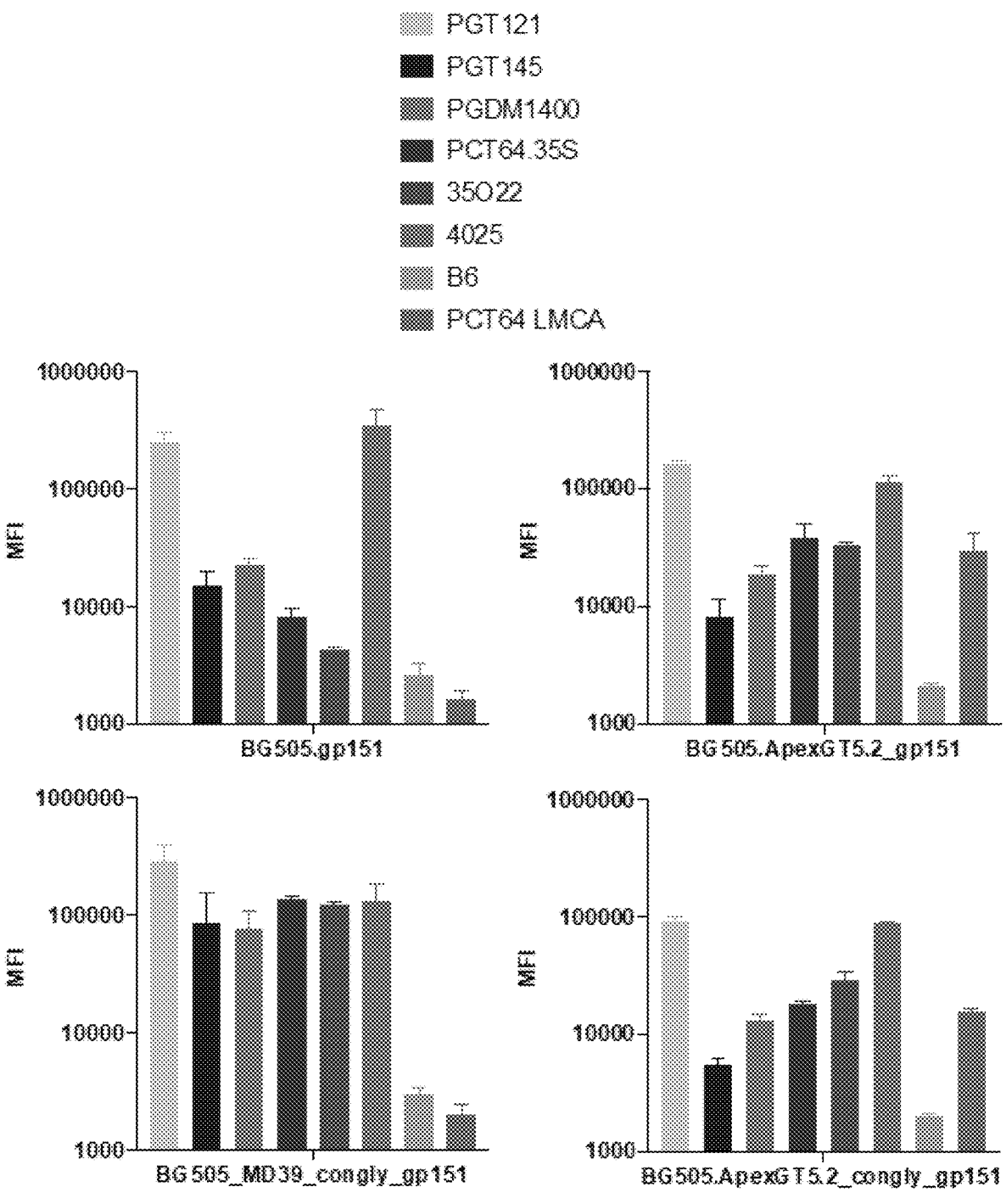
Figure 21:
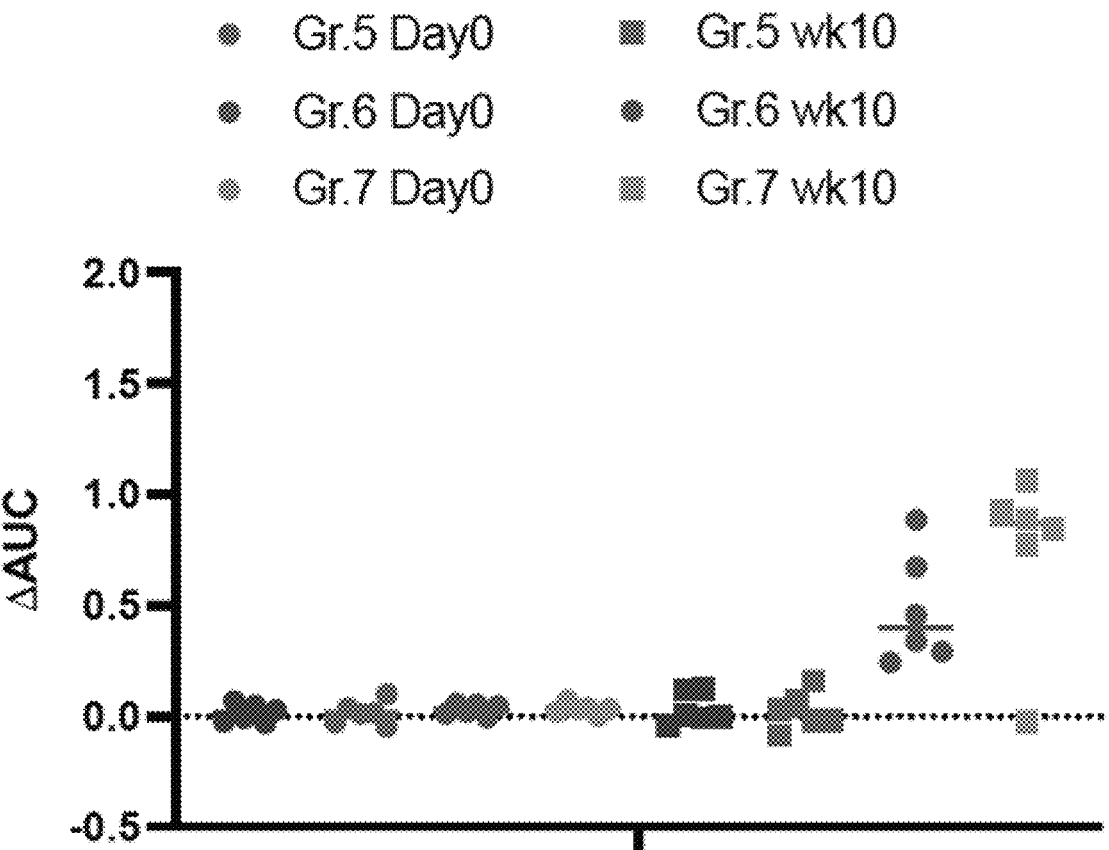
FIG. 21 shows epitope specific serological assays of BG505.ApexGT6.2 primed in NHPs. The ELISA plate was coated with RM19R antibody overnight at 4° C. and blocked by 5% skim milk in PBST with 1% FBS. ApexGT6.2 and epitope knock-out version of ApexGT6.2 trimers (ApexGT6.2_KO) were loaded onto the blocked plate and labelled by 1:100 ratio of solution with 3-fold dilutions of the indicated sera followed by peroxidase-conjugated anti-human IgG antibodies. Plates were developed for less than 10 minutes with TMB, stopped by addition of sulfuric acid, and optical densities at 450 nm and 570 nm were measured by a plate reader (BioTek). Data were normalized by subtracting the background, AUCs were calculated in graphpad prism. AAUC of each group was calculated by AUCs of ApexGT6.2 subtracted by AUCs of ApexGT6.2.KO. To note, group 2 (N=6) immunized with BG505 MD39.3 gp151 mRNA, group 5 (N=6) immunized with BG505 MD39.3 soluble trimer protein+SMNP adjuvant, group 6 (N=6) immunized with BG505 ApexGT6.2 congly soluble trimer protein+SMNP adjuvant, group 7 (N=6) immunized with BG505 ApexGT6.2_gp151 mRNA.
Figure 22:
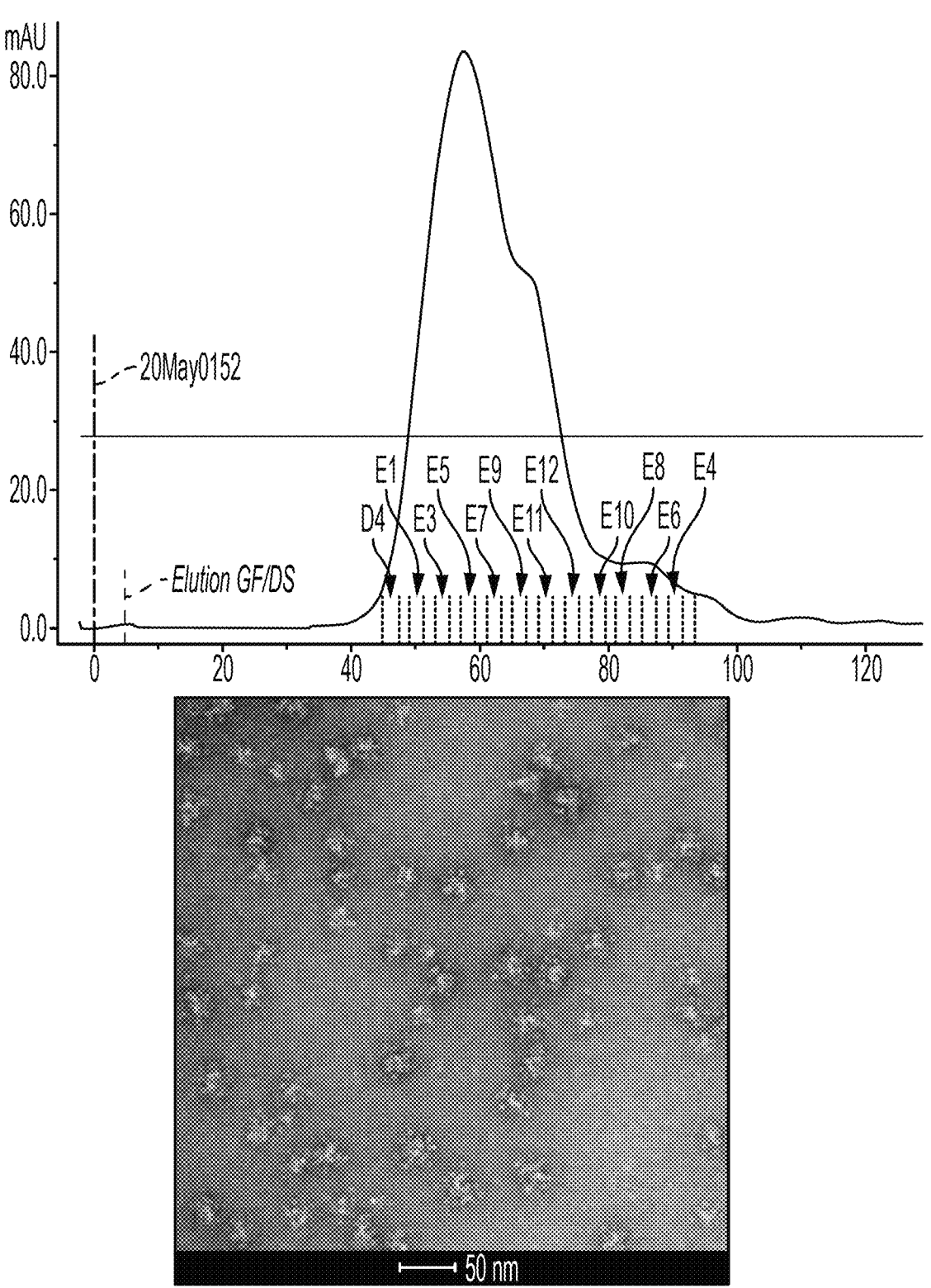
FIG. 22 shows a SEC profile and negative stain EM of core-g28v2 60mer. Core-g28v2 60mer was expressed in freestyle 293F cells and purified by lectin affinity column followed by size exclusion chromatography on a superose 6 column. nsEM was used to evaluate structural integrity. 0.01 mg/mL of sample was prepared in TBS buffer and uranyl formate was used as a negative stain reagent.
Figure 23:
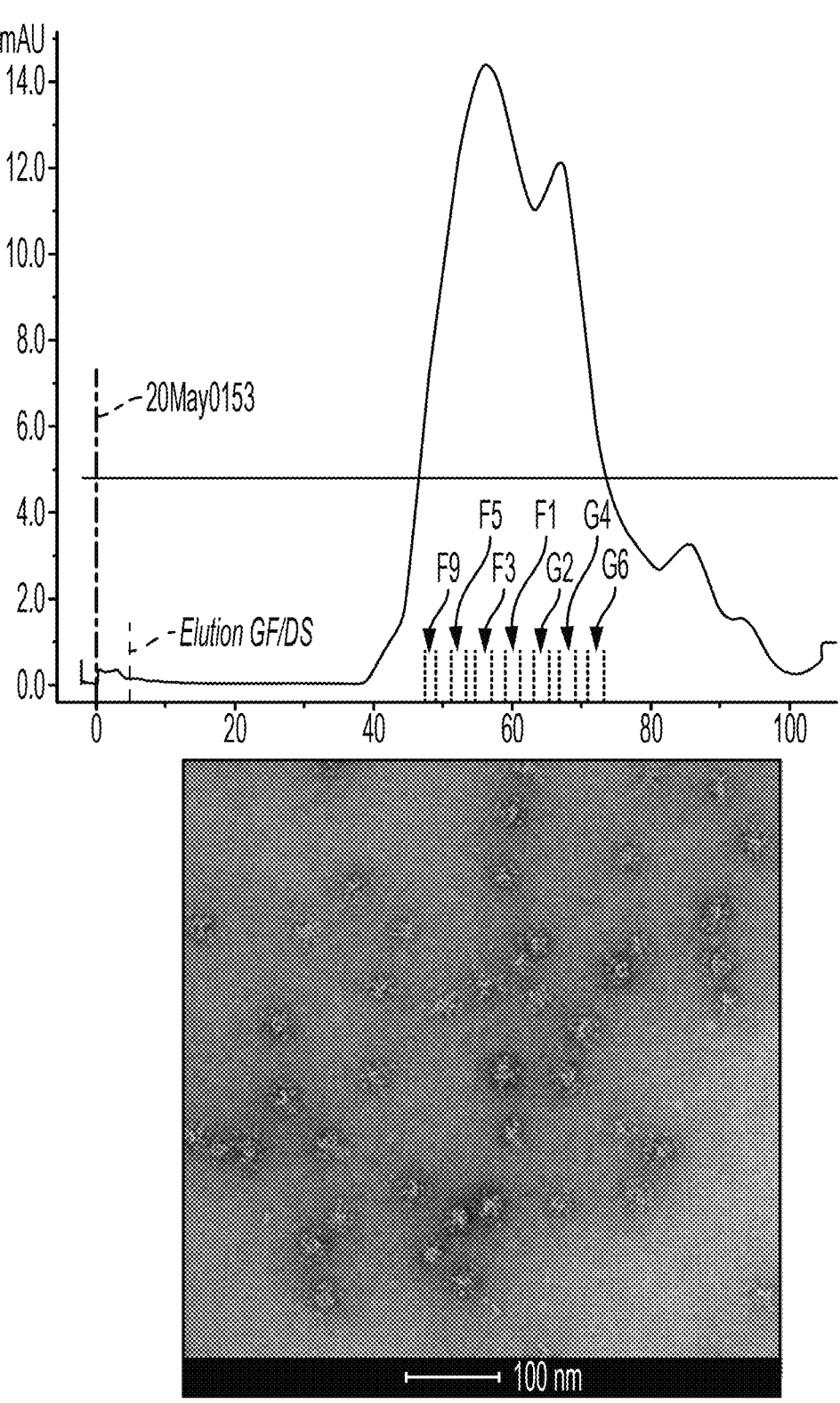
FIG. 23 shows a SEC profile and negative stain EM of core-g28v2 CD4KO 60mer. Core-g28v2 CD4KO 60mer was expressed in Freestyle 293F cells and purified by lectin affinity column followed by size exclusion chromatography on a superose 6 column. nsEM was used to evaluate structural integrity. 0.01 mg/mL of sample was prepared in TBS buffer and uranyl formate was used as a negative stain reagent.

The invention relates to improved HIV antigens, including germline-targeting designs, trimer stabilization designs, combinations of those two, trimers designed with modified surfaces helpful for immunization regimens, other types of trimer modifications (see, for example, examples of trimers with combined germline-targeting mutations and stabilization mutations and additional trimer modifications that add functionality and that can be combined with other types of modifications as described herein) and on development of trimer nanoparticles and membrane-bound trimers. The invention also encopasses combinations of any of the herein described modifications, such as but not limited to, combinations of stabilization and modified surfaces with nanoparticles or membrane-bound trimers.

The HIV envelope protein trimer is the target of broadly neutralizing antibodies (bNAbs). The high mannose patch, including the N332-linked glycan at the base of the V3 loop of gp120, is frequently targeted by bnAbs during natural infection and hence is an appealing vaccine epitope. Germline targeting has potential to initiate the elicitation of N332-dependent bnAbs by vaccination, but no immunogen has been reported to bind germline-reverted precursors of N332-dependent bnAbs.

VRC01-class antibodies are defined as those with a VH1-2 gene in the heavy chain and a five amino acid CDR3 in the light chain. The VH1-2 mouse employed here was originally developed by Ming Tian in the Fred Alt lab at Harvard and was first reported in Tian et al. Cell 2016. It is a stringent model system for inducing VRC01-class responses, in which Applicants have measured a VRC01-class precursor frequency of approximately 1 in 1 million naive B cells, which is similar to the frequency measured in humans as reported in Jardine et al. Science 2016 and Havenar-Daughton et al Science Translational Medicine 2018. eOD-GT8 60mer and derivatives are the only immunogens reported to be capable of priming VRC01-class responses in this model (Tian et al. Cell 2016; Duan et al Immunity 2018).

Some sequences contain a leader sequence (MGILPSPGMPALLSLVSLLSVLLMGCVAETG (SEQ ID NO: 1)) are cleaved during expression/secretion and is not present in the final expressed protein product. The embodiments contained herein are not limited to this particular leader sequence as different leader sequences could be used to serve the same purpose.

The invention also encompasses a protein having at least 90% homology or identity with the sequence of the protein of any one of the trimers disclosed herein. The invention also encompasses a protein having at least 95% homology or identity with the sequence of the protein of any one of trimers disclosed herein.

The invention also encompasses any nucleic acid encoding the protein of any one of the immunogens disclosed herein. The invention also encompasses a nucleic acid having at least 90% or 95% homology or identity with the sequence of said nucleic acid.

The present invention also encompasses methods for eliciting an immune response which may comprise systemically administering to an animal in need thereof an effective amount of the protein of any one of the trimers disclosed herein. The animal may be a mammal, advantageously a human.

Applicants have engineered novel eOD-GT8, eOD-GT11, and eOD-GT12 immunogens that exhibit major improved characteristics over previously described OD immunogens. In certain embodiments, the immunogens provide improved priming. In certain embodiments, the immunogens provide improved boost. In certain embodiments, the immunogens comprise additional and/or repositioned glycosylation sites as compared to native HIV antigens. In a non-limiting example, eOD-GT11 is a high affinity version of eOD-GT8. In a non-limiting example, eOD-GT11_N276+ and eOD-GT12_N276+, both of which include the N276 glycan, retain similar affinities for VRC01-class precursors as eOD- GT8, which does not include the N276 glycan. Exemplary eOD proteins incorporating such improvements include the following.

eOD-GT8_6G_60mer contains 6 additional glycosylation sites as compared to eOD-GT8_60mer and has improved immunogenicity. In certain embodiments, one or more of the glycosylation sites is repositioned.

In certain examples, glycosylation sites are added by insertion of amino acids. For example, certain 60mer proteins having a "g123" designation described herein comprise an insertion of two amino acids whereby one or more glycosylation sites is added. eOD-GT8_6G_g123_60mer contains three glycosylation sites ("g123") added to the base nanoparticle.

In certain examples, higher affinity versions are employed which may further include additional glycosylation sites. eOD-GT11 60mer is a high affinity version of eOD-GT8 60mer engineered by directed evolution and rational design. In certain embodiments, the eOD-GT11 60mer may comprise one, two, three, four, five, or six or additional glycans compared to eOD-GT8 60mer. One example, eOD-GT11_6G_60mer comprises 6 additional glycans. In certain embodiments, eOD variants are designed to keep one or more native glycans. One example, eOD-GT11-N276_6G_60mer, maintains the native glycan present at 276. In another example, eOD-GT12 N276 and eOD-GT12_N276 60mer both maintain the native glycan present at 276.

The invention includes resurfaced and epitope-modified variants. eOD-GT6-3mutB-cRSF01_60mer is a resurfaced and epitope-modified version of eOD-GT6, a precursor to eOD-GT8. eOD-GT6-3mutB-cRSF01 contains many mutations compared to eOD-GT6, and is designed to be useful as an improved booster after immunization with a GT8 priming immunogen, though its use is not so limited. For example, eOD-GT6-3mutB-cRSF01 can be used as a priming immunogen. Furthermore, eOD-GT6-3mutB-cRSF01 can be used as a booster subsequent to a variety of priming immunogens not limited to GT8.

In certain embodiments, resurfaced and epitope-modified variants comprise one, two, three, four, five, or six or more additional glycans compared to eOD-GT8 60mer. In certain embodiments, resurfaced and epitope-modified variants comprise three glycosylation sites ("g123") added to the base nanoparticle corresponding to glycosylation sites added in OD-GT8_6G_g123_60mer described above.

Core-r4g5_60mer is a heavily modified (resurfaced, glycan masked, and loop-trimmed) variant of the core gp120 designated "core-e-2CC HxB2 N276D" (see Jardine et al. Science 2015). The "core-e-2CC HxB2 N276D" combines additional design elements described herein. Core-r4g7-TH_60mer is similar to Core-r4g5_60mer but with additional glycan masking and with potential T-helper epitopes from BG505 SOSIP incorporated to improve priming of CD4 T helper cells. In certain embodiments, primed CD4 T helper cells are engaged by a subsequent boost with a BG505-SOSIP-based trimer.

MD39_link14_congly_Q is a BG505 SOSIP MD39 trimer with (a) "link14" linker in place of the cleavage site (see PCT/US2017/023854), (b) two glycan holes in BG505 filled ("congly"), and (c) glutamine (Q) residue at position 276. Q at position 276 is designed to be useful in boosting/shepherding regimens to induce VRC01-class bnAbs.

MD64_CPG9_Q is a circularly permutated (CP) and glycan-masked (G) variant of BG505 SOSIP MD64 (which itself is a further stabilized version of MD39) also with Q at position 276 designed for VRC01-class maturation.

BG505_MD39_gp160-dCT_link14_Q is a membrane-bound gp160 version of the soluble trimer BG505_SOSIP_MD39_link14. BG505_MD39_gp160-dCT_link14_congly_Q includes filling of BG505 glycan holes as in MD39_link14_congly_Q.

MD64_CPG9 is similar to MD64_CPG9_Q but without Q at position 276.

BG505_MD39_gp160-dCT_link14_congly is similar to BG505_MD39_gp160-dCT_link14_congly_Q but without Q at position 276.

MD39_link14_congly is similar to MD39_link14_congly_Q but without Q at position 276.

MD65 21mutJ_link14_congly (N332-GT5), which is designed to be BG18 germline-targeting soluble trimer, is similar to BG505 MD65 congly N332-GT5 (see U.S. Ser. No. 62/747,650, filed 18 Oct. 2018, further comprising link14 (see PCT/US2017/023854). MD65_21mutJ_gp160-dCT_link14_congly (N332-GT5) is similar to MD65_21mutJ_link14_congly (N332-GT5) but designed as a membrane-bound gp160 construct.

In various aspects, the invention involves improved immunogens, including but not limited to compositions, methods of treatment, methods of making, kits and the like. In certain embodiments, the invention may comprise eOD-GT8 d41m3 60mer. In certain embodiments, the invention involves immunogens that are improved in some aspect, for example relative to eOD-GT8 or relative to a different base immunogen. In certain embodiments the immunogen is glycan masked, such as, by for example the GT8-6G immunogen disclosed herein. In certain embodiments, masking is effected by mutating residues of a starting immunogen to add glycosylations sites corresponding to the glycosylation sites of the GT8-6G immunogen. In certain embodiments, the number of glycoslation sites added to the immunogen is one, two, three, four, five, six or more glycosylation sites. In certain embodiments, an immunogen may comprise glycosylation sites at one or more locations corresponding to glycosylation sites added to GT8-6G relative to GT8. In certain embodiments, masking is effected by substituting amino acids as in GT8-6G g123 disclosed herein to add glycosylation sites. In certain embodiments, masking is effected by mutating amino acids corresponding in position to those of GT8-6G g123 to increase glycosylation.

Further, in certain embodiments the antigen is engineered to display increased affinity. A non-limiting example is GT11 immunogen disclosed herein. According to the invention, in certain embodiments, immunogens engineered for increased affinity are further engineered as to glycan masking. In a non-limiting embodiment, increased affinity immunogens, such as GT11, which is a mutant of GT8, further comprise one, two, three, four, five, six or more additional glycosylation sites. In certain embodiments, the additional glycosylation sites correspond to the glycosylation sites added to GT8-6G relative to GT8. In certain increased affinity immunogens, there may be found amino acid substitutions that remove native glycosylation sites. In such cases, glycosylation sites can optionally be restored so that on or more native glycans is maintained.

In certain embodiments, immunogen monomers are presented in native configurations. For example, the invention provides HIV 60mer particles composed of monomers which may comprise the modifications described above. In certain embodiments, the monomers and particles are used to prime immune responses. In certain embodiments, the monomers and particles are used to boost immune responses.

In an aspect, the invention provides immunogens which are preferred for boosting though also useful for priming an immune response. In embodiments of the invention, the immunogens comprise modified or increased glycosylation as described herein. A nonlimiting example is GT6-3mutB-cRSF01-6G 60mer which is an eOD-GT6 60mer comprising an M3 mutation as described in PCT/US2016/038162. Another nonlimiting example is GT6-3mutB-cRSF01-6G g123 60mer which is an eOD-GT6 60mer with the M3 mutation described in PCT/US2016/038162.

In certain embodiments, invention provides core immunogens which are preferred for boosting though also useful for priming an immune response. A core gp120 is described in Jardine et al., Science, Jul. 10, 2015; 349 (6244): 156-161, doi: 10.1126/science.aac5894, published online 2015 Jun. 18. The invention includes improved core antigens. These examples include Core r4g5, which is a resurfaced, glycan masked, and loop-trimmed variant of gp120, and core-r4.0-Th-g7 lhqk-g123, which is similar to core-r4g5 but with additional glycan masking and potential T-helper epitopes for BG505 SOSIP.

In other embodiments, immunogens which are preferred for boosting though also useful for priming an immune response include, without limitation, MD39_link14_congly_Q, MD39_CPG9_Q (diff trimer with bottom glycan masking), BG505_MD39_gp160-dCT_link14_Q_m (variant of native membrane-bound; blocks bottom naturally), and BG505_MD39_gp160-dCT_link14_Q_congly_m (variant of native membrane-bound; blocks bottom naturally).

In another aspect, the invention provides trimer platforms. Non-limiting examples include native (control) trimers expressed from mRNA, such as MD64_CPG9 and BG505_MD39_gp160-dCT_link14_congly.

In other embodiments, trimer are provided, including but not limited to MD65 21mutJ_link14_congly, MD65_21mutJ_gp160-dCT_link14_congly, MT145K_link14, and MT145K_gp160-dCT_link14.

Sequences core-Hx_r4.0D_TH6_g28 and core-Hx_r4.0D_TH6_g28_60mer, the monomer and 60mer versions of core-Hx_r4.0D_TH6_g28, contain improvements on sequences: core_r4g7_TH6 (aka core-Hx_r4.0D_TH6_g7) and core_r4g7_TH6_60mer (aka core-Hx_r4.0D_TH6_g7_60mer_m). The core-Hx_r4.0D_TH6_g28 sequence has two additional N-linked glycosylation sites compared to the core-Hx_r4.0D_TH6_g7 sequence. The glycan moieties display at these glycosylation sites mask non-VRC01-class antibody binding and surprisingly improve the ability of the 60mer immunogen to boost VRC01-class responses.

Sequences core-Hx_r4.0D_TH6_g28_CD4KO and core-Hx r4.0D_TH6_g28_CD4KO_60mer, core-Hx_r4.0D_TH6_g28_Q276 and core-Hx r4.0D_TH6_g28_Q276_60mer, and core-Hx_r4.0D_TH6_g28_Q276_CD4KO and core-Hx r4.0D_TH6_g28_Q276_CD4KO_60mer are modifications of sequences core-Hx r4.0D_TH6 g28 and core-Hx_r4.0D_TH6_g28_60mer respectively.

Relative to sequences Hx_r4.0D_TH6_g28 and core-Hx_r4.0D_TH6_g28_60mer, sequences core-Hx_r4.0D_TH6 928_CD4KO and core-Hx_r4.0D_TH6_g28_CD4KO_60mer each contain a single point mutation to eliminate affinity for CD4 (CD4KO mutation).

Relative to sequences Hx_r4.0D_TH6_g28 and core-Hx_r4.0D_TH6_g28_60mer, sequences core-Hx_r4.0D_TH6_g28_Q276 and core-Hx_r4.0D_TH6 g28_Q276_60mer each contain a mutation to Q at position 276 that makes the gp120 Loop D closer to native (Q276 mutation).

Relative to sequences Hx_r4.0D_TH6 g28 and core-Hx_r4.0D_TH6_g28_60mer, core-Hx_r4.0D_TH6_ g28_Q276_CD4KO and core-Hx_r4.0D_TH6_ g28_Q276_CD4KO_60mer each contain both the CD4KO and Q276 mutations.

Sequences core-Hx_r4.0_g5_CD4KO and core-Hx_r4.0_g5_CD4KO_60mer, core-Hx_r4.0_g5_Q276 and core-Hx_r4.0_g5_Q276_60mer, and core-Hx_r4.0_g5_Q276_CD4KO and core-Hx_r4.0_g5_Q276_CD4KO_60mer are modifications of sequences core-Hx_r4.0_g5 and core-Hx_r4.0_g5_60mer respectively.

Relative to sequences core-Hx_r4.0_g5 and core-Hx_r4.0_g5_60mer, sequences core-Hx_r4.0_g5_CD4KO and core-Hx_r4.0_g5_CD4KO_60mer each contain a single point mutation to eliminate affinity for CD4 (CD4KO mutation).

Relative to sequences core-Hx_r4.0_g5 and core-Hx_r4.0_g5_60mer, sequences core-Hx_r4.0_g5_Q276 and core-Hx_r4.0_g5_Q276_60mer each contain a mutation to Q at position 276 that makes the gp120 Loop D closer to native (Q276 mutation).

Relative to sequences core-Hx_r4.0_g5 and core-Hx_r4.0_g5_60mer, sequences core-Hx_r4.0_g5_Q276_CD4KO and core-Hx_r4.0_g5_Q276_CD4KO_60mer each contain both the CD4KO and Q276 mutations.

The invention pertains to the identification, design, synthesis and isolation of mutant trimers disclosed herein as well as nucleic acids encoding the same. The present invention also relates to homologues, derivatives and variants of the sequences of the mutant trimers and nucleic acids encoding the same, wherein it is preferred that the homologue, derivative or variant have at least 50%, at least 60%, at least 70%, at least 75%, at least 80%, at least 85%, at least 90%, at least 93%, at least 95%, at least 97%, at least 98% or at least 99% homology or identity with the sequence of the mutant trimers and nucleic acids encoding the same. It is noted that within this specification, homology to sequences of the mutant proteins and nucleic acids encoding the same refers to the homology of the homologue, derivative or variant to the binding site of the mutant proteins and nucleic acids encoding the same.

The invention still further relates to nucleic acid sequences expressing the mutant immunogens disclosed herein, or homologues, variants or derivatives thereof. One of skill in the art will know, recognize and understand techniques used to create such. Additionally, one of skill in the art will be able to incorporate such a nucleic acid sequence into an appropriate vector, allowing for production of the amino acid sequence of mutant proteins and nucleic acids encoding the same or a homologue, variant or derivative thereof.

Where used herein and unless specifically indicated otherwise, the following terms are intended to have the following meanings in addition to any broader (or narrower) meanings the terms might enjoy in the art:

The term "isolated" or "non-naturally occurring" is used herein to indicate that the isolated moiety (e.g. peptide or compound) exists in a physical milieu distinct from that in which it occurs in nature. For example, the isolated peptide may be substantially isolated with respect to the complex cellular milieu in which it naturally occurs. The absolute level of purity is not critical, and those skilled in the art may readily determine appropriate levels of purity according to the use to which the peptide is to be put. The term "isolating" when used a step in a process is to be interpreted accordingly.

In many circumstances, the isolated moiety will form part of a composition (for example a more or less crude extract containing many other molecules and substances), buffer system, matrix or excipient, which may for example contain other components (including proteins, such as albumin).

In other circumstances, the isolated moiety may be purified to essential homogeneity, for example as determined by PAGE or column chromatography (for example HPLC or mass spectrometry). In preferred embodiments, the isolated peptide or nucleic acid of the invention is essentially the sole peptide or nucleic acid in a given composition.

In an advantageous embodiment, a tag may be utilized for purification or biotinylation. The tag for purification may be a his tag. In another embodiment, the tag for biotinylation may be an avi-tag. Other tags are contemplated for purification, however, purification may be accomplished without a tag. In another embodiment, antibody (such as, not limited to, a broadly neutralizing antibody) affinity columns are contemplated. In another embodiment, lectin columns are contemplated.

Native-like soluble trimers can be made by several methods that all involve stabilizing associations between envelope protein subunits. See, e.g., P. Dosenovic et al., "Immunization for HIV-1 broadly neutralizing antibodies in human Ig knockin mice," Cell, 161:1-11, 2015; Steichen et al., Immunity. 2016 Sep. 20;45 (3): 483-496. doi: 10.1016/j.immuni.2016.08.016. Epub 2016 Sep. 8.PMID: 27617678, Kulp et al., Nat Commun. 2017 Nov. 21;8 (1): 1655. doi: 10.1038/s41467-017-01549-6.PMID: 29162799 and R. W. Sanders et al., "HIV-1 neutralizing antibodies induced by native-like envelope trimers," Science, doi: 10.1126/science.aac4223, 2015.

The proteins and compounds of the invention need not be isolated in the sense defined above, however.

The term "pharmaceutical composition" is used herein to define a solid or liquid composition in a form, concentration and level of purity suitable for administration to a patient (e.g. a human patient) upon which administration it may elicit the desired physiological changes. The terms "immunogenic composition" and "immunological composition" and "immunogenic or immunological composition" cover any composition that elicits an immune response against the targeted pathogen, HIV. Terms such as "vaccinal composition" and "vaccine" and "vaccine composition" cover any composition that induces a protective immune response against the targeted pathogen or which efficaciously protects against the pathogen; for instance, after administration or injection, elicits a protective immune response against the targeted pathogen or provides efficacious protection against the pathogen. Accordingly, an immunogenic or immunological composition induces an immune response, which may, but need not, be a protective immune response. An immunogenic or immunological composition may be used in the treatment of individuals infected with the pathogen, e.g., to stimulate an immune response against the pathogen, such as by stimulating antibodies against the pathogen. Thus, an immunogenic or immunological composition may be a pharmaceutical composition. Furthermore, when the text speaks of "immunogen, antigen or epitope", an immunogen may be an antigen or an epitope of an antigen. A diagnostic composition is a composition containing a compound or antibody, e.g., a labeled compound or antibody, that is used for detecting the presence in a sample, such as a biological sample, e.g., blood, semen, vaginal fluid, etc., of an antibody that binds to the compound or an immunogen, antigen or epitope that binds to the antibody; for instance, an anti-HIV antibody or an HIV immunogen, antigen or epitope.

A "conservative amino acid change" is one in which the amino acid residue is replaced with an amino acid residue having a similar side chain. Families of amino acid residues having similar side chains have been defined in the art. These families include amino acids with basic side chains (e.g. lysine, arginine and histidine), acidic side chains (e.g. aspartic acid and glutamic acid), non-charged amino acids or polar side chains (e.g. glycine, asparagine, glutamine, serine, threonine, tyrosine and cysteine), non-polar side chains (e.g. alanine, valine, leucine, isoleucine, proline, phenylalanine, methionine and tryptophan), beta-branched side chains (e.g. threonine, valine and isoleucine), and aromatic side chains (e.g. tyrosine, phenylalanine, tryptophan and histidine).

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

(a) Fab, the fragment which contains a monovalent antigen-binding fragment of an antibody molecule may be produced by digestion of whole antibody with the enzyme papain to yield an intact light chain and a portion of one heavy chain;

(b) Fab', the fragment of an antibody molecule may be obtained by treating whole antibody with pepsin, followed by reduction, to yield an intact light chain and a portion of the heavy chain; two Fab' fragments are obtained per antibody molecule;

(c) F(ab')$_2$, the fragment of the antibody that may be obtained by treating whole antibody with the enzyme pepsin without subsequent reduction; F(ab')$_2$ is a dimer of two Fab' fragments held together by two disulfide bonds;

(d) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

Fabs, Fv and scFV may also be made recombinantly, i.e. expressed as Fab, Fv or scFV rather than cleaving an intact IgG.

A "neutralizing antibody" may inhibit the entry of HIV-1 virus for example SF162 and/or JR-CSF with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

An "isolated antibody" or "non-naturally occurring antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "monoclonal antibody" as used herein refers to an antibody obtained from a population of substantially homogeneous antibodies, i.e., the individual antibodies which may comprise the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

An "antibody fragment" may comprise a portion of an intact antibody, preferably the antigen binding or variable region of the intact antibody. Examples of antibody fragments include Fab, Fab', F(ab')₂, scFV and Fv fragments; diabodies; linear antibodies (see U.S. Pat. No. 5,641,870; Zapata et al., Protein Eng. 8 (10): 1057-1062 [1995]); single-chain antibody molecules; and multispecific antibodies formed from antibody fragments.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic--aspartate and glutamate; (2) basic--lysine, arginine, histidine; (3) non-polar--alanine, valine, leucine, isoleucine, proline, phenylalanine, methionine, tryptophan; and (4) uncharged polar--glycine, asparagine, glutamine, cysteine, serine threonine, tyrosine. Phenylalanine, tryptophan, and tyrosine are sometimes classified as aromatic amino acids. It is reasonably predictable that an isolated or non-naturally occurring replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid may be single-stranded, or partially or completely double-stranded (duplex). Duplex nucleic acids may be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the sequences of the invention, such as the mutant trimers, may be altered in these ways.

As regards codon optimization, the nucleic acid molecules of the invention have a nucleotide sequence that encodes the antigens of the invention and may be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens may be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention may readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87:2264-2268, modified as in Karlin & Altschul, Proc. Natl. Acad. Sci. USA 1993; 90:5873-5877.

Another example of a mathematical algorithm used for comparison of sequences is the algorithm of Myers & Miller, CABIOS 1988; 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 may be used. Yet another useful algorithm for identifying regions of local sequence similarity and alignment is the FASTA algorithm as described in Pearson & Lipman, Proc. Natl. Acad. Sci. USA 1988; 85:2444-2448.

Advantageous for use according to the present invention is the WU-BLAST (Washington University BLAST) version 2.0 software. WU-BLAST version 2.0 executable programs for several UNIX may platforms be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266:460-480; Altschul et al., Journal of Molecular Biology 1990; 215:403-410; Gish & States, 1993; Nature Genetics 3:266-272; Karlin & Altschul, 1993;Proc. Natl. Acad. Sci. USA 90:5873-5877; all of which are incorporated by reference herein).

The various recombinant nucleotide sequences and antibodies of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies of the present invention may be used in accordance with the present invention. In certain embodiments, the antibodies of the present invention may be used in vitro (such as using cell-free expression systems) and/or in cultured cells grown in vitro in order to produce the encoded HIV-antibodies, which may then be used for various applications such as in the production of proteinaceous vaccines. For such applications, any vector that allows expression of the antibodies in vitro and/or in cultured cells may be used.

For applications where it is desired that the antibodies be expressed in vivo, for example when the transgenes of the invention are used in DNA or DNA-containing vaccines, any vector that allows for the expression of the antibodies of the present invention and is safe for use in vivo may be used. In preferred embodiments the vectors used are safe for use in humans, mammals and/or laboratory animals.

For the antibodies of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" may be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention may be under the control of a constitutive promoter or of an inducible promoter, which initiates transcription only when exposed to some particular external stimulus, such as, without limitation, antibiotics such as tetracycline, hormones such as ecdysone, or heavy metals. The promoter may also be specific to a particular cell-type, tissue or organ. Many suitable promoters and enhancers are known in the art, and any such suitable promoter or enhancer may be used for expression of the transgenes of the invention. For example, suitable promoters and/or enhancers may be selected from the Eukaryotic Promoter Database (EPDB).

The vectors used in accordance with the present invention should typically be chosen such that they contain a suitable gene regulatory region, such as a promoter or enhancer, such that the antibodies of the invention may be expressed.

Any suitable vector may be used depending on the application. For example, plasmids, viral vectors, bacterial vectors, protozoal vectors, insect vectors, baculovirus expression vectors, yeast vectors, mammalian cell vectors, and the like, may be used. Suitable vectors may be selected by the skilled artisan taking into consideration the characteristics of the vector and the requirements for expressing the antibodies under the identified circumstances.

In an advantageous embodiment, IgG1 and Fab expression vectors may be utilized to reconstitute heavy and light chain constant regions if heavy and light chain genes of the antibodies of the present invention are cloned.

When the aim is to express the antibodies of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. Any vectors that are suitable for such uses may be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and may be used as gene delivery vectors.

The nucleotide sequences and vectors of the invention may be delivered to cells, for example if the aim is to express the HIV-1 antigens in cells in order to produce and isolate the expressed proteins, such as from cells grown in culture. For expressing the antibodies in cells any suitable transfection, transformation, or gene delivery methods may be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies may be carried out in any suitable type of host cells, such as bacterial cells, yeast, insect cells, and mammalian cells. The antibodies of the invention may also be expressed using including in vitro transcription/translation systems. All of such methods are well known by those skilled in the art, and one of skill in the art would readily be able to select a suitable method depending on the nature of the nucleotide sequences, vectors, and cell types used.

A synthetic mutant trimer may be chemically synthesized in whole or part using techniques that are well-known in the art (see, e.g., Kochendoerfer, G. G., 2001). Additionally, homologs and derivatives of the polypeptide may be also be synthesized.

Alternatively, methods which are well known to those skilled in the art may be used to construct expression vectors containing nucleic acid molecules that encode the polypeptide or homologs or derivatives thereof under appropriate transcriptional/translational control signals, for expression. These methods include in vitro recombinant DNA techniques, synthetic techniques and in vivo recombination/genetic recombination. See, for example, the techniques described in Maniatis et al., 1989.

The HIV envelope protein (Env) is the target of broadly neutralizing antibodies (bnAbs) in natural infection. Env is a membrane protein composed of a trimer of gp120 and gp41 subunits that contains a high degree of sequence diversity and a surface that is shielded by N-linked glycans. The bnAbs that target Env often have unusual features such as a long complementarity-determining region (CDR) H3, high levels of somatic hypermutation (SHM), and insertions and deletions (INDELS). Furthermore, most of the bnAbs recognize complex epitopes that are typically non-linear and have both protein and glycan components.

The most common epitope of bnAbs in HIV infected individuals is a high mannose glycan patch at the base of the variable loop V3 that includes a glycan linked to N332 (Landais et al. 2016 PLOS Pathog. 12, e1005369). PGT121 and its somatic relatives are an exceptionally potent family of bnAbs that target this epitope and PGT121 has been shown to protect macaques in SHIV challenge studies (Walker et al. 2011 Nature. 477, 466-470, Moldt et al. 2012 Proc Natl Acad Sci. 109, 18921-18925). The elicitation of high and sustained titers of PGT121-like antibodies by vaccination would therefore have a reasonable likelihood of providing protection against HIV in humans.

HIV Env proteins show no detectable affinity for predicted germline precursors of PGT121, suggesting that activation of appropriate precursors is a barrier to PGT121-like bnAb induction that could be addressed by germline-targeting immunogen design. In this view, vaccine induction of PGT121-like bnAbs might be achieved by a germline-targeting prime followed by boosts with progressively more native-like Env, similar to what has been proposed for elicitation of VRC01-class bnAbs (Jardine, Julien, Menis et al. 2013 Science. 340, 711-716; McGuire et al 2013 J Exp Med. 210, 655-663; Jardine, Ota, Sok et al. 2015 Science. 349, 156-161). BG505 SOSIP.664 was the first soluble native-like Env trimer (Sanders et al. 2013 PloS Pathog. 9, e1003618). In parallel with Applicants' germline-targeting effort a goal was to improve the expression, stability and antigenic profile of BG505 SOSIP.664 in order to have an enhanced trimer platform for germline targeting and boosting. Using a lentivirus-based method for displaying libraries of immunogens on the surface of mammalian cells, and guided by the known structure of BG505 SOSIP.664 (Julien et al. 2013 Science. 342, 1477-1483; Lyumkis et al. 2013 Science. 342, 1484-1490; Pancera et al. 2014 Nature. 514, 455-461) Applicants have engineered a series of soluble native-like trimers with improved yield, thermostability and antigenic profile, which have progressively increasing affinity for putative PGT121 germline precursors and intermediately mutated antibodies.

Applicants have demonstrated that structure-guided mammalian cell surface display can be used to engineer trimers containing native-like glycans. Native-like trimers have been developed that bind to predicted PGT121 germline precursors and intermediately mutated antibodies BG505 SOSIP trimers were engineered with improved yield, thermostability and antigenic profile. Tests of priming and boosting strategies are currently underway in PGT121-GL knock-in mice.

Apex germline-targeting trimers, ApexGTs, were designed primarily as the prime immunogens to elicit one of the V2 apex directed broadly neutralizing antibodies, PCT64, but also have good affinity for PG9/16 precursors.

Development of a vaccine that consistently primes PCT64-class responses required the design of germline-targeting trimers with appreciable affinity for diverse PCT64-class precursors. Compared to the previous designed ApexGT2, the GT5 trimer has improved binding affinity against one of mature PCT64 mAbs (35S) and the least mutated common ancestor (LMCA), and first time shows appreciable binding affinity against PCT64 inferred germline (iGL) with KD ~ 700 nM. As an improved Apex priming immunogen, ApexGT6 shows stronger binding affinity to PCT64 iGL and PG9 iGL. ApexGT6 also exhibits decent antigenic profile as soluble trimer proteins and membrane bound trimer mRNA.

Applicants claim sequences of different types of immunogen sequences. The sequences provided below are exemplary examples, the stabilizing mutations, modifications, (such as, but not limited to, cleavage-independent modifications), and/or a membrane anchoring strategy (such as, but not limited to, linker plus platelet-derived growth factor receptor (PDGFR)) described herein are applicable to any HIV strain or clade, such as but not limited to, those described below.

The present invention relates to non-naturally occurring proteins, which may be involved in forming immunogenic proteins of the present invention.

The invention relates to a non-naturally occurring protein which may comprise any one of the following sequences in Table 1.

TABLE 1 immunogenic proteins

```
191084_MD39_gp151_link14_BG505-TM_N276D
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVESHSGSGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISNWLWYIKIFIMIVGGLIGLRIVFAVLSVIHRVR** (SEQ ID NO: 2)

191084_MD39_gp151_link14_BG505-TM_N276D_CD4KO
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVESHSGSGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISNWLWYIKIFIMIVGGLIGLRIVFAVLSVIHRVR** (SEQ ID NO: 3)

191084_MD39_gp151_link14_BG505-TM_N276D_CD4KO_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVESHSGSGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISNWLWYIKIFIMIVGGLIGLRIVFAVLSVIHRVR** (SEQ ID NO: 4)

191084_MD39_gp151_link14_BG505-TM_N276D_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
```

TABLE 1-continued immunogenic proteins

```
CNSNITGLLLVRDGGATNNTDETFRPGGGNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISNWLWYIKIFIMIVGGLIGLRIVFAVLSVIHRVR** (SEQ ID NO: 4)

191084_MD39_gp151_link14_N276D
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISKWLWYIRIFIMIVGGLIGLRIVFTVLSIINRVR** (SEQ ID NO: 5)

191084_MD39_gp151_link14_N276D_CD4KO
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISKWLWYIRIFIMIVGGLIGLRIVFTVLSIINRVR** (SEQ ID NO: 6)

191084_MD39_gp151_link14_N276D_CD4KO_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISKWLWYIRIFIMIVGGLIGLRIVFTVLSIINRVR** (SEQ ID NO: 7)

191084_MD39_gp151_link14_N276D_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LDKWASLWNWFDISKWLWYIRIFIMIVGGLIGLRIVFTVLSIINRVR** (SEQ ID NO: 8)

191084_MD39_gp151_N276Q
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEQISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVERRRRRRAVGLGAVSIGFLGAAGSTMGAASVTLTVQARQLLSGIVQQQSNLL
RAPEPQQHLLKDTHWGIKQLQARVLAVEHYLKDQQLLGIWGCSGKLICCTTVPWNSS
WSNKSQNEIWDNMTWLQWDKEISNYTQLIYSLIEESQNQQEKNEQELLALDKWASL
WNWFDISKWLWYIRIFIMIVGGLIGLRIVFTVLSIINRVR** (SEQ ID NO: 9)
```

TABLE 1-continued immunogenic proteins

191084_MD39_gp151_N276Q_CD4KO
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEQISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVERRRRRAVGLGAVSIGFLGAAGSTMGAASVTLTVQARQLLSGIVQQQSNLL
RAPEPQQHLLKDTHWGIKQLQARVLAVEHYLKDQQLLGIWGCSGKLICCTTVPWNSS
WSNKSQNEIWDNMTWLQWDKEISNYTQLIYSLIEESQNQQEKNEQELLALDKWASL
WNWFDISKWLWYIRIFIMIVGGLIGLRIVFTVLSIINRVR** (SEQ ID NO: 10)

191084_MD39_gp151_NFL_N276Q
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEQISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVGGGGSGGGGSAVGLGAVSIGFLGAAGSTMGAASVTLTVQARQLLSGIVQQ
QSNLLRAPEPQQHLLKDTHWGIKQLQARVLAVEHYLKDQQLLGIWGCSGKLICCTTV
PWNSSWSNKSQNEIWDNMTWLQWDKEISNYTQLIYSLIEESQNQQEKNEQELLALDK
WASLWNWFDISKWLWYIRIFIMIVGGLIGLRIVFTVLSIINRVR** (SEQ ID NO: 11)

191084_MD39_gp151_NFL_N276Q_CD4KO
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEQISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVGGGGSGGGGSAVGLGAVSIGFLGAAGSTMGAASVTLTVQARQLLSGIVQQ
QSNLLRAPEPQQHLLKDTHWGIKQLQARVLAVEHYLKDQQLLGIWGCSGKLICCTTV
PWNSSWSNKSQNEIWDNMTWLQWDKEISNYTQLIYSLIEESQNQQEKNEQELLALDK
WASLWNWFDISKWLWYIRIFIMIVGGLIGLRIVFTVLSIINRVR** (SEQ ID NO: 12)

191084_MD39_link14_N276D
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LD (SEQ ID NO: 13)

191084_MD39_link14_N276D_CD4KO
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LD (SEQ ID NO: 14)

191084_MD39_link14_N276D_CD4KO_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR TABLE 1-continued immunogenic proteins CNSNITGLLLVRDGGATNNTDETFRPGGTNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LD (SEQ ID NO: 15)

191084_MD39_link14_N276D_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVESHSGSGGGSGSGGHAAVGLGAVSIGFLGAAGSTMGAASVTLTVQARQLLSGI
VQQQSNLLRAPEPQQHLLKDTHWGIKQLQARVLAVEHYLKDQQLLGIWGCSGKLICC
TTVPWNSSWSNKSQNEIWDNMTWLQWDKEISNYTQLIYSLIEESQNQQEKNEQELLA
LD (SEQ ID NO: 16)

191084_MD39_N197A_CD4KO_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCATS
VITQACPKVTFEPIPIHYCAPAGFAILKCKDKEFNGTGTCRNVSSVQCTHGIKPVVSTQ
LLLNGSLAEGQVIIRSENISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVERRRRRRAVGLGAVSIGFLGAAGSTMGAASVTLTVQARQLLSGIVQQQSNLL
RAPEPQQHLLKDTHWGIKQLQARVLAVEHYLKDQQLLGIWGCSGKLICCTTVPWNSS
WSNKSQNEIWDNMTWLQWDKEISNYTQLIYSLIEESQNQQEKNEQELLALDKWASL
WNWFDISKWLWYIRIFIMIVGGLIGLRIVFTVLSIINRVR** (SEQ ID NO: 17)

191084_MD39_N197A_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCATS
VITQACPKVTFEPIPIHYCAPAGFAILKCKDKEFNGTGTCRNVSSVQCTHGIKPVVSTQ
LLLNGSLAEGQVIIRSENISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVERRRRRRAVGLGAVSIGFLGAAGSTMGAASVTLTVQARQLLSGIVQQQSNLL
RAPEPQQHLLKDTHWGIKQLQARVLAVEHYLKDQQLLGIWGCSGKLICCTTVPWNSS
WSNKSQNEIWDNMTWLQWDKEISNYTQLIYSLIEESQNQQEKNEQELLALDKWASL
WNWFDISKWLWYIRIFIMIVGGLIGLRIVFTVLSIINRVR** (SEQ ID NO: 18)

191084_MD39_N276D_CD4KO_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVERRRRRRAVGLGAVSIGFLGAAGSTMGAASVTLTVQARQLLSGIVQQQSNLL
RAPEPQQHLLKDTHWGIKQLQARVLAVEHYLKDQQLLGIWGCSGKLICCTTVPWNSS
WSNKSQNEIWDNMTWLQWDKEISNYTQLIYSLIEESQNQQEKNEQELLALD (SEQ ID
NO: 19)

191084_MD39_N276D_congly
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKTLQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVERRRRRRAVGLGAVSIGFLGAAGSTMGAASVTLTVQARQLLSGIVQQQSNLL
RAPEPQQHLLKDTHWGIKQLQARVLAVEHYLKDQQLLGIWGCSGKLICCTTVPWNSS
WSNKSQNEIWDNMTWLQWDKEISNYTQLIYSLIEESQNQQEKNEQELLALD (SEQ ID
NO: 20)

TABLE 1-continued immunogenic proteins

191084_MD39_N276W_CD4KO_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEWISDNAKTIIVQLNESVPINCTRPNNNTVRGIHLGPGQTFFYT
DIIGDIRQAHCNVSESKWNKALQEVVKQLRQHWNKTIIFKSSSGGDLEITTHSFNCGGE
FFYCNTSGLFNSTWNIAGNRTNDTKSNETITLPCRIKQIVNVWQRVGQAIYAPPIAGVI
RCNSNITGLLLVRDGGATNNTDETFRPGGTNMRDNWRSELYKYKVVKIEPLGVAPTR
CRRRVVERRRRRAVGLGAVSIGFLGAAGSTMGAASVTLTVQARQLLSGIVQQQSNL
LRAPEPQQHLLKDTHWGIKQLQARVLAVEHYLKDQQLLGIWGCSGKLICCTTVPWNS
SWSNKSQNEIWDNMTWLQWDKEISNYTQLIYSLIEESQNQQEKNEQELLALDKWASL
WNWFDISKWLWYIRIFIMIVGGLIGLRIVFTVLSIINRVR** (SEQ ID NO: 21)

191084_MD39_N276W_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEWISDNAKTIIVQLNESVPINCTRPNNNTVRGIHLGPGQTFFYT
DIIGDIRQAHCNVSESKWNKALQEVVKQLRQHWNKTIIFKSSSGGDLEITTHSFNCGGE
FFYCNTSGLFNSTWNIAGNRTNDTKSNETITLPCRIKQIVNVWQRVGQAIYAPPIAGVI
RCNSNITGLLLVRDGGATNNTDETFRPGGGNMRDNWRSELYKYKVVKIEPLGVAPTR
CRRRVVERRRRRAVGLGAVSIGFLGAAGSTMGAASVTLTVQARQLLSGIVQQQSNL
LRAPEPQQHLLKDTHWGIKQLQARVLAVEHYLKDQQLLGIWGCSGKLICCTTVPWNS
SWSNKSQNEIWDNMTWLQWDKEISNYTQLIYSLIEESQNQQEKNEQELLALDKWASL
WNWFDISKWLWYIRIFIMIVGGLIGLRIVFTVLSIINRVR** (SEQ ID NO: 22)

191084_MD39_NFL_N197A_CD4KO_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCATS
VITQACPKVTFEPIPIHYCAPAGFAILKCKDKEFNGTGTCRNVSSVQCTHGIKPVVSTQ
LLLNGSLAEGQVIIRSENISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGTNMRDNWRSELYKYKVVKIEPLGVAPTRC
RRRVVGGGGGSGGGGSAVGLGAVSIGFLGAAGSTMGAASVTLTVQARQLLSGIVQQ
QSNLLRAPEPQQHLLKDTHWGIKQLQARVLAVEHYLKDQQLLGIWGCSGKLICCTTV
PWNSSWSNKSQNEIWDNMTWLQWDKEISNYTQLIYSLIEESQNQQEKNEQELLALDK
WASLWNWFDISKWLWYIRIFIMIVGGLIGLRIVFTVLSIINRVR** (SEQ ID NO: 23)

191084_MD39_NFL_N197A_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCATS
VITQACPKVTFEPIPIHYCAPAGFAILKCKDKEFNGTGTCRNVSSVQCTHGIKPVVSTQ
LLLNGSLAEGQVIIRSENISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRTNDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVGGGGGSGGGGSAVGLGAVSIGFLGAAGSTMGAASVTLTVQARQLLSGIVQQ
QSNLLRAPEPQQHLLKDTHWGIKQLQARVLAVEHYLKDQQLLGIWGCSGKLICCTTV
PWNSSWSNKSQNEIWDNMTWLQWDKEISNYTQLIYSLIEESQNQQEKNEQELLALDK
WASLWNWFDISKWLWYIRIFIMIVGGLIGLRIVFTVLSIINRVR** (SEQ ID NO: 24)

191084_MD39_NFL_N276W_CD4KO_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEWISDNAKTIIVQLNESVPINCTRPNNNTVRGIHLGPGQTFFYT
DIIGDIRQAHCNVSESKWNKALQEVVKQLRQHWNKTIIFKSSSGGDLEITTHSFNCGGE
FFYCNTSGLFNSTWNIAGNRTNDTKSNETITLPCRIKQIVNVWQRVGQAIYAPPIAGVI
RCNSNITGLLLVRDGGATNNTDETFRPGGTNMRDNWRSELYKYKVVKIEPLGVAPTR
CRRRVVGGGGGSGGGGSAVGLGAVSIGFLGAAGSTMGAASVTLTVQARQLLSGIVQ
QQSNLLRAPEPQQHLLKDTHWGIKQLQARVLAVEHYLKDQQLLGIWGCSGKLICCTT
VPWNSSWSNKSQNEIWDNMTWLQWDKEISNYTQLIYSLIEESQNQQEKNEQELLALD
KWASLWNWFDISKWLWYIRIFIMIVGGLIGLRIVFTVLSIINRVR** (SEQ ID NO: 25)

191084_MD39_NFL_N276W_gp151
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEWISDNAKTIIVQLNESVPINCTRPNNNTVRGIHLGPGQTFFYT
DIIGDIRQAHCNVSESKWNKALQEVVKQLRQHWNKTIIFKSSSGGDLEITTHSFNCGGE
FFYCNTSGLFNSTWNIAGNRTNDTKSNETITLPCRIKQIVNVWQRVGQAIYAPPIAGVI

TABLE 1-continued immunogenic proteins

RCNSNITGLLLVRDGGATNNTDETFRPGGGNMRDNWRSELYKYKVVKIEPLGVAPTR
CRRRVVGGGGGSGGGGSAVGLGAVSIGFLGAAGSTMGAASVTLTVQARQLLSGIVQ
QQSNLLRAPEPQQHLLKDTHWGIKQLQARVLAVEHYLKDQQLLGIWGCSGKLICCTT
VPWNSSWSNKSQNEIWDNMTWLQWDKEISNYTQLIYSLIEESQNQQEKNEQELLALD
KWASLWNWFDISKWLWYIRIFIMIVGGLIGLRIVFTVLSIINRVR** (SEQ ID NO: 26)

191084_SOSIP_MD39_N276D
TENLWVTVYYGVPVWRDAETTLFCASDAKAYDTEMHNVWATHACVPTDPNPQEID
LENVTEKFNMWKNNMVEQMHEDIISLWDQSLKPCVKLTPLCVTLNCTAITNDTRGNE
TGINRTVETTEMTNCSFNMTTELRDRKKKVNALFYKLDIVQIGENSSSQYRLINCNTS
VITQACPKVTFEPIPIHYCAPAGFAILKCKDKEFNGTGTCRNVSSVQCTHGIKPVVSTQ
LLLNGSLAEGQVIIRSEDISDNAKTIIVQLNESVPINCTRPNNNTVRGIHLGPGQTFFYTD
IIGDIRQAHCNVSESKWNKALQEVVKQLRQHWNKTIIFKSSSGGDLEITTHSFNCGGEF
FYCNTSGLFNSTWNIAGNRINDTKSNETITLPCRIKQIVNVWQRVGQAIYAPPIAGVIR
CNSNITGLLLVRDGGATNNTDETFRPGGGNMRDNWRSELYKYKVVKIEPLGVAPTRC
RRRVVERRRRRRAVGLGAVSIGFLGAAGSTMGAASVTLTVQARQLLSGIVQQQSNLL
RAPEPQQHLLKDTHWGIKQLQARVLAVEHYLKDQQLLGIWGCSGKLICCTTVPWNSS
WSNKSQNEIWDNMTWLQWDKEISNYTQLIYSLIEESQNQQEKNEQELLALD (SEQ ID
NO: 27)

BG505_ApexGT2.52 (soluble trimer for ApexGT2.52)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMGENSTNYRLINCNTSAITQACPKV
SFEPIPIHYCAPAGFAILKCKDKKFNGTGPCPSVSTVQCTHGIKPVVSTQLLLNGSLAEE
EVIIRSENITNNAKNILVQLNTPVQINCTRPNNNTVKSIRIGPGQAFYYTGDIIGDIRQAH
CNVSKATWNETLGKVVKQLRKHFGNNTIIRFAQSSGGDLEVTTHSFNCGGEFFYCNTS
GLFNSTWISNTSVQGSNSTGSNDSITLPCRIKQIINMWQRIGQAMYAPPIQGVIRCVSNI
TGLILTRDGGSTNSTTETFRPGGGDMRDNWRSELYKYKVVKIEPLGVAPTRCKRRVV
GRRRRRRAVGIGAVSLGFLGAAGSTMGAASMTLTVQARNLLSGIVQQQSNLLRAPEP
QQHLLKDTHWGIKQLQARVLAVEHYLRDQQLLGIWGCSGKLICCTNVPWNSSWSNR
NLSEIWDNMTWLQWDKEISNYTQIIYGLLEESQNQQEKNEQDLLALD (SEQ ID NO:
28)

BG505_ApexGT5.2 (soluble trimer for ApexGT5.2)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCPSVSTVQCTHGIKPVVSTQLLLNGSLAEE
EVIIRSENITNNAKNILVQLNTPVQINCTRPNNNTVKSIRIGPGQAFYYTGDIIGDIRQAH
CNVSKATWNETLGKVVKQLRKHFGNNTIIRFAQSSGGDLEVTTHSFNCGGEFFYCNTS
GLFNSTWISNTSVQGSNSTGSNDSITLPCRIKQIINMWQRIGQAMYAPPIQGVIRCVSNI
TGLILTRDGGSTNSTTETFRPGGGDMRDNWRSELYKYKVVKIEPLGVAPTRCKRRVV
GRRRRRRAVGIGAVSLGFLGAAGSTMGAASMTLTVQARNLLSGIVQQQSNLLRAPEP
QQHLLKDTHWGIKQLQARVLAVEHYLRDQQLLGIWGCSGKLICCTNVPWNSSWSNR
NLSEIWDNMTWLQWDKEISNYTQIIYGLLEESQNQQEKNEQDLLALD (SEQ ID NO:
29)

BG505_ApexGT5.2_congly (soluble trimer for ApexGT5.2, congly)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGRRRRRRAVGIGAVSLGFLGAAGSTMGAASMTLTVQARNLLSGIVQQQSNLLRAPE
PQQHLLKDTHWGIKQLQARVLAVEHYLRDQQLLGIWGCSGKLICCTNVPWNSSWSN
RNLSEIWDNMTWLQWDKEISNYTQIIYGLLEESQNQQEKNEQDLLALD (SEQ ID NO:
30)

BG505_ApexGT5.2_congly_CD4KO_link14 (soluble trimer for
ApexGT5.2, congly, link14, CD4KO)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGTDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD
(SEQ ID NO: 31)

TABLE 1-continued immunogenic proteins

BG505_ApexGT5.2_congly_link14 (soluble trimer for ApexGT5.2,
congly, link14)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD
(SEQ ID NO: 32)

BG505_ApexGT5.2_congly_CD4KO_link14
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGTDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD
(SEQ ID NO: 31)

BG505_ApexGT5.2_congly_CD4KO_gp151_link14
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGTDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR** (SEQ ID NO: 33)

BG505_ApexGT5.2_congly_CD4KO_link14
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGTDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD**
(SEQ ID NO: 34)

BG505_ApexGT5.2_congly_gp151
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR (SEQ ID NO: 35)

BG505_ApexGT5.2_congly_gp151 (membrane bound for ApexGT5.2,
congly, link14)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA TABLE 1-continued immunogenic proteins

```
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR (SEQ ID NO: 35)
```

```
BG505_ApexGT5.2_congly_gp151_link14
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR** (SEQ ID NO: 36)
```

```
BG505_ApexGT5.2_congly_link14
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD**
(SEQ ID NO: 37)
```

```
BG505_ApexGT5.2_congly_CD4KO_gp151 (membrane bound for
ApexGT5.2, congly, link14, CD4KO)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGTDMRDNWRSELYKYKVVKIEPLGVAPTRCKRRV
VGSHSGSGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR (SEQ ID NO: 38)
```

```
BG505_ApexGT5.2_gp151 (membrane bound for ApexGT5.2, link14)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNATTELRNKRQKVYSLFYRLDIVPMVDLWTNYRLINCNTSAITQACPKV
SFEPIPIHYCAPAGFAILKCKDKKFNGTGPCPSVSTVQCTHGIKPVVSTQLLLNGSLAE
EVIIRSENITNNAKNILVQLNTPVQINCTRPNNNTVKSIRIGPGQAFYYTGDIIGDIRQAH
CNVSKATWNETLGKVVKQLRKHFGNNTIIRFAQSSGGDLEVTTHSFNCGGEFFYCNTS
GLFNSTWISNTSVQGSNSTGSNDSITLPCRIKQIINMWQRIGQAMYAPPIQGVIRCVSNI
TGLILTRDGGSTNSTTETFRPGGGDMRDNWRSELYKYKVVKIEPLGVAPTRCKRRVV
GSHSGSGGSGSGGHAAVGIGAVSLGFLGAAGSTMGAASMTLTVQARNLLSGIVQQQS
NLLRAPEPQQHLLKDTHWGIKQLQARVLAVEHYLRDQQLLGIWGCSGKLICCTNVP
WNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR (SEQ ID NO: 39)
```

```
BG505_ApexGT6.2 (soluble trimer for ApexGT6.2)
AENLWVTVYYGVPVWKDAETTLFCASDAKAYETEKHNVWATHACVSTDPNPQEIHL
ENVTEEFNMWKNNMVEQMHEDIISLWDQSLKPCVKLTPLCVGLQCTNVTNNITDDM
RGELKNCSFNATTELRNKRQKVYSLFYRLDIVPMVDLWTNYRLISCNTSAITQACPKV
SFEPIPIHYCAPAGFAILKCKDKKFNGTGPCPSVSTVQCTHGIKPVVSTQLLLNGSLAEE
EVIIRSENITNNAKNILVQLNTPVQINCTRPNNNTVKSIRIGPGQAFYYTGDIIGDIRQAH
CNVSKATWNETLGKVVKQLRKHFGNNTIIRFAQSSGGDLEVTTHSFNCGGEFFYCNTS
GLFNSTWISNTSVQGSNSTGSNDSITLPCRIKQIINMWQRIGQAMYAPPIQGVIRCVSNI
TGLILTRDGGSTNSTTETFRPGGGDMRDNWRSELYKYKVVKIEPLGVAPTRCKRRVV
GRRRRRRAVGIGAVSLGFLGAAGSTMGAASMTLTVQARNLLSGIVQQQSNLLRAPEP
QQHLLKDTHWGIKQLQARVLAVEHYLRDQQLLGIWGCSGKLICCTNVPWNSSWSNR
NLSEIWDNMTWLQWDKEISNYTQIIYGLLEESQNQQEKNEQDLLALD (SEQ ID NO:
40)
```

TABLE 1-continued immunogenic proteins

BG505.ApexGT6.2_congly (soluble trimer for ApexGT6.2, congly)
AENLWVTVYYGVPVWKDAETTLFCASDAKAYETEKHNVWATHACVSTDPNPQEIHL
ENVTEEFNMWKNNMVEQMHEDIISLWDQSLKPCVKLTPLCVGLQCTNVTNNITDDM
RGELKNCSFNATTELRNKRQKVYSLFYRLDIVPMVDLWTNYRLISCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGRRRRRRAVGIGAVSLGFLGAAGSTMGAASMTLTVQARNLLSGIVQQQSNLLRAPE
PQQHLLKDTHWGIKQLQARVLAVEHYLRDQQLLGIWGCSGKLICCTNVPWNSSWSN
RNLSEIWDNMTWLQWDKEISNYTQIIYGLLEESQNQQEKNEQDLLALD (SEQ ID NO:
41)

BG505_ApexGT6.2_congly_CD4KO (soluble trimer for ApexGT6.2, congly, CD4KO)
AENLWVTVYYGVPVWKDAETTLFCASDAKAYETEKHNVWATHACVSTDPNPQEIHL
ENVTEEFNMWKNNMVEQMHEDIISLWDQSLKPCVKLTPLCVGLQCTNVTNNITDDM
RGELKNCSFNATTELRNKRQKVYSLFYRLDIVPMVDLWTNYRLISCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGTDMRDNWRSELYKYKVVKIEPLGVAPTRCKRRV
VGRRRRRRAVGIGAVSLGFLGAAGSTMGAASMTLTVQARNLLSGIVQQQSNLLRAPE
PQQHLLKDTHWGIKQLQARVLAVEHYLRDQQLLGIWGCSGKLICCTNVPWNSSWSN
RNLSEIWDNMTWLQWDKEISNYTQIIYGLLEESQNQQEKNEQDLLALD (SEQ ID NO:
42)

BG505_ApexGT6.2_congly_CD4KO_gp151 (membrane bound for ApexGT6.2, congly,
link14, CD4KO)
AENLWVTVYYGVPVWKDAETTLFCASDAKAYETEKHNVWATHACVSTDPNPQEIHL
ENVTEEFNMWKNNMVEQMHEDIISLWDQSLKPCVKLTPLCVGLQCTNVTNNITDDM
RGELKNCSFNATTELRNKRQKVYSLFYRLDIVPMVDLWTNYRLISCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGTDMRDNWRSELYKYKVVKIEPLGVAPTRCKRRV
VGSHSGSGGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR (SEQ ID NO: 43)

BG505_ApexGT6.2_congly_gp151 (membrane bound for ApexGT6.2, congly, link14)
AENLWVTVYYGVPVWKDAETTLFCASDAKAYETEKHNVWATHACVSTDPNPQEIHL
ENVTEEFNMWKNNMVEQMHEDIISLWDQSLKPCVKLTPLCVGLQCTNVTNNITDDM
RGELKNCSFNATTELRNKRQKVYSLFYRLDIVPMVDLWTNYRLISCNTSAITQACPKV
SFEPIPIHYCAPAGFAILKCKDKKFNGTGPCQNVSTVQCTHGIKPVVSTQLLLNGSLAE
EEVIIRSENITNNAKNILVQLNTSVQINCTRPNNNTVKSIRIGPGQAFYYTGDIIGDIRQA
HCNVSKATWNETLGKVVKQLRKHFGNNTIIRFAQSSGGDLEVTTHSFNCGGEFFYCN
TSGLFNSTWISNTSVQGSNSTGSNDSITLPCRIKQIINMWQRIGQAMYAPPIQGVIRCVS
NITGLILTRDGGSTNSTTETFRPGGGDMRDNWRSELYKYKVVKIEPLGVAPTRCKRRV
VGSHSGSGGGSGSGGHAAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR (SEQ ID NO: 44)

BG505_ApexGT6.2_gp151 (membrane bound for ApexGT6.2, link14)
AENLWVTVYYGVPVWKDAETTLFCASDAKAYETEKHNVWATHACVSTDPNPQEIHL
ENVTEEFNMWKNNMVEQMHEDIISLWDQSLKPCVKLTPLCVGLQCTNVTNNITDDM
RGELKNCSFNATTELRNKRQKVYSLFYRLDIVPMVDLWTNYRLISCNTSAITQACPKV
SFEPIPIHYCAPAGFAILKCKDKKFNGTGPCPSVSTVQCTHGIKPVVSTQLLLNGSLAEE
EVIIRSENITNNAKNILVQLNTPVQINCTRPNNNTVKSIRIGPGQAFYYTGDIIGDIRQAH
CNVSKATWNETLGKVVKQLRKHFGNNTIIRFAQSSGGDLEVTTHSFNCGGEFFYCNTS
GLFNSTWISNTSVQGSNSTGSNDSITLPCRIKQIINMWQRIGQAMYAPPIQGVIRCVSNI
TGLILTRDGGSTNSTTETFRPGGGDMRDNWRSELYKYKVVKIEPLGVAPTRCKRRVV
GSHSGSGGGSGSGGHAAVGIGAVSLGFLGAAGSTMGAASMTLTVQARNLLSGIVQQQS
NLLRAPEPQQHLLKDTHWGIKQLQARVLAVEHYLRDQQLLGIWGCSGKLICCTNVP
WNSSWSNRNLSEIWDNMTWLQWDKEISNYTQIIYGLLEESQNQQEKNEQDLLALDK
WASLWNWFDISNWLWYIKIFIMIVGGLIGLRIVFAVLSVIHRVR (SEQ ID NO: 45)

BG505_MD39.3_N197D_CD4KO_gp151
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCDTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN

TABLE 1-continued immunogenic proteins

```
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGTDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 46)
```

```
BG505_MD39.3_N197D_gp151
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCDTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 47)
```

```
BG505_MD39.3_N276Q_CD4KO_gp151
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSEQITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGTDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 48)
```

```
BG505_MD39.3_N276Q_gp151
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSEQITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 49)
```

```
BG505_MD39.3_N276W_CD4KO_gp151
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSEWITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGTDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 50)
```

```
BG505_MD39.3_N276W_gp151
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSEWITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV
APTRCKRRVVGSHSGSGGGSGSGGHAAVGIGAVSLGFLGAAGSTMGAASMTLTVQAR
```

TABLE 1-continued immunogenic proteins

NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 51)

BG505_MD39_gp151_link14_CD4KO4 (aka BG505 MD39.2 CD4KO gp151)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPNNNTVKSIRIGPGQAFYYTG
DIIGDIRQAHCNVSKATWNETLGKVVKQLRKHFGNNTIIRFAQSSGGDLEVTTHSFNC
GGEFFYCNTSGLFNSTWISNTSVQGSNSTGSNDSITLPCRIKQIINMWQRIGQAMYAPPI
QGVIRCVSNITGLILTRDGGSTNSTTETFRPGGTDMRDNWRSELYKYKVVKIEPLGVA
PTRCKRRVVGSHSGSGGGSGSGGHAAVGIGAVSLGFLGAAGSTMGAASMTLTVQARN
LLSGIVQQQSNLLRAPEPQQHLLKDTHWGIKQLQARVLAVEHYLRDQQLLGIWGCSG
KLICCTNVPWNSSWSNRNLSEIWDNMTWLQWDKEISNYTQIIYGLLEESQNQQEKNE
QDLLALDKWASLWNWFDISNWLWYIKIFIMIVGGLIGLRIVFAVLSVIHRVR** (SEQ
ID NO: 52)

BG505_MD39 gp151_link14_CD4KO4 (aka BG505 MD39.2 gp151)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPNNNTVKSIRIGPGQAFYYTG
DIIGDIRQAHCNVSKATWNETLGKVVKQLRKHFGNNTIIRFAQSSGGDLEVTTHSFNC
GGEFFYCNTSGLFNSTWISNTSVQGSNSTGSNDSITLPCRIKQIINMWQRIGQAMYAPPI
QGVIRCVSNITGLILTRDGGSTNSTTETFRPGGGDMRDNWRSELYKYKVVKIEPLGVA
PTRCKRRVVGSHSGSGGGSGSGGHAAVGIGAVSLGFLGAAGSTMGAASMTLTVQARN
LLSGIVQQQSNLLRAPEPQQHLLKDTHWGIKQLQARVLAVEHYLRDQQLLGIWGCSG
KLICCTNVPWNSSWSNRNLSEIWDNMTWLQWDKEISNYTQIIYGLLEESQNQQEKNE
QDLLALDKWASLWNWFDISNWLWYIKIFIMIVGGLIGLRIVFAVLSVIHRVR** (SEQ
ID NO: 53)

BG505_MD39_gp151_link14_congly (aka BG505 MD39.3 gp151)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 54)

BG505_MD39_gp151_link14_congly_CD4KO4 (aka BG505 MD39.3 CD4KO gp151)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGTDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 55)

BG505_MD39_gp160-dCT_link14_congly
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV TABLE 1-continued immunogenic proteins APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVRQGYSP
LS** (SEQ ID NO: 56)

BG505_MD39_gp160-dCT_link14_congly_Q
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSEQITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVRQGYSP
LS** (SEQ ID NO: 57)

BG505_MD39_gp160-dCT_link14_Q
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSEQITNNAKNILVQLNTPVQINCTRPNNNTVKSIRIGPGQAFYYTG
DIIGDIRQAHCNVSKATWNETLGKVVKQLRKHFGNNTIIRFAQSSGGDLEVTTHSFNC
GGEFFYCNTSGLFNSTWISNTSVQGSNSTGSNDSITLPCRIKQIINMWQRIGQAMYAPPI
QGVIRCVSNITGLILTRDGGSTNSTTETFRPGGGDMRDNWRSELYKYKVVKIEPLGVA
PTRCKRRVVGSHSGSGGGSGSGGHAAVGIGAVSLGFLGAAGSTMGAASMTLTVQARN
LLSGIVQQQSNLLRAPEPQQHLLKDTHWGIKQLQARVLAVEHYLRDQQLLGIWGCSG
KLICCTNVPWNSSWSNRNLSEIWDNMTWLQWDKEISNYTQIIYGLLEESQNQQEKNE
QDLLALDKWASLWNWFDISNWLWYIKIFIMIVGGLIGLRIVFAVLSVIHRVRQGYSPL
S** (SEQ ID NO: 58)

BG505_MD39_N332B9_gp151_L14
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYTPNLTSNM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPNNNTVKSIRIGPGQAFYYTG
DIIGDIRQAHCNVSKATWNETLGKVVKQLRKHFGNNTIIRFAQSSGGDLEVTTHSFNC
GGEFFYCNTSGLFNSTWISNTSVQGSNSTGSNDSITLPCRIKQIINMWQRIGQAMYAPPI
QGVIRCVSNITGLILTRDGGSTNSTTETFRPGGGDMRDNWRSELYKYKVVKIEPLGVA
PTRCKRRVVGSHSGSGGGSGSGGHAAVGIGAVSLGFLGAAGSTMGAASMTLTVQARN
LLSGIVQQQSNLLRAPEPQQHLLKDTHWGIKQLQARVLAVEHYLRDQQLLGIWGCSG
KLICCTNVPWNSSWSNRNLSEIWDNMTWLQWDKEISNYTQIIYGLLEESQNQQEKNE
QDLLALDKWASLWNWFDISNWLWYIKIFIMIVGGLIGLRIVFAVLSVIHRVR** (SEQ
ID NO: 59)

BG505_MD39_N332B11_gp151_link14_congly_CD4KO
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYTPNLTSMM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGDIRMAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGTDMRDNWRSELYKYKVVKIEPLGV
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 60)

BG505_MD39_N332B16_gp151_link14_congly_CD4KO
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYTEKLRSMM
KGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGHIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGTDMRDNWRSELYKYKVVKIEPLGV TABLE 1-continued immunogenic proteins

```
APTRCKRRVVGSHSGSGGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 61)

BG505_MD39_N332B22
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYTPNLTSMM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPNNNTVKSIRIGPGQAFYYTG
DIIGHIRMAHCNVSKATWNETLGKVVKQLRKHFGNNTIIRFAQSSGGDLEVTTHSFNC
GGEFFYCNTSGLFNSTWISNTSVQGSNSTGSNDSLILPCRIKQIINMWQRIGQAMYAPPI
QGVIRCVSNITGLILTRDGGSTNSTTETFRPGGGDMRDNWRSELYKYKVVKIEPLGVA
PTRCKRRVVGRRRRRRAVGIGAVSLGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD
(SEQ ID NO: 62)

BG505_MD39_N332B24
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYTPNLTSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPNNNTVKSIRIGPGQAFYYFG
DVLGDVRMAHCNISKATWNETLGKVVKQLRKHFGNNTIIRFAQSSGGDLEVTTHSFN
CGGEFFYCNTSGLFNSTWISNTSVQGSNSTGSNDSLILPCRIKQIINMWQRIGQAMYAP
PIQGVIRCVSNITGLILTRDGGSTNSTTETFRPGGGDMRDNWRSELYKYKVVKIEPLGV
APTRCKRRVVGRRRRRRAVGIGAVSLGFLGAAGSTMGAASMTLTVQARNLLSGIVQ
QQSNLLRAPEPQQHLLKDTHWGIKQLQARVLAVEHYLRDQQLLGIWGCSGKLICCTN
VPWNSSWSNRNLSEIWDNMTWLQWDKEISNYTQIIYGLLEESQNQQEKNEQDLLALD
(SEQ ID NO: 63)

BG505_MD64_N332B9
AENLWVTVYYGVPVWKDAETTLFCASDAKAYETEKHNVWATHECVPTDPNPQEIHL
ENVTEEFNMWKNNMVEQMHTDIIELWDQSLKPCVKLTPLCVTLQCTNYTPNLTSNM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPNNNTVKSIRIGPGQAFYYTG
DIIGDIRQAHCNVSKATWNETLGKVVKQLRKHFGNNTIIRFAQSSGGDLEVTTHSFNC
GGEFFYCNTSGLFNSTWISNTSVQGSNSTGSNDSITLPCRIKQIINMWQRIGQAMYAPPI
QGVIRCVSNITGLILTRDGGSTNSTTETFRPGGGDMRDNWRSELYKYKVVKIEPLGVA
PTRCKRRVVGRRRRRRAVGIGAVSLGFLGAAGSTMGAASMTLTVQARNLLSGIVQQ
QSNLLRAPEPQQHLLKLTVWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD
(SEQ ID NO: 64)

BG505_MD65_21mutJ_gp151_link14_congly_CD4KO
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPSNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCWIKQIINMWQRIGQAMYAP
PIQGVIRCVSNITGLILTRDGGSTNSTTETFRPGGTDMRDNWRSELYKYKVVKIEPLGV
APTRCKRRTVGSHSGSGGGSGSGGHAAAGIGASSDGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 65)

BG505_MD65_29mutA
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGQIMNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPSNISVKSIRIGPGQAFYYFGD
VLGHVRMAHCNISKATWNETLGKVVKQLRKHFGNNTIIRFAQSSGGDLEVTTHSFNC
GGEFFYCNTSLLFNSTWISNTSVQGSNSTGSNESLILPCWIKQIINMWQRIGQAMYAPPI
QGPINCVSNITGLILTRDGGSTNSTTETFRPGGGDMRDNWRSELYKYKVVKIEPLGVA
PTRCKRRTVGRRRRRRAAGIGASSDGFLGAAGSTMGAASMTLTVQARNLLSGIVQQQ
SNLLRAPEPQQHLLKDTHWGIKQLQARVLAVEHYLRDQQLLGIWGCSGKLICCTNVP
WNSSWSNRNLSEIWDNMTWLQWDKEISNYTQIIYGLLEESQNQQEKNEQDLLALD
(SEQ ID NO: 66)
```

TABLE 1-continued immunogenic proteins

BG505_MD65_29mutA_eG1
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYTPKLRSMM
RGQIMNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPSNISVKSIRIGPGQAFYYFGD
VLGHVRMAHCNISKATWNETLGKVVKQLRKHFGNNTIIRFAQSSGGDLEVTTHSFNC
GGEFFYCNTSLLFNSTWISNTSVQGSNSTGSNESLILPCWIKQIINMWQRIGQAMYAPPI
QGPINCVSNITGLILTRDGGSTNSTTETFRPGGGDMRDNWRSELYKYKVVKIEPLGVA
PTRCKRRTVGRRRRRRAAGIGASSDGFLGAAGSTMGAASMTLTVQARNLLSGIVQQQ
SNLLRAPEPQQHLLKDTHWGIKQLQARVLAVEHYLRDQQLLGIWGCSGKLICCTNVP
WNSSWSNRNLSEIWDNMTWLQWDKEISNYTQIIYGLLEESQNQQEKNEQDLLALD
(SEQ ID NO: 67)

BG505_MD65_29mutA_eG5
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGQIMNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPSNISVKSIRIGPGQAFYYFGN
VTGHVRMAHCNISKATWNETLGKVVKQLRKHFGNNTIIRFAQSSGGDLEVTTHSFNC
GGEFFYCNTSLLFNSTWISNTSVQGSNSTGSNESLILPCWIKQIINMWQRIGQAMYAPPI
QGPINCVSNITGLILTRDGGSTNSTTETFRPGGGDMRDNWRSELYKYKVVKIEPLGVA
PTRCKRRTVGRRRRRRAAGIGASSDGFLGAAGSTMGAASMTLTVQARNLLSGIVQQQ
SNLLRAPEPQQHLLKDTHWGIKQLQARVLAVEHYLRDQQLLGIWGCSGKLICCTNVP
WNSSWSNRNLSEIWDNMTWLQWDKEISNYTQIIYGLLEESQNQQEKNEQDLLALD
(SEQ ID NO: 68)

BG505_MD65_39mutA (N332-GT6)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGQIMNCSLNMTTELRDKKQKVYSLFYRRDVVQINENQGNRSNLSDKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPSNISVKSIRIGPGQAFYAVGD
VLGHVRMAHCNISKATWNETLGKVAKQLRKHFGNNTIIRFAQSSGADLEGTTHSFNC
GGEFFYCNTSLLFNSTWISNTSVQGSNSTGSNESLILPCWIKQIVNMWPRIGQAMYAPP
IQGPINCVSNITGLILTRDGGSTNSTTETFRPGGGDMRDNWRSELYKYKVVKIEPLGVA
PTRCKRRTVGRRRRRRAAGIGASSDGFLGAAGSTMGAASMTLTVQARNLLSGIVQQQ
SNLLRAPEPQQHLLKDTHWGIKQLQARVLAVEHYLRDQQLLGIWGCSGKLICCTNVP
WNSSWSNRNLSEIWDNMTWLQWDKEISNYTQIIYGLLEESQNQQEKNEQDLLALD
(SEQ ID NO: 69)

BG505_MD65_N332B23
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYTPNLTSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLNGSLAEEEVIIRSENITNNAKNILVQLNTPVQINCTRPSNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCWIKQIINMWQRIGQAMYAP
PIQGVIRCVSNITGLILTRDGGSTNSTTETFRPGGGDMRDNWRSELYKYKVVKIEPLGV
APTRCKRRTVGRRRRRRAAGIGASSDGFLGAAGSTMGAASMTLTVQARNLLSGIVQQ
QSNLLRAPEPQQHLLKDTHWGIKQLQARVLAVEHYLRDQQLLGIWGCSGKLICCTNV
PWNSSWSNRNLSEIWDNMTWLQWDKEISNYTQIIYGLLEESQNQQEKNEQDLLALD
(SEQ ID NO: 70)

core-g28v2_ferritin
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSTWSNESSNNINGSDNITLPCN
ISQNITMWCGVGKMNYSPPNSSNISCSSNITGLLLTRDGGVSNNETEIFRPGGGDMRD
NWRSELYKYKVVKIEPLGVAPTRGGGSGESQVRQQFSKDIEKLLNEQVNKEMQSSNL
YMSMSSWCYTHSLDGAGLFLFDHAAEEYEHAKKLIIFLNENNVPVQLTSISAPEHKFE
GLTQIFQKAYEHEQHISESINNIVDHAIKSKDHATFNFLQWYVAEQHEEEVLFKDILDK
IELIGNENHGLYLADQYVKGIAKSRKSGS* (SEQ ID NO: 71)

core-Hx_r4.0D_g30_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
GAENLWVTVYYGVPVWKDAETTLFCASDAKAYETEKHNVWATHACVPTDPNPQEI
HLENVTEEFNMCKNDMVEQMHKDICNLWNESLKPCNKTTGTSAITQACPKVSFEPIPI
HYCAPAGFAILKCNNNTFNGTGPCTNVSTVQCTHGIKPVVSTQLLLNGSLAEEEVIIRS TABLE 1-continued immunogenic proteins

```
CDFMDNAKTIIVQLNTSVEINCTAGNGTAHCNISGAKWNKTLKNISSKLRKQYGNNK
TIIFKQSSGGDPEIVTHWFNCGGEFFYCNSTQLFNSTWFNSTWSNESSNNTNGSDNITL
PCNISQIINMWCGVGKMNYSPPNSSNISCSSNITGLLLIRDGGVSNNETEIFRPGGGDM
RDNWRSELYKYKVVKIEPLGVAPTR* (SEQ ID NO: 72)
``` core-Hx_r4.0D_TH6_g7_60mer
```
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCVKLTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQFGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRDGGNSNNESEIFRPGGGDMRDN
WRSELYKYKVVKIEPLGVAPTR* (SEQ ID NO: 73)
``` core-Hx_r4.0D_TH6_g27_60mer
```
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
GAENLWVTVYYGVPVWKDAETTLFCASDAKAYETEKHNVWATHACVPTDPNPQEI
HLENVTEEFNMCKNDMVEQMHKDICNLWNESLKPCNKTTGTSAITQACPKVSFEPIPI
HYCAPAGFAILKCNNNTFNGTGPCTNVSTVQCTHGIKPVVSTQLLLNGSLAEEEVIIRS
CDFMDNAKTIIVQLNTSVEINCTAGNGTAHCNISGAKWNKTLKNISSKLRKQYGNNK
TIIFKQSSGGDPEIVTHWFNCGGEFFYCNSTQLFNSTWFNSNWSNESSNNINGSDNITL
PCNISQIINMWCGVGKMNYSPPNSSNISCSSNITGLLLTRDGGVSNNETEIFRPGGGDM
RDNWRSELYKYKVVKIEPLGVAPTR* (SEQ ID NO: 74)
``` core-Hx_r4.0D_TH6_g27_GT1.5_60mer
```
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRQGGNSNNETEIFRPGGGDMRDN
WRSELYKYKVVKIEPLGVAPTR* (SEQ ID NO: 75)
``` core-Hx_r4.0D_TH6_g27_GT1.7_60mer
```
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FTDNAKTIIVQLNTSVEINCTAGNGTAHCNISGAKWNKTLKNISSKLRKQFGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRQGGNSNDETEIFRPGGGDMRDN
WRSELYKYKVVKIEPLGVAPTR* (SEQ ID NO: 76)
``` core-Hx_r4.0D_TH6_g28v2_60mer (core-g28v2_60mer)
```
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
GAENLWVTVYYGVPVWKDAETTLFCASDAKAYETEKHNVWATHACVPTDPNPQEI
HLENVTEEFNMCKNDMVEQMHKDICNLWNESLKPCNKTTGTSAITQACPKVSFEPIPI
HYCAPAGFAILKCNNNTFNGTGPCTNVSTVQCTHGIKPVVSTQLLLNGSLAEEEVIIRS
CDFMDNAKTIIVQLNTSVEINCTAGNGTAHCNISGAKWNKTLKNISSKLRKQYGNNK
TIIFKQSSGGDPEIVTHWFNCGGEFFYCNSTQLFNSTWFNSTWSNESSNNINGSDNITL
PCNISQNITMWCGVGKMNYSPPNSSNISCSSNITGLLLTRDGGVSNNETEIFRPGGGDM
RDNWRSELYKYKVVKIEPLGVAPTR* (SEQ ID NO: 77)
``` core-Hx_r4.0D_TH6_g29_60mer
```
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
GAENLWVTVYYGVPVWKDAETTLFCASDAKAYETEKHNVWATHACVPTDPNPQEI
HLENVTEEFNMCKNDMVEQMHKDICNLWNESLKPCNKTTGTSAITQACPKVSFEPIPI
HYCAPAGFAILKCNNNTFNGTGPCTNVSTVQCTHGIKPVVSTQLLLNGSLAEEEVIIRS
CDFMDNAKTIIVQLNTSVEINCTAGNGTAHCNISGAKWNKTLKNISSKLRKQYGNNK
TIIFKQSSGGDPEIVTHWFNCGGEFFYCNSTQLFNSTWFNSTWSNESSNNINGSDNITL
PCNISQIINMWCGVGKMNYSPPNSSNISCSSNITGLLLTRDGGVSNNETEIFRPGGGDM
RDNWRSELYKYKVVKIEPLGVAPTR* (SEQ ID NO: 78)
```

TABLE 1-continued immunogenic proteins core r3.2 60mer (aka gp120core-e-2CC_c1_r3.2_N276D_V3_6_d41m3-60mer_m)
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
GVWKEATTTLFCASDAKAYDTEVHNVWATHACVPTDPNPQEVVLVNVTENFNWCK
NDMVEQMHKDICNLWEESLKPCVKLTGGSVITQACPKVSFEPIPIHYCAPAGYAILKC
NNNTFNGTGPCTNVSTVVCTHGIRPVVSSQLLLNGSLAEEKEVVIRSCDFTDNAKTIIVQ
LNTSVEINCAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCKVG
KMMYAPPVSGQIKCSSNITGLLLTRDGGNSNNESEIFRPGGGDMRDNWRSELYKYKV
VKIE** (SEQ ID NO: 79)

core r4g10 TH6 60mer (aka core-Hx_r4.0D_TH6_g10_d41m3_60mer)
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
GAENLWVTVYYGVPVWKDAETTLFCASDAKAYETEKHNVWATHACVPTDPNPQEI
HLENVTEEFNMCKNDMVEQMHKDICNLWNESLKPCNKTTGTSAITQACPKVSFEPIPI
HYCAPAGFAILKCNNNTFNGTGPCTNVSTVQCTHGIKPVVSTQLLLNGSLAEEEVIIRS
CDFMDNAKTIIVQLNTSVEINCTAGNGTAHCNISGAKWNKTLKNISSKLRKQFGNNKT
IIFKQSSGGDPEIVTHWFNCGGEFFYCNSTQLFNSTWFNSNWSNESSNNINGSDNITLP
CNISQNITMWCGVGKMNYSPPNSSNISCSSNITGLLLTRDGGNSNNESEIFRPGGGDMR
DNWRSELYKYKVVKIEPLGVAPTR** (SEQ ID NO: 80)

core r5g15 60mer (aka core-Hx_r4.0_g15_d41m3_60mer)
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
GVWKEATTTLFCASNATAYDNESHNVWATHACVPTDPNPNESVLVNVTENFSWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMNYSPPVSNQSKCSSNITGLLLTRDGGNSNNESEIFRPGGGDMRDNWRSELYKYKV
VKIE** (SEQ ID NO: 81)

core_r4g7_TH6 (aka core-Hx_r4.0D_TH6_g7)
AENLWVTVYYGVPVWKDAETTLFCASDAKAYETEKHNVWATHACVPTDPNPQEIHL
ENVTEEFNMCKNDMVEQMHKDICNLWNESLKPCVKLTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQFGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRDGGNSNNESEIFRPGGGDMRDN
WRSELYKYKVVKIEPLGVAPTR (SEQ ID NO: 82)

core_r4g7_TH6_60mer (aka core-Hx_r4.0D_TH6_g7_60mer_m)
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCVKLTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQFGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRDGGNSNNESEIFRPGGGDMRDN
WRSELYKYKVVKIEPLGVAPTR** (SEQ ID NO: 83)

core_r5g15 (aka core-Hx_r4.0_g15)
VWKEATTTLFCASNATAYDNESHNVWATHACVPTDPNPNESVLVNVTENFSWCKND
MVEQMHKDICNLWNESLKPCVKLTGGSVINQSCNKTSFEPIPIHYCAPAGYAILKCNN
NTFNGTGPCTNVSTVNCTHGIRPVVSSQLLLNGSLAEKEVVIRSCDFMDNAKTIIVQLN
TSVEINCTAGNGTAHCNISGAKWNKTLKRIASKLRKQFGNNKTIIFKQSSGGDPEIVTH
WFNCGGEFFYCNSTQLFNSTWFNSTWSTEGSNNTEGSDTITLPCKIKQIINMWCGVGK
MNYSPPVSNQSKCSSNITGLLLTRDGGNSNNESEIFRPGGGDMRDNWRSELYKYKVV
KIE (SEQ ID NO: 84)

core-Hx_r4.0_g5
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGGDMRDNWRSELYKYKV
VKIE (SEQ ID NO: 85)

core-Hx_r4.0_g5.2 (aka core-Hx_r4.0_g5_1G)
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN TABLE 1-continued immunogenic proteins

```
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 86)

core-Hx_r4.0_g5.2_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 87)

core-Hx_r4.0_g5.2_CD4KO (aka core-Hx_r4.0_g5_1G_CD4KO)
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 88)

core-Hx_r4.0_g5.2_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 89)

core-Hx_r4.0_g5.2_Q276
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 90)

core-Hx_r4.0_g5.2_Q276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 91)

core-Hx_r4.0_g5.2_Q276_CD4KO
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 92)

core-Hx_r4.0_g5.2_Q276_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCNKTTGGSVITQACNKTSFEPIPIHYCAPAGYAILKCN
```

TABLE 1-continued immunogenic proteins

NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 93)

core-Hx_r4.0_g5.3
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 94)

core-Hx_r4.0_g5.3_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 95)

core-Hx_r4.0_g5.3_CD4KO
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 96)

core-Hx_r4.0_g5.3_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 97)

core-Hx_r4.0_g5.3_Q276
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 98)

core-Hx_r4.0_g5.3_Q276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGGDMRDNWRSELYKYK
VVKIE (SEQ ID NO: 99)

core-Hx_r4.0_g5.3_Q276_CD4KO
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 100)

TABLE 1-continued immunogenic proteins core-Hx_r4.0_g5.3_Q276_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQNITMWCGV
GKMMYAPPVSNQSKCSSNITGLLLTRDGGNSNNESEIFRPGGTDMRDNWRSELYKYK
VVKIE (SEQ ID NO: 101)

core-Hx_r4.0_g5_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGGDMRDNWRSELYKYKV
VKIE (SEQ ID NO: 102)

core-Hx_r4.0_g5_CD4KO
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGTDMRDNWRSELYKYKV
VKIE (SEQ ID NO: 103)

core-Hx_r4.0_g5_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCDFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGTDMRDNWRSELYKYKV
VKIE (SEQ ID NO: 104)

core-Hx_r4.0_g5_N276
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCNFTDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGGDMRDNWRSELYKYKV
VKIE (SEQ ID NO: 105)

core-Hx_r4.0_g5_N276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCNFTDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGGDMRDNWRSELYKYKV
VKIE (SEQ ID NO: 106)

core-Hx_r4.0_g5_Q276
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGGDMRDNWRSELYKYKV
VKIE (SEQ ID NO: 107)

TABLE 1-continued immunogenic proteins core-Hx_r4.0_g5_Q276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGGDMRDNWRSELYKYKV
VKIE (SEQ ID NO: 108)

core-Hx_r4.0_g5_Q276_CD4KO
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGTDMRDNWRSELYKYKV
VKIE (SEQ ID NO: 109)

core-Hx_r4.0_g5_Q276_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
VWKEATTTLFCASDAKAYDNESHNVWATHACVPTDPNPNESVLVNVTENFHWCKN
DMVEQMHKDICNLWNESLKPCVKLTGGSVINQSCNKTSFEPIPIHYCAPAGYAILKCN
NNTFNGTGPCTNVSTVNCTHGIRPVVSSQLLLNGSLAEKEVVIRSCQFMDNAKTIIVQL
NTSVEINCTAGNGTAHCNISGAKWNKTLKRIASKLRKQFGNNKTIIFKQSSGGDPEIVT
HWFNCGGEFFYCNSTQLFNSTWFNSTWSTEGSNNTEGSDTITLPCKIKQIINMWCGVG
KMMYAPPVSNQSKCSSNITGLLLTRDGGNSNNESEIFRPGGTDMRDNWRSELYKYKV
VKIE (SEQ ID NO: 110)

core-Hx_r4.0D_TH6_g7_monomer
AENLWVTVYYGVPVWKDAETTLFCASDAKAYETEKHNVWATHACVPTDPNPQEIHL
ENVTEEFNMCKNDMVEQMHKDICNLWNESLKPCVKLTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQFGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRDGGNSNNESEIFRPGGGDMRDN
WRSELYKYKVVKIEPLGVAPTR* (SEQ ID NO: 111)

core-Hx_r4.0D_TH6_g27_monomer
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRDGGVSNNETEIFRPGGGDMRDN
WRSELYKYKVVKIEPLGVAPTR* (SEQ ID NO: 112)

core-Hx_r4.0D_TH6_g27_GT1.5_monomer
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRQGGNSNNETEIFRPGGGDMRDN
WRSELYKYKVVKIEPLGVAPTR* (SEQ ID NO: 113)

core-Hx_r4.0D_TH6_g27_GT1.7_monomer
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FTDNAKTIIVQLNTSVEINCTAGNGTAHCNISGAKWNKTLKNISSKLRKQFGNNKTIIF
KQSSGGDPEIVTHWFNCGGEFFYCNSTQLFNSTWFNSNWSNESSNNINGSDNITLPCN
ISQIINMWCGVGKMNYSPPNSSNISCSSNITGLLLTRQGGNSNDETEIFRPGGGDMRDN
WRSELYKYKVVKIEPLGVAPTR* (SEQ ID NO: 114)

core-Hx_r4.0_TH6_g28_N276
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCN
FTDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 115)

TABLE 1-continued

| immunogenic proteins |
| --- | core-Hx_r4.0_TH6_g28_N276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCN
FTDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNTNGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 116)

core-Hx_r4.0D_191084_TH6_g28_v1
AENLWVTVYYGVPVWRDAETTLFCASDAKAYDTEMHNVWATHACVPTDPNPQEIH
LENVTEEFNMCKNDMVEQMHKDICNLWNESLKPCNKTTGTSAITQACPKVSFEPIPIH
YCAPAGFAILKCNNNTFNGTGPCTNVSTVQCTHGIKPVVSTQLLLNGSLAEEEVIIRSC
DFMDNAKTIIVQLNTSVEINCTAGNGTAHCNISGAKWNKTLKNISSKLRKQYGNNKTI
IFKQSSGGDPEIVTHWFNCGGEFFYCNSTQLFNSTWFNSNWSNESSNNINGSDNITLPC
NISQNITMWCGVGKMNYSPPNSSNISCSSNITGLLLTRDGGVSNNETEIFRPGGGNMR
DNWRSELYKYKVVKIEPLGVAPTR (SEQ ID NO: 117)

core-Hx_r4.0D_191084_TH6_g28_v1_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWRDAETTLFCASDAKAYDTEMHNVWATHACVPTDPNPQEIH
LENVTEEFNMCKNDMVEQMHKDICNLWNESLKPCNKTTGTSAITQACPKVSFEPIPIH
YCAPAGFAILKCNNNTFNGTGPCTNVSTVQCTHGIKPVVSTQLLLNGSLAEEEVIIRSC
DFMDNAKTIIVQLNTSVEINCTAGNGTAHCNISGAKWNKTLKNISSKLRKQYGNNKTI
IFKQSSGGDPEIVTHWFNCGGEFFYCNSTQLFNSTWFNSNWSNESSNNINGSDNITLPC
NISQNITMWCGVGKMNYSPPNSSNISCSSNITGLLLTRDGGVSNNETEIFRPGGGNMR
DNWRSELYKYKVVKIEPLGVAPTR (SEQ ID NO: 118)

core-Hx_r4.0D_191084_TH6_g28_v2
AENLWVTVYYGVPVWRDAETTLFCASDAKAYDTEKHNVWATHACVPTDPNPQEIH
LENVTEEFNMCKNDMVEQMHKDICNLWNESLKPCNKTTGTSAITQACPKVSFEPIPIH
YCAPAGFAILKCNNNTFNGTGPCTNVSTVQCTHGIKPVVSTQLLLNGSLAEEEVIIRSC
DFMDNAKTIIVQLNTSVEINCTAGNGTAHCNISGAKWNKTLKNISSKLRKQYGNNKTI
IFKQSSGGDPEIVTHWFNCGGEFFYCNSTQLFNSTWFNSNWSNESSNNTNGSDNITLPC
NISQNITMWCGVGKMNYSPPNSSNISCSSNITGLLLTRDGGVSNNETEIFRPGGGNMR
DNWRSELYKYKVVKIEPLGVAPTR (SEQ ID NO: 119)

core-Hx_r4.0D_191084_TH6_g28_v2_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWRDAETTLFCASDAKAYDTEKHNVWATHACVPTDPNPQEIH
LENVTEEFNMCKNDMVEQMHKDICNLWNESLKPCNKTTGTSAITQACPKVSFEPIPIH
YCAPAGFAILKCNNNTFNGTGPCTNVSTVQCTHGIKPVVSTQLLLNGSLAEEEVIIRSC
DFMDNAKTIIVQLNTSVEINCTAGNGTAHCNISGAKWNKTLKNISSKLRKQYGNNKTI
IFKQSSGGDPEIVTHWFNCGGEFFYCNSTQLFNSTWFNSNWSNESSNNTNGSDNITLPC
NISQNITMWCGVGKMNYSPPNSSNISCSSNITGLLLTRDGGVSNNETEIFRPGGGNMR
DNWRSELYKYKVVKIEPLGVAPTR (SEQ ID NO: 120)

core-Hx_r4.0D_TH6_g28
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 121)

core-Hx_r4.0D_TH6_g28_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 122)

core-Hx_r4.0D_TH6_g28_CD4KO
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY TABLE 1-continued immunogenic proteins

```
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQNITMWCGVGKMNYSPPNSSNISCSSNITGLLLTRDGGVSNNETEIFRPGGTDMRDN
WRSELYKYKVVKIEPLGVAPTR (SEQ ID NO: 123)

core-Hx_r4.0D_TH6_g28_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNTNGSDNITLPCN
ISQNITMWCGVGKMNYSPPNSSNISCSSNITGLLLTRDGGVSNNETEIFRPGGTDMRDN
WRSELYKYKVVKIEPLGVAPTR (SEQ ID NO: 124)

core-Hx_r4.0D_TH6_g28_Q276
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCQ
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNTNGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 125)

core-Hx_r4.0D_TH6_g28_Q276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCQ
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 126)

core-Hx_r4.0D_TH6_g28_Q276_CD4KO
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCQ
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 125)

core-Hx_r4.0D_TH6_g28_Q276_CD4KO_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGSGGSGGSGG
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCQ
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSNWSNESSNNINGSDNITLPCN
ISQNITMWCGVGKMNYSPPNSSNISCSSNITGLLLTRDGGVSNNETEIFRPGGGDMRD
NWRSELYKYKVVKIEPLGVAPTR (SEQ ID NO: 126)

core-Hx_r4.0D_TH6_g28v2_monomer
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSTWSNESSNNTNGSDNITLPCN
ISQNITMWCGVGKMNYSPPNSSNISCSSNITGLLLTRDGGVSNNETEIFRPGGGDMRD
NWRSELYKYKVVKIEPLGVAPTR* (SEQ ID NO: 127)

core-Hx_r4.0D_TH6_g29_monomer
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSTWSNESSNNINGSDNITLPCN
ISQIINMWCGVGKMNYSPPNSSNISCSSNITGLLLTRDGGVSNNETEIFRPGGGDMRDN
WRSELYKYKVVKIEPLGVAPTR* (SEQ ID NO: 128)
```

TABLE 1-continued immunogenic proteins core-Hx_r4.0D_TH6_g30_monomer
AENLWVTVYYGVPVWKDAETTLFCASDAKAYETEKHNVWATHACVPTDPNPQEIHL
ENVTEEFNMCKNDMVEQMHKDICNLWNESLKPCNKTTGTSAITQACPKVSFEPIPIHY
CAPAGFAILKCNNNTFNGTGPCTNVSTVQCTHGIKPVVSTQLLLNGSLAEEEVIIRSCD
FMDNAKTIIVQLNTSVEINCTAGNGTAHCNISGAKWNKTLKNISSKLRKQYGNNKTIIF
KQSSGGDPEIVTHWFNCGGEFFYCNSTQLFNSTWFNSTWSNESSNNINGSDNITLPCN
ISQIINMWCGVGKMNYSPPNSSNISCSSNITGLLLIRDGGVSNNETEIFRPGGGDMRDN
WRSELYKYKVVKIEPLGVAPTR* (SEQ ID NO: 129)

eOD-GT11.15 6G 60mer (aka eOD-GT11.15_6G_d41m3_60mer_m)
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTITLP
CRPAPPPNCTSNITGLILTRQGGWSNDNTVIFRPSAGDWRDIARCNITGTVVSTQLFLN
GSLAENETVIRSRDWRDNQQSICVQLNTSVEINCTGNGTCNISRAKWNNTLKQIASKL
REQYGNKTVIFAPSSGGDPEFVNHSFNCGNVTFYCNSTQLFNSTWFNST** (SEQ ID
NO: 130)

eOD-GT11.15 6G N276 60mer (aka eOD-
GT11.15_N276_6G_d41m3_60mer_CORRECT_m)
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTITLP
CRPAPPPNCTSNITGLILTRQGGWSNDNTVIFRPSAGDWRDIARCNITGTVVSTQLFLN
GSLAENETVIRSRNWTDNQQSICVQLNTSVEINCTGNGTCNISRAKWNNTLKQIASKL
REQYGNKTVIFAPSSGGDPEFVNHSFNCGNVTFYCNSTQLFNSTWFNST** (SEQ ID
NO: 131)

eOD-GT6-3mutB-cRSF01_60mer_m
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTIELK
CEPAPPPSCSSNITGLILTRDGGVSNNETEIFRPSGGDMRDINSCNIAGPVRSTQLFLNGS
LAEKEVVIHSVDFRDNAKSICVQLNSSVTINCTGNGSCNISRAKWNKTLAEIANKLKK
TYGNRTIIFAQSSGGDPEFVTHSFDCNGKTFYCNSTQLFNSTWDNST** (SEQ ID NO:
132)

eOD-GT6-3mutB-cRSF01_N276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTIELK
CEPAPPPSCSSNITGLILTRDGGVSNNETEIFRPSGGDMRDINSCNIAGPVRSTQLFLNGS
LAEKEVVIHSVNFTDNAKSICVQLNSSVTINCTGNGSCNISRAKWNKTLAEIANKLKK
TYGNRTIIFAQSSGGDPEFVTHSFDCNGKTFYCNSTQLFNSTWDNST* (SEQ ID NO:
133)

eOD-GT6-3mutB-cRSF01_N276_E275_N460_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTIELK
CEPAPPPSCSSNITGLILTRDGGNSNNETEIFRPSGGDMRDINSCNIAGPVRSTQLFLNGS
LAEKEVVIHSENFTDNAKSICVQLNSSVTINCTGNGSCNISRAKWNKTLAEIANKLKKT
YGNRTIIFAQSSGGDPEFVTHSFDCNGKTFYCNSTQLFNSTWDNST* (SEQ ID NO: 134)

eOD-GT6-3mutB-cRSF01_N276_monomer
DTIELKCEPAPPPSCSSNITGLILTRDGGVSNNETEIFRPSGGDMRDINSCNIAGPVRSTQ
LFLNGSLAEKEVVIHSVNFTDNAKSICVQLNSSVTINCTGNGSCNISRAKWNKTLAEIA
NKLKKTYGNRTIIFAQSSGGDPEFVTHSFDCNGKTFYCNSTQLFNSTWDNST* (SEQ ID
NO: 135)

eOD-GT6-3mutB-cRSF01_N276_E275_N460_monomer
DTIELKCEPAPPPSCSSNITGLILTRDGGNSNNETEIFRPSGGDMRDINSCNIAGPVRSTQ
LFLNGSLAEKEVVIHSENFTDNAKSICVQLNSSVTINCTGNGSCNISRAKWNKTLAEIA
NKLKKTYGNRTIIFAQSSGGDPEFVTHSFDCNGKTFYCNSTQLFNSTWDNST* (SEQ ID
NO: 136)

eOD-GT8 6G 60mer (aka eOD-GT8_6G_d41m3_60mer_m)
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTITLP
CRPAPPPNCTSNITGLILTRQGGYSNDNTVIFRPSGGDWRDIARCNITGTVVSTQLFLN
GSLAENETVIRSEDWRDNAKSICVQLNTSVEINCTGNGTCNISRAKWNNTLKQIASKL
REQYGNKTIIFKPSSGGDPEFVNHSFNCGNVTFYCNSTQLFNSTWFNST** (SEQ ID
NO: 137)

eOD-GT8 6G g123 60mer (aka eOD-GT8_6G-60mer_g123_m)
MQIYEGKLTAEGLRFGIVASRANHALVDRLVEGAIDAIVRHGGREEDITLVRVCGSWE
IPVAAGELARKENISAVIAIGVLCRGATPSFDYIASEVSKGLADLSLELRKPITFGVITAD TABLE 1-continued immunogenic proteins TLEQAIEAAGTCHGNKGWEAALCAIEMANLFKSLRGGSNGTGGSGGSNGTGGDTITL
PCRPAPPPNCTSNITGLILTRQGGYSNDNTVIFRPSGGDWRDIARCNITGTVVSTQLFLN
GSLAENETVIRSEDWRDNAKSICVQLNTSVEINCTGNGTCNISRAKWNNTLKQIASKL
REQYGNKTIIFKPSSGGDPEFVNHSFNCGNVTFYCNSTQLFNSTWFNST** (SEQ ID
NO: 138)

eOD-GT8_d41m3_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGGDTITLP
CRPAPPPHCSSNITGLILTRQGGYSNDNTVIFRPSGGDWRDIARCQIAGTVVSTQLFLN
GSLAEEEVVIRSEDWRDNAKSICVQLNTSVEINCTGAGHCNISRAKWNNTLKQIASKL
REQYGNKTIIFKPSSGGDPEFVNHSFNCGGEFFYCDSTQLFNSTWFNST** (SEQ ID NO:
139)

GagIIIB_mut3
MGARASVLSGGELDRWEKIRLRPGGKKKYKLKHIVWASRELERFAVNPGLLETSEGC
RQILGQLQPSLQTGSEELRSLYNTVATLYCVHQRIEIKDTKEALDKIEEEQNKSKKKAQ
QAAADTGHSSQVSQNYPIVQNIQGQMVHQAISPRTLNAWVKVVEEKAFSPEVIPMFS
ALSEGATPQDLNTMLNTVGGHQAAMQMLKETINEEAAEWDRVHPVHAGPIAPGQM
REPRGSDIAGTTSTLQEQIGWMTNNPPIPVGEIYKRWIILGLNKIVRMYSPTSILDIRQGP
KEPFRDYVDRFYKTLRAEQASQEVKNWMTETLLVQNANPDCKTILKALGPAATLEE
MMTACQGVGGPGHKARVLAEAMSQATNTATIMMQRGNFRNQRKMVKCFNCGKEG
HTARNCRAPRKKGCWKCGKEGHQMKDCTERQANFLGKIWPSYKGRPGNFLQSRPEP
TAPPFLQSRPEPTAPPEESFRSGVETTTPPQKQEPIDKELYPLTSLRSLFGNDPSSQ (SEQ
ID NO: 140)

GT12.1_1G_N276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTITLP
CRPAPPPHCSSNITGLILTRQGGWNNDNTVIFRPSAGDWSDIARCQIAGTVVSTQLFLN
GSLAEEEVVIRSRNWTDNQQSICVQLNTSVEINCTGAGHCNISRAKWNNTLKQIASKL
REQYGNKTVIFAPSSGGDPEFVNHSFNCGGEFFYCNSTQLFNSTWFNST* (SEQ ID NO:
141)

GT12.1_1G_N276_D463Q_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTITLP
CRPAPPPHCSSNITGLILTRQGGWNNQNTVIFRPSAGDWSDIARCQIAGTVVSTQLFLN
GSLAEEEVVIRSRNWTDNQQSICVQLNTSVEINCTGAGHCNISRAKWNNTLKQIASKL
REQYGNKTVIFAPSSGGDPEFVNHSFNCGGEFFYCNSTQLFNSTWFNST* (SEQ ID NO:
142)

GT12.1_1G_N276_D463Q_N373M_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGDTITLP
CRPAPPPHCSSNITGLILTRQGGWNNQNTVIFRPSAGDWSDIARCQIAGTVVSTQLFLN
GSLAEEEVVIRSRNWTDNQQSICVQLNTSVEINCTGAGHCNISRAKWNNTLKQIASKL
REQYGNKTVIFAPSSGGDPEFVMHSFNCGGEFFYCNSTQLFNSTWFNST* (SEQ ID
NO: 143)

GT12.1_6G_N276_60mer
MQIYEGKLTAEGLRFGIVASRANHALVDRLVEGAIDAIVRHGGREEDITLVRVCGSWE
IPVAAGELARKEDIDAVIAIGVLCRGATPSFDYIASEVSKGLADLSLELRKPITFGVITA
DTLEQAIEAAGTCHGNKGWEAALCAIEMANLFKSLRGGSGGSGGSGGSGGGGDTITLP
CRPAPPPNCTSNITGLILTRQGGWNNDNTVIFRPSAGDWSDIARCNITGTVVSTQLFLN
GSLAENETVIRSRNWTDNQQSICVQLNTSVEINCTGNGTCNISRAKWNNTLKQIASKL
REQYGNKTVIFAPSSGGDPEFVNHSFNCGNVTFYCNSTQLFNSTWFNST* (SEQ ID
NO: 144)

GT12.1_1G_N276_monomer
DTITLPCRPAPPPHCSSNITGLILTRQGGWNNDNTVIFRPSAGDWSDIARCQIAGTVVST
QLFLNGSLAEEEVVIRSRNWTDNQQSICVQLNTSVEINCTGAGHCNISRAKWNNTLKQ
IASKLREQYGNKTVIFAPSSGGDPEFVNHSFNCGGEFFYCNSTQLFNSTWFNST* (SEQ
ID NO: 145)

GT12.1_1G_N276_D463Q_monomer
DTITLPCRPAPPPHCSSNITGLILTRQGGWNNQNTVIFRPSAGDWSDIARCQIAGTVVST
QLFLNGSLAEEEVVIRSRNWTDNQQSICVQLNTSVEINCTGAGHCNISRAKWNNTLKQ
IASKLREQYGNKTVIFAPSSGGDPEFVNHSFNCGGEFFYCNSTQLFNSTWFNST* (SEQ
ID NO: 146)

TABLE 1-continued immunogenic proteins

GT12.1_1G_N276_D463Q_N373M_monomer
DTITLPCRPAPPPHCSSNITGLILTRQGGWNNQNTVIFRPSAGDWSDIARCQIAGTVVST
QLFLNGSLAEEEVVIRSRNWTDNQQSICVQLNTSVEINCTGAGHCNISRAKWNNTLKQ
IASKLREQYGNKTVIFAPSSGGDPEFVMHSFNCGGEFFYCNSTQLFNSTWFNST* (SEQ
ID NO: 147)

GT12.1_6G_N276_monomer
DTITLPCRPAPPPNCTSNITGLILTRQGGWNNDNTVIFRPSAGDWSDIARCNITGTVVST
QLFLNGSLAENETVIRSRNWTDNQQSICVQLNTSVEINCTGNGTCNISRAKWNNTLKQ
IASKLREQYGNKTVIFAPSSGGDPEFVNHSFNCGNVTFYCNSTQLFNSTWFNST* (SEQ
ID NO: 148)

MD39_link14_congly (aka BG505_SOSIP_MD39_link14_congly_m)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV
APTRCKRRVVGSHSGSGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALD** (SEQ ID NO: 149)

MD39_link14_congly_Q (aka BG505_SOSIP_MD39_N276Q_link14_congly_m)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNVTNNITDDM
RGELKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSEQITNNAKNILVQLNTSVQINCTRPNNNTVKSIRIGPGQAFYYT
GDIIGDIRQAHCNVSKATWNETLGKVVKQLRKHFGNNTIIRFAQSSGGDLEVTTHSFN
CGGEFFYCNTSGLFNSTWISNTSVQGSNSTGSNDSITLPCRIKQIINMWQRIGQAMYAP
PIQGVIRCVSNITGLILTRDGGSTNSTTETFRPGGGDMRDNWRSELYKYKVVKIEPLGV
APTRCKRRVVGSHSGSGGSGSGGHAAVGIGAVSLGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALD** (SEQ ID NO: 150)

MD64_CPG9 (aka BG505_SOSIP_MD39C_CPG9_m)
GGNSSGSLGFLGAAGSTMGAASMTLTVQARNLLSGIVQQQSNLLRAPEPQQHLLKLT
VWGIKQLQARVLAVEHYLRDQQLLGIWGCSGKLICCTNVPWNSSWSNRNLSEIWDN
MTWLNWSKEISNYTQIIYGLLEESQNQNESNEQDLGGNGSGGGSGSGGNGSSGLWVT
VYYGVPVWKDAETTLFCASDAKAYETEKHNVWATHECVPTDPNSSEIHLENVTEEFN
MWKNNMVEQMHTDIIELWDQSLKPCVKLTPLCVTLQCTNVINNITDDMRGELKNCS
FNMTTELRDKKQKVYSLFYRLDVVQINENQGNRSNNSNKEYRLINCNTSAITQACPK
VSFEPIPIHYCAPAGFAILKCKDKKFNGTGPCQNVSTVQCTHGIKPVVSTQLLLNGSLA
EEEVIIRSENITNNAKNILVQLNTSVQINCTRPNNNTVKSIRIGPGQAFYYTGDIIGDIRQ
AHCNVSKATWNETLGKVVKQLRKHFGNNTIIRFAQSSGGDLEVTTHSFNCGGEFFYC
NTSGLFNSTWISNTSVQGSNSTGSNDSITLPCRIKQIINMWQRIGQAMYAPPIQGVIRCV
SNITGLILTRDGGSTNSTTETFRPGGGDMRDNWRSELYKYKVVKIEPLGVAPTRCNRS
** (SEQ ID NO: 151)

MD64_CPG9_Q (aka BG505_MD64_CPG9_N276Q_m)
GGNSSGSLGFLGAAGSTMGAASMTLTVQARNLLSGIVQQQSNLLRAPEPQQHLLKLT
VWGIKQLQARVLAVEHYLRDQQLLGIWGCSGKLICCTNVPWNSSWSNRNLSEIWDN
MTWLNWSKEISNYTQIIYGLLEESQNQNESNEQDLGGNGSGGGSGSGGNGSSGLWVT
VYYGVPVWKDAETTLFCASDAKAYETEKHNVWATHECVPTDPNSSEIHLENVTEEFN
MWKNNMVEQMHTDIIELWDQSLKPCVKLTPLCVTLQCTNVTNNITDDMRGELKNCS
FNMTTELRDKKQKVYSLFYRLDVVQINENQGNRSNNSNKEYRLINCNTSAITQACPK
VSFEPIPIHYCAPAGFAILKCKDKKFNGTGPCQNVSTVQCTHGIKPVVSTQLLLNGSLA
EEEVIIRSEQITNNAKNILVQLNTSVQINCTRPNNNTVKSIRIGPGQAFYYTGDIIGDIRQ
AHCNVSKATWNETLGKVVKQLRKHFGNNTIIRFAQSSGGDLEVTTHSFNCGGEFFYC
NTSGLFNSTWISNTSVQGSNSTGSNDSITLPCRIKQIINMWQRIGQAMYAPPIQGVIRCV
SNITGLILTRDGGSTNSTTETFRPGGGDMRDNWRSELYKYKVVKIEPLGVAPTRCNRS
** (SEQ ID NO: 152)

MD65_21mutJ_gp160-dCT_link14 (aka BG505_MD65_L14_21mutJ_gp160dCT_m)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLLNGSLAEEEVIIRSENITNNAKNILVQLNTPVQINCTRPSNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCWIKQIINMWQRIGQAMYAP
PIQGVIRCVSNITGLILTRDGGSTNSTTETFRPGGGDMRDNWRSELYKYKVVKIEPLGV
APTRCKRRTVGSHSGSGGSGSGGHAAAGIGASSDGFLGAAGSTMGAASMTLTVQAR

TABLE 1-continued immunogenic proteins

NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 153)

MD65_21mutJ_gp160-dCT_link14_congly
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPSNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCWIKQIINMWQRIGQAMYAP
PIQGVIRCVSNITGLILTRDGGSTNSTTETFRPGGGDMRDNWRSELYKYKVVKIEPLGV
APTRCKRRTVGSHSGSGGSGSGGHAAAGIGASSDGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALDKWASLWNWFDISNWLWYIKIFIMIVGGLIGLRIVFAVLSVIHRVR** (SEQ
ID NO: 154)

MD65_21mutJ_link14 (aka BG505_MD65_L14_21mutJ_m)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCPSVSTVQCTHGIKPVVSTQL
LLLNGSLAEEEVIIRSENITNNAKNILVQLNTPVQINCTRPSNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCWIKQIINMWQRIGQAMYAP
PIQGVIRCVSNITGLILTRDGGSTNSTTETFRPGGGDMRDNWRSELYKYKVVKIEPLGV
APTRCKRRTVGSHSGSGGSGSGGHAAAGIGASSDGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALD** (SEQ ID NO: 155)

MD65_21mutJ_link14_congly (aka BG505_MD65_L14_21mutJ_congly_m)
AENLWVTVYYGVPVWKDAETTLFCASDAKAYETEKHNVWATHACVPTDPNPQEIHL
ENVTEEFNMWKNNMVEQMHEDIISLWDQSLKPCVKLTPLCVTLQCTNYAPKLRSMM
RGEIKNCSFNMTTELRDKKQKVYSLFYRLDVVQINENQGNRSNNSNKEYRLINCNTS
AITQACPKVSFEPIPIHYCAPAGFAILKCKDKKFNGTGPCQNVSTVQCTHGIKPVVSTQ
LLLNGSLAEEEVIIRSENITNNAKNILVQLNTSVQINCTRPSNNTVKSIRIGPGQAFYYFG
DVLGHVRMAHCNISKATWNETLGKVVKQLRKHFGNNTIIRFAQSSGGDLEVTTHSFN
CGGEFFYCNTSGLFNSTWISNTSVQGSNSTGSNDSLILPCWIKQIINMWQRIGQAMYAP
PIQGVIRCVSNITGLILTRDGGSTNSTTETFRPGGGDMRDNWRSELYKYKVVKIEPLGV
APTRCKRRTVGSHSGSGGSGSGGHAAAGIGASSDGFLGAAGSTMGAASMTLTVQAR
NLLSGIVQQQSNLLRAPEPQQHLLKDTHWGIKQLQARVLAVEHYLRDQQLLGIWGCS
GKLICCTNVPWNSSWSNRNLSEIWDNMTWLQWDKEISNYTQIIYGLLEESQNQQEKN
EQDLLALD** (SEQ ID NO: 156)

SF162P3_MD64_B20.1
VEKLWVTVYYGVPAWKEATTTLFCASDAKAYDTEVHNVWATHECVPTDPNPQEIVL
ENVTENFNMWKNNMVEQMHEDIIELWDQSLEPCVKLTPLCVTLHCTNLENATNTTSS
NWKSMMRGEIKNCSFNVTTSIGNKMQKEYALFYRLDVVPIDNDNTSYNLINCNTSVIT
QACPKVSFEPIPIHYCAPAGFAILKCNDKKFNGSGPCINVSTVQCTHGIRPVVSTQLLLN
GSLAEEGVIIRSENFTDNVKTIIVQLKESVEINCTRPNNNTVKSIPIGPGKAFYYTGDIIG
DIRMAHCNISGEKWNNTLKQIVTKLQAQFENKTIVFKQSSGGDPEIVMHSFNCGGEFF
YCNSTQLFNSTWINTIGPNNTNGTITLPCRIKQIINRWQEVGKAMYAPPIRGQIRCSSNI
TGLLLTRDGGREVGNTTEIFRPGGGDMRDNWRSELYKYKVVKIEPLGVAPTKCKRRV
VQRRRRRRAVTLGAVSLGFLGAAGSTMGAASLTLTVQARQLLSGIVQQQNNLLRAPE
PQQRLLQLTVWGIKQLQARVLAVEHYLKDQQLLGIWGCSGKLICCTAVPWNASWSN
KSLDQIWNNMTWMEWEREIGNYTNLIYTLIEESQNQQEKNEQELLELD (SEQ ID NO:
157)

SF162P3_MD64_gp151_L14_B20.1
VEKLWVTVYYGVPAWKEATTTLFCASDAKAYDTEVHNVWATHECVPTDPNPQEIVL
ENVTENFNMWKNNMVEQMHEDIIELWDQSLEPCVKLTPLCVTLHCTNLENATNTTSS
NWKSMMRGEIKNCSFNVTTSIGNKMQKEYALFYRLDVVPIDNDNTSYNLINCNTSVIT
QACPKVSFEPIPIHYCAPAGFAILKCNDKKFNGSGPCINVSTVQCTHGIRPVVSTQLLLN
GSLAEEGVIIRSENFTDNVKTIIVQLKESVEINCTRPNNNTVKSIPIGPGKAFYYTGDIIG
DIRMAHCNISGEKWNNTLKQIVTKLQAQFENKTIVFKQSSGGDPEIVMHSFNCGGEFF
YCNSTQLFNSTWINTIGPNNTNGTITLPCRIKQIINRWQEVGKAMYAPPIRGQIRCSSNI
TGLLLTRDGGREVGNTTEIFRPGGGDMRDNWRSELYKYKVVKIEPLGVAPTKCKRRV
VQSHSGSGGSGSGGHAAVTLGAVSLGFLGAAGSTMGAASLTLTVQARQLLSGIVQQQ
NNLLRAPEPQQRLLQLTVWGIKQLQARVLAVEHYLKDQQLLGIWGCSGKLICCTAVP
WNASWSNKSLDQIWNNMTWMEWEREIGNYTNLIYTLIEESQNQQEKNEQELLELDK
WASLWNWFDISKWLWYIKIFIMIVGGLVGLRIVFTVLSIVNRVR** (SEQ ID NO: 158)

The protein may have at least 90% or 95% homology or identity with the sequence of the non-naturally occurring protein(s) of the invention.

The invention also encompasses trimers which may comprise any one of the non-naturally occurring protein(s) of the invention.

The proteins of the invention may comprise an additional cysteine and/or be fused to be a multimerization motif. The proteins of the invention may also comprise a tag for purification or biotinylation, such as a his tag or a avi-tag.

The invention also encompasses nucleic acids encoding the non-naturally occurring protein(s) of the present invention, including nucleic acids that may have at least 90% or 95% homology or identity with a nucleotide encoding the sequence of the non-naturally occurring protein(s) of the invention. In one embodiment, the nucleic acid may be a mRNA.

As used herein, at least three separate zoonotic transmissions resulted in the formation of three distinct HIV-1 groups: M (main), O (outlier), and N (non-M/non-O).

About 90% of HIV-1 infections are classified as group M and these are distributed worldwide. Group O infections are endemic to several west central African countries and represent 1 to 5% of all HIV-1 infection in those areas. Group N has only been identified in a small number of individuals in Cameroon.

Within the HIV-M group, there is a further division into at least ten subtypes or clades (groups of genetically related virus). Historically, the distribution of subtypes followed the geographic patterns listed below.

Clade or Subtype A: Central and East Africa as well as East European countries that were formerly part of the Soviet Union.

Clade or Subtype B: West and Central Europe, the Americas, Australia, South America, and several southeast Asian countries (Thailand, and Japan), as well as northern Africa and the Middle East.

Clade or Subtype C: Sub-Saharan Africa, India, and Brazil.

Clade or Subtype D: North Africa and the Middle East.

Clade or Subtype F: South and southeast Asia.

Clade or Subtype G: West and Central Africa.

Clade or Subtypes H, J, and K: Africa and the Middle East.

Additionally, different subtypes can combine genetic material to form a hybrid virus, known as a "circulating recombinant form" (CRFs), of which at least twenty have been identified (see, e.g., 2.Buonarguro L Human Immunodeficiency Virus Type 1 Subtype distribution in the worldwide epidemic: pathogenetic and therapeutic implications. J Virol 81 (19): 10209-19, 2007).

The present invention encompasses the stabilizing mutations, modifications, (such as, but not limited to, cleavage-independent modifications), and/or a membrane anchoring strategy (such as, but not limited to, linker plus platelet-derived growth factor receptor (PDGFR)) described herein to all groups and clades of HIV.

Types I and II are gp120 molecules (I) and gp140 trimer molecules (II) with mutations discovered to improve binding to germline-reverted and/or less-mutated versions of PGT121. The sequences in I and II can be employed in sequential immunization schemes to attempt to elicit PGT121-class bnAbs against HIV.

Type III are gp140 trimer molecules with stabilizing mutations to increase expression level and/or increase thermal melting temperature and/or improve antigenic profile, where a favorable antigenic profile means better affinity for broadly neutralizing antibodies and no or very weak affinity for non-neutralizing antibodies.

Type IV are combinations of mutations from II and III: these are gp140 trimers that contain both stabilizing mutations and germline-targeting mutations. In type IV Applicants have listed only a few important combinations, but the present invention encompasses all possible combinations of the mutations from II and III.

Type V are trimers with modified surfaces or of different strains than BG505, that can be employed in strategic boosting regimens.

Type VI are additional trimer modifications that add extra functionality and that can be combined with types II, III, IV or V.

Type VII are examples of native-like trimers from other HIV strains that have been stabilized by MD39 and Olio6 mutations, demonstrating the general applicability of the MD39 and Olio6 stabilizing mutations.

Type VIII are variants of BG505 MD39 that do not require cleavage by furin.

Applicants refer to these as "cleavage-independent" trimers.

Type IX are glycan masked trimers in which N-linked glycosylation sites have been added to cover the bottom and sides of the soluble trimer.

Type X are native-like trimers with variable loops V1, V2b and V4 modified to both minimize their lengths and maximize the number of glycosylation sites contained within them.

Type XI are BG505 MD39-based, single-component, self-assembling nanoparticles.

Type XII are BG505 MD39-based, membrane-bound native like trimers.

In one embodiment, the nucleic acids of the present invention may be delivered as a therapeutic mRNA.

Provided herein are isolated nucleic acids (e.g., modified mRNAs encoding a peptide described herein) which may comprise a translatable region and at least two different nucleoside modifications, wherein the nucleic acid exhibits reduced degradation in a cell into which the nucleic acid is introduced, relative to a corresponding unmodified nucleic acid. For example, the degradation rate of the nucleic acid is reduced by at least 10%, 20%, 30%, 40%, 50%, 60%, 70%, 80%, or 90%, compared to the degradation rate of the corresponding unmodified nucleic acid. In certain embodiments, the nucleic acid may comprise RNA, DNA, TNA, GNA, or a hybrid thereof. In certain embodiments, the nucleic acid comprises messenger RNA (mRNA). In certain embodiments, the mRNA does not substantially induce an innate immune response of the cell into which the mRNA is introduced. In certain embodiments, the mRNA may comprise at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxypseudouridine, and 4-methoxy-2-thio-pseudouridine. In certain embodiments, the mRNA may comprise at least one nucleoside selected from the group consisting of 5-aza-cytidine, pseudoisocytidine, 3-methyl-cytidine, N4-acetyl-cytidine, 5-formylcytidine, N4-methylcytidine, 5-hy-droxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocyti-dine, and 4-methoxy-1-methyl-pseudoisocytidine. In other embodiments, the mRNA may comprise at least one nucleo-side selected from the group consisting of 2-aminopurine, 2,6-diaminopurine, 7-deaza-adenine, 7-deaza-8-aza-ad-enine, 7-deaza-2-aminopurine, 7-deaza-8-aza-2-aminopu-rine, 7-deaza-2,6-diaminopurine, 7-deaza-8-aza-2,6-di-aminopurine, 1-methyladenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonyl-carbamoyladenosine, 2-methylthio-N6-threonyl carbamoy-ladenosine, N6,N6-dimethyladenosine, 7-methyladenine, 2-methylthio-adenine, and 2-methoxy-adenine. In yet other embodiments, the mRNA may comprise at least one nucleo-side selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleic acids provided herein comprise a 5' untranslated region (UTR) and/or a 3'UTR, wherein each of the two different nucleoside modifications are independently present in the 5'UTR and/or 3'UTR. In some embodiments, nucleic acids are provided herein, wherein at least one of the two different nucleoside modi-fications are present in the translatable region. In some embodiments, nucleic acids provided herein are capable of binding to at least one polypeptide that prevents or reduces an innate immune response of a cell into which the nucleic acid is introduced.

Further provided herein are isolated nucleic acids (e.g., modified mRNAs described herein) which may comprise (i) a translatable region encoding a peptide described herein, (ii) at least one nucleoside modification, and (iii) at least one intronic nucleotide sequence capable of being excised from the nucleic acid.

Further provided herein are isolated nucleic acids (e.g., modified mRNAs described herein) which may comprise (i) a translatable region encoding a peptide described herein, (ii) at least two different nucleoside modifications, and (iii) a degradation domain.

Further provided herein are non-enzymatically synthe-sized nucleic acids (e.g., modified mRNAs described herein) which may comprise at least one nucleoside modification, and which may comprise a translatable region encoding a peptide described herein. In certain embodiments, the non-enzymatically synthesized mRNA may comprise at least two different nucleoside modifications.

Further provided herein are isolated nucleic acids (e.g., modified mRNAs described herein) which may comprise a noncoding region and at least one nucleoside modification that reduces an innate immune response of a cell into which the nucleic acid is introduced, wherein the nucleic acid sequesters one or more translational machinery components. In certain embodiments, the isolated nucleic acids which may comprise a noncoding region and at least one nucleo-side modification described herein are provided in an amount effective to reduce protein expression in the cell. In certain embodiments, the translational machinery compo-nent is a ribosomal protein or a transfer RNA (tRNA). In certain embodiments, the nucleic acid may comprise a small nucleolar RNA (sno-RNA), microRNA (miRNA), small interfering RNA (siRNA) or Piwi-interacting RNA (piRNA).

Further provided herein are isolated nucleic acids (e.g., modified mRNAs described herein) which may comprise (i) a first translatable region, (ii) at least one nucleoside modi-fication, and (iii) an internal ribosome entry site (IRES). In certain embodiments, the IRES is obtained from a picorna-virus, a pest virus, a polio virus, an encephalomyocarditis virus, a foot-and-mouth disease virus, a hepatitis C virus, a classical swine fever virus, a murine leukemia virus, a simian immune deficiency virus or a cricket paralysis virus. In certain embodiments, the isolated nucleic acid further may comprise a second translatable region. In certain embodiments, the isolated nucleic acid further may com-prise a Kozak sequence. In some embodiments, the first translatable region encodes a peptide described herein. In some embodiments, the second translatable region encodes peptide described herein. In some embodiments, the first and the second translatable regions encode peptides described herein.

Provided herein are pharmaceutical compositions which may comprise: (i) an effective amount of a synthetic mes-senger ribonucleic acid (mRNA) encoding peptide described herein; and (ii) a pharmaceutically acceptable carrier, wherein i) the mRNA may comprise pseudouridine, 5'methyl-cytidine, or a combination thereof, or ii) the mRNA does not comprise a substantial amount of a nucleo-tide or nucleotides selected from the group consisting of uridine, cytidine, and a combination of uridine and cytidine, and wherein the composition is suitable for repeated admin-istration (e.g., intravenous administration) to a mammalian subject in need thereof. In some embodiments, Further provided herein are pharmaceutical compositions which may comprise and/or consisting essentially of: (i) an effective amount of a synthetic messenger ribonucleic acid (mRNA) encoding peptide described herein; (ii) a cell penetration agent; and (iii) a pharmaceutically acceptable carrier, wherein i) the mRNA may comprise pseudouridine, 5'methyl-cytidine or a combination thereof, or ii) the mRNA does not comprise a substantial amount of a nucleotide or nucleotides selected from the group consisting of uridine, cytidine, and a combination of uridine and cytidine, and wherein the composition is suitable for repeated adminis-tration (e.g., intravenous administration) to an animal (e.g., mammalian) subject in need thereof.

This invention provides nucleic acids, including RNAs such as mRNAs that contain one or more modified nucleo-sides (termed "modified nucleic acids"), which have useful properties including the lack of a substantial induction of the innate immune response of a cell into which the mRNA is introduced. Because these modified nucleic acids enhance the efficiency of protein production, intracellular retention of nucleic acids, and viability of contacted cells, as well as possess reduced immunogenicity, these nucleic acids having these properties are termed "enhanced nucleic acids" herein.

The term "nucleic acid," in its broadest sense, includes any compound and/or substance that is or can be incorporated into an oligonucleotide chain. Exemplary nucleic acids for use in accordance with the present invention include, but are not limited to, one or more of DNA, RNA, hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

Provided are modified nucleic acids containing a translatable region encoding a peptide described herein, and one, two, or more than two different nucleoside modifications. In some embodiments, the modified nucleic acid exhibits reduced degradation in a cell into which the nucleic acid is introduced, relative to a corresponding unmodified nucleic acid. For example, the degradation rate of the nucleic acid is reduced by at least 10%, 20%, 30%, 40%, 50%, 60%, 70%, 80%, or 90%, compared to the degradation rate of the corresponding unmodified nucleic acid. Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or a hybrid thereof. In preferred embodiments, the modified nucleic acid includes messenger RNAs (mRNAs). As described herein, the nucleic acids of the invention do not substantially induce an innate immune response of a cell into which the mRNA is introduced.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyluridine, 1-carboxymethyl-pseudouridine, 5-propynyluridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In certain embodiments it is desirable to intracellularly degrade a modified nucleic acid introduced into the cell, for example if precise timing of protein production is desired. Thus, the invention provides a modified nucleic acid containing a degradation domain, which is capable of being acted on in a directed manner within a cell.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 1-methyl-6-thio-guanosine, N2-methyl-6-thio-guanosine, and N2,N2-dimethyl-6-thio-guanosine.

Other components of nucleic acid are optional, and are beneficial in some embodiments. For example, a 5' untranslated region (UTR) and/or a 3'UTR are provided, wherein either or both may independently contain one or more different nucleoside modifications. In such embodiments, nucleoside modifications may also be present in the translatable region. Also provided are nucleic acids containing a Kozak sequence.

Further, nucleic acids encoding a peptide described herein, and containing an internal ribosome entry site (IRES) are provided herein. An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When nucleic acids are provided with an IRES, further optionally provided is a second translatable region. Examples of IRES sequences that can be used according to the invention include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

The therapeutic mRNAs as described, for example, in U.S. Pat. Nos. 9,464,124; 9,447,164; 9,428,535; 9,334,328; 9,303,079; 9,301,993; 9,295,689; 9,283,287; 9,271,996; 9,255,129; 9,254,311; 9,233,141; 9,221,891; 9,220,792; 9,220,755; 9,216,205; 9,192,651; 9,186,372; 9,181,319; 9,149,506; 9,114,113; 9,107,886; 9,095,552; 9,089,604; 9,061,059; 9,050,297; 8,999,380; 8,980,864; 8,822,663; 8,754,062; 8,710,200; 8,680,069 and 8,664,194 may be utilized for the present invention.

Methods for the chemical conjugation of polypeptides, carbohydrates, and/or lipids are well known in the art (see, for example, Hermanson. Bioconjugate Techniques (Academic Press; 1992); Aslam and Dent, eds. Bioconjugation: Protein coupling Techniques for the Biomedical Sciences (MacMillan: 1998); and Wong Chemistry of Protein Conjugation and Cross-linking (CRC Press: 1991)). For instance, primary amino groups may be incorporated by reaction with ethylenediamine in the presence of sodium cyanoborohydride and sulfhydryls may be introduced by reaction of cysteamin dihydrochloride followed by reduction with a standard disulfide reducing agent. Heterobifunctional crosslinkers, such as, for example, sulfosuccinimidyl (4-iodoacetyl) aminobenzoate, which link the epsilon amino group on the D-lysine residues of copolymers of D-lysine and D-glutamate to a sulfhydryl side chain from an amino terminal cysteine residue on the peptide to be coupled, may be used as well. Chemical conjugation also includes anything covalently bonded directly via side chain bonds or via a linker or spacer group.

The nanoparticle formulations may be a carbohydrate nanoparticle which may comprise a carbohydrate carrier and a modified nucleic acid molecule (e.g., mmRNA). As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; herein incorporated by reference in its entirety).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

The average diameter of the nanoparticle employed in the compositions of the invention can be at least one member selected from the group consisting of about 20 nanometers, about 25 nanometers, about 30 nanometers, about 40 nanometers, about 50 nanometers, about 75 nanometers, about 100 nanometers, about 125 nanometers, about 150 nanometers, about 175 nanometers and about 200 nanometers. In another embodiment, the average diameter of the particle is at least one member selected from the group consisting of between about 10 to about 200 nanometers, between about 0.5 to about 5 microns and between about 5 to about 10 microns. In another embodiment, the average diameter of the microparticle is selected from the group consisting of about 0.1 μm, about 0.2 μm, about 0.4 μm, about 0.5 μm, about 1 μm and about 2 μm.

Nanoparticles for use in the compositions of the invention can be made from lipids or other fatty acids (see, for example, U.S. Pat. Nos. 5,709,879; 6,342,226; 6,090,406; Lian, et al., J. of Pharma. Sci. 90:667-680 (2001) and van Slooten, et al., Pharm Res. 17:42-48 (2000)) and non-lipid compositions (see, for example, Kreuter, J. Anat. 189:503-505 (1996), the teachings of all of which are hereby incorporated by reference in their entirety). The compositions can be bilayer or multilamellar liposomes and phospholipid based. Polymerized nanoparticles, as described, for example, in U.S. Pat. No. 7,285,289, the teachings of which are incorporated by reference in their entirety.

Metallic oxide nanoparticles for use in the compositions of the invention can be chemically substituted with at least one reactive moiety capable of forming a thioether bond employing conventionally techniques as described herein and in U.S. Pat. No. 6,086,881, the teachings of which are hereby incorporated by reference in their entirety. The antigen described herein can be coupled in a single step onto the metallic oxide particles by the formation of at least one thioether bond or it may be synthesized or assembled stepwise onto the metallic oxide particles after the initial thioether bond formation. The chemical derivatization reagents for the metallic oxide particles can include organosilane reagents that provide thioalkane functionality or other groups that may readily be converted into thiols or thiol-reactive moieties. Organosilane reagents which may be utilized for this purpose may be, but are not limited to, 3-mercaptopropyltrimethoxysilane, 3-aminopropyltriethoxysilane, 3-iodopropyltrimethoxysilane, 2-chloroethyltrichlorosilane, 3-glycidoxypropyltrimethoxysilane, vinyltrichlorosilane and 3-acryloxypropyltrimethoxysilane. Moieties that include one or more disulfide components may also be joined to the metallic oxide particle surface and thereby provide the corresponding reactive moiety able to enter into and form a thioether bond and juncture. Exemplary nanoparticles for use in the compositions of the invention include at least one member selected from the group consisting of poly (D,L-lactide-co-glycolide, also referred to as "poly(lactic-co-glycolic acid) and bisacyloxypropylcysteine.

Nanoparticles for use in the compositions of the invention can be made of inorganic material. Nanoparticles for use in the compositions of the invention can be made of a polymer material, such as at least one member selected from the group consisting of polystyrene, brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, a carbohydrate, carboxymethyl cellulose, hydroxyethyl cellulose, agar, gel, proteinaceous polymer, polypeptide, eukaryotic and prokaryotic cells, viruses, lipid, metal, resin, latex, rubber, silicone (e.g., polydimethyldiphenyl siloxane), glass, ceramic, charcoal, kaolinite and bentonite.

It is noted that these therapeutics may be a chemical compound, a composition which may comprise a polypeptide of the present invention and/or antibody elicited by such a chemical compound and/or portion thereof or a pharmaceutically acceptable salt or a composition which may comprise a polypeptide of the invention, and may be administered alone or as an active ingredient in combination with pharmaceutically acceptable carriers, diluents, and vehicles, as well as other active ingredients.

The compounds or compositions may be administered orally, subcutaneously or parenterally including intravenous, intraarterial, intramuscular, intraperitoneally, and intranasal administration as well as intrathecal and infusion techniques.

It is noted that humans are treated generally longer than the mice or other experimental animals which treatment has a length proportional to the length of the disease process and drug effectiveness. The doses may be single doses or multiple doses over a period of several days, but single doses are preferred. Thus, one may scale up from animal experiments, e.g., rats, mice, and the like, to humans, by techniques from this disclosure and documents cited herein and the knowledge in the art, without undue experimentation.

In a particularly advantageous embodiment, the mRNAs of the present invention are administered in combinations of a prime dose followed by one or more boost doses over time. mRNA doses of about 100 μg are advantageous, however, dosages of about 10 μg to about 1000 μg, about 20 μg to about 900 µg, about 30 µg to about 800 µg, about 40 µg to about 700 µg, about 50 µg to about 600 µg, about 60 µg to about 500 µg, about about 70 µg to about 400 µg, about 80 µg to about 300 µg, or about 900 µg to about 200 µg, are contemplated. Varying combinations are presented below as non-limiting examples.

The treatment generally has a length proportional to the length of the disease process and drug effectiveness and the patient being treated.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier may be a solvent or dispersing medium containing, for example, water, ethanol, polyol (for example, glycerol, propylene glycol, liquid polyethylene glycol, and the like), suitable mixtures thereof, and vegetable oils.

Proper fluidity may be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, may be added. Prevention of the action of microorganisms may be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form may be brought about by the use of agents delaying absorption, for example, aluminum monostearate and gelatin. According to the present invention, however, any vehicle, diluent, or additive used would have to be compatible with the compounds.

Sterile injectable solutions may be prepared by incorporating the compounds utilized in practicing the present invention in the required amount of the appropriate solvent with various amounts of the other ingredients, as desired.

A pharmacological formulation of the present invention, e.g., which may comprise a therapeutic compound or polypeptide of the present invention, may be administered to the patient in an injectable formulation containing any compatible carrier, such as various vehicles, adjuvants, additives, and diluents; or the compounds utilized in the present invention may be administered parenterally to the patient in the form of slow-release subcutaneous implants or targeted delivery systems such as monoclonal antibodies, iontophoretic, polymer matrices, liposomes, and microspheres.

A pharmacological formulation of the compound and composition which may comprise a polypeptide utilized in the present invention may be administered orally to the patient. Conventional methods such as administering the compounds in tablets, suspensions, solutions, emulsions, capsules, powders, syrups and the like are usable. Known techniques, which deliver the compound orally or intravenously and retain the biological activity, are preferred.

In one embodiment, a formulation of the present invention may be administered initially, and thereafter maintained by further administration. For instance, a formulation of the invention may be administered in one type of composition and thereafter further administered in a different or the same type of composition. For example, a formulation of the invention may be administered by intravenous injection to bring blood levels to a suitable level. The patient's levels are then maintained by an oral dosage form, although other forms of administration, dependent upon the patient's condition, may be used. In the instance of a vaccine composition, the vaccine may be administered as a single dose, or the vaccine may incorporate set booster doses. For example, booster doses may comprise variants in order to provide protection against multiple clades of HIV.

The quantity to be administered will vary for the patient being treated and whether the administration is for treatment or prevention and will vary from a few micrograms to a few milligrams for an average 70 kg patient, e.g., 5 micrograms to 5 milligrams such as 500 micrograms, or about 100 ng/kg of body weight to 100 mg/kg of body weight per administration and preferably will be from 10 µg/kg to 10 mg/kg per administration. Typically, however, the antigen is present in an amount on, the order of micrograms to milligrams, or, about 0.001 to about 20 wt %, preferably about 0.01 to about 10 wt %, and most preferably about 0.05 to about 5 wt %.

Of course, for any composition to be administered to an animal or human, including the components thereof, and for any particular method of administration, it is preferred to determine therefor: toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable immunological response, such as by titrations of sera and analysis thereof for antibodies or antigens, e.g., by ELISA and/or RFFIT analysis. Such determinations do not require undue experimentation from the knowledge of the skilled artisan, this disclosure and the documents cited herein. And, the time for sequential administrations may be ascertained without undue experimentation. For instance, dosages may be readily ascertained by those skilled in the art from this disclosure and the knowledge in the art. Thus, the skilled artisan may readily determine the amount of compound and optional additives, vehicles, and/or carrier in compositions and to be administered in methods of the invention. Typically, an adjuvant or additive is commonly used as 0.001 to 50 wt % solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Such determinations do not require undue experimentation from the knowledge of the skilled artisan, this disclosure and the documents cited herein. And, the time for sequential administrations may be ascertained without undue experimentation.

Examples of compositions which may comprise a therapeutic of the invention include liquid preparations for orifice, e.g., oral, nasal, anal, vaginal, peroral, intragastric, mucosal (e.g., perlingual, alveolar, gingival, olfactory or respiratory mucosa) etc., administration such as suspensions, syrups or elixirs; and, preparations for parenteral, subcutaneous, intradermal, intramuscular or intravenous administration (e.g., injectable administration), such as sterile suspensions or emulsions. Such compositions may be in admixture with a suitable carrier, diluent, or excipient such as sterile water, physiological saline, glucose or the like. The compositions may also be lyophilized. The compositions may contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Compositions of the invention, are conveniently provided as liquid preparations, e.g., isotonic aqueous solutions, suspensions, emulsions or viscous compositions which may be buffered to a selected pH. If digestive tract absorption is preferred, compositions of the invention may be in the "solid" form of pills, tablets, capsules, caplets and the like, including "solid" preparations which are time-released or which have a liquid filling, e.g., gelatin covered liquid, whereby the gelatin is dissolved in the stomach for delivery to the gut. If nasal or respiratory (mucosal) administration is desired, compositions may be in a form and dispensed by a squeeze spray dispenser, pump dispenser or aerosol dispenser. Aerosols are usually under pressure by means of a hydrocarbon. Pump dispensers may preferably dispense a metered dose or, a dose having a particular particle size.

Compositions of the invention may contain pharmaceutically acceptable flavors and/or colors for rendering them more appealing, especially if they are administered orally. The viscous compositions may be in the form of gels, lotions, ointments, creams and the like (e.g., for transdermal administration) and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions may approach solid or gelatin forms, which are then easily administered as a swallowed pill for oral ingestion.

Liquid preparations are normally easier to prepare than gels, other viscous compositions, and solid compositions. Additionally, liquid compositions are somewhat more convenient to administer, especially by injection or orally. Viscous compositions, on the other hand, may be formulated within the appropriate viscosity range to provide longer contact periods with mucosa, such as the lining of the stomach or nasal mucosa.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the active compound. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions may be isotonic, i.e., it may have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount that will achieve the selected viscosity. Viscous compositions are normally prepared from solutions by the addition of such thickening agents.

A pharmaceutically acceptable preservative may be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems may be readily avoided by reference to standard texts or by simple experiments (not involving undue experimentation), from this disclosure and the documents cited herein.

It is generally envisaged that compounds and compositions of the invention will be administered by injection, as such compounds are to elicit anti-HIV antibodies, and the skilled artisan may, from this disclosure and the knowledge in the art, formulate compounds and compositions identified by herein methods for administration by injection and administer such compounds and compositions by injection.

The inventive compositions of this invention are prepared by mixing the ingredients following generally accepted procedures. For example the selected components may be simply mixed in a blender, or other standard device to produce a concentrated mixture which may then be adjusted to the final concentration and viscosity by the addition of water or thickening agent and possibly a buffer to control pH or an additional solute to control tonicity. Generally the pH may be from about 3 to 7.5. Compositions may be administered in dosages and by techniques well known to those skilled in the medical arts taking into consideration such factors as the age, sex, weight, and condition of the particular patient, and the composition form used for administration (e.g., solid vs. liquid). Dosages for humans or other mammals may be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Figure 24:
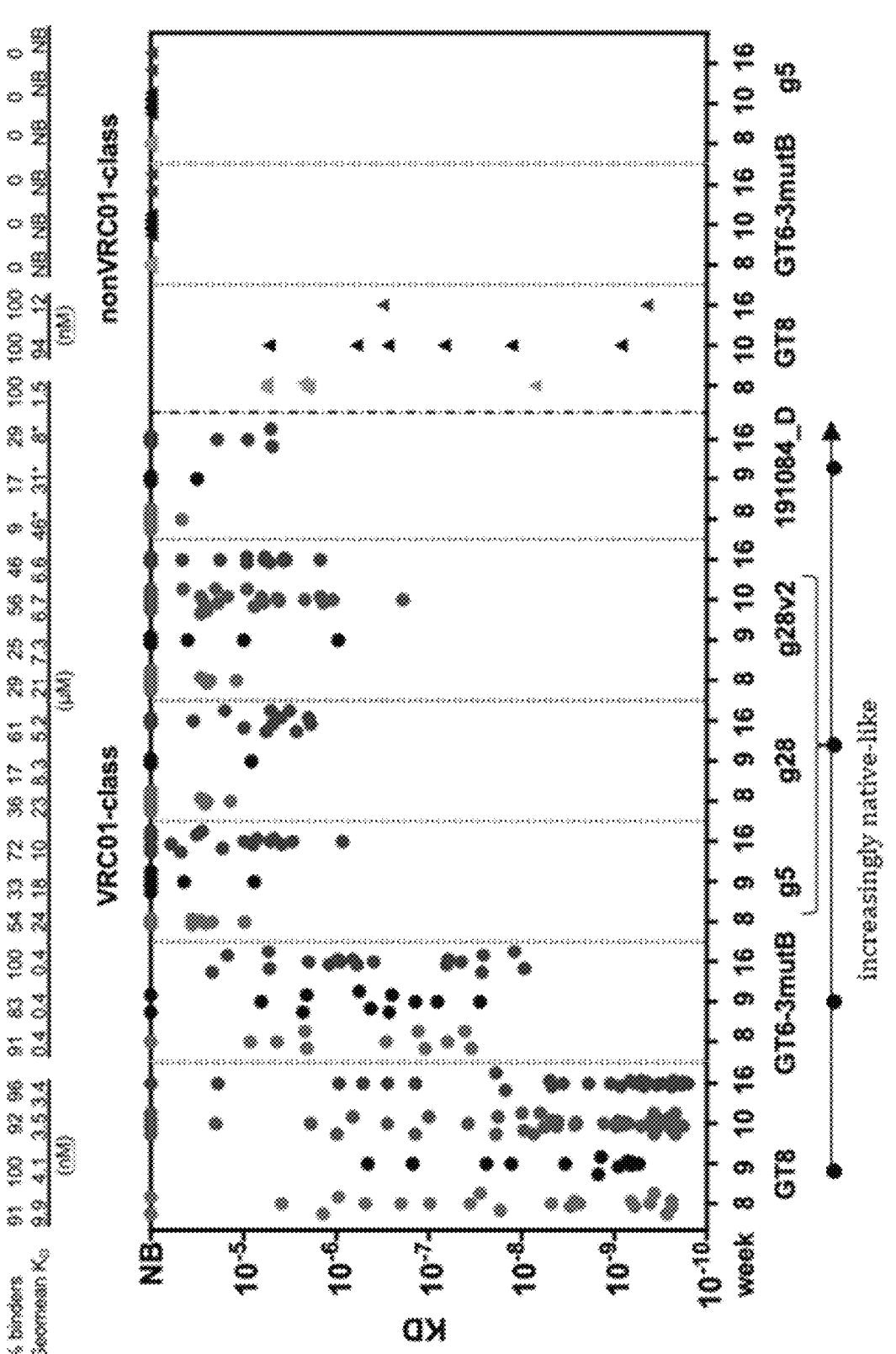
FIG. 24 shows boost candidates that bind G001 vaccine-induced VRC01-class mAbs and do not bind vaccine-induced non-VRC01-class mAbs. In human clinical trial G001, two shots of eOD-GT8 60mer were given at week 0 and week 8. Epitope specific IgG+ B cells were collected at week 8, 9, 10 and 16. Selected isolated B cell receptors (both VRC01-class and non-VRC01 class) were expressed as IgGs and binding to different boost candidates (eOD-GT8, eOD-GT6-3mutB, core-g5, core-g28, core-g28v2, 191084_D trimer) was measured by SPR. The Kps for each antigen were determined by capturing IgG on the SPR Chip and flowing antigens as analyte. For 191084_D trimer, avidity is in play, so the Kps do not reflect a monovalent interaction. NB means no binding at the top concentration of 50 μM. GT6-3mutB and core variants show weaker binding to VRC01 antibodies and show no binding to non-VRC01 antibodies.
Figure 25:
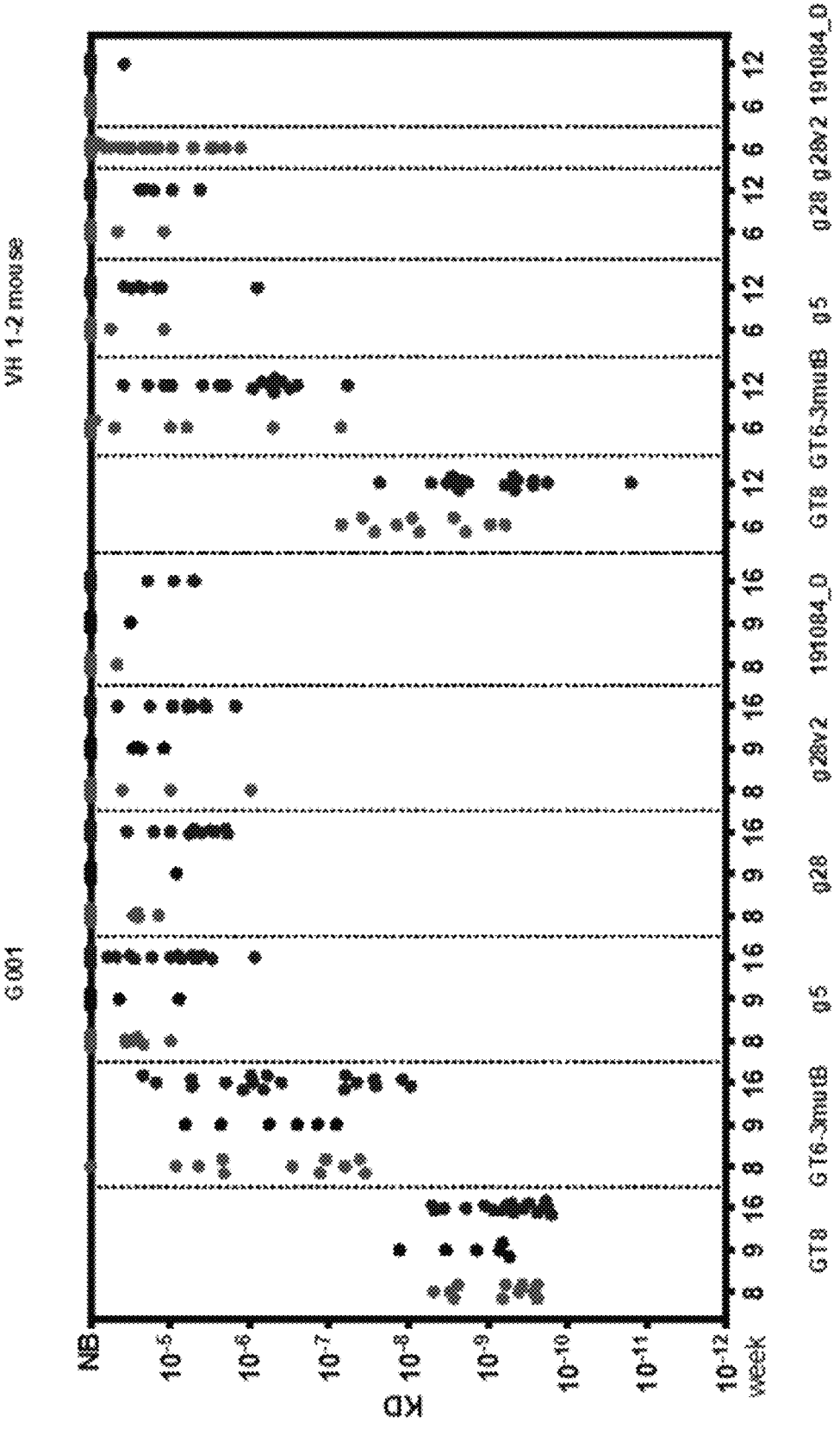
FIG. 25 shows evidence that the Alt VH1-2 mouse has strong relevance for testing boost candidates: Affinities of GT8-induced antibodies from the VH1-2 mouse are similar to those from G001. In human clinical trial G001, two shots of eOD-GT8 60mer were given at week 0 and week 8. Epitope specific IgG+ B cells were collected at week 8, 9, 10 and 16. In separate VH1-2 mouse immunization experiments, a single immunization of eOD-GT8 60mer was given at day 0, and epitope-specific B cells were sorted and sequenced at day 42 (week 6). Alternately, in the VH1-2 mouse, a single immunization of eOD-GT8 60mer was given at day 0, a placebo+adjuvant immunization was given at day 42, and epitope-specific B cells were sorted and sequenced at day 84 (week 12). The isolated B cell receptors were expressed as IgGs, and binding to different boost candidates (eOD-GT8, eOD-GT6-3mutB, core-g5, core-g28, core-g28v2,191084_D trimer) was measured by SPR. The Kps for each antigen were determined by capturing IgG on the SPR Chip and flowing antigens as analyte. For 191084_D trimer, avidity is in play, so the Kps do not reflect a monovalent interaction. NB means no binding at the top concentration of 50 µM. The binding affinities of boost candidates to GT8-induced antibodies appears similar using GT8-induced antibodies from humans (G001) and from the VH1-2 mouse. This suggests that the VH1-2 mouse may be an appropriate model system to test boost candidate immunization after GT8 priming and downselect boost candidates for human clinical testing. * avidity allowed for 191084 D data
Figure 26:
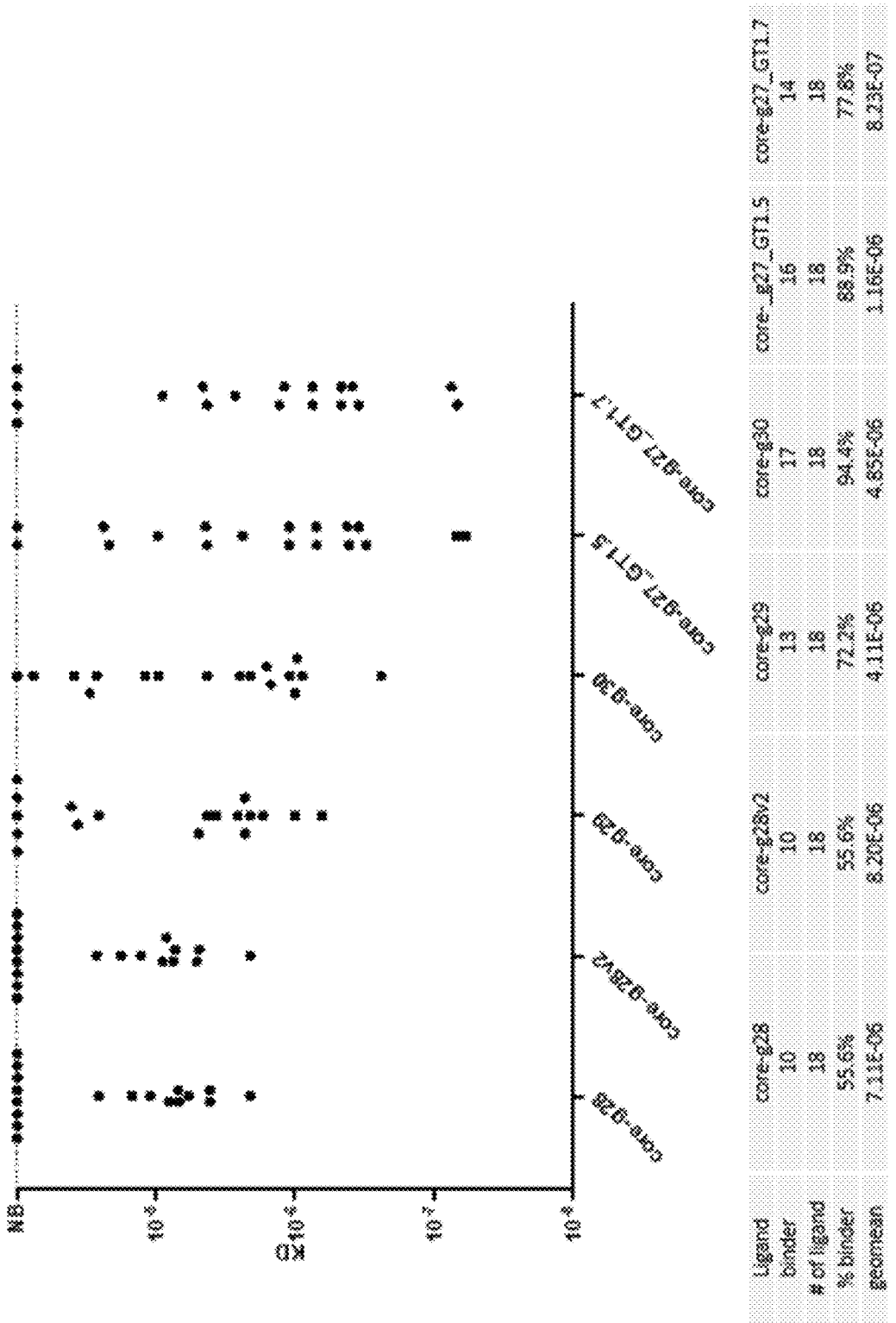
FIG. 26 shows SPR data for potential boost candidates. In human clinical trial G001, two shots of eOD-GT8 60mer were given at week 0 and week 8. Epitope specific IgG+ B cells were collected at different time points. The antibodies tested here are from the low dose group at week 16. The isolated B cell receptors were expressed as IgGs and binding to different boost candidates was measured by SPR. The Kps for each antigen were determined by capturing IgG on the SPR Chip and flowing antigens as analyte. NB means no binding at the top concentration of 50 µM.
Figure 28:
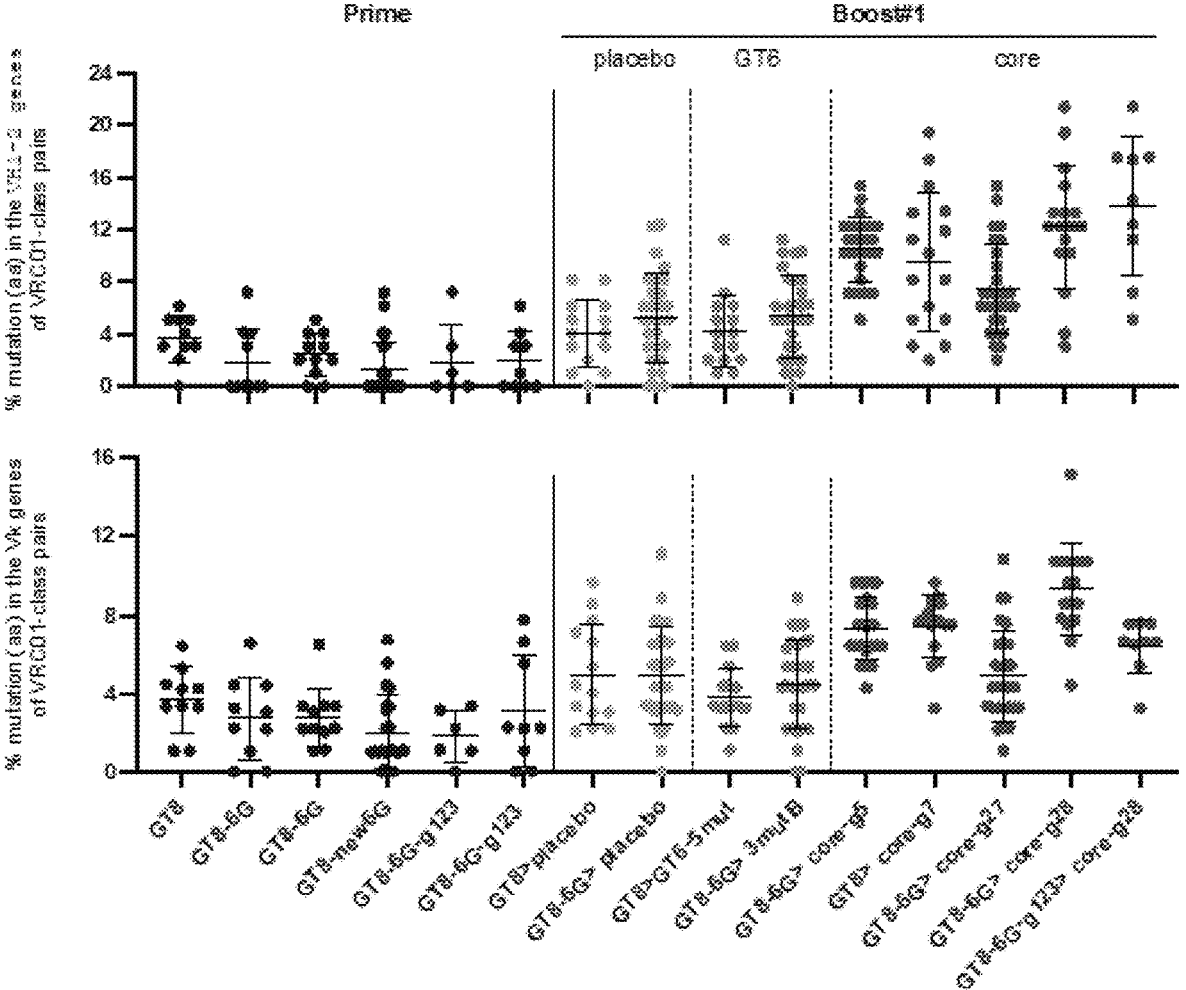
FIG. 28 shows a graphical display of % mutation data after priming or boosting in the VH1-2 mouse model. The data in this figure are from the same experiments as described in FIG. 6. Groups of VH1-2 mice were immunized with the indicated prime-boost regimen, and their B cells sorted and analyzed, as in FIG. 6. Sequences of isolated VRC01-class B cell receptors were analyzed for the % mutation in the VH gene (upper graph) and Vkappa gene (lower graph). GT8 60mer and its hyperglycosylated variants elicited similar low levels of mutation. Placebo and GT6 boost groups produced slightly higher mutation levels compared to priming alone. Mouse groups boosted with core-g5, core-g7, or core-g28 all showed evidence of increased maturation beyond the level achieved by the placebo boost or GT6 boost.
Figure 29:
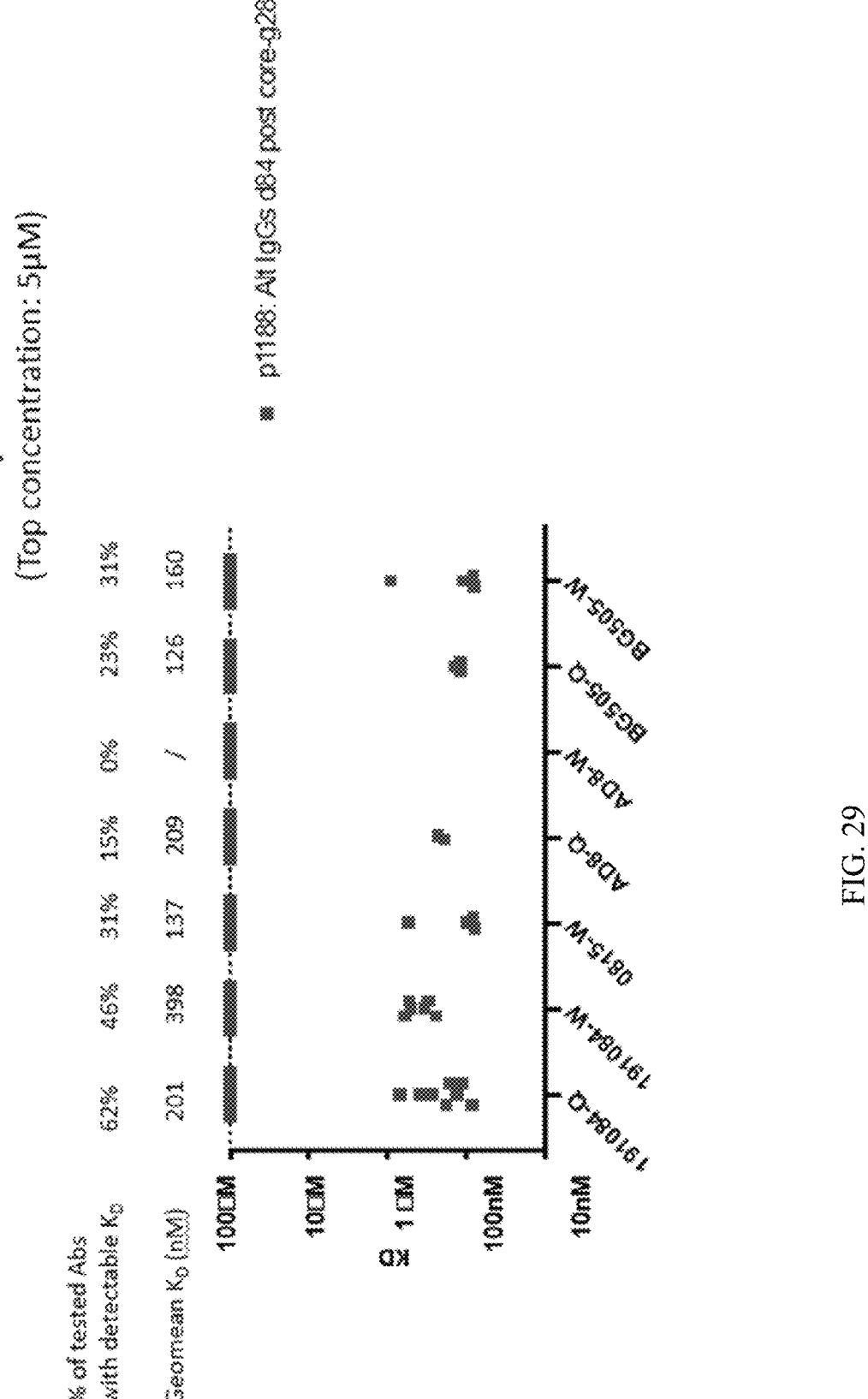
FIG. 29 shows binding affinities of candidate boost #2 immunogens for partially mature VRC01-class antibodies induced by immunization with adjuvanted eOD-GT8 60mer followed by core-g28 60mer in the VH1-2 mouse model. Antibodies were recovered from memory or GC B cells at 42 days after core-g28 60mer boosting (84 days after GT8 priming). Apparent affinities, expressed as dissociation constants (KD), were measured using a Biacore 8 k instrument. IgGs were captured onto CM3 sensor chips (GE Healthcare) using the human antibody capture kit (GE Healthcare), and serial dilutions of the indicated trimeric immunogens were passed over the surface. Data were analyzed using the Biacore Insight Evaluation software (GE Healthcare), and data were plotted in Prism (Graphpad). Each candidate boost #2 immunogen was tested for binding to the same set of antibodies. The percent of antibodies with detectable affinity, and the geomean apparent affinity among binders, are listed at the top of the graph. Candidate boost #2 immunogens do have appreciable affinity/avidity for core-g28 60mer-induced B cells, indicating their potential to bind and activate core-g28 60mer-induced memory B cells and induce further maturation of VRC01-class responses, if delivered as a boost after core-g28 60mer.

Measurement of binding affinities of eOD-GT8 or candidate boost immunogens. Binding affinities of eOD-GT8 or candidate boost immunogens for partially mature VRC01-class antibodies were measured by inducing a response by vaccination with adjuvanted eOD-GT8 60mer either in a human clinical trial (G001) or in a mouse model (VH1-2 mouse). Antibodies were recovered from memory B cells at the number of weeks after eOD-GT8 60mer immunization indicated on the x-axis of FIG. 1. Similar data is presented in FIGS. 24 and 25. Affinities, expressed as dissociation constants (KD), were measured using a Biacore 8 k instrument. IgGs were captured onto CM3 sensor chips (GE Healthcare) using the human antibody capture kit (GE Healthcare), and serial dilutions of the indicated monomeric immunogens were passed over the surface. Data were analyzed using the Biacore Insight Evaluation software (GE Healthcare), and data were plotted in Prism (Graphpad). Each analyte listed on the x-axis of FIG. 1 was tested for binding to the same set of antibodies. For each analyte, the percent of antibodies with detectable affinity, and the geomean affinity among binders, are listed at the top of the graph.

Biacore Insight Evaluation software (GE Healthcare) and data were plotted in Prism (Graphpad) and shown in FIG. 2. The data show that (i) both core-g5 and core-g28 have substantial affinity for mature and partially mature VRC01-class antibodies; (ii) the CD4KO mutation generally does not alter those affinities but does eliminate detectable CD4 binding; (iii) the N276Q mutation generally reduces affinity for immature VRC01-class antibodies but does not alter affinity for mature bnAbs; and (iv) the presence of N276 eliminates detectable affinity for the partially mature VRC01-class antibodies but does not alter affinity for mature bnAbs. Abbreviations: GT8, eOD-GT8; GT6-3mutB, eOD-GT6-3mutB-cRSF01; core-g5, core-Hx_r4.0_g5; core-g28, core-Hx_r4.0D_TH6_g28.

Measurement of biophysical properties of boost immunogen 60mer nanoparticles. To measure the biophysical properties of the boost immunogen 60mer nanoparticles, core-gp120 antigens were fused to Lumazine Synthase via a linker. DNA was transfected into FreeStyle 293 F cells and proteins were expressed at 37° C. for four days. Nanoparticles were purified using lectin beads followed by gel-filtration using a Superose 6 size-exclusion chromatography column (GE HealthCare). The results are shown in the Table below.

TABLE 2

| 60mer nanoparticle | EM for 60mer | NP fraction based on SEC after lectin | Yield after Lectin + SEC (mg/L) | Avg yield (mg/L) |
|---|---|---|---|---|
| core-Hx_r4.0D_TH6_g7_60mer | good | >75% | 2/4.4/2.8/2.6 | 2.95 |
| core-Hx_r4.0D_TH6_g28_60mer | good | 50%/70%/50% | 1.2/4.2/3.2 | 2.8 |
| core-Hx_r4.0_g5_60mer_m | good | 75% | 2/2.6/5.8 | 3.5 |
| core-Hx_r4.0_g15_d41m3_60mer | good | 60% | 4 | NA |
| core-4g7D_TH6_3mutB_60mer_m | good | 60% | 1.6/0.3/1.4 | 1.1 |

The fact that candidate boost immunogens do have appreciable affinity for eOD-GT8 60mer-induced B cells indicates that these immunogens have potential to bind and activate eOD-GT8 60mer-induced memory B cells and induce further maturation of VRC01-class responses, if delivered as a boost after eOD-GT8 60mer. The correspondence in affinities between humans (G001) and the mouse model (VH1-2 mouse) is striking and suggests that the results of boosting experiments in the mouse model may be predictive of human responses to boosting (i.e. boost candidates that succeed to increase maturation of VRC01-class responses in the mouse model would seem to have at least a reasonable probability of achieving similar results in humans).

Measurement of the binding affinities of core-gp120 boost immunogen candidates. Binding affinities of core-gp120 boost immunogen candidates for VRC01-class broadly neutralizing antibodies or CD4-IgG2. h-VRC01c antibodies were isolated from human memory B cells after one or two immunizations with adjuvanted eOD-GT8-60mer in the IA VI G001 Phase I clinical trial. m-VRC01c antibodies were isolated from mouse memory B cells after a single immunization with adjuvanted eOD-GT8 60mer in the VH1-2 mouse model from Tian et al. Cell 2016. Dissociation constants were measured using a Biacore 8 k instrument. IgGs were captured onto CM3 sensor chips (GE Healthcare) using the human antibody capture kit (GE Healthcare) and serial dilutions of the indicated monomeric immunogens were passed over the surface. Data were analyzed using the SEC-MALS analysis of core-gp120 60mer nanoparticles. The purified nanoparticles were assessed by size exclusion chromatography+multi-angle light scattering (SEC-MALS) using a Superose 6 10/300 column (GE Healthcare) at a flow rate of 0.5 mL/min followed by DAWN HELEOS II and Optilab T-rEX detectors (Wyatt Technology). The green line indicates the UV trace and the red line indicates the light scattering. The correction of the glycan molecular mass was applied through the protein-conjugate analysis. Measured and expected molecular weights, indicated, are in good agreement.

Analysis of the development of amino acid mutations in VH and Vkappa genes of VRC01-class pairs. Maturation of VRC01-class B cell receptors was induced by boosting with selected core-gp120 60mer protein nanoparticles in the VH1-2 mouse model from Tian et al Cell 2016. Groups of VH1-2 mice were immunized with the indicated prime-boost regimen, with all immunogens delivered via the IP route as 20 µg purified protein adjuvanted with Sigma adjuvant system according to the table below. At 42 days following the last immunization, five mice per group were sacrificed, their CD4-binding-site specific memory B cells from spleens and lymph nodes single-cell-sorted into 96-well plates, and the isolated BCRs sequenced by RT-PCR followed by Sanger sequencing. In each group, approximately 5-20% of heavy chain/light chain paired sequences were VRC01-class antibodies defined as those have a VH1-2 gene in the heavy chain and a five amino acid long CDR3 in the light chain. Applicants note the surprising finding that eOD-GT6-3mutB-cRSF01_60mer fails to increase matura-
tion of VRC01-class responses, even though as shown in
FIG. 1 this immunogen has considerably higher affinity for
GT8-induced memory B cells compared to the core-gp120
immunogens that do seem to increase maturation. This
important finding indicates that the criteria for a boost
immunogen to drive maturation are complex, and that higher
affinity is not necessarily the best trait or feature. Indeed,
Applicants' data suggest that there may be a sweet spot in
terms of the optimal affinity/avidity for a boost to drive
maturation, and Applicants' core-gp120 60mer immunogens
may be in that sweet spot as far as maturing responses after
a prime by eOD-GT8 60mer.

TABLE 3

| Immunization groups | Priming molecule | Boosting molecule |
|---|---|---|
| 1 | eOD-GT8_6G_60mer | — |
| 2 | eOD-GT8-d41-m3-60mer | — |
| 3 | eOD-GT8-d41-m3-60mer | placebo |
| 4 | eOD-GT8_6G_60mer | placebo |
| 5 | | eOD-GT6-3mutB-cRSF01_60mer |
| 6 | | core-Hx_r4.0D _TH6 _g7_60mer |
| 7 | | core-Hx_r4.0_g5_60mer |
| 8 | | core-Hx_r4.0D_TH6_g28_60mer |

Example 3

Figure 30:
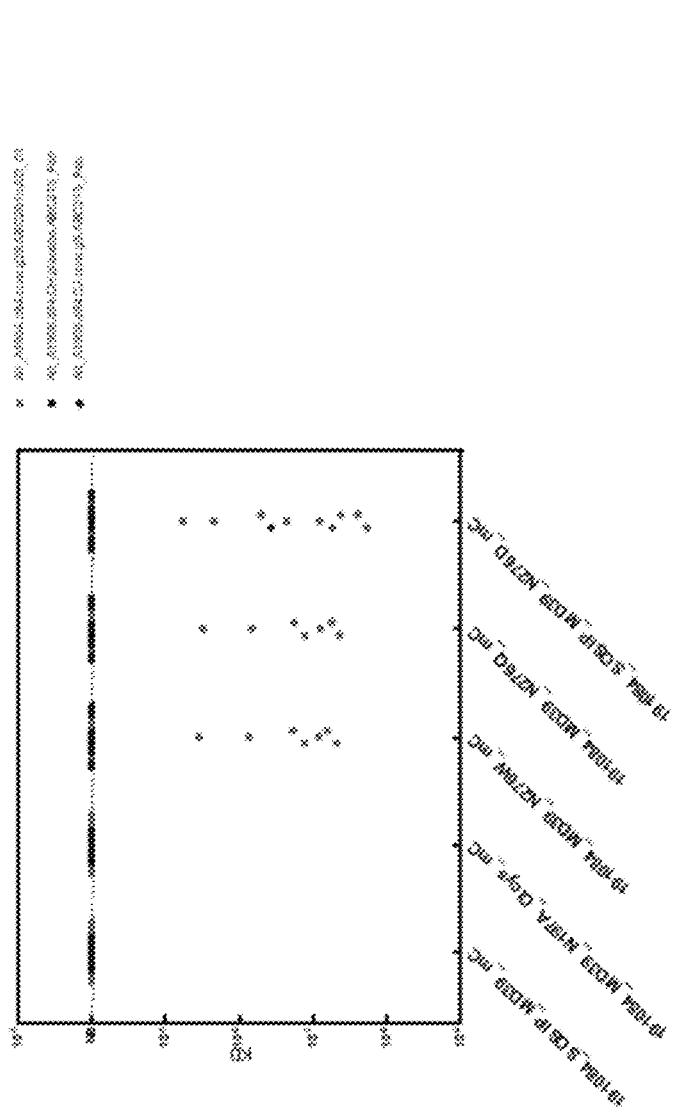
FIG. 30 shows binding affinities of boost #2 immunogen candidates for VRC01-class antibodies induced by eOD-GT8 60mer followed by core-g28 immunization in the VH1-2 mouse model. VRC01-class antibodies were isolated from mouse memory B cells after both boosting by core-g5 60mer or core-g28 60mer or placebo boosting. Dissociation constants (Kps) were measured using a Biacore 8 k instrument. Candidate boost #2 trimers were captured onto a sensor chips (GE Healthcare) using the Anti-His capture kit (GE Healthcare), and serial dilutions of the indicated Fabs were passed over the surface. Thus, the indicated Kps reflect monovalent interactions. Data were analyzed using the Biacore Insight Evaluation software (GE Healthcare) and data were plotted in Prism (Graphpad). The data show that only the core-g28-induced VRC01-class antibodies have substantial affinity for the indicated candidate boost #2 immunogens.
Figure 31:
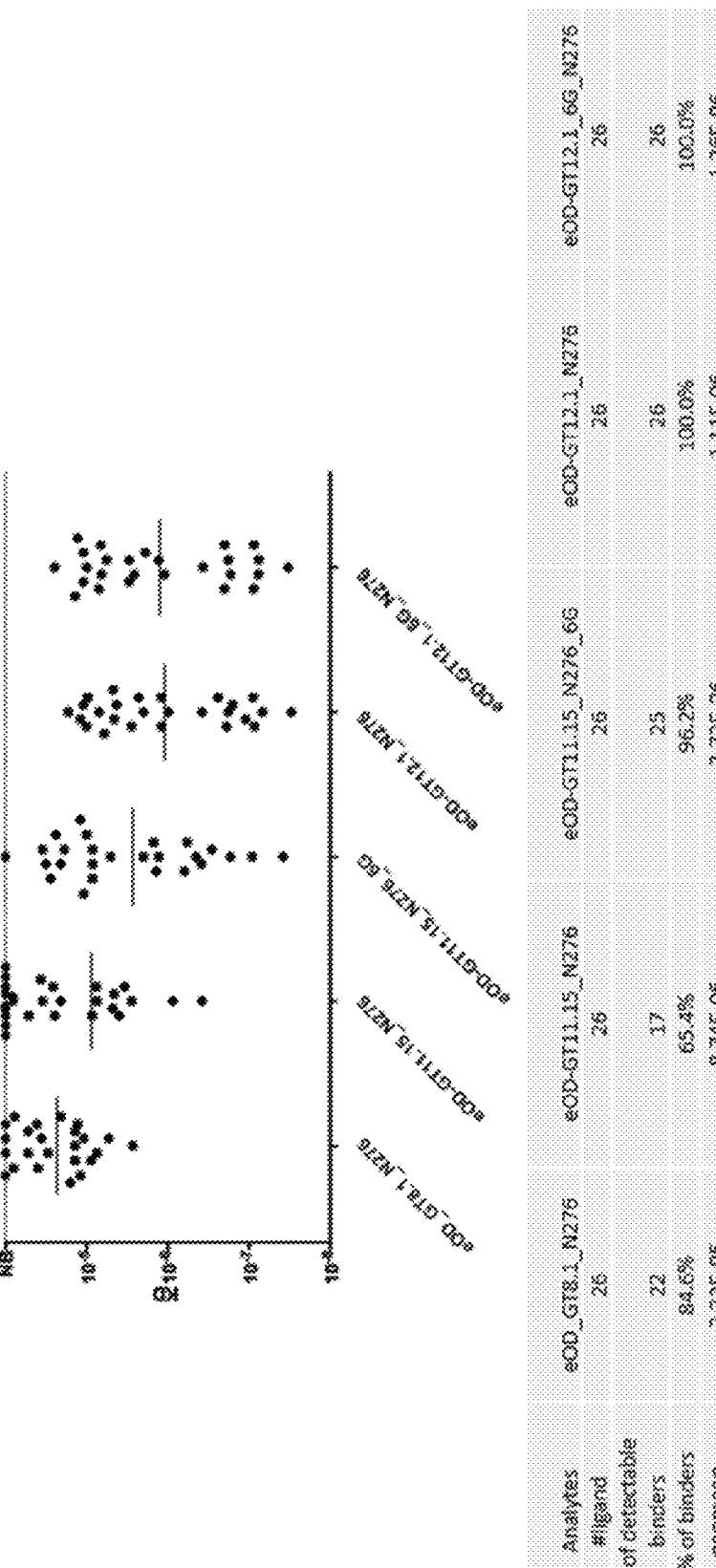
FIG. 31 shows eOD-GT11 and eOD-GT12 improve binding to VRC01 class Abs in the presence of the N276 glycan. eOD-GT8 was used as a probe to sort human naïve B cells. Epitope specific B cells were sorted and their B cell receptors (BCRs) sequenced. VRC01-class BCRs were expressed as IgGs, and binding to different priming candidates containing the N276 glycan (GT8.1_N276, GT11.15_N276, GT11.15_N276_6G, GT12.1_N276 and GT12.1_6G_N276) was measured by SPR. The Kps for each antigen were determined by capturing IgG on the SPR Chip and flowing the monomeric antigens as analytes. The top concentration of analytes was 50 µM. NB means no binding was detected at the top concentration. All the monomers tested here were expressed in freestyle 293F cells and purified by nickle affinity column followed by size exclusion chromatography on a superdex 75.
Figure 32:
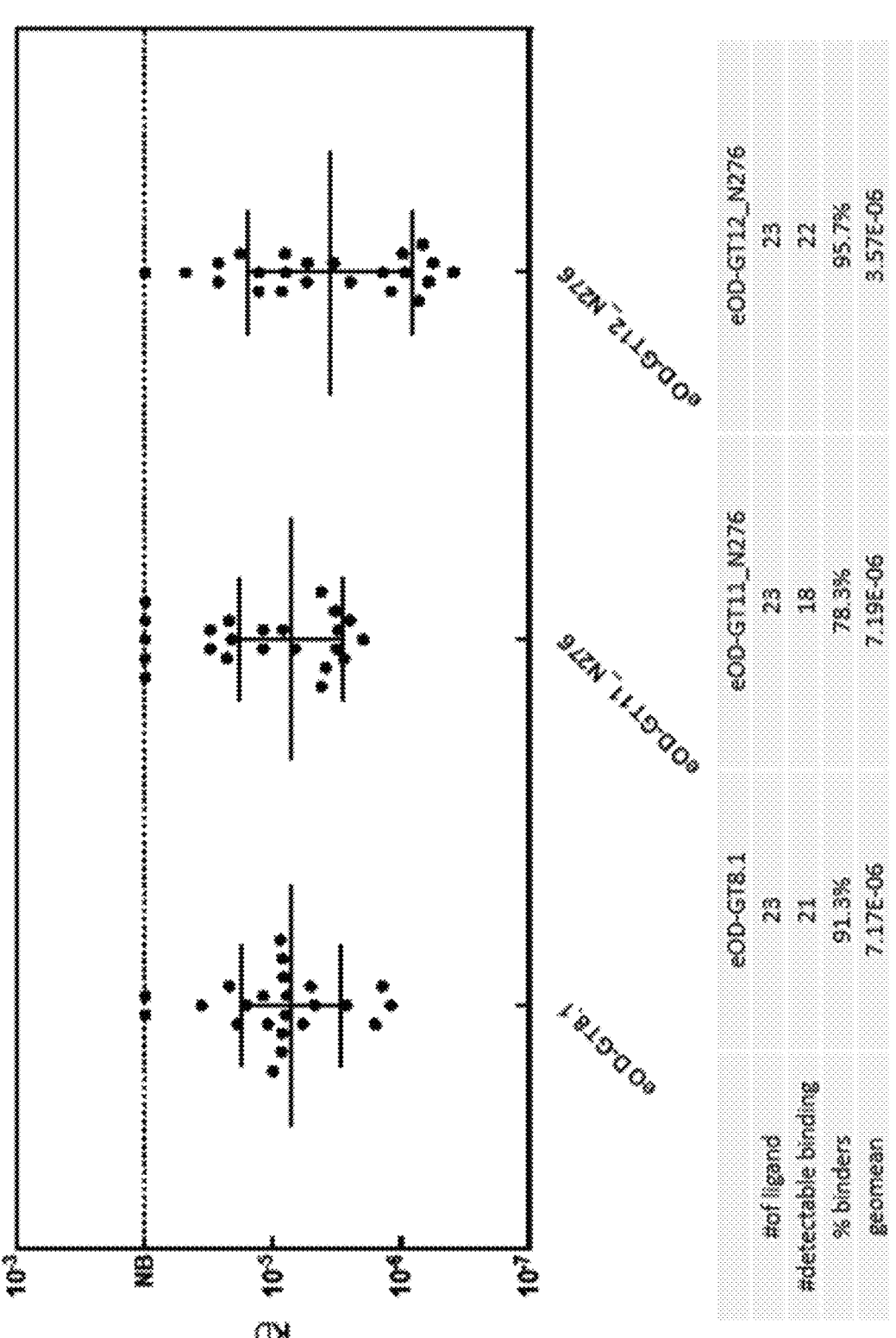
FIG. 32 shows eOD-GT12 improves binding to IOMA Abs. eOD-GT8 was used as a probe to sort human naïve B cells. Epitope specific B cells were sorted and their B cell receptors (BCRs) sequenced. Selected IOMA-like BCRs were expressed as IgGs, and binding to different prime candidates (GT8.1, GT11.15_N276, and GT12.1_N276) was measured by SPR. The Kps for each antigen were determined by capturing IgG on the SPR Chip and flowing the monomeric antigens as analytes. The top concentration of analytes was 50 M. NB means no binding was detected at the top concentration. All the monomers tested here were expressed in freestyle 293F cells and purified by nickle affinity column followed by size exclusion chromatography on a superdex 75.
Figure 34:
FIG. 34 shows antigenic profiles of membrane-bound 191084 trimers. Freestyle 293F cells were transfected with the indicated Env constructs. After 2 days, cells were labelled with the indicated antibodies, stained with AlexaFluor-647-conjugated anti-human IgG secondary antibody (Jackson ImmunoResearch) and Median fluorescence intensities of single cells were measured on a NovoCyte analyzer (ACEA Biosciences). Overall, membrane-bound 191084 trimers show the antigenic profile of a well folded native trimers. The 191084 isolate is highly sensitive to VRC01-class neutralization, therefore these membrane-bound 191084 trimers have utility as potential shepherding immunogens.
Figure 35:
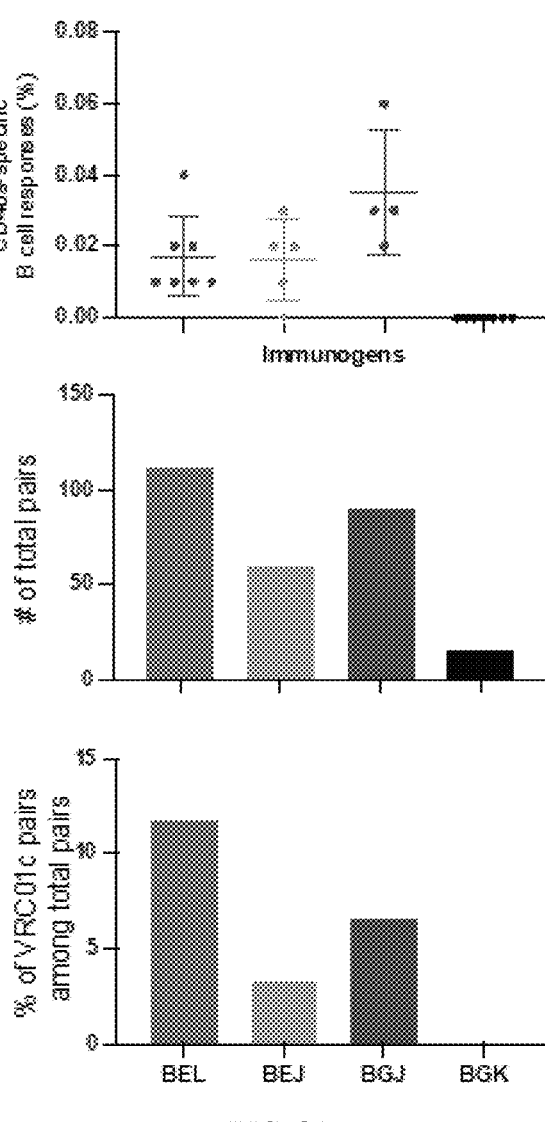
FIG. 35 shows groups of VH1-2 mice were immunized with the indicated prime-boost regimen, with all immunogens delivered via the IP route as 20 µg purified protein adjuvanted with Sigma adjuvant system. At 42 days following the last immunization, CD4-binding-site specific memory B cells from spleens and lymph nodes were single-cell-sorted into 96-well plates, and the isolated BCRs were sequenced by RT-PCR followed by Sanger sequencing. The upper plot shows the percent CD4bs-specific B cell responses in each group. The middle graph shows the total number of recovered BCR heavy-light paired sequences. The lower graph shows the percent VRC01-class pairs among the total pairs. The results suggest that the 191084-W trimer, in this case delivered on a ferritin nanoparticle, has utility for boosting VRC01-class responses after a GT8 prime and core-g5 60mer first boost. In contrast, the BG505-Q trimer, delivered on a similar ferritin nanoparticle, showed no evidence of boosting VRC01-class responses following a GT8 prime and core-g5 60mer boost.

Results supporting core-g28v2 60mer mRNA as boost 1
in G002. Boost candidates eOD-GT6-3mutB 60mer, various
core-gX 60mers, and trimer 191084-D, bound GT8-induced
VRC01-class Abs from G001 but did not bind non-VRC01-
class Abs from G001. core-g5,-g28,-g28v2 have similar
affinities. Alt VH1-2 mouse model is relevant for booster
testing because: precursor frequency in VH1-2 mouse is low,
~1 in 1.5 million (~5× lower than humans) and affinities of
GT8-induced antibodies from VH1-2 mouse are similar to
those from G001 (Example 1). Three different classes of
boost immunogens (high, medium, low affinity) in Alt
VH1-2 mouse were tested. It was found that: high-affinity
eOD-GT6 boosters did not cause more maturation than a
placebo boost, middle-affinity core-gp120 boosters selected
for increased mutation & generate Abs that bind to more
native-like trimers and low affinity trimer boosters showed
no evidence of boost. It was concluded core-gp120 60mer
current best boost platform after GT8 60mer prime. Fur-
thermore, boosting with core-g28 60mer after priming with
eOD-GT8 in the VH1-2 mouse elicited antibodies that could
react to more native-like trimer molecules, whereas boosting
with core-g5 60mer after priming with eOD-GT8 in the
same mouse model did not elicit such antibodies (FIG. 30).

g28v2 was a minor change from g28-α single aa mutation
caused a glycosylation site to move by two residues, from
less common HIV position to more common HIV position
and a glycan was outside the VRC01-epitope, within V4
loop, and repositioning may reduce undesired off-target
responses. g28v2 has similar affinities for VRC01-class
bnAbs and G001 Abs. Most importantly, g28v2 60mers
exhibited more efficient nanoparticle assembly (better SEC
traces) and higher nanoparticle yield compared to g28
60mers. Better assembly and yield may translate to better
immunogenicity if the immunogen is delivered by nucleic
acid or vector technology.

Example 4

This Example relates to a vaccine design to elicit broadly
neutralizing antibodies against HIV.
The IAVI G001 Phase I Trial: eOD-GT8 60mer/AS01B. It
was the first-in-human test of germline targeting. There was a self-assembling nanoparticle plus a strong adjuvant. The
first vaccination and last vaccination were one and a half
years apart. The primary endpoint was safety. A major
immunological endpoint was to determine if the vaccine
induces VRC01-class IgG+ B cells. A critical readout by B
cell sorting/sequencing at VRC and FHCRC was the first-
in-human use of this assay as the bottom-line endpoint.

TABLE 4

| Study Group | N | eOD-GT8 60mer dose | Week 0 | Week 8 |
|---|---|---|---|---|
| 1 (low dose) | 18 | 20 µg | eOD-GT8 60mer/AS01B | eOD-GT8 60mer/AS01B |
| | 6 | — | buffer | buffer |
| 2 (high dose) | 18 | 100 µg | eOD-GT8 60mer/AS01B | eOD-GT8 60mer/AS01B |
| | 6 | — | buffer | buffer |
| Total | 48 | | | |

The IAVI G001 sequences were analyzed as follows. All
sequences were from low+high dose groups and included
pre-immunization and seven post-immunization timepoints.
Sequences were filtered: partial reads and unproductive
sequences were eliminated, low quality sequences were
eliminated (Phred score cutoff), control sequences were
eliminated, doublet sequences were eliminated and the
sequences were restricted to epitope-specific sequences
(GT8++/KO-binders according to FACS). 11,399 heavy-
light paired sequences were analyzed that passed all filters.
There was a median of 303 H-L pairs per vaccine recipient
and 9 H-L pairs per placebo.

IAVI G001 major conclusions are as follows. eOD-GT8
60mer/AS01B is safe in humans. eOD-GT8 60mer/AS01B
induced VRC01-class responses in 97% (35/36) of vaccine
recipients. Proof of principle is established for germline
targeting in humans and supports extending the strategy to
other targets in HIV and other pathogens. eOD-GT8 60mer
is validated as a as candidate for VRC01-class HIV vaccine
prime. Evidence is provided that boosting-induced matura-
tion can be achieved in humans. Key reagents are provided
to help define VRC01 boost candidates for human testing.
This is the first HIV human vaccine trial to confirm an
intended mechanistic hypothesis and validates reductionist
philosophy.

To develop a highly effective HIV vaccine, Applicants
need to carry out many iterative human clinical trials. If
Applicants rely on GMP protein manufacture, progress is
limited by the relatively slow pace and high cost of manu-
facture.

IAVI G001 established proof of principle for germline-
targeting vaccine design in humans. Applicants believe that
this strategy is necessary to develop an HIV vaccine, but
doing so requires multiple iterative human clinical trials.
Applicants envision multiple trials until there is convergence
on a protective vaccine.

Having thus described in detail preferred embodiments of
the present invention, it is to be understood that the inven-
tion defined by the above paragraphs is not to be limited to
particular details set forth in the above description as many
apparent variations thereof are possible without departing
from the spirit or scope of the present invention.

What is claimed is:

1. A non-naturally occurring protein comprising an amino acid sequence selected from SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72 SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, and SEQ ID NO: 158.

2. A multimeric protein comprising the protein of claim 1.

3. The protein of claim 1 further comprising an additional cysteine.

4. The protein of claim 2 fused to a multimerization motif.

5. The protein of claim 1 further comprising a tag for purification or biotinylation.

6. The protein of claim 5 wherein the tag for purification is a his tag.

7. The protein of claim 5 wherein the tag for biotinylation is an avi-tag.

8. A nucleic acid encoding the protein of claim 1.

9. The nucleic acid of claim 8 wherein the nucleic acid is a mRNA.

10. A method for eliciting an immune response comprising systemically administering to an animal in need thereof an effective amount of the protein of claim 1.

11. The method of claim 10, wherein the animal is a mammal.

12. The method of claim 11, wherein the mammal is a human.

13. A method for eliciting an immune response for germline-targeting priming immunogens, boosting/shepherding immunogens to guide maturation, and/or trimer stabilization and presentation in a membrane-bound format, the method comprising administering an effective amount of the protein of claim 1 a subject in need thereof.

14. The method of claim 13, wherein the maturation is a VRC01-class response and/or PCT64-like or PG9-like response, and/or BG 18-like response.

15. The method of claim 13, wherein the germline is VRC01, PCT64, PG9 or BG18 or a combination thereof.

16. The non-naturally occurring protein of claim 1, wherein the amino acid sequence is selected from the group consisting of SEQ ID NO: 77, SEQ ID NO: 139, and SEQ ID NO: 153.

17. The non-naturally occurring protein of claim 1, wherein the amino acid sequence comprises one or more conservative amino acid substitutions.

18. The nucleic acid of claim 8, wherein the nucleic acid encodes a protein comprising one or more conservative amino acid substitutions.

19. The nucleic acid of claim 17, wherein the conservative amino acid substitution is a replacement of an amino acid residue with an amino acid residue having a similar side chain selected from:

(a) a basic side chain family;

(b) an acidic side chain family;

(c) a non-charged polar side chain family; and (d) a non-polar side chain family.

* * * * *

SEQUENCE LISTING

Sequence total quantity: 165
SEQ ID NO: 1              moltype = AA  length = 31
FEATURE                   Location/Qualifiers
REGION                    1..31
                          note = Description of Artificial Sequence: Synthetic
                           polypeptide
source                    1..31
                          mol_type = protein
                          organism = synthetic construct
SEQUENCE: 1
MGILPSPGMP ALLSLVSLLS VLLMGCVAET G                                       31

SEQ ID NO: 2              moltype = AA  length = 683
FEATURE                   Location/Qualifiers
REGION                    1..683
                          note = Description of Artificial Sequence: Synthetic
                           polypeptide
source                    1..683
                          mol_type = protein
                          organism = synthetic construct
SEQUENCE: 2
TENLWVTVYY GVPVWRDAET TLFCASDAKA YDTEMHNVWA THACVPTDPN PQEIDLENVT  60
EKFNMWKNNM VEQMHEDIIS LWDQSLKPCV KLTPLCVTLN CTAITNDTRG NETGINRTVE  120
TTEMTNCSFN MTTELRDRKK KVNALFYKLD IVQIGENSSS QYRLINCNTS VITQACPKVT  180
FEPIPIHYCA PAGFAILKCK DKEFNGTGTC RNVSSVQCTH GIKPVVSTQL LLNGSLAEGQ  240
VIIRSEDISD NAKTIIVQLN ESVPINCTRP NNNTVRGIHL GPGQTFFYTD IIGDIRQAHC  300
NVSESKWNKA LQEVVKQLRQ HWNKTIIFKS SSGGDLEITT HSFNCGGEFF YCNTSGLFNS  360
TWNIAGNRTN DTKSNETITL PCRIKQIVNV WQRVGQAIYA PPIAGVIRCN SNITGLLLVR  420
DGGATNNTDE TFRPGGGNMR DNWRSELYKY KVVKIEPLGV APTRCRRRVV ESHSGSGGSG  480
SGGHAAVGLG AVSIGFLGAA GSTMGAASVT LTVQARQLLS GIVQQQSNLL RAPEPQQHLL  540
KDTHWGIKQL QARVLAVEHY LKDQQLLGIW GCSGKLICCT TVPWNSSWSN KSQNEIWDNM  600
TWLQWDKEIS NYTQLIYSLI EESQNQQEKN EQELLALDKW ASLWNWFDIS NWLWYIKIFI  660
MIVGGLIGLR IVFAVLSVIH RVR                                          683

SEQ ID NO: 3              moltype = AA  length = 683
FEATURE                   Location/Qualifiers
REGION                    1..683
                          note = Description of Artificial Sequence: Synthetic
                           polypeptide
source                    1..683
                          mol_type = protein
                          organism = synthetic construct
SEQUENCE: 3
TENLWVTVYY GVPVWRDAET TLFCASDAKA YDTEMHNVWA THACVPTDPN PQEIDLENVT  60
EKFNMWKNNM VEQMHEDIIS LWDQSLKPCV KLTPLCVTLN CTAITNDTRG NETGINRTVE  120
TTEMTNCSFN MTTELRDRKK KVNALFYKLD IVQIGENSSS QYRLINCNTS VITQACPKVT  180
FEPIPIHYCA PAGFAILKCK DKEFNGTGTC RNVSSVQCTH GIKPVVSTQL LLNGSLAEGQ  240
VIIRSEDISD NAKTIIVQLN ESVPINCTRP NNNTVRGIHL GPGQTFFYTD IIGDIRQAHC  300
NVSESKWNKA LQEVVKQLRQ HWNKTIIFKS SSGGDLEITT HSFNCGGEFF YCNTSGLFNS  360
TWNIAGNRTN DTKSNETITL PCRIKQIVNV WQRVGQAIYA PPIAGVIRCN SNITGLLLVR  420
DGGATNNTDE TFRPGGTNMR DNWRSELYKY KVVKIEPLGV APTRCRRRVV ESHSGSGGSG  480
SGGHAAVGLG AVSIGFLGAA GSTMGAASVT LTVQARQLLS GIVQQQSNLL RAPEPQQHLL  540
KDTHWGIKQL QARVLAVEHY LKDQQLLGIW GCSGKLICCT TVPWNSSWSN KSQNEIWDNM  600
TWLQWDKEIS NYTQLIYSLI EESQNQQEKN EQELLALDKW ASLWNWFDIS NWLWYIKIFI  660
MIVGGLIGLR IVFAVLSVIH RVR                                          683

SEQ ID NO: 4              moltype = AA  length = 683
FEATURE                   Location/Qualifiers
REGION                    1..683
                          note = Description of Artificial Sequence: Synthetic
                           polypeptide
source                    1..683
                          mol_type = protein
                          organism = synthetic construct
SEQUENCE: 4
TENLWVTVYY GVPVWRDAET TLFCASDAKA YDTEMHNVWA THACVPTDPN PQEIDLENVT  60
EKFNMWKNNM VEQMHEDIIS LWDQSLKPCV KLTPLCVTLN CTAITNDTRG NETGINRTVE  120
TTEMTNCSFN MTTELRDRKK KVNALFYKLD IVQIGENSSS QYRLINCNTS VITQACPKVT  180
FEPIPIHYCA PAGFAILKCK DKEFNGTGTC RNVSSVQCTH GIKPVVSTQL LLNGSLAEGQ  240
VIIRSEDISD NAKTIIVQLN ESVPINCTRP NNNTVRGIHL GPGQTFFYTD IIGDIRQAHC  300
NVSESKWNKT LQEVVKQLRQ HWNKTIIFKS SSGGDLEITT HSFNCGGEFF YCNTSGLFNS  360
TWNIAGNRTN DTKSNETITL PCRIKQIVNV WQRVGQAIYA PPIAGVIRCN SNITGLLLVR  420
DGGATNNTDE TFRPGGGNMR DNWRSELYKY KVVKIEPLGV APTRCRRRVV ESHSGSGGSG  480
SGGHAAVGLG AVSIGFLGAA GSTMGAASVT LTVQARQLLS GIVQQQSNLL RAPEPQQHLL  540
KDTHWGIKQL QARVLAVEHY LKDQQLLGIW GCSGKLICCT TVPWNSSWSN KSQNEIWDNM  600
TWLQWDKEIS NYTQLIYSLI EESQNQQEKN EQELLALDKW ASLWNWFDIS NWLWYIKIFI  660
MIVGGLIGLR IVFAVLSVIH RVR                                          683

```
SEQ ID NO: 5              moltype = AA   length = 683
FEATURE                  Location/Qualifiers
REGION                   1..683
                         note = Description of Artificial Sequence: Synthetic
                         polypeptide
source                   1..683
                         mol_type = protein
                         organism = synthetic construct
SEQUENCE: 5
TENLWVTVYY GVPVWRDAET TLFCASDAKA YDTEMHNVWA THACVPTDPN PQEIDLENVT   60
EKFNMWKNNM VEQMHEDIIS LWDQSLKPCV KLTPLCVTLN CTAITNDTRG NETGINRTVE  120
TTEMTNCSFN MTTELRDRKK KVNALFYKLD IVQIGENSSS QYRLINCNTS VITQACPKVT  180
FEPIPIHYCA PAGFAILKCK DKEFNGTGTC RNVSSVQCTH GIKPVVSTQL LLNGSLAEGQ  240
VIIRSEDISD NAKTIIVQLN ESVPINCTRP NNNTVRGIHL GPGQTFFYTD IIGDIRQAHC  300
NVSESKWNKA LQEVVKQLRQ HWNKTIIFKS SSGGDLEITT HSFNCGGEFF YCNTSGLFNS  360
TWNIAGNRTN DTKSNETITL PCRIKQIVNV WQRVGQAIYA PPIAGVIRCN SNITGLLLVR  420
DGGATNNTDE TFRPGGGNMR DNWRSELYKY KVVKIEPLGV APTRCRRRVV ESHSGSGGSG  480
SGGHAAVGLG AVSIGFLGAA GSTMGAASVT LTVQARQLLS GIVQQQSNLL RAPEPQQHLL  540
KDTHWGIKQL QARVLAVEHY LKDQQLLGIW GCSGKLICCT TVPWNSSWSN KSQNEIWDNM  600
TWLQWDKEIS NYTQLIYSLI EESQNQQEKN EQELLALDKW ASLWNWFDIS KWLWYIRIFI  660
MIVGGLIGLR IVFTVLSIIN RVR                                          683

SEQ ID NO: 6              moltype = AA   length = 683
FEATURE                  Location/Qualifiers
REGION                   1..683
                         note = Description of Artificial Sequence: Synthetic
                         polypeptide
source                   1..683
                         mol_type = protein
                         organism = synthetic construct
SEQUENCE: 6
TENLWVTVYY GVPVWRDAET TLFCASDAKA YDTEMHNVWA THACVPTDPN PQEIDLENVT   60
EKFNMWKNNM VEQMHEDIIS LWDQSLKPCV KLTPLCVTLN CTAITNDTRG NETGINRTVE  120
TTEMTNCSFN MTTELRDRKK KVNALFYKLD IVQIGENSSS QYRLINCNTS VITQACPKVT  180
FEPIPIHYCA PAGFAILKCK DKEFNGTGTC RNVSSVQCTH GIKPVVSTQL LLNGSLAEGQ  240
VIIRSEDISD NAKTIIVQLN ESVPINCTRP NNNTVRGIHL GPGQTFFYTD IIGDIRQAHC  300
NVSESKWNKA LQEVVKQLRQ HWNKTIIFKS SSGGDLEITT HSFNCGGEFF YCNTSGLFNS  360
TWNIAGNRTN DTKSNETITL PCRIKQIVNV WQRVGQAIYA PPIAGVIRCN SNITGLLLVR  420
DGGATNNTDE TFRPGGTNMR DNWRSELYKY KVVKIEPLGV APTRCRRRVV ESHSGSGGSG  480
SGGHAAVGLG AVSIGFLGAA GSTMGAASVT LTVQARQLLS GIVQQQSNLL RAPEPQQHLL  540
KDTHWGIKQL QARVLAVEHY LKDQQLLGIW GCSGKLICCT TVPWNSSWSN KSQNEIWDNM  600
TWLQWDKEIS NYTQLIYSLI EESQNQQEKN EQELLALDKW ASLWNWFDIS KWLWYIRIFI  660
MIVGGLIGLR IVFTVLSIIN RVR                                          683

SEQ ID NO: 7              moltype = AA   length = 683
FEATURE                  Location/Qualifiers
REGION                   1..683
                         note = Description of Artificial Sequence: Synthetic
                         polypeptide
source                   1..683
                         mol_type = protein
                         organism = synthetic construct
SEQUENCE: 7
TENLWVTVYY GVPVWRDAET TLFCASDAKA YDTEMHNVWA THACVPTDPN PQEIDLENVT   60
EKFNMWKNNM VEQMHEDIIS LWDQSLKPCV KLTPLCVTLN CTAITNDTRG NETGINRTVE  120
TTEMTNCSFN MTTELRDRKK KVNALFYKLD IVQIGENSSS QYRLINCNTS VITQACPKVT  180
FEPIPIHYCA PAGFAILKCK DKEFNGTGTC RNVSSVQCTH GIKPVVSTQL LLNGSLAEGQ  240
VIIRSEDISD NAKTIIVQLN ESVPINCTRP NNNTVRGIHL GPGQTFFYTD IIGDIRQAHC  300
NVSESKWNKA LQEVVKQLRQ HWNKTIIFKS SSGGDLEITT HSFNCGGEFF YCNTSGLFNS  360
TWNIAGNRTN DTKSNETITL PCRIKQIVNV WQRVGQAIYA PPIAGVIRCN SNITGLLLVR  420
DGGATNNTDE TFRPGGTNMR DNWRSELYKY KVVKIEPLGV APTRCRRRVV ESHSGSGGSG  480
SGGHAAVGLG AVSIGFLGAA GSTMGAASVT LTVQARQLLS GIVQQQSNLL RAPEPQQHLL  540
KDTHWGIKQL QARVLAVEHY LKDQQLLGIW GCSGKLICCT TVPWNSSWSN KSQNEIWDNM  600
TWLQWDKEIS NYTQLIYSLI EESQNQQEKN EQELLALDKW ASLWNWFDIS KWLWYIRIFI  660
MIVGGLIGLR IVFTVLSIIN RVR                                          683

SEQ ID NO: 8              moltype = AA   length = 683
FEATURE                  Location/Qualifiers
REGION                   1..683
                         note = Description of Artificial Sequence: Synthetic
                         polypeptide
source                   1..683
                         mol_type = protein
                         organism = synthetic construct
SEQUENCE: 8
TENLWVTVYY GVPVWRDAET TLFCASDAKA YDTEMHNVWA THACVPTDPN PQEIDLENVT   60
EKFNMWKNNM VEQMHEDIIS LWDQSLKPCV KLTPLCVTLN CTAITNDTRG NETGINRTVE  120
TTEMTNCSFN MTTELRDRKK KVNALFYKLD IVQIGENSSS QYRLINCNTS VITQACPKVT  180
FEPIPIHYCA PAGFAILKCK DKEFNGTGTC RNVSSVQCTH GIKPVVSTQL LLNGSLAEGQ  240
```

-continued

```
VIIRSEDISD NAKTIIVQLN ESVPINCTRP NNNTVRGIHL GPGQTFFYTD IIGDIRQAHC   300
NVSESKWNKT LQEVVKQLRQ HWNKTIIFKS SSGGDLEITT HSFNCGGEFF YCNTSGLFNS   360
TWNIAGNRTN DTKSNETITL PCRIKQIVNV WQRVGQAIYA PPIAGVIRCN SNITGLLLVR   420
DGGATNNTDE TFRPGGGNMR DNWRSELYKY KVVKIEPLGV APTRCRRRVV ESHSGSGGSG   480
SGGHAAVGLG AVSIGFLGAA GSTMGAASVT LTVQARQLLS GIVQQQSNLL RAPEPQQHLL   540
KDTHWGIKQL QARVLAVEHY LKDQQLLGIW GCSGKLICCT TVPWNSSWSN KSQNEIWDNM   600
TWLQWDKEIS NYTQLIYSLI EESQNQQEKN EQELLALDKW ASLWNWFDIS KWLWYIRIFI   660
MIVGGLIGLR IVFTVLSIIN RVR                                          683

SEQ ID NO: 9              moltype = AA  length = 675
FEATURE                   Location/Qualifiers
REGION                    1..675
                          note = Description of Artificial Sequence: Synthetic
                           polypeptide
source                    1..675
                          mol_type = protein
                          organism = synthetic construct
SEQUENCE: 9
TENLWVTVYY GVPVWRDAET TLFCASDAKA YDTEMHNVWA THACVPTDPN PQEIDLENVT   60
EKFNMWKNNM VEQMHEDIIS LWDQSLKPCV KLTPLCVTLN CTAITNDTRG NETGINRTVE   120
TTEMTNCSFN MTTELRDRKK KVNALFYKLD IVQIGENSSS QYRLINCNTS VITQACPKVT   180
FEPIPIHYCA PAGFAILKCK DKEFNGTGTC RNVSSVQCTH GIKPVVSTQL LLNGSLAEGQ   240
VIIRSEQISD NAKTIIVQLN ESVPINCTRP NNNTVRGIHL GPGQTFFYTD IIGDIRQAHC   300
NVSESKWNKA LQEVVKQLRQ HWNKTIIFKS SSGGDLEITT HSFNCGGEFF YCNTSGLFNS   360
TWNIAGNRTN DTKSNETITL PCRIKQIVNV WQRVGQAIYA PPIAGVIRCN SNITGLLLVR   420
DGGATNNTDE TFRPGGGNMR DNWRSELYKY KVVKIEPLGV APTRCRRRVV ERRRRRAVG   480
LGAVSIGFLG AAGSTMGAAS VTLTVQARQL LSGIVQQQSN LLRAPEPQQH LLKDTHWGIK   540
QLQARVLAVE HYLKDQQLLG IWGCSGKLIC CTTVPWNSSW SNKSQNEIWD NMTWLQWDKE   600
ISNYTQLIYS LIEESQNQQE KNEQELLALD KWASLWNWFD ISKWLWYIRI FIMIVGGLIG   660
LRIVFTVLSI INRVR                                                   675

SEQ ID NO: 10             moltype = AA  length = 675
FEATURE                   Location/Qualifiers
REGION                    1..675
                          note = Description of Artificial Sequence: Synthetic
                           polypeptide
source                    1..675
                          mol_type = protein
                          organism = synthetic construct
SEQUENCE: 10
TENLWVTVYY GVPVWRDAET TLFCASDAKA YDTEMHNVWA THACVPTDPN PQEIDLENVT   60
EKFNMWKNNM VEQMHEDIIS LWDQSLKPCV KLTPLCVTLN CTAITNDTRG NETGINRTVE   120
TTEMTNCSFN MTTELRDRKK KVNALFYKLD IVQIGENSSS QYRLINCNTS VITQACPKVT   180
FEPIPIHYCA PAGFAILKCK DKEFNGTGTC RNVSSVQCTH GIKPVVSTQL LLNGSLAEGQ   240
VIIRSEQISD NAKTIIVQLN ESVPINCTRP NNNTVRGIHL GPGQTFFYTD IIGDIRQAHC   300
NVSESKWNKA LQEVVKQLRQ HWNKTIIFKS SSGGDLEITT HSFNCGGEFF YCNTSGLFNS   360
TWNIAGNRTN DTKSNETITL PCRIKQIVNV WQRVGQAIYA PPIAGVIRCN SNITGLLLVR   420
DGGATNNTDE TFRPGGTNMR DNWRSELYKY KVVKIEPLGV APTRCRRRVV ERRRRRAVG   480
LGAVSIGFLG AAGSTMGAAS VTLTVQARQL LSGIVQQQSN LLRAPEPQQH LLKDTHWGIK   540
QLQARVLAVE HYLKDQQLLG IWGCSGKLIC CTTVPWNSSW SNKSQNEIWD NMTWLQWDKE   600
ISNYTQLIYS LIEESQNQQE KNEQELLALD KWASLWNWFD ISKWLWYIRI FIMIVGGLIG   660
LRIVFTVLSI INRVR                                                   675

SEQ ID NO: 11             moltype = AA  length = 679
FEATURE                   Location/Qualifiers
REGION                    1..679
                          note = Description of Artificial Sequence: Synthetic
                           polypeptide
source                    1..679
                          mol_type = protein
                          organism = synthetic construct
SEQUENCE: 11
TENLWVTVYY GVPVWRDAET TLFCASDAKA YDTEMHNVWA THACVPTDPN PQEIDLENVT   60
EKFNMWKNNM VEQMHEDIIS LWDQSLKPCV KLTPLCVTLN CTAITNDTRG NETGINRTVE   120
TTEMTNCSFN MTTELRDRKK KVNALFYKLD IVQIGENSSS QYRLINCNTS VITQACPKVT   180
FEPIPIHYCA PAGFAILKCK DKEFNGTGTC RNVSSVQCTH GIKPVVSTQL LLNGSLAEGQ   240
VIIRSEQISD NAKTIIVQLN ESVPINCTRP NNNTVRGIHL GPGQTFFYTD IIGDIRQAHC   300
NVSESKWNKA LQEVVKQLRQ HWNKTIIFKS SSGGDLEITT HSFNCGGEFF YCNTSGLFNS   360
TWNIAGNRTN DTKSNETITL PCRIKQIVNV WQRVGQAIYA PPIAGVIRCN SNITGLLLVR   420
DGGATNNTDE TFRPGGGNMR DNWRSELYKY KVVKIEPLGV APTRCRRRVV GGGGGSGGGG   480
SAVGLGAVSI GFLGAAGSTM GAASVTLTVQ ARQLLSGIVQ QQSNLLRAPE PQQHLLKDTH   540
WGIKQLQARV LAVEHYLKDQ QLLGIWGCSG KLICCTTVPW NSSWSNKSQN EIWDNMTWLQ   600
WDKEISNYTQ LIYSLIEESQ NQQEKNEQEL LALDKWASLW NWFDISKWLW YIRIFIMIVG   660
GLIGLRIVFT VLSIINRVR                                               679

SEQ ID NO: 12             moltype = AA  length = 679
FEATURE                   Location/Qualifiers
REGION                    1..679
                          note = Description of Artificial Sequence: Synthetic
```

-continued

```
                          polypeptide
source                    1..679
                          mol_type = protein
                          organism = synthetic construct
SEQUENCE: 12
TENLWVTVYY GVPVWRDAET TLFCASDAKA YDTEMHNVWA THACVPTDPN PQEIDLENVT     60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEQISD NAKTIIVQLN ESVPINCTRP NNNTVRGIHL GPGQTFFYTD IIGDIRQAHC    300
NVSESKWNKA LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGTNMR DNWRSELYKY KVVKIEPLGV APTRCRRRVV GGGGSGGGG     480
SAVGLGAVSI GFLGAAGSTM GAASVTLTVQ ARQLLSGIVQ QQSNLLRAPE PQQHLLKDTH    540
WGIKQLQARV LAVEHYLKDQ QLLGIWGCSG KLICCTTVPW NSSWSNKSQN EIWDNMTWLQ    600
WDKEISNYTQ LIYSLIEESQ NQQEKNEQEL LALDKWASLW NWFDISKWLW YIRIFIMIVG    660
GLIGLRIVFT VLSIINRVR                                                 679

SEQ ID NO: 13             moltype = AA  length = 638
FEATURE                   Location/Qualifiers
REGION                    1..638
                          note = Description of Artificial Sequence: Synthetic
                           polypeptide
source                    1..638
                          mol_type = protein
                          organism = synthetic construct
SEQUENCE: 13
TENLWVTVYY GVPVWRDAET TLFCASDAKA YDTEMHNVWA THACVPTDPN PQEIDLENVT     60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEDISD NAKTIIVQLN ESVPINCTRP NNNTVRGIHL GPGQTFFYTD IIGDIRQAHC    300
NVSESKWNKA LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGGNMR DNWRSELYKY KVVKIEPLGV APTRCRRRVV ESHSGSGGSG    480
SGGHAAVGLG AVSIGFLGAA GSTMGAASVT LTVQARQLLS GIVQQQSNLL RAPEPQQHLL    540
KDTHWGIKQL QARVLAVEHY LKDQQLLGIW GCSGKLICCT TVPWNSSWSN KSQNEIWDNM    600
TWLQWDKEIS NYTQLIYSLI EESQNQQEKN EQELLALD                            638

SEQ ID NO: 14             moltype = AA  length = 638
FEATURE                   Location/Qualifiers
REGION                    1..638
                          note = Description of Artificial Sequence: Synthetic
                           polypeptide
source                    1..638
                          mol_type = protein
                          organism = synthetic construct
SEQUENCE: 14
TENLWVTVYY GVPVWRDAET TLFCASDAKA YDTEMHNVWA THACVPTDPN PQEIDLENVT     60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEDISD NAKTIIVQLN ESVPINCTRP NNNTVRGIHL GPGQTFFYTD IIGDIRQAHC    300
NVSESKWNKA LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGTNMR DNWRSELYKY KVVKIEPLGV APTRCRRRVV ESHSGSGGSG    480
SGGHAAVGLG AVSIGFLGAA GSTMGAASVT LTVQARQLLS GIVQQQSNLL RAPEPQQHLL    540
KDTHWGIKQL QARVLAVEHY LKDQQLLGIW GCSGKLICCT TVPWNSSWSN KSQNEIWDNM    600
TWLQWDKEIS NYTQLIYSLI EESQNQQEKN EQELLALD                            638

SEQ ID NO: 15             moltype = AA  length = 638
FEATURE                   Location/Qualifiers
REGION                    1..638
                          note = Description of Artificial Sequence: Synthetic
                           polypeptide
source                    1..638
                          mol_type = protein
                          organism = synthetic construct
SEQUENCE: 15
TENLWVTVYY GVPVWRDAET TLFCASDAKA YDTEMHNVWA THACVPTDPN PQEIDLENVT     60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEDISD NAKTIIVQLN ESVPINCTRP NNNTVRGIHL GPGQTFFYTD IIGDIRQAHC    300
NVSESKWNKT LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGTNMR DNWRSELYKY KVVKIEPLGV APTRCRRRVV ESHSGSGGSG    480
SGGHAAVGLG AVSIGFLGAA GSTMGAASVT LTVQARQLLS GIVQQQSNLL RAPEPQQHLL    540
KDTHWGIKQL QARVLAVEHY LKDQQLLGIW GCSGKLICCT TVPWNSSWSN KSQNEIWDNM    600
```

```
TWLQWDKEIS NYTQLIYSLI EESQNQQEKN EQELLALD                              638

SEQ ID NO: 16          moltype = AA   length = 638
FEATURE                Location/Qualifiers
REGION                 1..638
                       note = Description of Artificial Sequence: Synthetic
                        polypeptide
source                 1..638
                       mol_type = protein
                       organism = synthetic construct
SEQUENCE: 16
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE      120
TTEMTNCSFN MTTELRDRKK KVNALFYKLD IVQIGENSSS QYRLINCNTS VITQACPKVT      180
FEPIPIHYCA PAGFAILKCK DKEFNGTGTC RNVSSVQCTH GIKPVVSTQL LLNGSLAEGQ      240
VIIRSEDISD NAKTIIVQLN ESVPINCTRP NNNTVRGIHL GPGQTFFYTD IIGDIRQAHC      300
NVSESKWNKT LQEVVKQLRQ HWNKTIIFKS SSGGDLEITT HSFNCGGEFF YCNTSGLFNS      360
TWNIAGNRTN DTKSNETITL PCRIKQIVNV WQRVGQAIYA PPIAGVIRCN SNITGLLLVR      420
DGGATNNTDE TFRPGGGNMR DNWRSELYKY KVVKIEPLGV APTRCRRRVV ESHSGSGGSG      480
SGGHAAVGLG AVSIGFLGAA GSTMGAASVT LTVQARQLLS GIVQQQSNLL RAPEPQQHLL      540
KDTHWGIKQL QARVLAVEHY LKDQQLLGIW GCSGKLICCT TVPWNSSWSN KSQNEIWDNM      600
TWLQWDKEIS NYTQLIYSLI EESQNQQEKN EQELLALD                              638

SEQ ID NO: 17          moltype = AA   length = 675
FEATURE                Location/Qualifiers
REGION                 1..675
                       note = Description of Artificial Sequence: Synthetic
                        polypeptide
source                 1..675
                       mol_type = protein
                       organism = synthetic construct
SEQUENCE: 17
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE      120
TTEMTNCSFN MTTELRDRKK KVNALFYKLD IVQIGENSSS QYRLINCATS VITQACPKVT      180
FEPIPIHYCA PAGFAILKCK DKEFNGTGTC RNVSSVQCTH GIKPVVSTQL LLNGSLAEGQ      240
VIIRSENISD NAKTIIVQLN ESVPINCTRP NNNTVRGIHL GPGQTFFYTD IIGDIRQAHC      300
NVSESKWNKA LQEVVKQLRQ HWNKTIIFKS SSGGDLEITT HSFNCGGEFF YCNTSGLFNS      360
TWNIAGNRTN DTKSNETITL PCRIKQIVNV WQRVGQAIYA PPIAGVIRCN SNITGLLLVR      420
DGGATNNTDE TFRPGGTNMR DNWRSELYKY KVVKIEPLGV APTRCRRRVV ERRRRRRAVG      480
LGAVSIGFLG AAGSTMGAAS VTLTVQARQL LSGIVQQQSN LLRAPEPQQH LLKDTHWGIK      540
QLQARVLAVE HYLKDQQLLG IWGCSGKLIC CTTVPWNSSW SNKSQNEIWD NMTWLQWDKE      600
ISNYTQLIYS LIEESQNQQE KNEQELLALD KWASLWNWFD ISKWLWYIRI FIMIVGGLIG      660
LRIVFTVLSI INRVR                                                       675

SEQ ID NO: 18          moltype = AA   length = 675
FEATURE                Location/Qualifiers
REGION                 1..675
                       note = Description of Artificial Sequence: Synthetic
                        polypeptide
source                 1..675
                       mol_type = protein
                       organism = synthetic construct
SEQUENCE: 18
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE      120
TTEMTNCSFN MTTELRDRKK KVNALFYKLD IVQIGENSSS QYRLINCATS VITQACPKVT      180
FEPIPIHYCA PAGFAILKCK DKEFNGTGTC RNVSSVQCTH GIKPVVSTQL LLNGSLAEGQ      240
VIIRSENISD NAKTIIVQLN ESVPINCTRP NNNTVRGIHL GPGQTFFYTD IIGDIRQAHC      300
NVSESKWNKA LQEVVKQLRQ HWNKTIIFKS SSGGDLEITT HSFNCGGEFF YCNTSGLFNS      360
TWNIAGNRTN DTKSNETITL PCRIKQIVNV WQRVGQAIYA PPIAGVIRCN SNITGLLLVR      420
DGGATNNTDE TFRPGGGNMR DNWRSELYKY KVVKIEPLGV APTRCRRRVV ERRRRRRAVG      480
LGAVSIGFLG AAGSTMGAAS VTLTVQARQL LSGIVQQQSN LLRAPEPQQH LLKDTHWGIK      540
QLQARVLAVE HYLKDQQLLG IWGCSGKLIC CTTVPWNSSW SNKSQNEIWD NMTWLQWDKE      600
ISNYTQLIYS LIEESQNQQE KNEQELLALD KWASLWNWFD ISKWLWYIRI FIMIVGGLIG      660
LRIVFTVLSI INRVR                                                       675

SEQ ID NO: 19          moltype = AA   length = 630
FEATURE                Location/Qualifiers
REGION                 1..630
                       note = Description of Artificial Sequence: Synthetic
                        polypeptide
source                 1..630
                       mol_type = protein
                       organism = synthetic construct
SEQUENCE: 19
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE      120
TTEMTNCSFN MTTELRDRKK KVNALFYKLD IVQIGENSSS QYRLINCNTS VITQACPKVT      180
```

```
FEPIPIHYCA PAGFAILKCK DKEFNGTGTC RNVSSVQCTH GIKPVVSTQL LLNGSLAEGQ    240
VIIRSEDISD NAKTIIVQLN ESVPINCTRP NNNTVRGIHL GPGQTFFYTD IIGDIRQAHC    300
NVSESKWNKT LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGTNMR DNWRSELYKY KVVKIEPLGV APTRCRRRVV ERRRRRAVG     480
LGAVSIGFLG AAGSTMGAAS VTLTVQARQL LSGIVQQQSN LLRAPEPQQH LLKDTHWGIK    540
QLQARVLAVE HYLKDQQLLG IWGCSGKLIC CTTVPWNSSW SNKSQNEIWD NMTWLQWDKE    600
ISNYTQLIYS LIEESQNQQE KNEQELLALD                                    630
```

```
SEQ ID NO: 20             moltype = AA  length = 630
FEATURE                   Location/Qualifiers
REGION                    1..630
                          note = Description of Artificial Sequence: Synthetic
                           polypeptide
source                    1..630
                          mol_type = protein
                          organism = synthetic construct
SEQUENCE: 20
TENLWVTVYY GVPVWRDAET TLFCASDAKA YDTEMHNVWA THACVPTDPN PQEIDLENVT    60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEDISD NAKTIIVQLN ESVPINCTRP NNNTVRGIHL GPGQTFFYTD IIGDIRQAHC    300
NVSESKWNKT LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGNMR DNWRSELYKY KVVKIEPLGV APTRCRRRVV ERRRRRAVG      480
LGAVSIGFLG AAGSTMGAAS VTLTVQARQL LSGIVQQQSN LLRAPEPQQH LLKDTHWGIK    540
QLQARVLAVE HYLKDQQLLG IWGCSGKLIC CTTVPWNSSW SNKSQNEIWD NMTWLQWDKE    600
ISNYTQLIYS LIEESQNQQE KNEQELLALD                                    630
```

```
SEQ ID NO: 21             moltype = AA  length = 675
FEATURE                   Location/Qualifiers
REGION                    1..675
                          note = Description of Artificial Sequence: Synthetic
                           polypeptide
source                    1..675
                          mol_type = protein
                          organism = synthetic construct
SEQUENCE: 21
TENLWVTVYY GVPVWRDAET TLFCASDAKA YDTEMHNVWA THACVPTDPN PQEIDLENVT    60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEWISD NAKTIIVQLN ESVPINCTRP NNNTVRGIHL GPGQTFFYTD IIGDIRQAHC    300
NVSESKWNKA LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGTNMR DNWRSELYKY KVVKIEPLGV APTRCRRRVV ERRRRRAVG     480
LGAVSIGFLG AAGSTMGAAS VTLTVQARQL LSGIVQQQSN LLRAPEPQQH LLKDTHWGIK    540
QLQARVLAVE HYLKDQQLLG IWGCSGKLIC CTTVPWNSSW SNKSQNEIWD NMTWLQWDKE    600
ISNYTQLIYS LIEESQNQQE KNEQELLALD KWASLWNWFD ISKWLWYIRI FIMIVGGLIG    660
LRIVFTVLSI INRVR                                                    675
```

```
SEQ ID NO: 22             moltype = AA  length = 675
FEATURE                   Location/Qualifiers
REGION                    1..675
                          note = Description of Artificial Sequence: Synthetic
                           polypeptide
source                    1..675
                          mol_type = protein
                          organism = synthetic construct
SEQUENCE: 22
TENLWVTVYY GVPVWRDAET TLFCASDAKA YDTEMHNVWA THACVPTDPN PQEIDLENVT    60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEWISD NAKTIIVQLN ESVPINCTRP NNNTVRGIHL GPGQTFFYTD IIGDIRQAHC    300
NVSESKWNKA LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGGNMR DNWRSELYKY KVVKIEPLGV APTRCRRRVV ERRRRRAVG     480
LGAVSIGFLG AAGSTMGAAS VTLTVQARQL LSGIVQQQSN LLRAPEPQQH LLKDTHWGIK    540
QLQARVLAVE HYLKDQQLLG IWGCSGKLIC CTTVPWNSSW SNKSQNEIWD NMTWLQWDKE    600
ISNYTQLIYS LIEESQNQQE KNEQELLALD KWASLWNWFD ISKWLWYIRI FIMIVGGLIG    660
LRIVFTVLSI INRVR                                                    675
```

```
SEQ ID NO: 23             moltype = AA  length = 679
FEATURE                   Location/Qualifiers
REGION                    1..679
                          note = Description of Artificial Sequence: Synthetic
                           polypeptide
```

-continued

```
source                    1..679
                          mol_type = protein
                          organism = synthetic construct
SEQUENCE: 23
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE     120
TTEMTNCSFN MTTELRDRKK KVNALFYKLD IVQIGENSSS QYRLINCATS VITQACPKVT     180
FEPIPIHYCA PAGFAILKCK DKEFNGTGTC RNVSSVQCTH GIKPVVSTQL LLNGSLAEGQ     240
VIIRSENISD NAKTIIVQLN ESVPINCTRP NNNTVRGIHL GPGQTFFYTD IIGDIRQAHC     300
NVSESKWNKA LQEVVKQLRQ HWNKTIIFKS SSGGDLEITT HSFNCGGEFF YCNTSGLFNS     360
TWNIAGNRTN DTKSNETITL PCRIKQIVNV WQRVGQAIYA PPIAGVIRCN SNITGLLLVR     420
DGGATNNTDE TFRPGGTNMR DNWRSELYKY KVVKIEPLGV APTRCRRRVV GGGGGSGGGG     480
SAVGLGAVSI GFLGAAGSTM GAASVTLTVQ ARQLLSGIVQ QQSNLLRAPE PQQHLLKDTH     540
WGIKQLQARV LAVEHYLKDQ QLLGIWGCSG KLICCTTVPW NSSWSNKSQN EIWDNMTWLQ     600
WDKEISNYTQ LIYSLIEESQ NQQEKNEQEL LALDKWASLW NWFDISKWLW YIRIFIMIVG     660
GLIGLRIVFT VLSIINRVR                                                  679

SEQ ID NO: 24              moltype = AA   length = 679
FEATURE                   Location/Qualifiers
REGION                    1..679
                          note = Description of Artificial Sequence: Synthetic
                          polypeptide
source                    1..679
                          mol_type = protein
                          organism = synthetic construct
SEQUENCE: 24
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE     120
TTEMTNCSFN MTTELRDRKK KVNALFYKLD IVQIGENSSS QYRLINCATS VITQACPKVT     180
FEPIPIHYCA PAGFAILKCK DKEFNGTGTC RNVSSVQCTH GIKPVVSTQL LLNGSLAEGQ     240
VIIRSENISD NAKTIIVQLN ESVPINCTRP NNNTVRGIHL GPGQTFFYTD IIGDIRQAHC     300
NVSESKWNKA LQEVVKQLRQ HWNKTIIFKS SSGGDLEITT HSFNCGGEFF YCNTSGLFNS     360
TWNIAGNRTN DTKSNETITL PCRIKQIVNV WQRVGQAIYA PPIAGVIRCN SNITGLLLVR     420
DGGATNNTDE TFRPGGGNMR DNWRSELYKY KVVKIEPLGV APTRCRRRVV GGGGGSGGGG     480
SAVGLGAVSI GFLGAAGSTM GAASVTLTVQ ARQLLSGIVQ QQSNLLRAPE PQQHLLKDTH     540
WGIKQLQARV LAVEHYLKDQ QLLGIWGCSG KLICCTTVPW NSSWSNKSQN EIWDNMTWLQ     600
WDKEISNYTQ LIYSLIEESQ NQQEKNEQEL LALDKWASLW NWFDISKWLW YIRIFIMIVG     660
GLIGLRIVFT VLSIINRVR                                                  679

SEQ ID NO: 25              moltype = AA   length = 679
FEATURE                   Location/Qualifiers
REGION                    1..679
                          note = Description of Artificial Sequence: Synthetic
                          polypeptide
source                    1..679
                          mol_type = protein
                          organism = synthetic construct
SEQUENCE: 25
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE     120
TTEMTNCSFN MTTELRDRKK KVNALFYKLD IVQIGENSSS QYRLINCATS VITQACPKVT     180
FEPIPIHYCA PAGFAILKCK DKEFNGTGTC RNVSSVQCTH GIKPVVSTQL LLNGSLAEGQ     240
VIIRSEWISD NAKTIIVQLN ESVPINCTRP NNNTVRGIHL GPGQTFFYTD IIGDIRQAHC     300
NVSESKWNKA LQEVVKQLRQ HWNKTIIFKS SSGGDLEITT HSFNCGGEFF YCNTSGLFNS     360
TWNIAGNRTN DTKSNETITL PCRIKQIVNV WQRVGQAIYA PPIAGVIRCN SNITGLLLVR     420
DGGATNNTDE TFRPGGTNMR DNWRSELYKY KVVKIEPLGV APTRCRRRVV GGGGGSGGGG     480
SAVGLGAVSI GFLGAAGSTM GAASVTLTVQ ARQLLSGIVQ QQSNLLRAPE PQQHLLKDTH     540
WGIKQLQARV LAVEHYLKDQ QLLGIWGCSG KLICCTTVPW NSSWSNKSQN EIWDNMTWLQ     600
WDKEISNYTQ LIYSLIEESQ NQQEKNEQEL LALDKWASLW NWFDISKWLW YIRIFIMIVG     660
GLIGLRIVFT VLSIINRVR                                                  679

SEQ ID NO: 26              moltype = AA   length = 679
FEATURE                   Location/Qualifiers
REGION                    1..679
                          note = Description of Artificial Sequence: Synthetic
                          polypeptide
source                    1..679
                          mol_type = protein
                          organism = synthetic construct
SEQUENCE: 26
TENLWVTVYY GVPVWRDAET TLFCASDAKA YDTEMHNVWA THACVPTDPN PQEIDLENVT      60
EKFNMWKNNM VEQMHEDIIS LWDQSLKPCV KLTPLCVTLN CTAITNDTRG NETGINRTVE     120
TTEMTNCSFN MTTELRDRKK KVNALFYKLD IVQIGENSSS QYRLINCNTS VITQACPKVT     180
FEPIPIHYCA PAGFAILKCK DKEFNGTGTC RNVSSVQCTH GIKPVVSTQL LLNGSLAEGQ     240
VIIRSEWISD NAKTIIVQLN ESVPINCTRP NNNTVRGIHL GPGQTFFYTD IIGDIRQAHC     300
NVSESKWNKA LQEVVKQLRQ HWNKTIIFKS SSGGDLEITT HSFNCGGEFF YCNTSGLFNS     360
TWNIAGNRTN DTKSNETITL PCRIKQIVNV WQRVGQAIYA PPIAGVIRCN SNITGLLLVR     420
DGGATNNTDE TFRPGGGNMR DNWRSELYKY KVVKIEPLGV APTRCRRRVV GGGGGSGGGG     480
SAVGLGAVSI GFLGAAGSTM GAASVTLTVQ ARQLLSGIVQ QQSNLLRAPE PQQHLLKDTH     540
```

```
WGIKQLQARV LAVEHYLKDQ QLLGIWGCSG KLICCTTVPW NSSWSNKSQN EIWDNMTWLQ    600
WDKEISNYTQ LIYSLIEESQ NQQEKNEQEL LALDKWASLW NWFDISKWLW YIRIFIMIVG    660
GLIGLRIVFT VLSIINRVR                                                 679

SEQ ID NO: 27               moltype = AA   length = 630
FEATURE                     Location/Qualifiers
REGION                      1..630
                            note = Description of Artificial Sequence: Synthetic
                             polypeptide
source                      1..630
                            mol_type = protein
                            organism = synthetic construct
SEQUENCE: 27
TENLWVTVYY GVPVWRDAET TLFCASDAKA YDTEMHNVWA THACVPTDPN PQEIDLENVT    60
EKFNMWKNNM VEQMHEDIIS LWDQSLKPCV KLTPLCVTLN CTAITNDTRG NETGINRTVE    120
TTEMTNCSFN MTTELRDRKK KVNALFYKLD IVQIGENSSS QYRLINCNTS VITQACPKVT    180
FEPIPIHYCA PAGFAILKCK DKEFNGTGTC RNVSSVQCTH GIKPVVSTQL LLNGSLAEGQ    240
VIIRSEDISD NAKTIIVQLN ESVPINCTRP NNNTVRGIHL GPGQTFFYTD IIGDIRQAHC    300
NVSESKWNKA LQEVVKQLRQ HWNKTIIFKS SSGGDLEITT HSFNCGGEFF YCNTSGLFNS    360
TWNIAGNRTN DTKSNETITL PCRIKQIVNV WQRVGQAIYA PPIAGVIRCN SNITGLLLVR    420
DGGATNNTDE TFRPGGGNMR DNWRSELYKY KVVKIEPLGV APTRCRRRVV ERRRRRRAVG    480
LGAVSIGFLG AAGSTMGAAS VTLTVQARQL LSGIVQQQSN LLRAPEPQQH LLKDTHWGIK    540
QLQARVLAVE HYLKDQQLLG IWGCSGKLIC CTTVPWNSSW SNKSQNEIWD NMTWLQWDKE    600
ISNYTQLIYS LIEESQNQQE KNEQELLALD                                     630

SEQ ID NO: 28               moltype = AA   length = 626
FEATURE                     Location/Qualifiers
REGION                      1..626
                            note = Description of Artificial Sequence: Synthetic
                             polypeptide
source                      1..626
                            mol_type = protein
                            organism = synthetic construct
SEQUENCE: 28
AENLWVTVYY GVPVWKDAET TLFCASDAKA YETEKHNVWA THACVPTDPN PQEIHLENVT    60
EEFNMWKNNM VEQMHEDIIS LWDQSLKPCV KLTPLCVTLQ CTNVTNNITD DMRGELKNCS    120
FNATTELRNK RQKVYSLFYR LDIVPMGENS TNYRLINCNT SAITQACPKV SFEPIPIHYC    180
APAGFAILKC KDKKFNGTGP CPSVSTVQCT HGIKPVVSTQ LLLNGSLAEE EVIIRSENIT    240
NNAKNILVQL NTPVQINCTR PNNNTVKSIR IGPGQAFYYT GDIIGDIRQA HCNVSKATWN    300
ETLGKVVKQL RKHFGNNTII RFAQSSGGDL EVTTHSFNCG GEFFYCNTSG LFNSTWISNT    360
SVQGSNSTGS NDSITLPCRI KQIINMWQRI GQAMYAPPIQ GVIRCVSNIT GLILTRDGGS    420
TNSTTETFRP GGGDMRDNWR SELYKYKVVK IEPLGVAPTR CKRRVVGRRR RRRAVGIGAV    480
SLGFLGAAGS TMGAASMTLT VQARNLLSGI VQQQSNLLRA PEPQQHLLKD THWGIKQLQA    540
RVLAVEHYLR DQQLLGIWGC SGKLICCTNV PWNSSWSNRN LSEIWDNMTW LQWDKEISNY    600
TQIIYGLLEE SQNQQEKNEQ DLLALD                                         626

SEQ ID NO: 29               moltype = AA   length = 626
FEATURE                     Location/Qualifiers
REGION                      1..626
                            note = Description of Artificial Sequence: Synthetic
                             polypeptide
source                      1..626
                            mol_type = protein
                            organism = synthetic construct
SEQUENCE: 29
AENLWVTVYY GVPVWKDAET TLFCASDAKA YETEKHNVWA THACVPTDPN PQEIHLENVT    60
EEFNMWKNNM VEQMHEDIIS LWDQSLKPCV KLTPLCVTLQ CTNVTNNITD DMRGELKNCS    120
FNATTELRNK RQKVYSLFYR LDIVPMVDLW TNYRLINCNT SAITQACPKV SFEPIPIHYC    180
APAGFAILKC KDKKFNGTGP CPSVSTVQCT HGIKPVVSTQ LLLNGSLAEE EVIIRSENIT    240
NNAKNILVQL NTPVQINCTR PNNNTVKSIR IGPGQAFYYT GDIIGDIRQA HCNVSKATWN    300
ETLGKVVKQL RKHFGNNTII RFAQSSGGDL EVTTHSFNCG GEFFYCNTSG LFNSTWISNT    360
SVQGSNSTGS NDSITLPCRI KQIINMWQRI GQAMYAPPIQ GVIRCVSNIT GLILTRDGGS    420
TNSTTETFRP GGGDMRDNWR SELYKYKVVK IEPLGVAPTR CKRRVVGRRR RRRAVGIGAV    480
SLGFLGAAGS TMGAASMTLT VQARNLLSGI VQQQSNLLRA PEPQQHLLKD THWGIKQLQA    540
RVLAVEHYLR DQQLLGIWGC SGKLICCTNV PWNSSWSNRN LSEIWDNMTW LQWDKEISNY    600
TQIIYGLLEE SQNQQEKNEQ DLLALD                                         626

SEQ ID NO: 30               moltype = AA   length = 626
FEATURE                     Location/Qualifiers
REGION                      1..626
                            note = Description of Artificial Sequence: Synthetic
                             polypeptide
source                      1..626
                            mol_type = protein
                            organism = synthetic construct
SEQUENCE: 30
AENLWVTVYY GVPVWKDAET TLFCASDAKA YETEKHNVWA THACVPTDPN PQEIHLENVT    60
EEFNMWKNNM VEQMHEDIIS LWDQSLKPCV KLTPLCVTLQ CTNVTNNITD DMRGELKNCS    120
FNATTELRNK RQKVYSLFYR LDIVPMVDLW TNYRLINCNT SAITQACPKV SFEPIPIHYC    180
```

```
APAGFAILKC KDKKFNGTGP CQNVSTVQCT HGIKPVVSTQ LLLNGSLAEE EVIIRSENIT   240
NNAKNILVQL NTSVQINCTR PNNNTVKSIR IGPGQAFYYT GDIIGDIRQA HCNVSKATWN   300
ETLGKVVKQL RKHFGNNTII RFAQSSGGDL EVTTHSFNCG GEFFYCNTSG LFNSTWISNT   360
SVQGSNSTGS NDSITLPCRI KQIINMWQRI GQAMYAPPIQ GVIRCVSNIT GLILTRDGGS   420
TNSTTETFRP GGGDMRDNWR SELYKYKVVK IEPLGVAPTR CKRRVVGRRR RRRAVGIGAV   480
SLGFLGAAGS TMGAASMTLT VQARNLLSGI VQQQSNLLRA PEPQQHLLKD THWGIKQLQA   540
RVLAVEHYLR DQQLLGIWGC SGKLICCTNV PWNSSWSNRN LSEIWDNMTW LQWDKEISNY   600
TQIIYGLLEE SQNQQEKNEQ DLLALD                                        626
```

```
SEQ ID NO: 31              moltype = AA  length = 634
FEATURE                    Location/Qualifiers
REGION                     1..634
                           note = Description of Artificial Sequence: Synthetic
                            polypeptide
source                     1..634
                           mol_type = protein
                           organism = synthetic construct
SEQUENCE: 31
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS   120
FNATTELRNK RQKVYSLFYR LDIVPMVDLW TNYRLINCNT SAITQACPKV SFEPIPIHYC   180
APAGFAILKC KDKKFNGTGP CQNVSTVQCT HGIKPVVSTQ LLLNGSLAEE EVIIRSENIT   240
NNAKNILVQL NTSVQINCTR PNNNTVKSIR IGPGQAFYYT GDIIGDIRQA HCNVSKATWN   300
ETLGKVVKQL RKHFGNNTII RFAQSSGGDL EVTTHSFNCG GEFFYCNTSG LFNSTWISNT   360
SVQGSNSTGS NDSITLPCRI KQIINMWQRI GQAMYAPPIQ GVIRCVSNIT GLILTRDGGS   420
TNSTTETFRP GGTDMRDNWR SELYKYKVVK IEPLGVAPTR CKRRVVGSHS GSGGSGSGGH   480
AAVGIGAVSL GFLGAAGSTM GAASMTLTVQ ARNLLSGIVQ QQSNLLRAPE PQQHLLKDTH   540
WGIKQLQARV LAVEHYLRDQ QLLGIWGCSG KLICCTNVPW NSSWSNRNLS EIWDNMTWLQ   600
WDKEISNYTQ IIYGLLEESQ NQQEKNEQDL LALD                               634
```

```
SEQ ID NO: 32              moltype = AA  length = 634
FEATURE                    Location/Qualifiers
REGION                     1..634
                           note = Description of Artificial Sequence: Synthetic
                            polypeptide
source                     1..634
                           mol_type = protein
                           organism = synthetic construct
SEQUENCE: 32
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS   120
FNATTELRNK RQKVYSLFYR LDIVPMVDLW TNYRLINCNT SAITQACPKV SFEPIPIHYC   180
APAGFAILKC KDKKFNGTGP CQNVSTVQCT HGIKPVVSTQ LLLNGSLAEE EVIIRSENIT   240
NNAKNILVQL NTSVQINCTR PNNNTVKSIR IGPGQAFYYT GDIIGDIRQA HCNVSKATWN   300
ETLGKVVKQL RKHFGNNTII RFAQSSGGDL EVTTHSFNCG GEFFYCNTSG LFNSTWISNT   360
SVQGSNSTGS NDSITLPCRI KQIINMWQRI GQAMYAPPIQ GVIRCVSNIT GLILTRDGGS   420
TNSTTETFRP GGGDMRDNWR SELYKYKVVK IEPLGVAPTR CKRRVVGSHS GSGGSGSGGH   480
AAVGIGAVSL GFLGAAGSTM GAASMTLTVQ ARNLLSGIVQ QQSNLLRAPE PQQHLLKDTH   540
WGIKQLQARV LAVEHYLRDQ QLLGIWGCSG KLICCTNVPW NSSWSNRNLS EIWDNMTWLQ   600
WDKEISNYTQ IIYGLLEESQ NQQEKNEQDL LALD                               634
```

```
SEQ ID NO: 33              moltype = AA  length = 679
FEATURE                    Location/Qualifiers
REGION                     1..679
                           note = Description of Artificial Sequence: Synthetic
                            polypeptide
source                     1..679
                           mol_type = protein
                           organism = synthetic construct
SEQUENCE: 33
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS   120
FNATTELRNK RQKVYSLFYR LDIVPMVDLW TNYRLINCNT SAITQACPKV SFEPIPIHYC   180
APAGFAILKC KDKKFNGTGP CQNVSTVQCT HGIKPVVSTQ LLLNGSLAEE EVIIRSENIT   240
NNAKNILVQL NTSVQINCTR PNNNTVKSIR IGPGQAFYYT GDIIGDIRQA HCNVSKATWN   300
ETLGKVVKQL RKHFGNNTII RFAQSSGGDL EVTTHSFNCG GEFFYCNTSG LFNSTWISNT   360
SVQGSNSTGS NDSITLPCRI KQIINMWQRI GQAMYAPPIQ GVIRCVSNIT GLILTRDGGS   420
TNSTTETFRP GGTDMRDNWR SELYKYKVVK IEPLGVAPTR CKRRVVGSHS GSGGSGSGGH   480
AAVGIGAVSL GFLGAAGSTM GAASMTLTVQ ARNLLSGIVQ QQSNLLRAPE PQQHLLKDTH   540
WGIKQLQARV LAVEHYLRDQ QLLGIWGCSG KLICCTNVPW NSSWSNRNLS EIWDNMTWLQ   600
WDKEISNYTQ IIYGLLEESQ NQQEKNEQDL LALDKWASLW NWFDISNWLW YIKIFIMIVG   660
GLIGLRIVFA VLSVIHRVR                                                679
```

```
SEQ ID NO: 34              moltype = AA  length = 634
FEATURE                    Location/Qualifiers
REGION                     1..634
                           note = Description of Artificial Sequence: Synthetic
                            polypeptide
source                     1..634
```

```
                              mol_type = protein
                              organism = synthetic construct
SEQUENCE: 34
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNATTELRNK RQKVYSLFYR LDIVPMVDLW TNYRLINCNT SAITQACPKV SFEPIPIHYC  180
APAGFAILKC KDKKFNGTGP CQNVSTVQCT HGIKPVVSTQ LLLNGSLAEE EVIIRSENIT  240
NNAKNILVQL NTSVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGTDMRDNWR SELYKYKVVK IEPLGVAPTR CKRRVVGSHS GSGGSGSGGH  480
AAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                             634

SEQ ID NO: 35              moltype = AA  length = 679
FEATURE                    Location/Qualifiers
REGION                     1..679
                           note = Description of Artificial Sequence: Synthetic
                            polypeptide
source                     1..679
                           mol_type = protein
                           organism = synthetic construct
SEQUENCE: 35
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNATTELRNK RQKVYSLFYR LDIVPMVDLW TNYRLINCNT SAITQACPKV SFEPIPIHYC  180
APAGFAILKC KDKKFNGTGP CQNVSTVQCT HGIKPVVSTQ LLLNGSLAEE EVIIRSENIT  240
NNAKNILVQL NTSVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGGDMRDNWR SELYKYKVVK IEPLGVAPTR CKRRVVGSHS GSGGSGSGGH  480
AAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALDKWASLW NWFDISNWLW YIKIFIMIVG  660
GLIGLRIVFA VLSVIHRVR                                              679

SEQ ID NO: 36              moltype = AA  length = 679
FEATURE                    Location/Qualifiers
REGION                     1..679
                           note = Description of Artificial Sequence: Synthetic
                            polypeptide
source                     1..679
                           mol_type = protein
                           organism = synthetic construct
SEQUENCE: 36
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNATTELRNK RQKVYSLFYR LDIVPMVDLW TNYRLINCNT SAITQACPKV SFEPIPIHYC  180
APAGFAILKC KDKKFNGTGP CQNVSTVQCT HGIKPVVSTQ LLLNGSLAEE EVIIRSENIT  240
NNAKNILVQL NTSVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGGDMRDNWR SELYKYKVVK IEPLGVAPTR CKRRVVGSHS GSGGSGSGGH  480
AAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALDKWASLW NWFDISNWLW YIKIFIMIVG  660
GLIGLRIVFA VLSVIHRVR                                              679

SEQ ID NO: 37              moltype = AA  length = 634
FEATURE                    Location/Qualifiers
REGION                     1..634
                           note = Description of Artificial Sequence: Synthetic
                            polypeptide
source                     1..634
                           mol_type = protein
                           organism = synthetic construct
SEQUENCE: 37
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNATTELRNK RQKVYSLFYR LDIVPMVDLW TNYRLINCNT SAITQACPKV SFEPIPIHYC  180
APAGFAILKC KDKKFNGTGP CQNVSTVQCT HGIKPVVSTQ LLLNGSLAEE EVIIRSENIT  240
NNAKNILVQL NTSVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGGDMRDNWR SELYKYKVVK IEPLGVAPTR CKRRVVGSHS GSGGSGSGGH  480
AAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                             634
```

-continued

```
SEQ ID NO: 38               moltype = AA  length = 679
FEATURE                     Location/Qualifiers
REGION                      1..679
                            note = Description of Artificial Sequence: Synthetic
                             polypeptide
source                      1..679
                            mol_type = protein
                            organism = synthetic construct
SEQUENCE: 38
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNATTELRNK RQKVYSLFYR LDIVPMVDLW TNYRLINCNT SAITQACPKV SFEPIPIHYC  180
APAGFAILKC KDKKFNGTGP CQNVSTVQCT HGIKPVVSTQ LLLNGSLAEE EVIIRSENIT  240
NNAKNILVQL NTSVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGTDMRDNWR SELYKYKVVK IEPLGVAPTR CKRRVVGSHS GSGGSGSGGH  480
AAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALDKWASLW NWFDISNWLW YIKIFIMIVG  660
GLIGLRIVFA VLSVIHRVR                                              679

SEQ ID NO: 39               moltype = AA  length = 679
FEATURE                     Location/Qualifiers
REGION                      1..679
                            note = Description of Artificial Sequence: Synthetic
                             polypeptide
source                      1..679
                            mol_type = protein
                            organism = synthetic construct
SEQUENCE: 39
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNATTELRNK RQKVYSLFYR LDIVPMVDLW TNYRLINCNT SAITQACPKV SFEPIPIHYC  180
APAGFAILKC KDKKFNGTGP CPSVSTVQCT HGIKPVVSTQ LLLNGSLAEE EVIIRSENIT  240
NNAKNILVQL NTPVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGGDMRDNWR SELYKYKVVK IEPLGVAPTR CKRRVVGSHS GSGGSGSGGH  480
AAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALDKWASLW NWFDISNWLW YIKIFIMIVG  660
GLIGLRIVFA VLSVIHRVR                                              679

SEQ ID NO: 40               moltype = AA  length = 626
FEATURE                     Location/Qualifiers
REGION                      1..626
                            note = Description of Artificial Sequence: Synthetic
                             polypeptide
source                      1..626
                            mol_type = protein
                            organism = synthetic construct
SEQUENCE: 40
AENLWVTVYY GVPVWKDAET TLFCASDAKA YETEKHNVWA THACVSTDPN PQEIHLENVT   60
EEFNMWKNNM VEQMHEDIIS LWDQSLKPCV KLTPLCVGLQ CTNVTNNITD DMRGELKNCS  120
FNATTELRNK RQKVYSLFYR LDIVPMVDLW TNYRLISCNT SAITQACPKV SFEPIPIHYC  180
APAGFAILKC KDKKFNGTGP CPSVSTVQCT HGIKPVVSTQ LLLNGSLAEE EVIIRSENIT  240
NNAKNILVQL NTPVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGGDMRDNWR SELYKYKVVK IEPLGVAPTR CKRRVVGRRR RRRAVGIGAV  480
SLGFLGAAGS TMGAASMTLT VQARNLLSGI VQQQSNLLRA PEPQQHLLKD THWGIKQLQA  540
RVLAVEHYLR DQQLLGIWGC SGKLICCTNV PWNSSWSNRN LSEIWDNMTW LQWDKEISNY  600
TQIIYGLLEE SQNQQEKNEQ DLLALD                                      626

SEQ ID NO: 41               moltype = AA  length = 626
FEATURE                     Location/Qualifiers
REGION                      1..626
                            note = Description of Artificial Sequence: Synthetic
                             polypeptide
source                      1..626
                            mol_type = protein
                            organism = synthetic construct
SEQUENCE: 41
AENLWVTVYY GVPVWKDAET TLFCASDAKA YETEKHNVWA THACVSTDPN PQEIHLENVT   60
EEFNMWKNNM VEQMHEDIIS LWDQSLKPCV KLTPLCVGLQ CTNVTNNITD DMRGELKNCS  120
FNATTELRNK RQKVYSLFYR LDIVPMVDLW TNYRLISCNT SAITQACPKV SFEPIPIHYC  180
APAGFAILKC KDKKFNGTGP CQNVSTVQCT HGIKPVVSTQ LLLNGSLAEE EVIIRSENIT  240
```

```
NNAKNILVQL NTSVQINCTR PNNNTVKSIR IGPGQAFYYT GDIIGDIRQA HCNVSKATWN    300
ETLGKVVKQL RKHFGNNTII RFAQSSGGDL EVTTHSFNCG GEFFYCNTSG LFNSTWISNT    360
SVQGSNSTGS NDSITLPCRI KQIINMWQRI GQAMYAPPIQ GVIRCVSNIT GLILTRDGGS    420
TNSTTETFRP GGGDMRDNWR SELYKYKVVK IEPLGVAPTR CKRRVVGRRR RRRAVGIGAV    480
SLGFLGAAGS TMGAASMTLT VQARNLLSGI VQQQSNLLRA PEPQQHLLKD THWGIKQLQA    540
RVLAVEHYLR DQQLLGIWGC SGKLICCTNV PWNSSWSNRN LSEIWDNMTW LQWDKEISNY    600
TQIIYGLLEE SQNQQEKNEQ DLLALD                                        626
```

SEQ ID NO: 42            moltype = AA  length = 626
FEATURE                  Location/Qualifiers
REGION                   1..626
                         note = Description of Artificial Sequence: Synthetic
                          polypeptide
source                   1..626
                         mol_type = protein
                         organism = synthetic construct
SEQUENCE: 42

```
AENLWVTVYY GVPVWKDAET TLFCASDAKA YETEKHNVWA THACVSTDPN PQEIHLENVT    60
EEFNMWKNNM VEQMHEDIIS LWDQSLKPCV KLTPLCVGLQ CTNVTNNITD DMRGELKNCS    120
FNATTELRNK RQKVYSLFYR LDIVPMVDLW TNYRLISCNT SAITQACPKV SFEPIPIHYC    180
APAGFAILKC KDKKFNGTGP CQNVSTVQCT HGIKPVVSTQ LLLNGSLAEE EVIIRSENIT    240
NNAKNILVQL NTSVQINCTR PNNNTVKSIR IGPGQAFYYT GDIIGDIRQA HCNVSKATWN    300
ETLGKVVKQL RKHFGNNTII RFAQSSGGDL EVTTHSFNCG GEFFYCNTSG LFNSTWISNT    360
SVQGSNSTGS NDSITLPCRI KQIINMWQRI GQAMYAPPIQ GVIRCVSNIT GLILTRDGGS    420
TNSTTETFRP GGTDMRDNWR SELYKYKVVK IEPLGVAPTR CKRRVVGRRR RRRAVGIGAV    480
SLGFLGAAGS TMGAASMTLT VQARNLLSGI VQQQSNLLRA PEPQQHLLKD THWGIKQLQA    540
RVLAVEHYLR DQQLLGIWGC SGKLICCTNV PWNSSWSNRN LSEIWDNMTW LQWDKEISNY    600
TQIIYGLLEE SQNQQEKNEQ DLLALD                                        626
```

SEQ ID NO: 43            moltype = AA  length = 679
FEATURE                  Location/Qualifiers
REGION                   1..679
                         note = Description of Artificial Sequence: Synthetic
                          polypeptide
source                   1..679
                         mol_type = protein
                         organism = synthetic construct
SEQUENCE: 43

```
AENLWVTVYY GVPVWKDAET TLFCASDAKA YETEKHNVWA THACVSTDPN PQEIHLENVT    60
EEFNMWKNNM VEQMHEDIIS LWDQSLKPCV KLTPLCVGLQ CTNVTNNITD DMRGELKNCS    120
FNATTELRNK RQKVYSLFYR LDIVPMVDLW TNYRLISCNT SAITQACPKV SFEPIPIHYC    180
APAGFAILKC KDKKFNGTGP CQNVSTVQCT HGIKPVVSTQ LLLNGSLAEE EVIIRSENIT    240
NNAKNILVQL NTSVQINCTR PNNNTVKSIR IGPGQAFYYT GDIIGDIRQA HCNVSKATWN    300
ETLGKVVKQL RKHFGNNTII RFAQSSGGDL EVTTHSFNCG GEFFYCNTSG LFNSTWISNT    360
SVQGSNSTGS NDSITLPCRI KQIINMWQRI GQAMYAPPIQ GVIRCVSNIT GLILTRDGGS    420
TNSTTETFRP GGTDMRDNWR SELYKYKVVK IEPLGVAPTR CKRRVVGSHS GSGGGSGSGGH    480
AAVGIGAVSL GFLGAAGSTM GAASMTLTVQ ARNLLSGIVQ QQSNLLRAPE PQQHLLKDTH    540
WGIKQLQARV LAVEHYLRDQ QLLGIWGCSG KLICCTNVPW NSSWSNRNLS EIWDNMTWLQ    600
WDKEISNYTQ IIYGLLEESQ NQQEKNEQDL LALDKWASLW NWFDISNWLW YIKIFIMIVG    660
GLIGLRIVFA VLSVIHRVR                                                679
```

SEQ ID NO: 44            moltype = AA  length = 679
FEATURE                  Location/Qualifiers
REGION                   1..679
                         note = Description of Artificial Sequence: Synthetic
                          polypeptide
source                   1..679
                         mol_type = protein
                         organism = synthetic construct
SEQUENCE: 44

```
AENLWVTVYY GVPVWKDAET TLFCASDAKA YETEKHNVWA THACVSTDPN PQEIHLENVT    60
EEFNMWKNNM VEQMHEDIIS LWDQSLKPCV KLTPLCVGLQ CTNVTNNITD DMRGELKNCS    120
FNATTELRNK RQKVYSLFYR LDIVPMVDLW TNYRLISCNT SAITQACPKV SFEPIPIHYC    180
APAGFAILKC KDKKFNGTGP CQNVSTVQCT HGIKPVVSTQ LLLNGSLAEE EVIIRSENIT    240
NNAKNILVQL NTSVQINCTR PNNNTVKSIR IGPGQAFYYT GDIIGDIRQA HCNVSKATWN    300
ETLGKVVKQL RKHFGNNTII RFAQSSGGDL EVTTHSFNCG GEFFYCNTSG LFNSTWISNT    360
SVQGSNSTGS NDSITLPCRI KQIINMWQRI GQAMYAPPIQ GVIRCVSNIT GLILTRDGGS    420
TNSTTETFRP GGGDMRDNWR SELYKYKVVK IEPLGVAPTR CKRRVVGSHS GSGGGSGSGGH    480
AAVGIGAVSL GFLGAAGSTM GAASMTLTVQ ARNLLSGIVQ QQSNLLRAPE PQQHLLKDTH    540
WGIKQLQARV LAVEHYLRDQ QLLGIWGCSG KLICCTNVPW NSSWSNRNLS EIWDNMTWLQ    600
WDKEISNYTQ IIYGLLEESQ NQQEKNEQDL LALDKWASLW NWFDISNWLW YIKIFIMIVG    660
GLIGLRIVFA VLSVIHRVR                                                679
```

SEQ ID NO: 45            moltype = AA  length = 679
FEATURE                  Location/Qualifiers
REGION                   1..679
                         note = Description of Artificial Sequence: Synthetic
                          polypeptide
source                   1..679

```
                         mol_type = protein
                         organism = synthetic construct
SEQUENCE: 45
AENLWVTVYY GVPVWKDAET TLFCASDAKA YETEKHNVWA THACVSTDPN PQEIHLENVT   60
EEFNMWKNNM VEQMHEDIIS LWDQSLKPCV KLTPLCVGLQ CTNVTNNITD DMRGELKNCS  120
FNATTELRNK RQKVYSLFYR LDIVPMVDLW TNYRLISCNT SAITQACPKV SFEPIPIHYC  180
APAGFAILKC KDKKFNGTGP CPSVSTVQCT HGIKPVVSTQ LLLNGSLAEE EVIIRSENIT  240
NNAKNILVQL NTPVQINCTR PNNNTVKSIR IGPGQAFYYT GDIIGDIRQA HCNVSKATWN  300
ETLGKVVKQL RKHFGNNTII RFAQSSGGDL EVTTHSFNCG GEFFYCNTSG LFNSTWISNT  360
SVQGSNSTGS NDSITLPCRI KQIINMWQRI GQAMYAPPIQ GVIRCVSNIT GLILTRDGGS  420
TNSTTETFRP GGGDMRDNWR SELYKYKVVK IEPLGVAPTR CKRRVVGSHS GSGGSGSGGH  480
AAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALDKWASLW NWFDISNWLW YIKIFIMIVG  660
GLIGLRIVFA VLSVIHRVR                                              679

SEQ ID NO: 46          moltype = AA  length = 687
FEATURE                Location/Qualifiers
REGION                 1..687
                       note = Description of Artificial Sequence: Synthetic
                        polypeptide
source                 1..687
                       mol_type = protein
                       organism = synthetic construct
SEQUENCE: 46
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCDTSA ITQACPKVSF  180
EPIPIHYCAP AGFAILKCKD KKFNGTGPCQ NVSTVQCTHG IKPVVSTQLL LNGSLAEEEV  240
IIRSENITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG TDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                     687

SEQ ID NO: 47          moltype = AA  length = 687
FEATURE                Location/Qualifiers
REGION                 1..687
                       note = Description of Artificial Sequence: Synthetic
                        polypeptide
source                 1..687
                       mol_type = protein
                       organism = synthetic construct
SEQUENCE: 47
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCDTSA ITQACPKVSF  180
EPIPIHYCAP AGFAILKCKD KKFNGTGPCQ NVSTVQCTHG IKPVVSTQLL LNGSLAEEEV  240
IIRSENITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                     687

SEQ ID NO: 48          moltype = AA  length = 687
FEATURE                Location/Qualifiers
REGION                 1..687
                       note = Description of Artificial Sequence: Synthetic
                        polypeptide
source                 1..687
                       mol_type = protein
                       organism = synthetic construct
SEQUENCE: 48
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSEQITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG TDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
```

```
WDNMTWLQWD KEISNYTQII YGLLEESQNQ QEKNEQDLLA LDKWASLWNW FDISNWLWYI  660
KIFIMIVGGL IGLRIVFAVL SVIHRVR                                       687

SEQ ID NO: 49            moltype = AA  length = 687
FEATURE                  Location/Qualifiers
REGION                   1..687
                         note = Description of Artificial Sequence: Synthetic
                          polypeptide
source                   1..687
                         mol_type = protein
                         organism = synthetic construct
SEQUENCE: 49
AENLWVTVYY GVPVWKDAET TLFCASDAKA YETEKHNVWA THACVPTDPN PQEIHLENVT  60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSEQITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                       687

SEQ ID NO: 50            moltype = AA  length = 687
FEATURE                  Location/Qualifiers
REGION                   1..687
                         note = Description of Artificial Sequence: Synthetic
                          polypeptide
source                   1..687
                         mol_type = protein
                         organism = synthetic construct
SEQUENCE: 50
AENLWVTVYY GVPVWKDAET TLFCASDAKA YETEKHNVWA THACVPTDPN PQEIHLENVT  60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSEWITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG TDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                       687

SEQ ID NO: 51            moltype = AA  length = 687
FEATURE                  Location/Qualifiers
REGION                   1..687
                         note = Description of Artificial Sequence: Synthetic
                          polypeptide
source                   1..687
                         mol_type = protein
                         organism = synthetic construct
SEQUENCE: 51
AENLWVTVYY GVPVWKDAET TLFCASDAKA YETEKHNVWA THACVPTDPN PQEIHLENVT  60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSEWITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                       687

SEQ ID NO: 52            moltype = AA  length = 687
FEATURE                  Location/Qualifiers
REGION                   1..687
                         note = Description of Artificial Sequence: Synthetic
                          polypeptide
source                   1..687
                         mol_type = protein
                         organism = synthetic construct
SEQUENCE: 52
AENLWVTVYY GVPVWKDAET TLFCASDAKA YETEKHNVWA THACVPTDPN PQEIHLENVT  60
```

```
EEFNMWKNNM VEQMHEDIIS LWDQSLKPCV KLTPLCVTLQ CTNVTNNITD DMRGELKNCS   120
FNMTTELRDK KQKVYSLFYR LDVVQINENQ GNRSNNSNKE YRLINCNTSA ITQACPKVSF   180
EPIPIHYCAP AGFAILKCKD KKFNGTGPCP SVSTVQCTHG IKPVVSTQLL LNGSLAEEEV   240
IIRSENITNN AKNILVQLNT PVQINCTRPN NNTVKSIRIG PGQAFYYTGD IIGDIRQAHC   300
NVSKATWNET LGKVVKQLRK HFGNNTIIRF AQSSGGDLEV TTHSFNCGGE FFYCNTSGLF   360
NSTWISNTSV QGSNSTGSND SITLPCRIKQ IINMWQRIGQ AMYAPPIQGV IRCVSNITGL   420
ILTRDGGSTN STTETFRPGG TDMRDNWRSE LYKYKVVKIE PLGVAPTRCK RRVVGSHSGS   480
GGSGSGGHAA VGIGAVSLGF LGAAGSTMGA ASMTLTVQAR NLLSGIVQQQ SNLLRAPEPQ   540
QHLLKDTHWG IKQLQARVLA VEHYLRDQQL LGIWGCSGKL ICCTNVPWNS SWSNRNLSEI   600
WDNMTWLQWD KEISNYTQII YGLLEESQNQ QEKNEQDLLA LDKWASLWNW FDISNWLWYI   660
KIFIMIVGGL IGLRIVFAVL SVIHRVR                                       687
```

SEQ ID NO: 53               moltype = AA  length = 687
FEATURE                     Location/Qualifiers
REGION                      1..687
                            note = Description of Artificial Sequence: Synthetic
                             polypeptide
source                      1..687
                            mol_type = protein
                            organism = synthetic construct
SEQUENCE: 53

```
AENLWVTVYY GVPVWKDAET TLFCASDAKA YETEKHNVWA THACVPTDPN PQEIHLENVT    60
EEFNMWKNNM VEQMHEDIIS LWDQSLKPCV KLTPLCVTLQ CTNVTNNITD DMRGELKNCS   120
FNMTTELRDK KQKVYSLFYR LDVVQINENQ GNRSNNSNKE YRLINCNTSA ITQACPKVSF   180
EPIPIHYCAP AGFAILKCKD KKFNGTGPCP SVSTVQCTHG IKPVVSTQLL LNGSLAEEEV   240
IIRSENITNN AKNILVQLNT PVQINCTRPN NNTVKSIRIG PGQAFYYTGD IIGDIRQAHC   300
NVSKATWNET LGKVVKQLRK HFGNNTIIRF AQSSGGDLEV TTHSFNCGGE FFYCNTSGLF   360
NSTWISNTSV QGSNSTGSND SITLPCRIKQ IINMWQRIGQ AMYAPPIQGV IRCVSNITGL   420
ILTRDGGSTN STTETFRPGG GDMRDNWRSE LYKYKVVKIE PLGVAPTRCK RRVVGSHSGS   480
GGSGSGGHAA VGIGAVSLGF LGAAGSTMGA ASMTLTVQAR NLLSGIVQQQ SNLLRAPEPQ   540
QHLLKDTHWG IKQLQARVLA VEHYLRDQQL LGIWGCSGKL ICCTNVPWNS SWSNRNLSEI   600
WDNMTWLQWD KEISNYTQII YGLLEESQNQ QEKNEQDLLA LDKWASLWNW FDISNWLWYI   660
KIFIMIVGGL IGLRIVFAVL SVIHRVR                                       687
```

SEQ ID NO: 54               moltype = AA  length = 687
FEATURE                     Location/Qualifiers
REGION                      1..687
                            note = Description of Artificial Sequence: Synthetic
                             polypeptide
source                      1..687
                            mol_type = protein
                            organism = synthetic construct
SEQUENCE: 54

```
AENLWVTVYY GVPVWKDAET TLFCASDAKA YETEKHNVWA THACVPTDPN PQEIHLENVT    60
EEFNMWKNNM VEQMHEDIIS LWDQSLKPCV KLTPLCVTLQ CTNVTNNITD DMRGELKNCS   120
FNMTTELRDK KQKVYSLFYR LDVVQINENQ GNRSNNSNKE YRLINCNTSA ITQACPKVSF   180
EPIPIHYCAP AGFAILKCKD KKFNGTGPCQ NVSTVQCTHG IKPVVSTQLL LNGSLAEEEV   240
IIRSENITNN AKNILVQLNT SVQINCTRPN NNTVKSIRIG PGQAFYYTGD IIGDIRQAHC   300
NVSKATWNET LGKVVKQLRK HFGNNTIIRF AQSSGGDLEV TTHSFNCGGE FFYCNTSGLF   360
NSTWISNTSV QGSNSTGSND SITLPCRIKQ IINMWQRIGQ AMYAPPIQGV IRCVSNITGL   420
ILTRDGGSTN STTETFRPGG GDMRDNWRSE LYKYKVVKIE PLGVAPTRCK RRVVGSHSGS   480
GGSGSGGHAA VGIGAVSLGF LGAAGSTMGA ASMTLTVQAR NLLSGIVQQQ SNLLRAPEPQ   540
QHLLKDTHWG IKQLQARVLA VEHYLRDQQL LGIWGCSGKL ICCTNVPWNS SWSNRNLSEI   600
WDNMTWLQWD KEISNYTQII YGLLEESQNQ QEKNEQDLLA LDKWASLWNW FDISNWLWYI   660
KIFIMIVGGL IGLRIVFAVL SVIHRVR                                       687
```

SEQ ID NO: 55               moltype = AA  length = 687
FEATURE                     Location/Qualifiers
REGION                      1..687
                            note = Description of Artificial Sequence: Synthetic
                             polypeptide
source                      1..687
                            mol_type = protein
                            organism = synthetic construct
SEQUENCE: 55

```
AENLWVTVYY GVPVWKDAET TLFCASDAKA YETEKHNVWA THACVPTDPN PQEIHLENVT    60
EEFNMWKNNM VEQMHEDIIS LWDQSLKPCV KLTPLCVTLQ CTNVTNNITD DMRGELKNCS   120
FNMTTELRDK KQKVYSLFYR LDVVQINENQ GNRSNNSNKE YRLINCNTSA ITQACPKVSF   180
EPIPIHYCAP AGFAILKCKD KKFNGTGPCQ NVSTVQCTHG IKPVVSTQLL LNGSLAEEEV   240
IIRSENITNN AKNILVQLNT SVQINCTRPN NNTVKSIRIG PGQAFYYTGD IIGDIRQAHC   300
NVSKATWNET LGKVVKQLRK HFGNNTIIRF AQSSGGDLEV TTHSFNCGGE FFYCNTSGLF   360
NSTWISNTSV QGSNSTGSND SITLPCRIKQ IINMWQRIGQ AMYAPPIQGV IRCVSNITGL   420
ILTRDGGSTN STTETFRPGG TDMRDNWRSE LYKYKVVKIE PLGVAPTRCK RRVVGSHSGS   480
GGSGSGGHAA VGIGAVSLGF LGAAGSTMGA ASMTLTVQAR NLLSGIVQQQ SNLLRAPEPQ   540
QHLLKDTHWG IKQLQARVLA VEHYLRDQQL LGIWGCSGKL ICCTNVPWNS SWSNRNLSEI   600
WDNMTWLQWD KEISNYTQII YGLLEESQNQ QEKNEQDLLA LDKWASLWNW FDISNWLWYI   660
KIFIMIVGGL IGLRIVFAVL SVIHRVR                                       687
```

SEQ ID NO: 56               moltype = AA  length = 694

```
FEATURE                 Location/Qualifiers
REGION                  1..694
                        note = Description of Artificial Sequence: Synthetic
                         polypeptide
source                  1..694
                        mol_type = protein
                        organism = synthetic construct
SEQUENCE: 56
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSENITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVRQGY SPLS                             694

SEQ ID NO: 57           moltype = AA  length = 694
FEATURE                 Location/Qualifiers
REGION                  1..694
                        note = Description of Artificial Sequence: Synthetic
                         polypeptide
source                  1..694
                        mol_type = protein
                        organism = synthetic construct
SEQUENCE: 57
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSEQITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVRQGY SPLS                             694

SEQ ID NO: 58           moltype = AA  length = 694
FEATURE                 Location/Qualifiers
REGION                  1..694
                        note = Description of Artificial Sequence: Synthetic
                         polypeptide
source                  1..694
                        mol_type = protein
                        organism = synthetic construct
SEQUENCE: 58
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSEQITNN AKNILVQLNT PVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVRQGY SPLS                             694

SEQ ID NO: 59           moltype = AA  length = 687
FEATURE                 Location/Qualifiers
REGION                  1..687
                        note = Description of Artificial Sequence: Synthetic
                         polypeptide
source                  1..687
                        mol_type = protein
                        organism = synthetic construct
SEQUENCE: 59
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYTPNLTS NMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPN NNTVKSIRIG PGQAFYYTGD IIGDIRQAHC  300
```

```
NVSKATWNET LGKVVKQLRK HFGNNTIIRF AQSSGGDLEV TTHSFNCGGE FFYCNTSGLF   360
NSTWISNTSV QGSNSTGSND SITLPCRIKQ IINMWQRIGQ AMYAPPIQGV IRCVSNITGL   420
ILTRDGGSTN STTETFRPGG GDMRDNWRSE LYKYKVVKIE PLGVAPTRCK RRVVGSHSGS   480
GGSGSGGHAA VGIGAVSLGF LGAAGSTMGA ASMTLTVQAR NLLSGIVQQQ SNLLRAPEPQ   540
QHLLKDTHWG IKQLQARVLA VEHYLRDQQL LGIWGCSGKL ICCTNVPWNS SWSNRNLSEI   600
WDNMTWLQWD KEISNYTQII YGLLEESQNQ QEKNEQDLLA LDKWASLWNW FDISNWLWYI   660
KIFIMIVGGL IGLRIVFAVL SVIHRVR                                       687

SEQ ID NO: 60             moltype = AA   length = 687
FEATURE                   Location/Qualifiers
REGION                    1..687
                          note = Description of Artificial Sequence: Synthetic
                           polypeptide
source                    1..687
                          mol_type = protein
                          organism = synthetic construct
SEQUENCE: 60
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYTPNLTS MMRGELKNCS   120
FNMTTELRDK KQKVYSLFYR LDVVQINENQ GNRSNNSNKE YRLINCNTSA ITQACPKVSF   180
EPIPIHYCAP AGFAILKCKD KKFNGTGPCQ NVSTVQCTHG IKPVVSTQLL LNGSLAEEEV   240
IIRSENITNN AKNILVQLNT SVQINCTRPN NNTVKSIRIG PGQAFYYTGD IIGDIRMAHC   300
NVSKATWNET LGKVVKQLRK HFGNNTIIRF AQSSGGDLEV TTHSFNCGGE FFYCNTSGLF   360
NSTWISNTSV QGSNSTGSND SITLPCRIKQ IINMWQRIGQ AMYAPPIQGV IRCVSNITGL   420
ILTRDGGSTN STTETFRPGG TDMRDNWRSE LYKYKVVKIE PLGVAPTRCK RRVVGSHSGS   480
GGSGSGGHAA VGIGAVSLGF LGAAGSTMGA ASMTLTVQAR NLLSGIVQQQ SNLLRAPEPQ   540
QHLLKDTHWG IKQLQARVLA VEHYLRDQQL LGIWGCSGKL ICCTNVPWNS SWSNRNLSEI   600
WDNMTWLQWD KEISNYTQII YGLLEESQNQ QEKNEQDLLA LDKWASLWNW FDISNWLWYI   660
KIFIMIVGGL IGLRIVFAVL SVIHRVR                                       687

SEQ ID NO: 61             moltype = AA   length = 687
FEATURE                   Location/Qualifiers
REGION                    1..687
                          note = Description of Artificial Sequence: Synthetic
                           polypeptide
source                    1..687
                          mol_type = protein
                          organism = synthetic construct
SEQUENCE: 61
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYTEKLRS MMKGELKNCS   120
FNMTTELRDK KQKVYSLFYR LDVVQINENQ GNRSNNSNKE YRLINCNTSA ITQACPKVSF   180
EPIPIHYCAP AGFAILKCKD KKFNGTGPCQ NVSTVQCTHG IKPVVSTQLL LNGSLAEEEV   240
IIRSENITNN AKNILVQLNT SVQINCTRPN NNTVKSIRIG PGQAFYYTGD IIGHIRQAHC   300
NVSKATWNET LGKVVKQLRK HFGNNTIIRF AQSSGGDLEV TTHSFNCGGE FFYCNTSGLF   360
NSTWISNTSV QGSNSTGSND SITLPCRIKQ IINMWQRIGQ AMYAPPIQGV IRCVSNITGL   420
ILTRDGGSTN STTETFRPGG TDMRDNWRSE LYKYKVVKIE PLGVAPTRCK RRVVGSHSGS   480
GGSGSGGHAA VGIGAVSLGF LGAAGSTMGA ASMTLTVQAR NLLSGIVQQQ SNLLRAPEPQ   540
QHLLKDTHWG IKQLQARVLA VEHYLRDQQL LGIWGCSGKL ICCTNVPWNS SWSNRNLSEI   600
WDNMTWLQWD KEISNYTQII YGLLEESQNQ QEKNEQDLLA LDKWASLWNW FDISNWLWYI   660
KIFIMIVGGL IGLRIVFAVL SVIHRVR                                       687

SEQ ID NO: 62             moltype = AA   length = 634
FEATURE                   Location/Qualifiers
REGION                    1..634
                          note = Description of Artificial Sequence: Synthetic
                           polypeptide
source                    1..634
                          mol_type = protein
                          organism = synthetic construct
SEQUENCE: 62
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYTPNLTS MMRGELKNCS   120
FNMTTELRDK KQKVYSLFYR LDVVQINENQ GNRSNNSNKE YRLINCNTSA ITQACPKVSF   180
EPIPIHYCAP AGFAILKCKD KKFNGTGPCP SVSTVQCTHG IKPVVSTQLL LNGSLAEEEV   240
IIRSENITNN AKNILVQLNT PVQINCTRPN NNTVKSIRIG PGQAFYYTGD IIGHIRMAHC   300
NVSKATWNET LGKVVKQLRK HFGNNTIIRF AQSSGGDLEV TTHSFNCGGE FFYCNTSGLF   360
NSTWISNTSV QGSNSTGSND SLILPCRIKQ IINMWQRIGQ AMYAPPIQGV IRCVSNITGL   420
ILTRDGGSTN STTETFRPGG GDMRDNWRSE LYKYKVVKIE PLGVAPTRCK RRVVGRRRRR   480
RAVGIGAVSL GFLGAAGSTM GAASMTLTVQ ARNLLSGIVQ QQSNLLRAPE PQQHLLKDTH   540
WGIKQLQARV LAVEHYLRDQ QLLGIWGCSG KLICCTNVPW NSSWSNRNLS EIWDNMTWLQ   600
WDKEISNYTQ IIYGLLEESQ NQQEKNEQDL LALD                               634

SEQ ID NO: 63             moltype = AA   length = 634
FEATURE                   Location/Qualifiers
REGION                    1..634
                          note = Description of Artificial Sequence: Synthetic
                           polypeptide
source                    1..634
```

```
                              mol_type = protein
                              organism = synthetic construct
SEQUENCE: 63
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYTPNLTS MMRGEIKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPN NNTVKSIRIG PGQAFYYFGD VLGDVRMAHC  300
NISKATWNET LGKVVKQLRK HFGNNTIIRF AQSSGGDLEV TTHSFNCGGE FFYCNTSGLF  360
NSTWISNTSV QGSNSTGSND SLILPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGRRRRR  480
RAVGIGAVSL GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                             634

SEQ ID NO: 64            moltype = AA   length = 634
FEATURE                  Location/Qualifiers
REGION                   1..634
                         note = Description of Artificial Sequence: Synthetic
                          polypeptide
source                   1..634
                         mol_type = protein
                         organism = synthetic construct
SEQUENCE: 64
AENLWVTVYY GVPVWKDAET TLFCASDAKA YETEKHNVWA THECVPTDPN PQEIHLENVT   60
EEFNMWKNNM VEQMHTDIIE LWDQSLKPCV KLTPLCVTLQ CTNYTPNLTS MMRGEIKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPN NNTVKSIRIG PGQAFYYFGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGRRRRR  480
RAVGIGAVSL GFLGAAGSTM GAASMTLTVQ ARNLLSGIVQ QQSNLLRAPE PQQHLLKLTV  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                             634

SEQ ID NO: 65            moltype = AA   length = 687
FEATURE                  Location/Qualifiers
REGION                   1..687
                         note = Description of Artificial Sequence: Synthetic
                          polypeptide
source                   1..687
                         mol_type = protein
                         organism = synthetic construct
SEQUENCE: 65
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYAPKLRS MMRGEIKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSENITNN AKNILVQLNT SVQINCTRPS NNTVKSIRIG PGQAFYYFGD VLGHVRMAHC  300
NISKATWNET LGKVVKQLRK HFGNNTIIRF AQSSGGDLEV TTHSFNCGGE FFYCNTSGLF  360
NSTWISNTSV QGSNSTGSND SLILPCWIKQ IINMWQRIGQ AMYAPPIQGV IRCVSNITGL  420
ILTRDGGSTN STTETFRPGG TDMRDNWRSE LYKYKVVKIE PLGVAPTRCK RRTVGSHSGS  480
GGSGSGGHAA AGIGASSDGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                     687

SEQ ID NO: 66            moltype = AA   length = 634
FEATURE                  Location/Qualifiers
REGION                   1..634
                         note = Description of Artificial Sequence: Synthetic
                          polypeptide
source                   1..634
                         mol_type = protein
                         organism = synthetic construct
SEQUENCE: 66
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYAPKLRS MMRGQIMNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPS NISVKSIRIG PGQAFYYFGD VLGHVRMAHC  300
NISKATWNET LGKVVKQLRK HFGNNTIIRF AQSSGGDLEV TTHSFNCGGE FFYCNTSLLF  360
NSTWISNTSV QGSNSTGSNE SLILPCWIKQ IINMWQRIGQ AMYAPPIQGP INCVSNITGL  420
ILTRDGGSTN STTETFRPGG GDMRDNWRSE LYKYKVVKIE PLGVAPTRCK RRTVGRRRRR  480
RAAGIGASSD GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                             634
```

```
SEQ ID NO: 67          moltype = AA   length = 634
FEATURE                Location/Qualifiers
REGION                 1..634
                       note = Description of Artificial Sequence: Synthetic
                       polypeptide
source                 1..634
                       mol_type = protein
                       organism = synthetic construct
SEQUENCE: 67
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYTPKLRS MMRGQIMNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPS NISVKSIRIG PGQAFYYFGD VLGHVRMAHC  300
NISKATWNET LGKVVKQLRK HFGNNTIIRF AQSSGGDLEV TTHSFNCGGE FFYCNTSLLF  360
NSTWISNTSV QGSNSTGSNE SLILPCWIKQ IINMWQRIGQ AMYAPPIQGP INCVSNITGL  420
ILTRDGGSTN STTETFRPGG GDMRDNWRSE LYKYKVVKIE PLGVAPTRCK RRTVGRRRRR  480
RAAGIGASSD GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                              634

SEQ ID NO: 68          moltype = AA   length = 634
FEATURE                Location/Qualifiers
REGION                 1..634
                       note = Description of Artificial Sequence: Synthetic
                       polypeptide
source                 1..634
                       mol_type = protein
                       organism = synthetic construct
SEQUENCE: 68
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYAPKLRS MMRGQIMNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPS NISVKSIRIG PGQAFYYFGN VTGHVRMAHC  300
NISKATWNET LGKVVKQLRK HFGNNTIIRF AQSSGGDLEV TTHSFNCGGE FFYCNTSLLF  360
NSTWISNTSV QGSNSTGSNE SLILPCWIKQ IINMWQRIGQ AMYAPPIQGP INCVSNITGL  420
ILTRDGGSTN STTETFRPGG GDMRDNWRSE LYKYKVVKIE PLGVAPTRCK RRTVGRRRRR  480
RAAGIGASSD GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                              634

SEQ ID NO: 69          moltype = AA   length = 634
FEATURE                Location/Qualifiers
REGION                 1..634
                       note = Description of Artificial Sequence: Synthetic
                       polypeptide
source                 1..634
                       mol_type = protein
                       organism = synthetic construct
SEQUENCE: 69
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYAPKLRS MMRGQIMNCS  120
LNMTTELRDK KQKVYSLFYR RDVVQINENQ GNRSNLSDKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPS NISVKSIRIG PGQAFYAVGD VLGHVRMAHC  300
NISKATWNET LGKVAKQLRK HFGNNTIIRF AQSSGADLEG TTHSFNCGGE FFYCNTSLLF  360
NSTWISNTSV QGSNSTGSNE SLILPCWIKQ IVNMWPRIGQ AMYAPPIQGP INCVSNITGL  420
ILTRDGGSTN STTETFRPGG GDMRDNWRSE LYKYKVVKIE PLGVAPTRCK RRTVGRRRRR  480
RAAGIGASSD GFLGAAGSTM GAASMTLTVQ ARNLLSGIVQ QQSNLLRAPE PQQHLLKDTH  540
WGIKQLQARV LAVEHYLRDQ QLLGIWGCSG KLICCTNVPW NSSWSNRNLS EIWDNMTWLQ  600
WDKEISNYTQ IIYGLLEESQ NQQEKNEQDL LALD                              634

SEQ ID NO: 70          moltype = AA   length = 634
FEATURE                Location/Qualifiers
REGION                 1..634
                       note = Description of Artificial Sequence: Synthetic
                       polypeptide
source                 1..634
                       mol_type = protein
                       organism = synthetic construct
SEQUENCE: 70
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYTPNLTS MMRGEIKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPS NNTVKSIRIG PGQAFYYFGD VLGHVRMAHC  300
NISKATWNET LGKVVKQLRK HFGNNTIIRF AQSSGGDLEV TTHSFNCGGE FFYCNTSGLF  360
NSTWISNTSV QGSNSTGSND SLILPCWIKQ IINMWQRIGQ AMYAPPIQGV IRCVSNITGL  420
```

-continued

```
ILTRDGGSTN STTETFRPGG GDMRDNWRSE LYKYKVVKIE PLGVAPTRCK RRTVGRRRRR   480
RAAGIGASSD GFLGAAGSTM GAASMTLTVQ ARNLLSGIVQ QQSNLLRAPE PQQHLLKDTH   540
WGIKQLQARV LAVEHYLRDQ QLLGIWGCSG KLICCTNVPW NSSWSNRNLS EIWDNMTWLQ   600
WDKEISNYTQ IIYGLLEESQ NQQEKNEQDL LALD                              634

SEQ ID NO: 71               moltype = AA   length = 551
FEATURE                     Location/Qualifiers
REGION                      1..551
                            note = Description of Artificial Sequence: Synthetic
                             polypeptide
source                      1..551
                            mol_type = protein
                            organism = synthetic construct
SEQUENCE: 71
AENLWVTVYY GVPVWKDAET TLFCASDAKA YETEKHNVWA THACVPTDPN PQEIHLENVT   60
EEFNMCKNDM VEQMHKDICN LWNESLKPCN KTTGTSAITQ ACPKVSFEPI PIHYCAPAGF   120
AILKCNNNTF NGTGPCTNVS TVQCTHGIKP VVSTQLLLNG SLAEEEVIIR SCDFMDNAKT   180
IIVQLNTSVE INCTAGNGTA HCNISGAKWN KTLKNISSKL RKQYGNNKTI IFKQSSGGDP   240
EIVTHWFNCG GEFFYCNSTQ LFNSTWFNST WSNESSNNTN GSDNITLPCN ISQNITMWCG   300
VGKMNYSPPN SSNISCSSNI TGLLLTRDGG VSNNETEIFR PGGGDMRDNW RSELYKYKVV   360
KIEPLGVAPT RGGGSGESQV RQQFSKDIEK LLNEQVNKEM QSSNLYMSMS SWCYTHSLDG   420
AGLFLFDHAA EEYEHAKKLI IFLNENNVPV QLTSISAPEH KFEGLTQIFQ KAYEHEQHIS   480
ESINNIVDHA IKSKDHATFN FLQWYVAEQH EEEVLFKDIL DKIELIGNEN HGLYLADQYV   540
KGIAKSRKSG S                                                       551

SEQ ID NO: 72               moltype = AA   length = 546
FEATURE                     Location/Qualifiers
REGION                      1..546
                            note = Description of Artificial Sequence: Synthetic
                             polypeptide
source                      1..546
                            mol_type = protein
                            organism = synthetic construct
SEQUENCE: 72
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGAENLW   180
VTVYYGVPVW KDAETTLFCA SDAKAYETEK HNVWATHACV PTDPNPQEIH LENVTEEFNM   240
CKNDMVEQMH KDICNLWNES LKPCNKTTGT SAITQACPKV SFEPIPIHYC APAGFAILKC   300
NNNTFNGTGP CTNVSTVQCT HGIKPVVSTQ LLLNGSLAEE EVIIRSCDFM DNAKTIIVQL   360
NTSVEINCTA GNGTAHCNIS GAKWNKTLKN ISSKLRKQYG NNKTIIFKQS SGGDPEIVTH   420
WFNCGGEFFY CNSTQLFNST WFNSTWSNES SNNTNGSDNI TLPCNISQII NMWCGVGKMN   480
YSPPNSSNIS CSSNITGLLL IRDGGVSNNE TEIFRPGGGD MRDNWRSELY KYKVVKIEPL   540
GVAPTR                                                             546

SEQ ID NO: 73               moltype = AA   length = 545
FEATURE                     Location/Qualifiers
REGION                      1..545
                            note = Description of Artificial Sequence: Synthetic
                             polypeptide
source                      1..545
                            mol_type = protein
                            organism = synthetic construct
SEQUENCE: 73
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGAENLWV   180
TVYYGVPVWK DAETTLFCAS DAKAYETEKH NVWATHACVP TDPNPQEIHL ENVTEEFNMC   240
KNDMVEQMHK DICNLWNESL KPCVKLTGTS AITQACPKVS FEPIPIHYCA PAGFAILKCN   300
NNTFNGTGPC TNVSTVQCTH GIKPVVSTQL LLNGSLAEEE VIIRSCDFMD NAKTIIVQLN   360
TSVEINCTAG NGTAHCNISG AKWNKTLKNI SSKLRKQFGN NKTIIFKQSS GGDPEIVTHW   420
FNCGGEFFYC NSTQLFNSTW FNSNWSNESS NNTNGSDNIT LPCNISQIIN MWCGVGKMNY   480
SPPNSSNISC SSNITGLLLT RDGGNSNNES EIFRPGGGDM RDNWRSELYK YKVVKIEPLG   540
VAPTR                                                              545

SEQ ID NO: 74               moltype = AA   length = 546
FEATURE                     Location/Qualifiers
REGION                      1..546
                            note = Description of Artificial Sequence: Synthetic
                             polypeptide
source                      1..546
                            mol_type = protein
                            organism = synthetic construct
SEQUENCE: 74
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGAENLW   180
VTVYYGVPVW KDAETTLFCA SDAKAYETEK HNVWATHACV PTDPNPQEIH LENVTEEFNM   240
CKNDMVEQMH KDICNLWNES LKPCNKTTGT SAITQACPKV SFEPIPIHYC APAGFAILKC   300
```

```
NNNTFNGTGP CTNVSTVQCT HGIKPVVSTQ LLLNGSLAEE EVIIRSCDFM DNAKTIIVQL   360
NTSVEINCTA GNGTAHCNIS GAKWNKTLKN ISSKLRKQYG NNKTIIFKQS SGGDPEIVTH   420
WFNCGGEFFY CNSTQLFNST WFNSNWSNES SNNTNGSDNI TLPCNISQII NMWCGVGKMN   480
YSPPNSSNIS CSSNITGLLL TRDGGVSNNE TEIFRPGGGD MRDNWRSELY KYKVVKIEPL   540
GVAPTR                                                              546

SEQ ID NO: 75             moltype = AA  length = 545
FEATURE                   Location/Qualifiers
REGION                    1..545
                          note = Description of Artificial Sequence: Synthetic
                           polypeptide
source                    1..545
                          mol_type = protein
                          organism = synthetic construct
SEQUENCE: 75
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGAENLWV   180
TVYYGVPVWK DAETTLFCAS DAKAYETEKH NVWATHACVP TDPNPQEIHL ENVTEEFNMC   240
KNDMVEQMHK DICNLWNESL KPCNKTTGTS AITQACPKVS FEPIPIHYCA PAGFAILKCN   300
NNTFNGTGPC TNVSTVQCTH GIKPVVSTQL LLNGSLAEEE VIIRSCDFMD NAKTIIVQLN   360
TSVEINCTAG NGTAHCNISG AKWNKTLKNI SSKLRKQYGN NKTIIFKQSS GGDPEIVTHW   420
FNCGGEFFYC NSTQLFNSTW FNSNWSNESS NNTNGSDNIT LPCNISQIIN MWCGVGKMNY   480
SPPNSSNISC SSNITGLLLT RQGGNSNNET EIFRPGGGDM RDNWRSELYK YKVVKIEPLG   540
VAPTR                                                              545

SEQ ID NO: 76             moltype = AA  length = 545
FEATURE                   Location/Qualifiers
REGION                    1..545
                          note = Description of Artificial Sequence: Synthetic
                           polypeptide
source                    1..545
                          mol_type = protein
                          organism = synthetic construct
SEQUENCE: 76
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGAENLWV   180
TVYYGVPVWK DAETTLFCAS DAKAYETEKH NVWATHACVP TDPNPQEIHL ENVTEEFNMC   240
KNDMVEQMHK DICNLWNESL KPCNKTTGTS AITQACPKVS FEPIPIHYCA PAGFAILKCN   300
NNTFNGTGPC TNVSTVQCTH GIKPVVSTQL LLNGSLAEEE VIIRSCDFTD NAKTIIVQLN   360
TSVEINCTAG NGTAHCNISG AKWNKTLKNI SSKLRKQFGN NKTIIFKQSS GGDPEIVTHW   420
FNCGGEFFYC NSTQLFNSTW FNSNWSNESS NNTNGSDNIT LPCNISQIIN MWCGVGKMNY   480
SPPNSSNISC SSNITGLLLT RQGGNSNDET EIFRPGGGDM RDNWRSELYK YKVVKIEPLG   540
VAPTR                                                              545

SEQ ID NO: 77             moltype = AA  length = 546
FEATURE                   Location/Qualifiers
REGION                    1..546
                          note = Description of Artificial Sequence: Synthetic
                           polypeptide
source                    1..546
                          mol_type = protein
                          organism = synthetic construct
SEQUENCE: 77
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGAENLW   180
VTVYYGVPVW KDAETTLFCA SDAKAYETEK HNVWATHACV PTDPNPQEIH LENVTEEFNM   240
CKNDMVEQMH KDICNLWNES LKPCNKTTGT SAITQACPKV SFEPIPIHYC APAGFAILKC   300
NNNTFNGTGP CTNVSTVQCT HGIKPVVSTQ LLLNGSLAEE EVIIRSCDFM DNAKTIIVQL   360
NTSVEINCTA GNGTAHCNIS GAKWNKTLKN ISSKLRKQYG NNKTIIFKQS SGGDPEIVTH   420
WFNCGGEFFY CNSTQLFNST WFNSTWSNES SNNTNGSDNI TLPCNISQNI TMWCGVGKMN   480
YSPPNSSNIS CSSNITGLLL TRDGGVSNNE TEIFRPGGGD MRDNWRSELY KYKVVKIEPL   540
GVAPTR                                                              546

SEQ ID NO: 78             moltype = AA  length = 546
FEATURE                   Location/Qualifiers
REGION                    1..546
                          note = Description of Artificial Sequence: Synthetic
                           polypeptide
source                    1..546
                          mol_type = protein
                          organism = synthetic construct
SEQUENCE: 78
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGAENLW   180
VTVYYGVPVW KDAETTLFCA SDAKAYETEK HNVWATHACV PTDPNPQEIH LENVTEEFNM   240
```

```
CKNDMVEQMH KDICNLWNES LKPCNKTTGT SAITQACPKV SFEPIPIHYC APAGFAILKC   300
NNNTFNGTGP CTNVSTVQCT HGIKPVVSTQ LLLNGSLAEE EVIIRSCDFM DNAKTIIVQL   360
NTSVEINCTA GNGTAHCNIS GAKWNKTLKN ISSKLRKQYG NNKTIIFKQS SGGDPEIVTH   420
WFNCGGEFFY CNSTQLFNST WFNSTWSNES SNNTNGSDNI TLPCNISQII NMWCGVGKMN   480
YSPPNSSNIS CSSNITGLLL TRDGGVSNNE TEIFRPGGGD MRDNWRSELY KYKVVKIEPL   540
GVAPTR                                                             546

SEQ ID NO: 79           moltype = AA  length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
SEQUENCE: 79
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGVWKEA   180
TTTLFCASDA KAYDTEVHNV WATHACVPTD PNPQEVVLVN VTENFNWCKN DMVEQMHKDI   240
CNLWEESLKP CVKLTGGSVI TQACPKVSFE PIPIHYCAPA GYAILKCNNN TFNGTGPCTN   300
VSTVVCTHGI RPVVSSQLLL NGSLAEKEVV IRSCDFTDNA KTIIVQLNTS VEINCAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQIINMWC KVGKMMYAPP VSGQIKCSSN   480
ITGLLLTRDG GNSNNESEIF RPGGGDMRDN WRSELYKYKV VKIE                    524

SEQ ID NO: 80           moltype = AA  length = 546
FEATURE                 Location/Qualifiers
REGION                  1..546
                        note = Description of Artificial Sequence: Synthetic
                         polypeptide
source                  1..546
                        mol_type = protein
                        organism = synthetic construct
SEQUENCE: 80
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGAENLW   180
VTVYYGVPVW KDAETTLFCA SDAKAYETEK HNVWATHACV PTDPNPQEIH LENVTEEFNM   240
CKNDMVEQMH KDICNLWNES LKPCNKTTGT SAITQACPKV SFEPIPIHYC APAGFAILKC   300
NNNTFNGTGP CTNVSTVQCT HGIKPVVSTQ LLLNGSLAEE EVIIRSCDFM DNAKTIIVQL   360
NTSVEINCTA GNGTAHCNIS GAKWNKTLKN ISSKLRKQFG NNKTIIFKQS SGGDPEIVTH   420
WFNCGGEFFY CNSTQLFNST WFNSNWSNES SNNTNGSDNI TLPCNISQNI TMWCGVGKMN   480
YSPPNSSNIS CSSNITGLLL TRDGGNSNNE SEIFRPGGGD MRDNWRSELY KYKVVKIEPL   540
GVAPTR                                                             546

SEQ ID NO: 81           moltype = AA  length = 525
FEATURE                 Location/Qualifiers
REGION                  1..525
                        note = Description of Artificial Sequence: Synthetic
                         polypeptide
source                  1..525
                        mol_type = protein
                        organism = synthetic construct
SEQUENCE: 81
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGGVWKEA   180
TTTLFCASNA TAYDNESHNV WATHACVPTD PNPNESVLVN VTENFSWCKN DMVEQMHKDI   240
CNLWNESLKP CVKLTGGSVI NQSCNKTSFE PIPIHYCAPA GYAILKCNNN TFNGTGPCTN   300
VSTVNCTHGI RPVVSSQLLL NGSLAEKEVV IRSCDFMDNA KTIIVQLNTS VEINCTAGNG   360
TAHCNISGAK WNKTLKRIAS KLRKQFGNNK TIIFKQSSGG DPEIVTHWFN CGGEFFYCNS   420
TQLFNSTWFN STWSTEGSNN TEGSDTITLP CKIKQIINMW CGVGKMNYSP PVSNQSKCSS   480
NITGLLLTRD GGNSNNESEI FRPGGGDMRD NWRSELYKYK VVKIE                   525

SEQ ID NO: 82           moltype = AA  length = 371
FEATURE                 Location/Qualifiers
REGION                  1..371
                        note = Description of Artificial Sequence: Synthetic
                         polypeptide
source                  1..371
                        mol_type = protein
                        organism = synthetic construct
SEQUENCE: 82
AENLWVTVYY GVPVWKDAET TLFCASDAKA YETEKHNVWA THACVPTDPN PQEIHLENVT   60
EEFNMCKNDM VEQMHKDICN LWNESLKPCV KLTGTSAITQ ACPKVSFEPI PIHYCAPAGF   120
AILKCNNNTF NGTGPCTNVS TVQCTHGIKP VVSTQLLLNG SLAEEEVIIR SCDFMDNAKT   180
IIVQLNTSVE INCTAGNGTA HCNISGAKWN KTLKNISSKL RKQFGNNKTI IFKQSSGGDP   240
EIVTHWFNCG GEFFYCNSTQ LFNSTWFNSN WSNESSNNTN GSDNITLPCN ISQIINMWCG   300
```

-continued

```
VGKMNYSPPN SSNISCSSNI TGLLLTRDGG NSNNESEIFR PGGGDMRDNW RSELYKYKVV  360
KIEPLGVAPT R                                                       371

SEQ ID NO: 83           moltype = AA  length = 545
FEATURE                 Location/Qualifiers
REGION                  1..545
                        note = Description of Artificial Sequence: Synthetic
                         polypeptide
source                  1..545
                        mol_type = protein
                        organism = synthetic construct
SEQUENCE: 83
MQIYEGKLTA EGLRFGIVAS RANHALVDRL VEGAIDAIVR HGGREEDITL VRVCGSWEIP  60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGSG GSGGAENLWV  180
TVYYGVPVWK DAETTLFCAS DAKAYETEKH NVWATHACVP TDPNPQEIHL ENVTEEFNMC  240
KNDMVEQMHK DICNLWNESL KPCVKLTGTS AITQACPKVS FEPIPIHYCA PAGFAILKCN  300
NNTFNGTGPC TNVSTVQCTH GIKPVVSTQL LLNGSLAEEE VIIRSCDFMD NAKTIIVQLN  360
TSVEINCTAG NGTAHCNISG AKWNKTLKNI SSKLRKQFGN NKTIIFKQSS GGDPEIVTHW  420
FNCGGEFFYC NSTQLFNSTW FNSNWSNESS NNTNGSDNIT LPCNISQIIN MWCGVGKMNY  480
SPPNSSNISC SSNITGLLLT RDGGNSNNES EIFRPGGGDM RDNWRSELYK YKVVKIEPLG  540
VAPTR                                                             545

SEQ ID NO: 84           moltype = AA  length = 350
FEATURE                 Location/Qualifiers
REGION                  1..350
                        note = Description of Artificial Sequence: Synthetic
                         polypeptide
source                  1..350
                        mol_type = protein
                        organism = synthetic construct
SEQUENCE: 84
VWKEATTTLF CASNATAYDN ESHNVWATHA CVPTDPNPNE SVLVNVTENF SWCKNDMVEQ  60
MHKDICNLWN ESLKPCVKLT GGSVINQSCN KTSFEPIPIH YCAPAGYAIL KCNNNTFNGT  120
GPCTNVSTVN CTHGIRPVVS SQLLLNGSLA EKEVVIRSCD FMDNAKTIIV QLNTSVEINC  180
TAGNGTAHCN ISGAKWNKTL KRIASKLRKQ FGNNKTIIFK QSSGGDPEIV THWFNCGGEF  240
FYCNSTQLFN STWFNSTWST EGSNNTEGSD TITLPCKIKQ IINMWCGVGK MNYSPPVSNQ  300
SKCSSNITGL LLTRDGGNSN NESEIFRPGG GDMRDNWRSE LYKYKVVKIE            350

SEQ ID NO: 85           moltype = AA  length = 350
FEATURE                 Location/Qualifiers
REGION                  1..350
                        note = Description of Artificial Sequence: Synthetic
                         polypeptide
source                  1..350
                        mol_type = protein
                        organism = synthetic construct
SEQUENCE: 85
VWKEATTTLF CASDAKAYDN ESHNVWATHA CVPTDPNPNE SVLVNVTENF HWCKNDMVEQ  60
MHKDICNLWN ESLKPCVKLT GGSVINQSCN KTSFEPIPIH YCAPAGYAIL KCNNNTFNGT  120
GPCTNVSTVN CTHGIRPVVS SQLLLNGSLA EKEVVIRSCD FMDNAKTIIV QLNTSVEINC  180
TAGNGTAHCN ISGAKWNKTL KRIASKLRKQ FGNNKTIIFK QSSGGDPEIV THWFNCGGEF  240
FYCNSTQLFN STWFNSTWST EGSNNTEGSD TITLPCKIKQ IINMWCGVGK MMYAPPVSNQ  300
SKCSSNITGL LLTRDGGNSN NESEIFRPGG GDMRDNWRSE LYKYKVVKIE            350

SEQ ID NO: 86           moltype = AA  length = 350
FEATURE                 Location/Qualifiers
REGION                  1..350
                        note = Description of Artificial Sequence: Synthetic
                         polypeptide
source                  1..350
                        mol_type = protein
                        organism = synthetic construct
SEQUENCE: 86
VWKEATTTLF CASDAKAYDN ESHNVWATHA CVPTDPNPNE SVLVNVTENF HWCKNDMVEQ  60
MHKDICNLWN ESLKPCNKTT GGSVITQACN KTSFEPIPIH YCAPAGYAIL KCNNNTFNGT  120
GPCTNVSTVN CTHGIRPVVS SQLLLNGSLA EKEVVIRSCD FMDNAKTIIV QLNTSVEINC  180
TAGNGTAHCN ISGAKWNKTL KRIASKLRKQ FGNNKTIIFK QSSGGDPEIV THWFNCGGEF  240
FYCNSTQLFN STWFNSTWST EGSNNTEGSD TITLPCKIKQ NITMWCGVGK MMYAPPVSNQ  300
SKCSSNITGL LLTRDGGNSN NESEIFRPGG GDMRDNWRSE LYKYKVVKIE            350

SEQ ID NO: 87           moltype = AA  length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
```

```
SEQUENCE: 87
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC NKTTGGSVIT QACNKTSFEP IPIHYCAPAG YAILKCNNNT FNGTGPCTNV   300
STVNCTHGIR PVVSSQLLLN GSLAEKEVVI RSCDFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQNITMWC GVGKMMYAPP VSNQSKCSSN   480
ITGLLLTRDG GNSNNESEIF RPGGGDMRDN WRSELYKYKV VKIE                    524

SEQ ID NO: 88          moltype = AA  length = 350
FEATURE                Location/Qualifiers
REGION                 1..350
                       note = Description of Artificial Sequence: Synthetic
                        polypeptide
source                 1..350
                       mol_type = protein
                       organism = synthetic construct
SEQUENCE: 88
VWKEATTTLF CASDAKAYDN ESHNVWATHA CVPTDPNPNE SVLVNVTENF HWCKNDMVEQ    60
MHKDICNLWN ESLKPCNKTT GGSVITQACN KTSFEPIPIH YCAPAGYAIL KCNNNTFNGT   120
GPCTNVSTVN CTHGIRPVVS SQLLLNGSLA EKEVVIRSCD FMDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ NITMWCGVGK MMYAPPVSNQ   300
SKCSSNITGL LLTRDGGNSN NESEIFRPGG TDMRDNWRSE LYKYKVVKIE             350

SEQ ID NO: 89          moltype = AA  length = 524
FEATURE                Location/Qualifiers
REGION                 1..524
                       note = Description of Artificial Sequence: Synthetic
                        polypeptide
source                 1..524
                       mol_type = protein
                       organism = synthetic construct
SEQUENCE: 89
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC NKTTGGSVIT QACNKTSFEP IPIHYCAPAG YAILKCNNNT FNGTGPCTNV   300
STVNCTHGIR PVVSSQLLLN GSLAEKEVVI RSCDFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQNITMWC GVGKMMYAPP VSNQSKCSSN   480
ITGLLLTRDG GNSNNESEIF RPGGTDMRDN WRSELYKYKV VKIE                    524

SEQ ID NO: 90          moltype = AA  length = 350
FEATURE                Location/Qualifiers
REGION                 1..350
                       note = Description of Artificial Sequence: Synthetic
                        polypeptide
source                 1..350
                       mol_type = protein
                       organism = synthetic construct
SEQUENCE: 90
VWKEATTTLF CASDAKAYDN ESHNVWATHA CVPTDPNPNE SVLVNVTENF HWCKNDMVEQ    60
MHKDICNLWN ESLKPCNKTT GGSVITQACN KTSFEPIPIH YCAPAGYAIL KCNNNTFNGT   120
GPCTNVSTVN CTHGIRPVVS SQLLLNGSLA EKEVVIRSCQ FMDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ NITMWCGVGK MMYAPPVSNQ   300
SKCSSNITGL LLTRDGGNSN NESEIFRPGG GDMRDNWRSE LYKYKVVKIE             350

SEQ ID NO: 91          moltype = AA  length = 524
FEATURE                Location/Qualifiers
REGION                 1..524
                       note = Description of Artificial Sequence: Synthetic
                        polypeptide
source                 1..524
                       mol_type = protein
                       organism = synthetic construct
SEQUENCE: 91
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC NKTTGGSVIT QACNKTSFEP IPIHYCAPAG YAILKCNNNT FNGTGPCTNV   300
STVNCTHGIR PVVSSQLLLN GSLAEKEVVI RSCQFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQNITMWC GVGKMMYAPP VSNQSKCSSN   480
```

```
ITGLLLTRDG GNSNNESEIF RPGGGDMRDN WRSELYKYKV VKIE                    524

SEQ ID NO: 92           moltype = AA  length = 350
FEATURE                 Location/Qualifiers
REGION                  1..350
                        note = Description of Artificial Sequence: Synthetic
                        polypeptide
source                  1..350
                        mol_type = protein
                        organism = synthetic construct
SEQUENCE: 92
VWKEATTTLF CASDAKAYDN ESHNVWATHA CVPTDPNPNE SVLVNVTENF HWCKNDMVEQ  60
MHKDICNLWN ESLKPCNKTT GGSVITQACN KTSFEPIPIH YCAPAGYAIL KCNNNTFNGT  120
GPCTNVSTVN CTHGIRPVVS SQLLLNGSLA EKEVVIRSCQ FMDNAKTIIV QLNTSVEINC  180
TAGNGTAHCN ISGAKWNKTL KRIASKLRKQ FGNNKTIIFK QSSGGDPEIV THWFNCGGEF  240
FYCNSTQLFN STWFNSTWST EGSNNTEGSD TITLPCKIKQ NITMWCGVGK MMYAPPVSNQ  300
SKCSSNITGL LLTRDGGNSN NESEIFRPGG TDMRDNWRSE LYKYKVVKIE            350

SEQ ID NO: 93           moltype = AA  length = 524
FEATURE                 Location/Qualifiers
REGION                  1..524
                        note = Description of Artificial Sequence: Synthetic
                        polypeptide
source                  1..524
                        mol_type = protein
                        organism = synthetic construct
SEQUENCE: 93
MQIYEGKLTA EGLRFGIVAS RANHALVDRL VEGAIDAIVR HGGREEDITL VRVCGSWEIP  60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGSG GSGGVWKEAT  180
TTLFCASDAK AYDNESHNVW ATHACVPTDP NPNESVLVNV TENFHWCKND MVEQMHKDIC  240
NLWNESLKPC NKTTGGSVIT QACNKTSFEP IPIHYCAPAG YAILKCNNNT FNGTGPCTNV  300
STVNCTHGIR PVVSSQLLLN GSLAEKEVVI RSCQFMDNAK TIIVQLNTSV EINCTAGNGT  360
AHCNISGAKW NKTLKRIASK LRKQFGNNKT IIFKQSSGGD PEIVTHWFNC GGEFFYCNST  420
QLFNSTWFNS TWSTEGSNNT EGSDTITLPC KIKQNITMWC GVGKMMYAPP VSNQSKCSSN  480
ITGLLLTRDG GNSNNESEIF RPGGTDMRDN WRSELYKYKV VKIE                  524

SEQ ID NO: 94           moltype = AA  length = 350
FEATURE                 Location/Qualifiers
REGION                  1..350
                        note = Description of Artificial Sequence: Synthetic
                        polypeptide
source                  1..350
                        mol_type = protein
                        organism = synthetic construct
SEQUENCE: 94
VWKEATTTLF CASDAKAYDN ESHNVWATHA CVPTDPNPNE SVLVNVTENF HWCKNDMVEQ  60
MHKDICNLWN ESLKPCVKLT GGSVINQSCN KTSFEPIPIH YCAPAGYAIL KCNNNTFNGT  120
GPCTNVSTVN CTHGIRPVVS SQLLLNGSLA EKEVVIRSCD FMDNAKTIIV QLNTSVEINC  180
TAGNGTAHCN ISGAKWNKTL KRIASKLRKQ FGNNKTIIFK QSSGGDPEIV THWFNCGGEF  240
FYCNSTQLFN STWFNSTWST EGSNNTEGSD TITLPCKIKQ NITMWCGVGK MMYAPPVSNQ  300
SKCSSNITGL LLTRDGGNSN NESEIFRPGG GDMRDNWRSE LYKYKVVKIE            350

SEQ ID NO: 95           moltype = AA  length = 524
FEATURE                 Location/Qualifiers
REGION                  1..524
                        note = Description of Artificial Sequence: Synthetic
                        polypeptide
source                  1..524
                        mol_type = protein
                        organism = synthetic construct
SEQUENCE: 95
MQIYEGKLTA EGLRFGIVAS RANHALVDRL VEGAIDAIVR HGGREEDITL VRVCGSWEIP  60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGSG GSGGVWKEAT  180
TTLFCASDAK AYDNESHNVW ATHACVPTDP NPNESVLVNV TENFHWCKND MVEQMHKDIC  240
NLWNESLKPC VKLTGGSVIN QSCNKTSFEP IPIHYCAPAG YAILKCNNNT FNGTGPCTNV  300
STVNCTHGIR PVVSSQLLLN GSLAEKEVVI RSCDFMDNAK TIIVQLNTSV EINCTAGNGT  360
AHCNISGAKW NKTLKRIASK LRKQFGNNKT IIFKQSSGGD PEIVTHWFNC GGEFFYCNST  420
QLFNSTWFNS TWSTEGSNNT EGSDTITLPC KIKQNITMWC GVGKMMYAPP VSNQSKCSSN  480
ITGLLLTRDG GNSNNESEIF RPGGGDMRDN WRSELYKYKV VKIE                  524

SEQ ID NO: 96           moltype = AA  length = 350
FEATURE                 Location/Qualifiers
REGION                  1..350
                        note = Description of Artificial Sequence: Synthetic
                        polypeptide
source                  1..350
                        mol_type = protein
``` organism = synthetic construct
SEQUENCE: 96
VWKEATTTLF CASDAKAYDN ESHNVWATHA CVPTDPNPNE SVLVNVTENF HWCKNDMVEQ    60
MHKDICNLWN ESLKPCVKLT GGSVINQSCN KTSFEPIPIH YCAPAGYAIL KCNNNTFNGT   120
GPCTNVSTVN CTHGIRPVVS SQLLLNGSLA EKEVVIRSCD FMDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ NITMWCGVGK MMYAPPVSNQ   300
SKCSSNITGL LLTRDGGNSN NESEIFRPGG TDMRDNWRSE LYKYKVVKIE             350

SEQ ID NO: 97          moltype = AA  length = 524
FEATURE                Location/Qualifiers
REGION                 1..524
                       note = Description of Artificial Sequence: Synthetic
                        polypeptide
source                 1..524
                       mol_type = protein
                       organism = synthetic construct
SEQUENCE: 97
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCDFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQNITMWC GVGKMMYAPP VSNQSKCSSN   480
ITGLLLTRDG GNSNNESEIF RPGGTDMRDN WRSELYKYK VKIE                    524

SEQ ID NO: 98          moltype = AA  length = 350
FEATURE                Location/Qualifiers
REGION                 1..350
                       note = Description of Artificial Sequence: Synthetic
                        polypeptide
source                 1..350
                       mol_type = protein
                       organism = synthetic construct
SEQUENCE: 98
VWKEATTTLF CASDAKAYDN ESHNVWATHA CVPTDPNPNE SVLVNVTENF HWCKNDMVEQ    60
MHKDICNLWN ESLKPCVKLT GGSVINQSCN KTSFEPIPIH YCAPAGYAIL KCNNNTFNGT   120
GPCTNVSTVN CTHGIRPVVS SQLLLNGSLA EKEVVIRSCQ FMDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ NITMWCGVGK MMYAPPVSNQ   300
SKCSSNITGL LLTRDGGNSN NESEIFRPGG GDMRDNWRSE LYKYKVVKIE             350

SEQ ID NO: 99          moltype = AA  length = 524
FEATURE                Location/Qualifiers
REGION                 1..524
                       note = Description of Artificial Sequence: Synthetic
                        polypeptide
source                 1..524
                       mol_type = protein
                       organism = synthetic construct
SEQUENCE: 99
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCQFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQNITMWC GVGKMMYAPP VSNQSKCSSN   480
ITGLLLTRDG GNSNNESEIF RPGGGDMRDN WRSELYKYKV VKIE                   524

SEQ ID NO: 100         moltype = AA  length = 350
FEATURE                Location/Qualifiers
REGION                 1..350
                       note = Description of Artificial Sequence: Synthetic
                        polypeptide
source                 1..350
                       mol_type = protein
                       organism = synthetic construct
SEQUENCE: 100
VWKEATTTLF CASDAKAYDN ESHNVWATHA CVPTDPNPNE SVLVNVTENF HWCKNDMVEQ    60
MHKDICNLWN ESLKPCVKLT GGSVINQSCN KTSFEPIPIH YCAPAGYAIL KCNNNTFNGT   120
GPCTNVSTVN CTHGIRPVVS SQLLLNGSLA EKEVVIRSCQ FMDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ NITMWCGVGK MMYAPPVSNQ   300
SKCSSNITGL LLTRDGGNSN NESEIFRPGG TDMRDNWRSE LYKYKVVKIE             350

```
SEQ ID NO: 101          moltype = AA   length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
SEQUENCE: 101
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCQFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQNITMWC GVGKMMYAPP VSNQSKCSSN   480
ITGLLLTRDG GNSNNESEIF RPGGTDMRDN WRSELYKYKV VKIE                    524

SEQ ID NO: 102          moltype = AA   length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
SEQUENCE: 102
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCDFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQIINMWC GVGKMMYAPP VSNQSKCSSN   480
ITGLLLTRDG GNSNNESEIF RPGGGDMRDN WRSELYKYKV VKIE                    524

SEQ ID NO: 103          moltype = AA   length = 350
FEATURE                 Location/Qualifiers
REGION                  1..350
                        note = Description of Artificial Sequence: Synthetic
                         polypeptide
source                  1..350
                        mol_type = protein
                        organism = synthetic construct
SEQUENCE: 103
VWKEATTTLF CASDAKAYDN ESHNVWATHA CVPTDPNPNE SVLVNVTENF HWCKNDMVEQ    60
MHKDICNLWN ESLKPCVKLT GGSVINQSCN KTSFEPIPIH YCAPAGYAIL KCNNNTFNGT   120
GPCTNVSTVN CTHGIRPVVS SQLLLNGSLA EKEVVIRSCD FMDNAKTIIV QLNTSVEINC   180
TAGNTAHCN ISGAKWNKTL KRIASKLRKQ FGNNKTIIFK QSSGGDPEIV THWFNCGGEF   240
FYCNSTQLFN STWFNSTWST EGSNNTEGSN TITLPCKIKQ IINMWCGVGK MMYAPPVSNQ   300
SKCSSNITGL LLTRDGGNSN NESEIFRPGG TDMRDNWRSE LYKYKVVKIE             350

SEQ ID NO: 104          moltype = AA   length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
SEQUENCE: 104
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCDFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQIINMWC GVGKMMYAPP VSNQSKCSSN   480
ITGLLLTRDG GNSNNESEIF RPGGTDMRDN WRSELYKYKV VKIE                    524

SEQ ID NO: 105          moltype = AA   length = 350
FEATURE                 Location/Qualifiers
REGION                  1..350
                        note = Description of Artificial Sequence: Synthetic
                         polypeptide
source                  1..350
```

```
                          mol_type = protein
                          organism = synthetic construct
SEQUENCE: 105
VWKEATTTLF CASDAKAYDN ESHNVWATHA CVPTDPNPNE SVLVNVTENF HWCKNDMVEQ    60
MHKDICNLWN ESLKPCVKLT GGSVINQSCN KTSFEPIPIH YCAPAGYAIL KCNNNTFNGT   120
GPCTNVSTVN CTHGIRPVVS SQLLLNGSLA EKEVVIRSCN FTDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ IINMWCGVGK MMYAPPVSNQ   300
SKCSSNITGL LLTRDGGNSN NESEIFRPGG GDMRDNWRSE LYKYKVVKIE             350

SEQ ID NO: 106          moltype = AA  length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
SEQUENCE: 106
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCNFTDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQIINMWC GVGKMMYAPP VSNQSKCSSN   480
ITGLLLTRDG GNSNNESEIF RPGGGDMRDN WRSELYKYKV VKIE                    524

SEQ ID NO: 107          moltype = AA  length = 350
FEATURE                 Location/Qualifiers
REGION                  1..350
                        note = Description of Artificial Sequence: Synthetic
                         polypeptide
source                  1..350
                        mol_type = protein
                        organism = synthetic construct
SEQUENCE: 107
VWKEATTTLF CASDAKAYDN ESHNVWATHA CVPTDPNPNE SVLVNVTENF HWCKNDMVEQ    60
MHKDICNLWN ESLKPCVKLT GGSVINQSCN KTSFEPIPIH YCAPAGYAIL KCNNNTFNGT   120
GPCTNVSTVN CTHGIRPVVS SQLLLNGSLA EKEVVIRSCQ FMDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ IINMWCGVGK MMYAPPVSNQ   300
SKCSSNITGL LLTRDGGNSN NESEIFRPGG GDMRDNWRSE LYKYKVVKIE             350

SEQ ID NO: 108          moltype = AA  length = 524
FEATURE                 Location/Qualifiers
REGION                  1..524
                        note = Description of Artificial Sequence: Synthetic
                         polypeptide
source                  1..524
                        mol_type = protein
                        organism = synthetic construct
SEQUENCE: 108
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCQFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQIINMWC GVGKMMYAPP VSNQSKCSSN   480
ITGLLLTRDG GNSNNESEIF RPGGGDMRDN WRSELYKYKV VKIE                    524

SEQ ID NO: 109          moltype = AA  length = 350
FEATURE                 Location/Qualifiers
REGION                  1..350
                        note = Description of Artificial Sequence: Synthetic
                         polypeptide
source                  1..350
                        mol_type = protein
                        organism = synthetic construct
SEQUENCE: 109
VWKEATTTLF CASDAKAYDN ESHNVWATHA CVPTDPNPNE SVLVNVTENF HWCKNDMVEQ    60
MHKDICNLWN ESLKPCVKLT GGSVINQSCN KTSFEPIPIH YCAPAGYAIL KCNNNTFNGT   120
GPCTNVSTVN CTHGIRPVVS SQLLLNGSLA EKEVVIRSCQ FMDNAKTIIV QLNTSVEINC   180
TAGNGTAHCN ISGAKWNKTL KRIASKLRKQ FGNNKTIIFK QSSGGDPEIV THWFNCGGEF   240
FYCNSTQLFN STWFNSTWST EGSNNTEGSD TITLPCKIKQ IINMWCGVGK MMYAPPVSNQ   300
SKCSSNITGL LLTRDGGNSN NESEIFRPGG TDMRDNWRSE LYKYKVVKIE             350
```

```
SEQ ID NO: 110              moltype = AA   length = 524
FEATURE                     Location/Qualifiers
REGION                      1..524
                            note = Description of Artificial Sequence: Synthetic
                             polypeptide
source                      1..524
                            mol_type = protein
                            organism = synthetic construct
SEQUENCE: 110
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGVWKEAT   180
TTLFCASDAK AYDNESHNVW ATHACVPTDP NPNESVLVNV TENFHWCKND MVEQMHKDIC   240
NLWNESLKPC VKLTGGSVIN QSCNKTSFEP IPIHYCAPAG YAILKCNNNT FNGTGPCTNV   300
STVNCTHGIR PVVSSQLLLN GSLAEKEVVI RSCQFMDNAK TIIVQLNTSV EINCTAGNGT   360
AHCNISGAKW NKTLKRIASK LRKQFGNNKT IIFKQSSGGD PEIVTHWFNC GGEFFYCNST   420
QLFNSTWFNS TWSTEGSNNT EGSDTITLPC KIKQIINMWC GVGKMMYAPP VSNQSKCSSN   480
ITGLLLTRDG GNSNNESEIF RPGGTDMRDN WRSELYKYKV VKIE                    524

SEQ ID NO: 111              moltype = AA   length = 371
FEATURE                     Location/Qualifiers
REGION                      1..371
                            note = Description of Artificial Sequence: Synthetic
                             polypeptide
source                      1..371
                            mol_type = protein
                            organism = synthetic construct
SEQUENCE: 111
AENLWVTVYY GVPVWKDAET TLFCASDAKA YETEKHNVWA THACVPTDPN PQEIHLENVT    60
EEFNMCKNDM VEQMHKDICN LWNESLKPCV KLTGTSAITQ ACPKVSFEPI PIHYCAPAGF   120
AILKCNNNTF NGTGPCTNVS TVQCTHGIKP VVSTQLLLNG SLAEEEVIIR SCDFMDNAKT   180
IIVQLNTSVE INCTAGNGTA HCNISGAKWN KTLKNISSKL RKQFGNNKTI IFKQSSGGDP   240
EIVTHWFNCG GEFFYCNSTQ LFNSTWFNSN WSNESSNNTN GSDNITLPCN ISQIINMWCG   300
VGKMNYSPPN SSNISCSSNI TGLLLTRDGG NSNNESEIFR PGGGDMRDNW RSELYKYKVV   360
KIEPLGVAPT R                                                        371

SEQ ID NO: 112              moltype = AA   length = 371
FEATURE                     Location/Qualifiers
REGION                      1..371
                            note = Description of Artificial Sequence: Synthetic
                             polypeptide
source                      1..371
                            mol_type = protein
                            organism = synthetic construct
SEQUENCE: 112
AENLWVTVYY GVPVWKDAET TLFCASDAKA YETEKHNVWA THACVPTDPN PQEIHLENVT    60
EEFNMCKNDM VEQMHKDICN LWNESLKPCN KTTGTSAITQ ACPKVSFEPI PIHYCAPAGF   120
AILKCNNNTF NGTGPCTNVS TVQCTHGIKP VVSTQLLLNG SLAEEEVIIR SCDFMDNAKT   180
IIVQLNTSVE INCTAGNGTA HCNISGAKWN KTLKNISSKL RKQYGNNKTI IFKQSSGGDP   240
EIVTHWFNCG GEFFYCNSTQ LFNSTWFNSN WSNESSNNTN GSDNITLPCN ISQIINMWCG   300
VGKMNYSPPN SSNISCSSNI TGLLLTRDGG VSNNETEIFR PGGGDMRDNW RSELYKYKVV   360
KIEPLGVAPT R                                                        371

SEQ ID NO: 113              moltype = AA   length = 371
FEATURE                     Location/Qualifiers
REGION                      1..371
                            note = Description of Artificial Sequence: Synthetic
                             polypeptide
source                      1..371
                            mol_type = protein
                            organism = synthetic construct
SEQUENCE: 113
AENLWVTVYY GVPVWKDAET TLFCASDAKA YETEKHNVWA THACVPTDPN PQEIHLENVT    60
EEFNMCKNDM VEQMHKDICN LWNESLKPCN KTTGTSAITQ ACPKVSFEPI PIHYCAPAGF   120
AILKCNNNTF NGTGPCTNVS TVQCTHGIKP VVSTQLLLNG SLAEEEVIIR SCDFMDNAKT   180
IIVQLNTSVE INCTAGNGTA HCNISGAKWN KTLKNISSKL RKQYGNNKTI IFKQSSGGDP   240
EIVTHWFNCG GEFFYCNSTQ LFNSTWFNSN WSNESSNNTN GSDNITLPCN ISQIINMWCG   300
VGKMNYSPPN SSNISCSSNI TGLLLTRQGG NSNNETEIFR PGGGDMRDNW RSELYKYKVV   360
KIEPLGVAPT R                                                        371

SEQ ID NO: 114              moltype = AA   length = 371
FEATURE                     Location/Qualifiers
REGION                      1..371
                            note = Description of Artificial Sequence: Synthetic
                             polypeptide
source                      1..371
                            mol_type = protein
                            organism = synthetic construct
```

```
SEQUENCE: 114
AENLWVTVYY GVPVWKDAET TLFCASDAKA YETEKHNVWA THACVPTDPN PQEIHLENVT   60
EEFNMCKNDM VEQMHKDICN LWNESLKPCN KTTGTSAITQ ACPKVSFEPI PIHYCAPAGF  120
AILKCNNNTF NGTGPCTNVS TVQCTHGIKP VVSTQLLLNG SLAEEEVIIR SCDFTDNAKT  180
IIVQLNTSVE INCTAGNGTA HCNISGAKWN KTLKNISSKL RKQFGNNKTI IFKQSSGGDP  240
EIVTHWFNCG GEFFYCNSTQ LFNSTWFNSN WSNESSNNTN GSDNITLPCN ISQIINMWCG  300
VGKMNYSPPN SSNISCSSNI TGLLLTRQGG NSNDETEIFR PGGGDMRDNW RSELYKYKVV  360
KIEPLGVAPT R                                                       371

SEQ ID NO: 115             moltype = AA  length = 371
FEATURE                    Location/Qualifiers
REGION                     1..371
                           note = Description of Artificial Sequence: Synthetic
                            polypeptide
source                     1..371
                           mol_type = protein
                           organism = synthetic construct
SEQUENCE: 115
AENLWVTVYY GVPVWKDAET TLFCASDAKA YETEKHNVWA THACVPTDPN PQEIHLENVT   60
EEFNMCKNDM VEQMHKDICN LWNESLKPCN KTTGTSAITQ ACPKVSFEPI PIHYCAPAGF  120
AILKCNNNTF NGTGPCTNVS TVQCTHGIKP VVSTQLLLNG SLAEEEVIIR SCNFTDNAKT  180
IIVQLNTSVE INCTAGNGTA HCNISGAKWN KTLKNISSKL RKQYGNNKTI IFKQSSGGDP  240
EIVTHWFNCG GEFFYCNSTQ LFNSTWFNSN WSNESSNNTN GSDNITLPCN ISQNITMWCG  300
VGKMNYSPPN SSNISCSSNI TGLLLTRDGG VSNNETEIFR PGGGDMRDNW RSELYKYKVV  360
KIEPLGVAPT R                                                       371

SEQ ID NO: 116             moltype = AA  length = 545
FEATURE                    Location/Qualifiers
REGION                     1..545
                           note = Description of Artificial Sequence: Synthetic
                            polypeptide
source                     1..545
                           mol_type = protein
                           organism = synthetic construct
SEQUENCE: 116
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGSG GSGGAENLWV  180
TVYYGVPVWK DAETTLFCAS DAKAYETEKH NVWATHACVP TDPNPQEIHL ENVTEEFNMC  240
KNDMVEQMHK DICNLWNESL KPCNKTTGTS AITQACPKVS FEPIPIHYCA PAGFAILKCN  300
NNTFNGTGPC TNVSTVQCTH GIKPVVSTQL LLNGSLAEEE VIIRSCNFTD NAKTIIVQLN  360
TSVEINCTAG NGTAHCNISG AKWNKTLKNI SSKLRKQYGN NKTIIFKQSS GGDPEIVTHW  420
FNCGGEFFYC NSTQLFNSTW FNSNWSNESS NNTNGSDNIT LPCNISQNIT MWCGVGKMNY  480
SPPNSSNISC SSNITGLLLT RDGGVSNNET EIFRPGGGDM RDNWRSELYK YKVVKIEPLG  540
VAPTR                                                              545

SEQ ID NO: 117             moltype = AA  length = 371
FEATURE                    Location/Qualifiers
REGION                     1..371
                           note = Description of Artificial Sequence: Synthetic
                            polypeptide
source                     1..371
                           mol_type = protein
                           organism = synthetic construct
SEQUENCE: 117
AENLWVTVYY GVPVWRDAET TLFCASDAKA YDTEMHNVWA THACVPTDPN PQEIHLENVT   60
EEFNMCKNDM VEQMHKDICN LWNESLKPCN KTTGTSAITQ ACPKVSFEPI PIHYCAPAGF  120
AILKCNNNTF NGTGPCTNVS TVQCTHGIKP VVSTQLLLNG SLAEEEVIIR SCDFMDNAKT  180
IIVQLNTSVE INCTAGNGTA HCNISGAKWN KTLKNISSKL RKQYGNNKTI IFKQSSGGDP  240
EIVTHWFNCG GEFFYCNSTQ LFNSTWFNSN WSNESSNNTN GSDNITLPCN ISQNITMWCG  300
VGKMNYSPPN SSNISCSSNI TGLLLTRDGG VSNNETEIFR PGGGNMRDNW RSELYKYKVV  360
KIEPLGVAPT R                                                       371

SEQ ID NO: 118             moltype = AA  length = 545
FEATURE                    Location/Qualifiers
REGION                     1..545
                           note = Description of Artificial Sequence: Synthetic
                            polypeptide
source                     1..545
                           mol_type = protein
                           organism = synthetic construct
SEQUENCE: 118
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGSG GSGGAENLWV  180
TVYYGVPVWR DAETTLFCAS DAKAYDTEMH NVWATHACVP TDPNPQEIHL ENVTEEFNMC  240
KNDMVEQMHK DICNLWNESL KPCNKTTGTS AITQACPKVS FEPIPIHYCA PAGFAILKCN  300
NNTFNGTGPC TNVSTVQCTH GIKPVVSTQL LLNGSLAEEE VIIRSCDFMD NAKTIIVQLN  360
TSVEINCTAG NGTAHCNISG AKWNKTLKNI SSKLRKQYGN NKTIIFKQSS GGDPEIVTHW  420
```

```
FNCGGEFFYC NSTQLFNSTW FNSNWSNESS NNTNGSDNIT LPCNISQNIT MWCGVGKMNY   480
SPPNSSNISC SSNITGLLLT RDGGVSNNET EIFRPGGGNM RDNWRSELYK YKVVKIEPLG   540
VAPTR                                                              545

SEQ ID NO: 119            moltype = AA   length = 371
FEATURE                   Location/Qualifiers
REGION                    1..371
                          note = Description of Artificial Sequence: Synthetic
                           polypeptide
source                    1..371
                          mol_type = protein
                          organism = synthetic construct
SEQUENCE: 119
AENLWVTVYY GVPVWRDAET TLFCASDAKA YDTEKHNVWA THACVPTDPN PQEIHLENVT   60
EEFNMCKNDM VEQMHKDICN LWNESLKPCN KTTGTSAITQ ACPKVSFEPI PIHYCAPAGF   120
AILKCNNNTF NGTGPCTNVS TVQCTHGIKP VVSTQLLLNG SLAEEEVIIR SCDFMDNAKT   180
IIVQLNTSVE INCTAGNGTA HCNISGAKWN KTLKNISSKL RKQYGNNKTI IFKQSSGGDP   240
EIVTHWFNCG GEFFYCNSTQ LFNSTWFNSN WSNESSNNTN GSDNITLPCN ISQNITMWCG   300
VGKMNYSPPN SSNISCSSNI TGLLLTRDGG VSNNETEIFR PGGGNMRDNW RSELYKYKVV   360
KIEPLGVAPT R                                                       371

SEQ ID NO: 120            moltype = AA   length = 545
FEATURE                   Location/Qualifiers
REGION                    1..545
                          note = Description of Artificial Sequence: Synthetic
                           polypeptide
source                    1..545
                          mol_type = protein
                          organism = synthetic construct
SEQUENCE: 120
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGAENLWV   180
TVYYGVPVWR DAETTLFCAS DAKAYDTEKH NVWATHACVP TDPNPQEIHL ENVTEEFNMC   240
KNDMVEQMHK DICNLWNESL KPCNKTTGTS AITQACPKVS FEPIPIHYCA PAGFAILKCN   300
NNTFNGTGPC TNVSTVQCTH GIKPVVSTQL LLNGSLAEEE VIIRSCDFMD NAKTIIVQLN   360
TSVEINCTAG NGTAHCNISG AKWNKTLKNI SSKLRKQYGN NKTIIFKQSS GGDPEIVTHW   420
FNCGGEFFYC NSTQLFNSTW FNSNWSNESS NNTNGSDNIT LPCNISQNIT MWCGVGKMNY   480
SPPNSSNISC SSNITGLLLT RDGGVSNNET EIFRPGGGNM RDNWRSELYK YKVVKIEPLG   540
VAPTR                                                              545

SEQ ID NO: 121            moltype = AA   length = 371
FEATURE                   Location/Qualifiers
REGION                    1..371
                          note = Description of Artificial Sequence: Synthetic
                           polypeptide
source                    1..371
                          mol_type = protein
                          organism = synthetic construct
SEQUENCE: 121
AENLWVTVYY GVPVWKDAET TLFCASDAKA YETEKHNVWA THACVPTDPN PQEIHLENVT   60
EEFNMCKNDM VEQMHKDICN LWNESLKPCN KTTGTSAITQ ACPKVSFEPI PIHYCAPAGF   120
AILKCNNNTF NGTGPCTNVS TVQCTHGIKP VVSTQLLLNG SLAEEEVIIR SCDFMDNAKT   180
IIVQLNTSVE INCTAGNGTA HCNISGAKWN KTLKNISSKL RKQYGNNKTI IFKQSSGGDP   240
EIVTHWFNCG GEFFYCNSTQ LFNSTWFNSN WSNESSNNTN GSDNITLPCN ISQNITMWCG   300
VGKMNYSPPN SSNISCSSNI TGLLLTRDGG VSNNETEIFR PGGGDMRDNW RSELYKYKVV   360
KIEPLGVAPT R                                                       371

SEQ ID NO: 122            moltype = AA   length = 545
FEATURE                   Location/Qualifiers
REGION                    1..545
                          note = Description of Artificial Sequence: Synthetic
                           polypeptide
source                    1..545
                          mol_type = protein
                          organism = synthetic construct
SEQUENCE: 122
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGSG GSGGAENLWV   180
TVYYGVPVWK DAETTLFCAS DAKAYETEKH NVWATHACVP TDPNPQEIHL ENVTEEFNMC   240
KNDMVEQMHK DICNLWNESL KPCNKTTGTS AITQACPKVS FEPIPIHYCA PAGFAILKCN   300
NNTFNGTGPC TNVSTVQCTH GIKPVVSTQL LLNGSLAEEE VIIRSCDFMD NAKTIIVQLN   360
TSVEINCTAG NGTAHCNISG AKWNKTLKNI SSKLRKQYGN NKTIIFKQSS GGDPEIVTHW   420
FNCGGEFFYC NSTQLFNSTW FNSNWSNESS NNTNGSDNIT LPCNISQNIT MWCGVGKMNY   480
SPPNSSNISC SSNITGLLLT RDGGVSNNET EIFRPGGGDM RDNWRSELYK YKVVKIEPLG   540
VAPTR                                                              545

SEQ ID NO: 123            moltype = AA   length = 371
```

```
FEATURE           Location/Qualifiers
REGION            1..371
                  note = Description of Artificial Sequence: Synthetic
                   polypeptide
source            1..371
                  mol_type = protein
                  organism = synthetic construct
SEQUENCE: 123
AENLWVTVYY GVPVWKDAET TLFCASDAKA YETEKHNVWA THACVPTDPN PQEIHLENVT      60
EEFNMCKNDM VEQMHKDICN LWNESLKPCN KTTGTSAITQ ACPKVSFEPI PIHYCAPAGF     120
AILKCNNNTF NGTGPCTNVS TVQCTHGIKP VVSTQLLLNG SLAEEEVIIR SCDFMDNAKT     180
IIVQLNTSVE INCTAGNGTA HCNISGAKWN KTLKNISSKL RKQYGNNKTI IFKQSSGGDP     240
EIVTHWFNCG GEFFYCNSTQ LFNSTWFNSN WSNESSNNTN GSDNITLPCN ISQNITMWCG     300
VGKMNYSPPN SSNISCSSNI TGLLLTRDGG VSNNETEIFR PGGTDMRDNW RSELYKYKVV     360
KIEPLGVAPT R                                                          371

SEQ ID NO: 124    moltype = AA  length = 545
FEATURE           Location/Qualifiers
REGION            1..545
                  note = Description of Artificial Sequence: Synthetic
                   polypeptide
source            1..545
                  mol_type = protein
                  organism = synthetic construct
SEQUENCE: 124
MQIYEGKLTA EGLRFGIVAS RANHALVDRL VEGAIDAIVR HGGREEDITL VRVCGSWEIP      60
VAAGELARKE DIDAVIAIGV LCRGATPSFD YIASEVSKGL ADLSLELRKP ITFGVITADT     120
LEQAIEAAGT CHGNKGWEAA LCAIEMANLF KSLRGGSGGS GGSGGSGGSG GSGGAENLWV     180
TVYYGVPVWK DAETTLFCAS DAKAYETEKH NVWATHACVP TDPNPQEIHL ENVTEEFNMC     240
KNDMVEQMHK DICNLWNESL KPCNKTTGTS AITQACPKVS FEPIPIHYCA PAGFAILKCN     300
NNTFNGTGPC TNVSTVQCTH GIKPVVSTQL LLNGSLAEEE VIIRSCDFMD NAKTIIVQLN     360
TSVEINCTAG NGTAHCNISG AKWNKTLKNI SSKLRKQYGN NKTIIFKQSS GGDPEIVTHW     420
FNCGGEFFYC NSTQLFNSTW FNSNWSNESS NNTNGSDNIT LPCNISQNIT MWCGVGKMNY     480
SPPNSSNISC SSNITGLLLT RDGGVSNNET EIFRPGGTDM RDNWRSELYK YKVVKIEPLG     540
VAPTR                                                                 545

SEQ ID NO: 125    moltype = AA  length = 371
FEATURE           Location/Qualifiers
REGION            1..371
                  note = Description of Artificial Sequence: Synthetic
                   polypeptide
source            1..371
                  mol_type = protein
                  organism = synthetic construct
SEQUENCE: 125
AENLWVTVYY GVPVWKDAET TLFCASDAKA YETEKHNVWA THACVPTDPN PQEIHLENVT      60
EEFNMCKNDM VEQMHKDICN LWNESLKPCN KTTGTSAITQ ACPKVSFEPI PIHYCAPAGF     120
AILKCNNNTF NGTGPCTNVS TVQCTHGIKP VVSTQLLLNG SLAEEEVIIR SCQFMDNAKT     180
IIVQLNTSVE INCTAGNGTA HCNISGAKWN KTLKNISSKL RKQYGNNKTI IFKQSSGGDP     240
EIVTHWFNCG GEFFYCNSTQ LFNSTWFNSN WSNESSNNTN GSDNITLPCN ISQNITMWCG     300
VGKMNYSPPN SSNISCSSNI TGLLLTRDGG VSNNETEIFR PGGGDMRDNW RSELYKYKVV     360
KIEPLGVAPT R                                                          371

SEQ ID NO: 126    moltype = AA  length = 545
FEATURE           Location/Qualifiers
REGION            1..545
                  note = Description of Artificial Sequence: Synthetic
                   polypeptide
source            1..545
                  mol_type = protein
                  organism = synthetic construct
SEQUENCE: 126
MQIYEGKLTA EGLRFGIVAS RANHALVDRL VEGAIDAIVR HGGREEDITL VRVCGSWEIP      60
VAAGELARKE DIDAVIAIGV LCRGATPSFD YIASEVSKGL ADLSLELRKP ITFGVITADT     120
LEQAIEAAGT CHGNKGWEAA LCAIEMANLF KSLRGGSGGS GGSGGSGGSG GSGGAENLWV     180
TVYYGVPVWK DAETTLFCAS DAKAYETEKH NVWATHACVP TDPNPQEIHL ENVTEEFNMC     240
KNDMVEQMHK DICNLWNESL KPCNKTTGTS AITQACPKVS FEPIPIHYCA PAGFAILKCN     300
NNTFNGTGPC TNVSTVQCTH GIKPVVSTQL LLNGSLAEEE VIIRSCQFMD NAKTIIVQLN     360
TSVEINCTAG NGTAHCNISG AKWNKTLKNI SSKLRKQYGN NKTIIFKQSS GGDPEIVTHW     420
FNCGGEFFYC NSTQLFNSTW FNSNWSNESS NNTNGSDNIT LPCNISQNIT MWCGVGKMNY     480
SPPNSSNISC SSNITGLLLT RDGGVSNNET EIFRPGGGDM RDNWRSELYK YKVVKIEPLG     540
VAPTR                                                                 545

SEQ ID NO: 127    moltype = AA  length = 371
FEATURE           Location/Qualifiers
REGION            1..371
                  note = Description of Artificial Sequence: Synthetic
                   polypeptide
source            1..371
```

```
                                mol_type = protein
                                organism = synthetic construct
SEQUENCE: 127
AENLWVTVYY GVPVWKDAET TLFCASDAKA YETEKHNVWA THACVPTDPN PQEIHLENVT   60
EEFNMCKNDM VEQMHKDICN LWNESLKPCN KTTGTSAITQ ACPKVSFEPI PIHYCAPAGF  120
AILKCNNNTF NGTGPCTNVS TVQCTHGIKP VVSTQLLLNG SLAEEEVIIR SCDFMDNAKT  180
IIVQLNTSVE INCTAGNGTA HCNISGAKWN KTLKNISSKL RKQYGNNKTI IFKQSSGGDP  240
EIVTHWFNCG GEFFYCNSTQ LFNSTWFNST WSNESSNNTN GSDNITLPCN ISQNITMWCG  300
VGKMNYSPPN SSNISCSSNI TGLLLTRDGG VSNNETEIFR PGGGDMRDNW RSELYKYKVV  360
KIEPLGVAPT R                                                       371

SEQ ID NO: 128            moltype = AA  length = 371
FEATURE                   Location/Qualifiers
REGION                    1..371
                          note = Description of Artificial Sequence: Synthetic
                           polypeptide
source                    1..371
                          mol_type = protein
                          organism = synthetic construct
SEQUENCE: 128
AENLWVTVYY GVPVWKDAET TLFCASDAKA YETEKHNVWA THACVPTDPN PQEIHLENVT   60
EEFNMCKNDM VEQMHKDICN LWNESLKPCN KTTGTSAITQ ACPKVSFEPI PIHYCAPAGF  120
AILKCNNNTF NGTGPCTNVS TVQCTHGIKP VVSTQLLLNG SLAEEEVIIR SCDFMDNAKT  180
IIVQLNTSVE INCTAGNGTA HCNISGAKWN KTLKNISSKL RKQYGNNKTI IFKQSSGGDP  240
EIVTHWFNCG GEFFYCNSTQ LFNSTWFNST WSNESSNNTN GSDNITLPCN ISQIINMWCG  300
VGKMNYSPPN SSNISCSSNI TGLLLTRDGG VSNNETEIFR PGGGDMRDNW RSELYKYKVV  360
KIEPLGVAPT R                                                       371

SEQ ID NO: 129            moltype = AA  length = 371
FEATURE                   Location/Qualifiers
REGION                    1..371
                          note = Description of Artificial Sequence: Synthetic
                           polypeptide
source                    1..371
                          mol_type = protein
                          organism = synthetic construct
SEQUENCE: 129
AENLWVTVYY GVPVWKDAET TLFCASDAKA YETEKHNVWA THACVPTDPN PQEIHLENVT   60
EEFNMCKNDM VEQMHKDICN LWNESLKPCN KTTGTSAITQ ACPKVSFEPI PIHYCAPAGF  120
AILKCNNNTF NGTGPCTNVS TVQCTHGIKP VVSTQLLLNG SLAEEEVIIR SCDFMDNAKT  180
IIVQLNTSVE INCTAGNGTA HCNISGAKWN KTLKNISSKL RKQYGNNKTI IFKQSSGGDP  240
EIVTHWFNCG GEFFYCNSTQ LFNSTWFNST WSNESSNNTN GSDNITLPCN ISQIINMWCG  300
VGKMNYSPPN SSNISCSSNI TGLLLIRDGG VSNNETEIFR PGGGDMRDNW RSELYKYKVV  360
KIEPLGVAPT R                                                       371

SEQ ID NO: 130            moltype = AA  length = 341
FEATURE                   Location/Qualifiers
REGION                    1..341
                          note = Description of Artificial Sequence: Synthetic
                           polypeptide
source                    1..341
                          mol_type = protein
                          organism = synthetic construct
SEQUENCE: 130
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPNCTSNITG LILTRQGGWS NDNTVIFRPS AGDWRDIARC NITGTVVSTQ LFLNGSLAEN  240
ETVIRSRDWR DNQQSICVQL NTSVEINCTG NGTCNISRAK WNNTLKQIAS KLREQYGNKT  300
VIFAPSSGGD PEFVNHSFNC GNVTFYCNST QLFNSTWFNS T                      341

SEQ ID NO: 131            moltype = AA  length = 341
FEATURE                   Location/Qualifiers
REGION                    1..341
                          note = Description of Artificial Sequence: Synthetic
                           polypeptide
source                    1..341
                          mol_type = protein
                          organism = synthetic construct
SEQUENCE: 131
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPNCTSNITG LILTRQGGWS NDNTVIFRPS AGDWRDIARC NITGTVVSTQ LFLNGSLAEN  240
ETVIRSRNWT DNQQSICVQL NTSVEINCTG NGTCNISRAK WNNTLKQIAS KLREQYGNKT  300
VIFAPSSGGD PEFVNHSFNC GNVTFYCNST QLFNSTWFNS T                      341

SEQ ID NO: 132            moltype = AA  length = 341
FEATURE                   Location/Qualifiers
```

-continued

```
REGION                    1..341
                          note = Description of Artificial Sequence: Synthetic
                           polypeptide
source                    1..341
                          mol_type = protein
                          organism = synthetic construct
SEQUENCE: 132
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGGD TIELKCEPAP   180
PPSCSSNITG LILTRDGGVS NNETEIFRPS GGDMRDINSC NIAGPVRSTQ LFLNGSLAEK   240
EVVIHSVDFR DNAKSICVQL NSSVTINCTG NGSCNISRAK WNKTLAEIAN KLKKTYGNRT   300
IIFAQSSGGD PEFVTHSFDC NGKTFYCNST QLFNSTWDNS T                       341

SEQ ID NO: 133           moltype = AA  length = 341
FEATURE                  Location/Qualifiers
REGION                    1..341
                          note = Description of Artificial Sequence: Synthetic
                           polypeptide
source                    1..341
                          mol_type = protein
                          organism = synthetic construct
SEQUENCE: 133
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGGD TIELKCEPAP   180
PPSCSSNITG LILTRDGGVS NNETEIFRPS GGDMRDINSC NIAGPVRSTQ LFLNGSLAEK   240
EVVIHSVNFT DNAKSICVQL NSSVTINCTG NGSCNISRAK WNKTLAEIAN KLKKTYGNRT   300
IIFAQSSGGD PEFVTHSFDC NGKTFYCNST QLFNSTWDNS T                       341

SEQ ID NO: 134           moltype = AA  length = 341
FEATURE                  Location/Qualifiers
REGION                    1..341
                          note = Description of Artificial Sequence: Synthetic
                           polypeptide
source                    1..341
                          mol_type = protein
                          organism = synthetic construct
SEQUENCE: 134
MQIYEGKLTA EGLRFGIVAS RANHALVDRL VEGAIDAIVR HGGREEDITL VRVCGSWEIP    60
VAAGELARKE DIDAVIAIGV LCRGATPSFD YIASEVSKGL ADLSLELRKP ITFGVITADT   120
LEQAIEAAGT CHGNKGWEAA LCAIEMANLF KSLRGGSGGS GGSGGSGGGD TIELKCEPAP   180
PPSCSSNITG LILTRDGGNS NNETEIFRPS GGDMRDINSC NIAGPVRSTQ LFLNGSLAEK   240
EVVIHSENFT DNAKSICVQL NSSVTINCTG NGSCNISRAK WNKTLAEIAN KLKKTYGNRT   300
IIFAQSSGGD PEFVTHSFDC NGKTFYCNST QLFNSTWDNS T                       341

SEQ ID NO: 135           moltype = AA  length = 172
FEATURE                  Location/Qualifiers
REGION                    1..172
                          note = Description of Artificial Sequence: Synthetic
                           polypeptide
source                    1..172
                          mol_type = protein
                          organism = synthetic construct
SEQUENCE: 135
DTIELKCEPA PPPSCSSNIT GLILTRDGGV SNNETEIFRP SGGDMRDINS CNIAGPVRST    60
QLFLNGSLAE KEVVIHSVNF TDNAKSICVQ LNSSVTINCT GNGSCNISRA KWNKTLAEIA   120
NKLKKTYGNR TIIFAQSSGG DPEFVTHSFD CNGKTFYCNS TQLFNSTWDN ST           172

SEQ ID NO: 136           moltype = AA  length = 172
FEATURE                  Location/Qualifiers
REGION                    1..172
                          note = Description of Artificial Sequence: Synthetic
                           polypeptide
source                    1..172
                          mol_type = protein
                          organism = synthetic construct
SEQUENCE: 136
DTIELKCEPA PPPSCSSNIT GLILTRDGGN SNNETEIFRP SGGDMRDINS CNIAGPVRST    60
QLFLNGSLAE KEVVIHSENF TDNAKSICVQ LNSSVTINCT GNGSCNISRA KWNKTLAEIA   120
NKLKKTYGNR TIIFAQSSGG DPEFVTHSFD CNGKTFYCNS TQLFNSTWDN ST           172

SEQ ID NO: 137           moltype = AA  length = 341
FEATURE                  Location/Qualifiers
REGION                    1..341
                          note = Description of Artificial Sequence: Synthetic
                           polypeptide
source                    1..341
                          mol_type = protein
```

```
                              organism = synthetic construct
SEQUENCE: 137
MQIYEGKLTA EGLRFGIVAS RANHALVDRL VEGAIDAIVR HGGREEDITL VRVCGSWEIP  60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPNCTSNITG LILTRQGGYS NDNTVIFRPS GGDWRDIARC NITGTVVSTQ LFLNGSLAEN  240
ETVIRSEDWR DNAKSICVQL NTSVEINCTG NGTCNISRAK WNNTLKQIAS KLREQYGNKT  300
IIFKPSSGGD PEFVNHSFNC GNVTFYCNST QLFNSTWFNS T                     341

SEQ ID NO: 138          moltype = AA  length = 343
FEATURE                 Location/Qualifiers
REGION                  1..343
                        note = Description of Artificial Sequence: Synthetic
                         polypeptide
source                  1..343
                        mol_type = protein
                        organism = synthetic construct
SEQUENCE: 138
MQIYEGKLTA EGLRFGIVAS RANHALVDRL VEGAIDAIVR HGGREEDITL VRVCGSWEIP  60
VAAGELARKE NISAVIAIGV LCRGATPSFD YIASEVSKGL ADLSLELRKP ITFGVITADT  120
LEQAIEAAGT CHGNKGWEAA LCAIEMANLF KSLRGGSNGT GGSGGSNGTG GDTITLPCRP  180
APPPNCTSNI TGLILTRQGG YSNDNTVIFR PSGGDWRDIA RCNITGTVVS TQLFLNGSLA  240
ENETVIRSED WRDNAKSICV QLNTSVEINC TGNGTCNISR AKWNNTLKQI ASKLREQYGN  300
KTIIFKPSSG GDPEFVNHSF NCGNVTFYCN STQLFNSTWF NST                   343

SEQ ID NO: 139          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 139
MQIYEGKLTA EGLRFGIVAS RANHALVDRL VEGAIDAIVR HGGREEDITL VRVCGSWEIP  60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPHCSSNITG LILTRQGGYS NDNTVIFRPS GGDWRDIARC QIAGTVVSTQ LFLNGSLAEE  240
EVVIRSEDWR DNAKSICVQL NTSVEINCTG AGHCNISRAK WNNTLKQIAS KLREQYGNKT  300
IIFKPSSGGD PEFVNHSFNC GGEFFYCDST QLFNSTWFNS T                     341

SEQ ID NO: 140          moltype = AA  length = 512
FEATURE                 Location/Qualifiers
REGION                  1..512
                        note = Description of Artificial Sequence: Synthetic
                         polypeptide
source                  1..512
                        mol_type = protein
                        organism = synthetic construct
SEQUENCE: 140
MGARASVLSG GELDRWEKIR LRPGGKKKYK LKHIVWASRE LERFAVNPGL LETSEGCRQI  60
LGQLQPSLQT GSEELRSLYN TVATLYCVHQ RIEIKDTKEA LDKIEEEQNK SKKKAQQAAA  120
DTGHSSQVSQ NYPIVQNIQG QMVHQAISPR TLNAWVKVVE EKAFSPEVIP MFSALSEGAT  180
PQDLNTMLNT VGGHQAAMQM LKETINEEAA EWDRVHPVHA GPIAPGQMRE PRGSDIAGTT  240
STLQEQIGWM TNNPPIPVGE IYKRWIILGL NKIVRMYSPT SILDIRQGPK EPFRDYVDRF  300
YKTLRAEQAS QEVKNWMTET LLVQNANPDC KTILKALGPA ATLEEMMTAC QGVGGPGHKA  360
RVLAEAMSQA TNTATIMMQR GNFRNQRKMV KCFNCGKEGH TARNCRAPRK KGCWKCGKEG  420
HQMKDCTERQ ANFLGKIWPS YKGRPGNFLQ SRPEPTAPPF LQSRPEPTAP PEESFRSGVE  480
TTTPPQKQEP IDKELYPLTS LRSLFGNDPS SQ                               512

SEQ ID NO: 141          moltype = AA  length = 341
FEATURE                 Location/Qualifiers
REGION                  1..341
                        note = Description of Artificial Sequence: Synthetic
                         polypeptide
source                  1..341
                        mol_type = protein
                        organism = synthetic construct
SEQUENCE: 141
MQIYEGKLTA EGLRFGIVAS RANHALVDRL VEGAIDAIVR HGGREEDITL VRVCGSWEIP  60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPHCSSNITG LILTRQGGWN NDNTVIFRPS AGDWSDIARC QIAGTVVSTQ LFLNGSLAEE  240
EVVIRSRNWT DNQQSICVQL NTSVEINCTG AGHCNISRAK WNNTLKQIAS KLREQYGNKT  300
VIFAPSSGGD PEFVNHSFNC GGEFFYCNST QLFNSTWFNS T                     341

SEQ ID NO: 142          moltype = AA  length = 341
FEATURE                 Location/Qualifiers
REGION                  1..341
```

```
                          note = Description of Artificial Sequence: Synthetic
                           polypeptide
source                    1..341
                          mol_type = protein
                          organism = synthetic construct
SEQUENCE: 142
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPHCSSNITG LILTRQGGWN NQNTVIFRPS AGDWSDIARC QIAGTVVSTQ LFLNGSLAEE  240
EVVIRSRNWT DNQQSICVQL NTSVEINCTG AGHCNISRAK WNNTLKQIAS KLREQYGNKT  300
VIFAPSSGGD PEFVNHSFNC GGEFFYCNST QLFNSTWFNS T                     341

SEQ ID NO: 143           moltype = AA  length = 341
FEATURE                  Location/Qualifiers
REGION                   1..341
                         note = Description of Artificial Sequence: Synthetic
                          polypeptide
source                   1..341
                         mol_type = protein
                         organism = synthetic construct
SEQUENCE: 143
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPHCSSNITG LILTRQGGWN NQNTVIFRPS AGDWSDIARC QIAGTVVSTQ LFLNGSLAEE  240
EVVIRSRNWT DNQQSICVQL NTSVEINCTG AGHCNISRAK WNNTLKQIAS KLREQYGNKT  300
VIFAPSSGGD PEFVMHSFNC GGEFFYCNST QLFNSTWFNS T                     341

SEQ ID NO: 144           moltype = AA  length = 341
FEATURE                  Location/Qualifiers
REGION                   1..341
                         note = Description of Artificial Sequence: Synthetic
                          polypeptide
source                   1..341
                         mol_type = protein
                         organism = synthetic construct
SEQUENCE: 144
MQIYEGKLTA EGLRFGIVAS RANHALVDRL VEGAIDAIVR HGGREEDITL VRVCGSWEIP   60
VAAGELARKE DIDAVIAIGV LCRGATPSFD YIASEVSKGL ADLSLELRKP ITFGVITADT  120
LEQAIEAAGT CHGNKGWEAA LCAIEMANLF KSLRGGSGGS GGSGGSGGGD TITLPCRPAP  180
PPNCTSNITG LILTRQGGWN NDNTVIFRPS AGDWSDIARC NITGTVVSTQ LFLNGSLAEN  240
ETVIRSRNWT DNQQSICVQL NTSVEINCTG NGTCNISRAK WNNTLKQIAS KLREQYGNKT  300
VIFAPSSGGD PEFVNHSFNC GNVTFYCNST QLFNSTWFNS T                     341

SEQ ID NO: 145           moltype = AA  length = 172
FEATURE                  Location/Qualifiers
REGION                   1..172
                         note = Description of Artificial Sequence: Synthetic
                          polypeptide
source                   1..172
                         mol_type = protein
                         organism = synthetic construct
SEQUENCE: 145
DTITLPCRPA PPPHCSSNIT GLILTRQGGW NNDNTVIFRP SAGDWSDIAR CQIAGTVVST   60
QLFLNGSLAE EEVVIRSRNW TDNQQSICVQ LNTSVEINCT GAGHCNISRA KWNNTLKQIA  120
SKLREQYGNK TVIFAPSSGG DPEFVNHSFN CGGEFFYCNS TQLFNSTWFN ST          172

SEQ ID NO: 146           moltype = AA  length = 172
FEATURE                  Location/Qualifiers
REGION                   1..172
                         note = Description of Artificial Sequence: Synthetic
                          polypeptide
source                   1..172
                         mol_type = protein
                         organism = synthetic construct
SEQUENCE: 146
DTITLPCRPA PPPHCSSNIT GLILTRQGGW NNQNTVIFRP SAGDWSDIAR CQIAGTVVST   60
QLFLNGSLAE EEVVIRSRNW TDNQQSICVQ LNTSVEINCT GAGHCNISRA KWNNTLKQIA  120
SKLREQYGNK TVIFAPSSGG DPEFVNHSFN CGGEFFYCNS TQLFNSTWFN ST          172

SEQ ID NO: 147           moltype = AA  length = 172
FEATURE                  Location/Qualifiers
REGION                   1..172
                         note = Description of Artificial Sequence: Synthetic
                          polypeptide
source                   1..172
                         mol_type = protein
                         organism = synthetic construct
```

```
SEQUENCE: 147
DTITLPCRPA PPPHCSSNIT GLILTRQGGW NNQNTVIFRP SAGDWSDIAR CQIAGTVVST  60
QLFLNGSLAE EEVVIRSRNW TDNQQSICVQ LNTSVEINCT GAGHCNISRA KWNNTLKQIA  120
SKLREQYGNK TVIFAPSSGG DPEFVMHSFN CGGEFFYCNS TQLFNSTWFN ST          172

SEQ ID NO: 148          moltype = AA  length = 172
FEATURE                 Location/Qualifiers
REGION                  1..172
                        note = Description of Artificial Sequence: Synthetic
                         polypeptide
source                  1..172
                        mol_type = protein
                        organism = synthetic construct
SEQUENCE: 148
DTITLPCRPA PPPNCTSNIT GLILTRQGGW NNDNTVIFRP SAGDWSDIAR CNITGTVVST  60
QLFLNGSLAE NETVIRSRNW TDNQQSICVQ LNTSVEINCT GNGTCNISRA KWNNTLKQIA  120
SKLREQYGNK TVIFAPSSGG DPEFVNHSFN CGNVTFYCNS TQLFNSTWFN ST          172

SEQ ID NO: 149          moltype = AA  length = 642
FEATURE                 Location/Qualifiers
REGION                  1..642
                        note = Description of Artificial Sequence: Synthetic
                         polypeptide
source                  1..642
                        mol_type = protein
                        organism = synthetic construct
SEQUENCE: 149
AENLWVTVYY GVPVWKDAET TLFCASDAKA YETEKHNVWA THACVPTDPN PQEIHLENVT  60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSENITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LD                     642

SEQ ID NO: 150          moltype = AA  length = 642
FEATURE                 Location/Qualifiers
REGION                  1..642
                        note = Description of Artificial Sequence: Synthetic
                         polypeptide
source                  1..642
                        mol_type = protein
                        organism = synthetic construct
SEQUENCE: 150
AENLWVTVYY GVPVWKDAET TLFCASDAKA YETEKHNVWA THACVPTDPN PQEIHLENVT  60
EEFNMWKNNM VEQMHEDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSEQITNN AKNILVQLNT SVQINCTRPN NNTVKSIRIG PGQAFYYTGD IIGDIRQAHC  300
NVSKATWNET LGKVVKQLRK HFGNNTIIRF AQSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGSHSGS  480
GGSGSGGHAA VGIGAVSLGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LD                     642

SEQ ID NO: 151          moltype = AA  length = 635
FEATURE                 Location/Qualifiers
REGION                  1..635
                        note = Description of Artificial Sequence: Synthetic
                         polypeptide
source                  1..635
                        mol_type = protein
                        organism = synthetic construct
SEQUENCE: 151
GGNSSGSLGF LGAAGSTMGA ASMTLTVQAR NLLSGIVQQQ SNLLRAPEPQ QHLLKLTVWG  60
IKQLQARVLA VEHYLRDQQL LGIWGCSGKL ICCTNVPWNS SWSNRNLSEI WDNMTWLNWS  120
KEISNYTQII YGLLEESQNQ NESNEQDLGG NGSGGGSGSG GNGSSGLWVT VYYGVPVWKD  180
AETTLFCASD AKAYETEKHN VWATHECVPT DPNSSEIHLE NVTEEFNMWK NNMVEQMHTD  240
IIELWDQSLK PCVKLTPLCV TLQCTNVTNN ITDDMRGELK NCSFNMTTEL RDKKQKVYSL  300
FYRLDVVQIN ENQGNRSNNS NKEYRLINCN TSAITQACPK VSFEPIPIHY CAPAGFAILK  360
CKDKKFNGTG PCQNVSTVQC THGIKPVVST QLLLNGSLAE EEVIIRSENI TNNAKNILVQ  420
LNTSVQINCT RPNNNTVKSI RIGPGQAFYY TGDIIGDIRQ AHCNVSKATW NETLGKVVKQ  480
LRKHFGNNTI IRFAQSSGGD LEVTTHSFNC GGEFFYCNTS GLFNSTWISN TSVQGSNSTG  540
SNDSITLPCR IKQIINMWQR IGQAMYAPPI QGVIRCVSNI TGLILTRDGG STNSTTETFR  600
```

```
PGGGDMRDNW RSELYKYKVV KIEPLGVAPT RCNRS                          635

SEQ ID NO: 152        moltype = AA  length = 635
FEATURE               Location/Qualifiers
REGION                1..635
                      note = Description of Artificial Sequence: Synthetic
                       polypeptide
source                1..635
                      mol_type = protein
                      organism = synthetic construct
SEQUENCE: 152
GGNSSGSLGF LGAAGSTMGA ASMTLTVQAR NLLSGIVQQQ SNLLRAPEPQ QHLLKLTVWG   60
IKQLQARVLA VEHYLRDQQL LGIWGCSGKL ICCTNVPWNS SWSNRNLSEI WDNMTWLNWS  120
KEISNYTQII YGLLEESQNQ NESNEQDLGG NGSGGGSGSG GNGSSGLWVT VYYGVPVWKD  180
AETTLFCASD AKAYETEKHN VWATHECVPT DPNSSEIHLE NVTEEFNMWK NNMVEQMHTD  240
IIELWDQSLK PCVKLTPLCV TLQCTNVTNN ITDDMRGELK NCSFNMTTEL RDKKQKVYSL  300
FYRLDVVQIN ENQGNRSNNS NKEYRLINCN TSAITQACPK VSFEPIPIHY CAPAGFAILK  360
CKDKKFNGTG PCQNVSTVQC THGIKPVVST QLLLNGSLAE EEVIIRSEQI TNNAKNILVQ  420
LNTSVQINCT RPNNNTVKSI RIGPGQAFYY TGDIIGDIRQ AHCNVSKATW NETLGKVVKQ  480
LRKHFGNNTI IRFAQSSGGD LEVTTHSFNC GGEFFYCNTS GLFNSTWISN TSVQGSNSTG  540
SNDSITLPCR IKQIINMWQR IGQAMYAPPI QGVIRCVSNI TGLILTRDGG STNSTTETFR  600
PGGGDMRDNW RSELYKYKVV KIEPLGVAPT RCNRS                          635

SEQ ID NO: 153        moltype = AA  length = 687
FEATURE               Location/Qualifiers
REGION                1..687
                      note = Description of Artificial Sequence: Synthetic
                       polypeptide
source                1..687
                      mol_type = protein
                      organism = synthetic construct
SEQUENCE: 153
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYAPKLRS MMRGEIKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
IIRSENITNN AKNILVQLNT PVQINCTRPS NNTVKSIRIG PGQAFYYFGD VLGHVRMAHC  300
NISKATWNET LGKVVKQLRK HFGNNTIIRF AQSSGGDLEV TTHSFNCGGE FFYCNTSGLF  360
NSTWISNTSV QGSNSTGSND SLILPCWIKQ IINMWQRIGQ AMYAPPIQGV IRCVSNITGL  420
ILTRDGGSTN STTETFRPGG GDMRDNWRSE LYKYKVVKIE PLGVAPTRCK RRTVGSHSGS  480
GGSGSGGHAA AGIGASSDGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                   687

SEQ ID NO: 154        moltype = AA  length = 687
FEATURE               Location/Qualifiers
REGION                1..687
                      note = Description of Artificial Sequence: Synthetic
                       polypeptide
source                1..687
                      mol_type = protein
                      organism = synthetic construct
SEQUENCE: 154
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYAPKLRS MMRGEIKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSENITNN AKNILVQLNT SVQINCTRPS NNTVKSIRIG PGQAFYYFGD VLGHVRMAHC  300
NISKATWNET LGKVVKQLRK HFGNNTIIRF AQSSGGDLEV TTHSFNCGGE FFYCNTSGLF  360
NSTWISNTSV QGSNSTGSND SLILPCWIKQ IINMWQRIGQ AMYAPPIQGV IRCVSNITGL  420
ILTRDGGSTN STTETFRPGG GDMRDNWRSE LYKYKVVKIE PLGVAPTRCK RRTVGSHSGS  480
GGSGSGGHAA AGIGASSDGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LDKWASLWNW FDISNWLWYI  660
KIFIMIVGGL IGLRIVFAVL SVIHRVR                                   687

SEQ ID NO: 155        moltype = AA  length = 642
FEATURE               Location/Qualifiers
REGION                1..642
                      note = Description of Artificial Sequence: Synthetic
                       polypeptide
source                1..642
                      mol_type = protein
                      organism = synthetic construct
SEQUENCE: 155
AENLWVTVYY GVPVWKDAET TLFCASDAKA YETEKHNVWA THACVPTDPN PQEIHLENVT   60
EEFNMWKNNM VEQMHEDIIS LWDQSLKPCV KLTPLCVTLQ CTNYAPKLRS MMRGEIKNCS  120
FNMTTELRDK KQKVYSLFYR LDVVQINENQ GNRSNNSNKE YRLINCNTSA ITQACPKVSF  180
```

```
EPIPIHYCAP AGFAILKCKD KKFNGTGPCP SVSTVQCTHG IKPVVSTQLL LNGSLAEEEV  240
IIRSENITNN AKNILVQLNT PVQINCTRPS NNTVKSIRIG PGQAFYYFGD VLGHVRMAHC  300
NISKATWNET LGKVVKQLRK HFGNNTIIRF AQSSGGDLEV TTHSFNCGGE FFYCNTSGLF  360
NSTWISNTSV QGSNSTGSND SLILPCWIKQ IINMWQRIGQ AMYAPPIQGV IRCVSNITGL  420
ILTRDGGSTN STTETFRPGG GDMRDNWRSE LYKYKVVKIE PLGVAPTRCK RRTVGSHSGS  480
GGSGSGGHAA AGIGASSDGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LD                     642

SEQ ID NO: 156         moltype = AA  length = 642
FEATURE                Location/Qualifiers
REGION                 1..642
                       note = Description of Artificial Sequence: Synthetic
                        polypeptide
source                 1..642
                       mol_type = protein
                       organism = synthetic construct
SEQUENCE: 156
AENLWVTVYY GVPVWKDAET TLFCASDAKA YETEKHNVWA THACVPTDPN PQEIHLENVT  60
EEFNMWKNNM VEQMHEDIIS LWDQSLKPCV KLTPLCVTLQ CTNYAPKLRS MMRGEIKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCQ NVSTVQCTHG IKPVVSTQLL LNGSLAEEEV  240
IIRSENITNN AKNILVQLNT SVQINCTRPS NNTVKSIRIG PGQAFYYFGD VLGHVRMAHC  300
NISKATWNET LGKVVKQLRK HFGNNTIIRF AQSSGGDLEV TTHSFNCGGE FFYCNTSGLF  360
NSTWISNTSV QGSNSTGSND SLILPCWIKQ IINMWQRIGQ AMYAPPIQGV IRCVSNITGL  420
ILTRDGGSTN STTETFRPGG GDMRDNWRSE LYKYKVVKIE PLGVAPTRCK RRTVGSHSGS  480
GGSGSGGHAA AGIGASSDGF LGAAGSTMGA ASMTLTVQAR NLLSGIVQQQ SNLLRAPEPQ  540
QHLLKDTHWG IKQLQARVLA VEHYLRDQQL LGIWGCSGKL ICCTNVPWNS SWSNRNLSEI  600
WDNMTWLQWD KEISNYTQII YGLLEESQNQ QEKNEQDLLA LD                     642

SEQ ID NO: 157         moltype = AA  length = 628
FEATURE                Location/Qualifiers
REGION                 1..628
                       note = Description of Artificial Sequence: Synthetic
                        polypeptide
source                 1..628
                       mol_type = protein
                       organism = synthetic construct
SEQUENCE: 157
VEKLWVTVYY GVPAWKEATT TLFCASDAKA YDTEVHNVWA THECVPTDPN PQEIVLENVT  60
ENFNMWKNNM VEQMHEDIIE LWDQSLEPCV KLTPLCVTLH CTNLENATNT TSSNWKSMMR  120
GEIKNCSFNV TTSIGNKMQK EYALFYRLDV VPIDNDNTSY NLINCNTSVI TQACPKVSFE  180
PIPIHYCAPA GFAILKCNDK KFNGSGPCIN VSTVQCTHGI RPVVSTQLLL NGSLAEEGVI  240
IRSENFTDNV KTIIVQLKES VEINCTRPNN NTVKSIPIGP GKAFYYTGDI IGDIRMAHCN  300
ISGEKWNNTL KQIVTKLQAQ FENKTIVFKQ SSGGDPEIVM HSFNCGGEFF YCNSTQLFNS  360
TWNNTIGPNN TNGTITLPCR IKQIINRWQE VGKAMYAPPI RGQIRCSSNI TGLLLTRDGG  420
REVGNTTEIF RPGGGDMRDN WRSELYKYKV VKIEPLGVAP TKCKRRVVQR RRRRRAVTLG  480
AVSLGFLGAA GSTMGAASLT LTVQARQLLS GIVQQQNNLL RAPEPQQRLL QLTVWGIKQL  540
QARVLAVEHY LKDQQLLGIW GCSGKLICCT AVPWNASWSN KSLDQIWNNM TWMEWEREIG  600
NYTNLIYTLI EESQNQQEKN EQELLELD                                     628

SEQ ID NO: 158         moltype = AA  length = 681
FEATURE                Location/Qualifiers
REGION                 1..681
                       note = Description of Artificial Sequence: Synthetic
                        polypeptide
source                 1..681
                       mol_type = protein
                       organism = synthetic construct
SEQUENCE: 158
VEKLWVTVYY GVPAWKEATT TLFCASDAKA YDTEVHNVWA THECVPTDPN PQEIVLENVT  60
ENFNMWKNNM VEQMHEDIIE LWDQSLEPCV KLTPLCVTLH CTNLENATNT TSSNWKSMMR  120
GEIKNCSFNV TTSIGNKMQK EYALFYRLDV VPIDNDNTSY NLINCNTSVI TQACPKVSFE  180
PIPIHYCAPA GFAILKCNDK KFNGSGPCIN VSTVQCTHGI RPVVSTQLLL NGSLAEEGVI  240
IRSENFTDNV KTIIVQLKES VEINCTRPNN NTVKSIPIGP GKAFYYTGDI IGDIRMAHCN  300
ISGEKWNNTL KQIVTKLQAQ FENKTIVFKQ SSGGDPEIVM HSFNCGGEFF YCNSTQLFNS  360
TWNNTIGPNN TNGTITLPCR IKQIINRWQE VGKAMYAPPI RGQIRCSSNI TGLLLTRDGG  420
REVGNTTEIF RPGGGDMRDN WRSELYKYKV VKIEPLGVAP TKCKRRVVQS HSGSGGSGSG  480
GHAAVTLGAV SLGFLGAAGS TMGAASLTLT VQARQLLSGI VQQQNNLLRA PEPQQRLLQL  540
TVWGIKQLQA RVLAVEHYLK DQQLLGIWGC SGKLICCTAV PWNASWSNKS LDQIWNNMTW  600
MEWEREIGNY TNLIYTLIEE SQNQQEKNEQ ELLELDKWAS LWNWFDISKW LWYIKIFIMI  660
VGGLVGLRIV FTVLSIVNRV R                                           681

SEQ ID NO: 159         moltype = AA  length = 25
FEATURE                Location/Qualifiers
REGION                 1..25
                       note = Description of Artificial Sequence: Synthetic peptide
source                 1..25
                       mol_type = protein
```

-continued

```
                          organism = synthetic construct
SEQUENCE: 159
MTGVERGDFW SDDYSQHYNT YLIDV                                    25

SEQ ID NO: 160          moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 160
YYDFWSGYYT                                                     10

SEQ ID NO: 161          moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 161
YYYYYYMDV                                                       9

SEQ ID NO: 162          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 162
TTGVETYDFW SGYDDHYYDY YFRDV                                    25

SEQ ID NO: 163          moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 163
TTGVEYYDFW SGYYDHYYYY YYMDV                                    25

SEQ ID NO: 164          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 164
VREAGGPDYR NGYNYYDFYD GYYNYHYMDV                               30

SEQ ID NO: 165          moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 165
AREAGGPDYR NGYNYYDFWS GYYYYYYMDV                               30
```